US012751726B2

(12) United States Patent
McGinley et al.

(10) Patent No.: US 12,751,726 B2
(45) Date of Patent: Oct. 6, 2026

(54) ANKLE REPLACEMENT SYSTEM AND METHOD

(71) Applicant: Wright Medical Technology, Inc., Memphis, TN (US)

(72) Inventors: Shawn McGinley, Arlington, TN (US); Robert M. Howles, Bartlett, TN (US); Daniel E. Free, Oakland, TN (US); Vinay D. Patel, Memphis, TN (US); Ramon Luna, Arlington, TN (US); Matthew D. Schultz, Orlando, FL (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 441 days.

(21) Appl. No.: 18/495,844

(22) Filed: Oct. 27, 2023

(65) Prior Publication Data

US 2024/0050108 A1 Feb. 15, 2024

Related U.S. Application Data

(60) Division of application No. 17/402,760, filed on Aug. 16, 2021, now Pat. No. 11,864,778, which is a
(Continued)

(51) Int. Cl.
*A61B 17/17* (2006.01)
*A61B 17/15* (2006.01)
(Continued)

(52) U.S. Cl.
CPC .......... *A61B 17/1739* (2013.01); *A61B 17/15* (2013.01); *A61B 17/1682* (2013.01);
(Continued)

(58) Field of Classification Search
CPC ............ A61B 17/1739; A61B 17/1775; A61B 17/1682; A61F 2/4202; A61F 2/4606
See application file for complete search history.

(56) References Cited

U.S. PATENT DOCUMENTS

| | | |
|---|---|---|
| 3,839,742 A | 10/1974 | Link |
| 3,872,519 A | 3/1975 | Giannestras et al. |

(Continued)

FOREIGN PATENT DOCUMENTS

| | | |
|---|---|---|
| EP | 2967697 | 4/2018 |
| JP | H11500035 | 1/1999 |

(Continued)

OTHER PUBLICATIONS

Search report issued for European U.S. Appl. No. 13/198,280 dated Feb. 5, 2014. *cited in parent.

(Continued)

*Primary Examiner* — Matthew J Lawson
(74) *Attorney, Agent, or Firm* — DUANE MORRIS LLP

(57) ABSTRACT

A system that provides a guide arm, a ratchet arm frame configured to be coupled to the guide arm, a ratchet arm configured to be coupled to the ratchet arm frame, and a sagittal sizing guide body configured to be coupled to the ratchet arm. The sagittal sizing guide body includes a first radiopaque object disposed at a first position and a second radiopaque object disposed at a second position that is spaced apart from the first position. The first radiopaque object has a length that corresponds to a length of a second prosthesis component. When the surgical alignment system is positioned for use on a patient, the first radiopaque object identifies a location at which a first resection of a first bone is to be performed. The second radiopaque object has a profile that corresponds to a profile of a first prosthesis component for installation on a second bone.

30 Claims, 86 Drawing Sheets

Related U.S. Application Data division of application No. 15/982,337, filed on May 17, 2018, now Pat. No. 11,116,524, which is a continuation of application No. 14/448,242, filed on Jul. 31, 2014, now Pat. No. 9,993,255, which is a continuation of application No. PCT/US2014/027448, filed on Mar. 14, 2014, which is a continuation-in-part of application No. 14/100,799, filed on Dec. 9, 2013, now Pat. No. 9,480,571.

(60) Provisional application No. 61/846,831, filed on Jul. 16, 2013, provisional application No. 61/782,507, filed on Mar. 14, 2013, provisional application No. 61/746,393, filed on Dec. 27, 2012.

(51) Int. Cl.

| | |
|---|---|
| ***A61B 17/16*** | (2006.01) |
| ***A61B 17/84*** | (2006.01) |
| ***A61B 17/88*** | (2006.01) |
| ***A61B 90/00*** | (2016.01) |
| ***A61F 2/42*** | (2006.01) |
| ***A61F 2/46*** | (2006.01) |
| *A61B 17/56* | (2006.01) |
| *A61B 17/90* | (2006.01) |
| *A61F 2/30* | (2006.01) |

(52) U.S. Cl.

CPC ............ *A61B 17/846* (2013.01); *A61B 17/88* (2013.01); *A61B 90/39* (2016.02); *A61F 2/4202* (2013.01); *A61F 2/4606* (2013.01); *A61F 2/4637* (2013.01); *A61F 2/4684* (2013.01); *A61B 17/1703* (2013.01); *A61B 17/1775* (2016.11); *A61B 2017/564* (2013.01); *A61B 17/90* (2021.08); *A61B 2090/3966* (2016.02); *A61F 2002/30387* (2013.01); *A61F 2002/30878* (2013.01); *A61F 2002/4205* (2013.01); *A61F 2002/4207* (2013.01); *A61F 2002/4687* (2013.01)

(56) References Cited

U.S. PATENT DOCUMENTS 3,886,599 A 6/1975 Schlein
3,889,300 A 6/1975 Smith
3,896,502 A 7/1975 Lennox
3,896,503 A 7/1975 Freeman et al.
3,975,778 A 8/1976 Newton, III
3,987,500 A 10/1976 Schlein
4,021,864 A 5/1977 Waugh
4,069,518 A 1/1978 Groth, Jr. et al.
4,156,944 A 6/1979 Schreiber et al.
4,166,292 A 9/1979 Bokros
4,204,284 A 5/1980 Koeneman
4,232,404 A 11/1980 Samuelson et al.
4,309,778 A 1/1982 Buechel et al.
4,470,158 A 9/1984 Pappas et al.
4,661,069 A 4/1987 Weissman
4,755,185 A 7/1988 Tarr
4,913,144 A 4/1990 Del Medico
4,968,316 A 11/1990 Hergenroeder
5,041,139 A 8/1991 Brånemark
5,190,544 A 3/1993 Chapman et al.
5,312,412 A 5/1994 Whipple
5,326,365 A 7/1994 Alvine
5,342,368 A 8/1994 Petersen
5,354,300 A 10/1994 Goble et al.
5,364,402 A 11/1994 Mumme et al.
5,423,825 A 6/1995 Levine
5,476,466 A 12/1995 Barrette et al.
5,601,563 A 2/1997 Burke et al.
5,634,927 A 6/1997 Houston et al.
5,667,511 A 9/1997 Vendrely et al.
5,674,223 A 10/1997 Cipolletti et al.
5,678,996 A 10/1997 Dawson
5,683,470 A 11/1997 Johnson et al.
5,688,279 A 11/1997 McNulty et al.
5,735,904 A 4/1998 Pappas
5,766,259 A 6/1998 Sammarco
5,776,200 A 7/1998 Johnson et al.
5,817,097 A 10/1998 Howard et al.
5,824,106 A 10/1998 Fournal
5,879,389 A 3/1999 Koshino
5,885,299 A 3/1999 Winslow et al.
5,888,203 A 3/1999 Goldberg
5,897,559 A 4/1999 Masini
5,935,132 A 8/1999 Bettuchi et al.
6,002,859 A 12/1999 DiGioia, III et al.
6,033,405 A 3/2000 Winslow et al.
6,102,952 A 8/2000 Koshino
6,183,519 B1 2/2001 Bonnin et al.
6,245,109 B1 6/2001 Mendes et al.
6,342,056 B1 1/2002 Mac-Thiong et al.
6,409,767 B1 6/2002 Pericéet al.
6,436,146 B1 8/2002 Hassler et al.
6,478,800 B1 11/2002 Fraser et al.
6,520,964 B2 2/2003 Tallarida et al.
6,530,930 B1 3/2003 Marino et al.
6,610,067 B2 8/2003 Tallarida et al.
6,610,095 B1 8/2003 Pope et al.
6,620,168 B1 9/2003 Lombardo et al.
6,645,215 B1 11/2003 McGovern et al.
6,663,669 B1 12/2003 Reiley
6,673,116 B2 1/2004 Reiley
6,679,917 B2 1/2004 Ek
6,719,799 B1 4/2004 Kropf
6,824,567 B2 11/2004 Tornier et al.
6,852,130 B2 2/2005 Keller et al.
6,860,902 B2 3/2005 Reiley
6,863,691 B2 3/2005 Short et al.
6,875,222 B2 4/2005 Long et al.
6,875,236 B2 4/2005 Reiley
6,926,739 B1 8/2005 O'Connor et al.
6,939,380 B2 9/2005 Guzman
6,942,670 B2 9/2005 Heldreth et al.
7,001,394 B2 2/2006 Gundlapalli et al.
7,011,687 B2 3/2006 Deffenbaugh et al.
7,025,790 B2 4/2006 Parks et al.
7,163,541 B2 1/2007 Ek
7,238,190 B2 7/2007 Schon et al.
7,252,684 B2 8/2007 Dearnaley
7,314,488 B2 1/2008 Reiley
7,323,012 B1 1/2008 Stone et al.
7,476,227 B2 1/2009 Tornier et al.
7,481,814 B1 1/2009 Metzger
7,485,147 B2 2/2009 Papps et al.
7,534,246 B2 5/2009 Reiley et al.
7,618,421 B2 11/2009 Axelson, Jr. et al.
7,625,409 B2 12/2009 Saltzman et al.
7,641,697 B2 1/2010 Reiley
7,648,508 B2 1/2010 Lutz et al.
7,678,151 B2 3/2010 Ek
7,713,305 B2 5/2010 Ek
7,717,920 B2 5/2010 Reiley
7,744,601 B2 6/2010 Rosa et al.
7,763,027 B2 7/2010 Irving
7,763,080 B2 7/2010 Southworth
7,803,158 B2 9/2010 Hayden
7,850,698 B2 12/2010 Straszheim-Morley et al.
7,896,883 B2 3/2011 Ek et al.
7,896,885 B2 3/2011 Miniaci et al.
7,909,882 B2 3/2011 Stinnette
7,963,996 B2 6/2011 Saltzman et al.
8,002,841 B2 8/2011 Hasselman
8,012,217 B2 9/2011 Strzepa et al.
8,034,114 B2 10/2011 Reiley
8,034,115 B2 10/2011 Reiley
8,048,164 B2 11/2011 Reiley
8,110,006 B2 2/2012 Reiley
8,114,091 B2 2/2012 Ratron et al.
8,167,888 B2 5/2012 Steffensmeier

(56) References Cited

U.S. PATENT DOCUMENTS 8,172,850 B2 5/2012 McMinn
8,177,841 B2 5/2012 Ek
8,268,007 B2 9/2012 Barsoum et al.
8,303,667 B2 11/2012 Younger
8,313,492 B2 11/2012 Wong et al.
8,323,346 B2 12/2012 Tepic
8,337,503 B2 12/2012 Lian
8,361,159 B2 1/2013 Ek
8,475,463 B2 7/2013 Lian
8,491,596 B2 7/2013 Long et al.
8,652,180 B2 2/2014 Federspiel et al.
8,808,303 B2 * 8/2014 Stemniski ............. A61F 2/4202 606/96
9,186,154 B2 11/2015 Li
9,326,780 B2 5/2016 Wong et al.
9,675,471 B2 6/2017 Bojarski et al.
9,775,639 B2 10/2017 Hanson et al.
9,907,561 B2 3/2018 Luna et al.
10,034,678 B2 7/2018 Park et al.
10,039,558 B2 8/2018 Park et al.
10,206,588 B2 2/2019 Park et al.
10,456,179 B2 10/2019 Luna et al.
10,881,417 B2 * 1/2021 Mahfouz ................ A61B 17/15
10,888,336 B2 1/2021 McGinley et al.
11,633,195 B2 4/2023 Dhillon
11,653,938 B2 * 5/2023 Siegler ............... A61B 17/1775 606/87
2002/0082607 A1 6/2002 Heldreth et al.
2002/0133164 A1 9/2002 Williamson
2002/0173853 A1 11/2002 Corl, III et al.
2003/0208280 A1 11/2003 Tohidi
2003/0236522 A1 12/2003 Long et al.
2004/0030399 A1 2/2004 Asencio
2004/0039394 A1 * 2/2004 Conti ..................... A61B 17/15 606/87
2004/0068322 A1 4/2004 Ferree
2004/0167631 A1 8/2004 Luchesi et al.
2004/0186585 A1 9/2004 Feiwell
2004/0216259 A1 11/2004 Ponziani
2004/0236431 A1 11/2004 Sekel
2005/0004676 A1 1/2005 Schon et al.
2005/0075643 A1 4/2005 Schwab et al.
2005/0165408 A1 7/2005 Puno et al.
2005/0192674 A1 9/2005 Ferree
2005/0216008 A1 9/2005 Zwirnmann
2006/0009857 A1 1/2006 Gibbs et al.
2006/0020345 A1 1/2006 O'Connor et al.
2006/0036237 A1 2/2006 Steffensmeier
2006/0116679 A1 6/2006 Lutz et al.
2006/0142870 A1 6/2006 Robinson et al.
2006/0235541 A1 10/2006 Hodorek
2006/0247788 A1 11/2006 Ross
2007/0038303 A1 2/2007 Myerson et al.
2007/0100346 A1 5/2007 Wyss et al.
2007/0112431 A1 5/2007 Kofoed
2007/0162025 A1 7/2007 Tornier et al.
2007/0173944 A1 7/2007 Keller et al.
2007/0173947 A1 7/2007 Ratron et al.
2007/0213830 A1 9/2007 Ammann et al.
2007/0233129 A1 10/2007 Bertagnoli et al.
2007/0276400 A1 11/2007 Moore et al.
2008/0015602 A1 1/2008 Axelson
2008/0097617 A1 4/2008 Fellinger et al.
2008/0103603 A1 5/2008 Hintermann
2008/0109081 A1 5/2008 Bao et al.
2008/0195233 A1 8/2008 Ferrari et al.
2008/0215156 A1 9/2008 Duggal et al.
2008/0287954 A1 11/2008 Kunz et al.
2008/0312745 A1 12/2008 Keller et al.
2009/0043310 A1 2/2009 Rasmussen
2009/0054992 A1 2/2009 Landes et al.
2009/0062801 A1 3/2009 VanMeter
2009/0082875 A1 3/2009 Long
2009/0105767 A1 4/2009 Reiley
2009/0105840 A1 4/2009 Reiley
2009/0182433 A1 7/2009 Reiley et al.
2009/0198341 A1 8/2009 Choi et al.
2009/0234360 A1 9/2009 Alexander
2009/0276052 A1 11/2009 Regala et al.
2009/0299416 A1 12/2009 Hanni et al.
2010/0010493 A1 1/2010 Dower
2010/0023066 A1 1/2010 Long et al.
2010/0023126 A1 1/2010 Grotz
2010/0057216 A1 3/2010 Gannoe et al.
2010/0069910 A1 3/2010 Hasselman
2010/0198355 A1 8/2010 Kofoed et al.
2010/0241126 A1 9/2010 Ghijselings
2010/0241237 A1 9/2010 Pappas
2010/0262150 A1 10/2010 Lian
2010/0305572 A1 12/2010 Saltzman et al.
2010/0331984 A1 12/2010 Barsoum et al.
2011/0015636 A1 1/2011 Katrana et al.
2011/0029090 A1 2/2011 Zannis et al.
2011/0035018 A1 2/2011 Deffenbaugh et al.
2011/0035019 A1 2/2011 Goswami et al.
2011/0106268 A1 5/2011 Deffenbaugh et al.
2011/0125200 A1 5/2011 Hanson et al.
2011/0125275 A1 5/2011 Lipman et al.
2011/0125284 A1 5/2011 Gabbrielli et al.
2011/0152868 A1 6/2011 Kourtis et al.
2011/0152869 A1 6/2011 Ek et al.
2011/0166608 A1 7/2011 Duggal et al.
2011/0190829 A1 8/2011 Duggal et al.
2011/0218542 A1 9/2011 Lian
2011/0253151 A1 10/2011 Tochigi et al.
2011/0276052 A1 11/2011 Hasselman
2011/0295380 A1 12/2011 Long
2012/0010718 A1 1/2012 Still
2012/0046753 A1 2/2012 Cook et al.
2012/0053644 A1 3/2012 Landry et al.
2012/0071802 A1 3/2012 Reiley et al.
2012/0083789 A1 4/2012 Blakemore et al.
2012/0109131 A1 5/2012 Vasarhelyi et al.
2012/0109326 A1 5/2012 Perler
2012/0130376 A1 * 5/2012 Loring .................. A61B 17/15 606/90
2012/0136443 A1 5/2012 Wenzel
2012/0185057 A1 7/2012 Abidi et al.
2012/0191210 A1 7/2012 Ratron et al.
2012/0239045 A1 9/2012 Li
2012/0245645 A1 9/2012 Hanson et al.
2012/0245701 A1 9/2012 Zak et al.
2012/0271430 A1 10/2012 Arnett et al.
2012/0277745 A1 11/2012 Lizee
2013/0041473 A1 2/2013 Rouyer et al.
2013/0046313 A1 2/2013 Lian
2013/0090662 A1 4/2013 Hanson et al.
2013/0116797 A1 5/2013 Coulange et al.
2013/0316562 A1 11/2013 Nagasaka et al.
2016/0135815 A1 5/2016 Loring et al.
2016/0367270 A1 12/2016 Garlock et al.
2016/0374697 A1 * 12/2016 Kehres ............... A61B 17/1739 606/87
2017/0112509 A9 * 4/2017 Lancianese ........ A61B 17/1682
2020/0352580 A1 * 11/2020 Saltzman ........... A61B 17/1775

FOREIGN PATENT DOCUMENTS

JP 2006150055 6/2006
JP 2007-518453 7/2007
JP 2007-519477 7/2007
JP 2011526189 10/2011
JP 2012518517 8/2012
JP 2013500810 1/2013
JP 2013511358 4/2013
JP 2014-131738 7/2014
JP 2007536011 12/2017
WO WO 01/66021 A1 9/2001
WO WO 2005/011523 A2 2/2005
WO WO 2006/023824 3/2006
WO WO 2006/099270 9/2006
WO WO 2007/084846 7/2007
WO WO 2009/158522 12/2009
WO WO 2010099142 9/2010

(56) References Cited

FOREIGN PATENT DOCUMENTS

| | | | |
|---|---|---|---|
| WO | WO 2011015863 | | 2/2011 |
| WO | 2011072249 | A1 | 6/2011 |
| WO | WO 2011/151657 | | 12/2011 |
| WO | WO 2012088036 | | 6/2012 |
| WO | WO 2012116089 | | 8/2012 |

OTHER PUBLICATIONS

International Search Report for International patent application No. PCT/US2014/027448 dated Jul. 7, 2014. *cited in parent.

International Preliminary Report on Patentability issued for International patent application No. PCT/US2014/027448, Sep. 15, 2015, 8 pages. *cited in parent.

Partial European Search Report issued in connection with European patent application No. 14768333.8, Oct. 26, 2016, 6 pages. *cited in parent.

Patent Examination Report No. 1 issued in connection with Australian patent application No. 2015202080, Jul. 5, 2016, 4 pages. *cited in parent.

First Office Action issued for Japanese patent application No. 2016-117842, Sep. 12, 2017, 5 pages. *cited in parent.

Extended European Sean Report and Opinion in connection with European Patent Application No. 14768333.8, Jan. 30, 2017, 10 pages *cited in parent.

Final Office Action issued in connection with corresponding Japanese Patent Application No. 2016-502443, May 15, 2018, 3 pages.

European Search Report issued in connection with European Patent Application No. 18160378.8, Jun. 29, 2018.

Examination Report No. 1 issued in connection with corresponding Australian Patent Application No. 20182000073, Dec. 24, 2018, 3 pages.

First Office Action issued in connection with corresponding Japanese Patent Application No. 2018-092289, Mar. 5, 2019, 2 pages.

First Office Action issued in connection with corresponding Japanese Patent Application No. 2018-178853, Sep. 3, 2018, 3 pages.

Office Action in corresponding Canadian Patent Application No. 2,904,652, Jun. 2, 2020, 6 pages.

First Examination Report issued in corresponding Australian Patent Application No. 2019213412, Sep. 3, 2020, 5 pages.

First Office Action issued in connection with corresponding Japanese Patent Application No. 2020-016447, Apr. 6, 2021, 4 pages.

First Examination Report issued in connection with Australian Patent Application No. 202106853, 3 pages, Jul. 13, 2022.

Laurence W. McKeen, Handbook of Polymer Applications in Medicine and Medical Devices (2014), 38 pages.

Bonasia, D. E. et al., Total ankle replacement: Why, When and How?, The lowa Orthopaedic J., 30, (2010), 12 pages.

Clare, Michael P. et al., Preoperative Considerations in Ankle Replacement Surgery, Foot and Ankle Clinic, vol. 7 (2002), 12 pages.

Cenni, Francesco et al., Position of the Prosthesis Components in Total Ankle Replacement and the Effect on Motion at the Replaced Joint, Int'l Orthopaedics, vol. 36(3) (2012), 8 pages.

Steeves, Mark et al., How Pilot-Hole Size Affects Bone-Screw Pullout Strength in Human Cadaveric Cancellous Bone, Canadian J.of Surgery, vol. 48(3) (2005), 6 pages.

Howell, Joel D., Early Clinical Use of the X-Ray, Transactions of the Am. Clinical and Climatological Ass'n, vol. 127 (2016), 10 pages.

Hofstetter, R. et al., Fluoroscopy as an Imaging Means for Computer-Assisted Surgical Navigation, Computer Aided Surgery, vol. 4 (1999), 14 pages.

Jennings, John D. et al., Intraoperative Fluoroscopy Improves Component Position During Anterior Hip Arthroplasty, SLACK Inc., vol. 38(11) (2015), 6 pages.

Roberts, Timothy T. et al., History of the Orthopedic Screw, Orthopedics, vol. 36(1) (2013), 4 pages.

Non-Final Office Action issued in connection with U.S. Appl. No. 16/047,425, Apr. 24, 2020, 8 pages.

Response to Non-Final Office Action filed in connection with U.S. Appl. No. 16/047,425, Sep. 8, 2020, 19 pages.

Notice of Allowance issued in connection with U.S. Appl. No. 16/047,425, Oct. 20, 2020, 8 pages.

Non-Final Office Action issued in connection with U.S. Appl. No. 14/446,921, Jun. 16, 2017, 20 pages.

Response to Non-Final Office Action filed in connection with U.S. Appl. No. 14/446,921, Sep. 15, 2017, 14 pages.

Notice of Allowance issued in connection with U.S. Appl. No. 14/446,921, Oct. 25, 2017, 6 pages.

Petition for Inter Partes Review issued in connection with U.S. Pat. No. 10,888,336, 88 pages, Oct. 4, 2022.

Petition for Inter Partes Review issued in connection with U.S. Pat. No. 9,907,561, 86 pages, Oct. 4, 2022.

* cited by examiner

ANKLE REPLACEMENT SYSTEM AND METHOD

CROSS-REFERENCE TO RELATED APPLICATIONS

This application is a divisional of U.S. patent application Ser. No. 17/402,760, filed Aug. 16, 2021, which is a divisional of U.S. patent application Ser. No. 15/982,337, filed May 17, 2018 (U.S. Pat. No. 11,116,524), which is a continuation of U.S. patent application Ser. No. 14/448,242, filed Jul. 31, 2014 (U.S. Pat. No. 9,993,255), which is a continuation of International Patent Application PCT/US2014/027448, filed Mar. 14, 2014, which claims priority to U.S. Provisional Patent Application No. 61/782,507, filed Mar. 14, 2013, and to U.S. Provisional Patent Application No. 61/846,831, filed Jul. 16, 2013, and is a continuation-in-part of U.S. patent application Ser. No. 14/100,799, filed Dec. 9, 2013 (U.S. Pat. No. 9,480,471), which claims priority to U.S. Provisional Patent Application No. 61/746,393, filed Dec. 27, 2012, the entireties of which are herein incorporated by reference.

This disclosure relates to prosthetics generally, and more specifically to systems and methods for total ankle replacement.

BACKGROUND

The ankle is a joint that acts much like a hinge. The joint is formed by the union of three bones. The ankle bone is the talus. The top of the talus fits inside a socket that is formed by the lower end of the tibia, and the fibula, the small bone of the lower leg. Arthritis, bone degeneration, and/or injury can cause ankle joint deterioration resulting in pain, reduced range of motion, and decreased quality of life. In many cases, physicians are recommending ankle replacement surgery with an implant as an option. Consequently, improved systems and methods of providing ankle replacement surgery are desirable.

SUMMARY

In some embodiments, a surgical alignment system includes a guide arm, a ratchet arm frame configured to be coupled slidably to the guide arm, a ratchet arm configured to be coupled to the ratchet arm frame, and a sagittal sizing guide body configured to be coupled to the ratchet arm. The sagittal sizing guide body includes a first radiopaque object disposed at a first position and a second radiopaque object disposed at a second position that is spaced apart from the first position.

In some embodiments, a method includes coupling a guide arm to a first fixture coupled to a first bone and inserting an end of the guide arm into an opening defined by a ratchet arm frame. The ratchet arm frame is coupled to a ratchet arm that extends in a first longitudinal direction that is different from a direction in which the guide arm extends along its length. The ratchet arm is inserted into a channel defined by a sagittal sizing guide body to couple the sagittal sizing guide body to the ratchet arm. The sagittal sizing guide body includes a first radiopaque object disposed at a first position and a second radiopaque object disposed at a second position that is spaced apart from the first position.

In some embodiments, a method includes inserting a dovetail extension of a coronal sizing and drill guide into a cavity of a dovetail joint of an adjustment block that is coupled to a tibia, securing the dovetail extension within the cavity, and using fluoroscopy to check a size of a radiopaque element of the coronal sizing and drill guide relative to at least the tibia. The radiopaque element has a size and shape that corresponds to a profile of a prosthesis component of a first type having a first size when viewed in an anterior-posterior direction.

In some embodiments, a surgical positioning system includes a first component including an elongate shaft coupled to a head. The head is configured to be disposed in a joint between a first bone and a second bone. A second component includes diverging first and second portions. The first portion defines a hole that is sized and configured to receive the shaft of the first component. The second portion defines a first channel on a first side. A third component is configured to be coupled to the second component. The third component includes a base and a pointer extension. The base includes a protrusion that is sized and configured to be received slidably within the first slot.

In some embodiments, a method includes inserting a head of a first component of a surgical positioning system into a joint between a first bone and a second bone and sliding a second component of the surgical positioning system onto a shaft of the first component. The second component includes diverging first and second portions. The first portion defines a hole that is sized and configured to receive the shaft of the first component, and the second portion defines a first channel on a first side. A third component of the surgical positioning system is slid into engagement with the second component by inserting a protrusion of the third component into the first channel defined by the second component.

In some embodiments, a cutting system includes a cutting base having a body defining a slot, a first set of holes, and a second set of holes. The first set of holes being positioned along a first flange extending away from the slot in a first direction, and the second set of holes being positioned along a second flange extending from the slot in a second direction that is opposite the first direction. A first cutting guide has a body defining a plurality of holes that overlap one another to form a slot having a width that is smaller than a width of the slot defined by the cutting base. The first cutting guide includes a set of pegs that extend inferiorly from the first cutting guide and are sized and configured to be received with the first set of holes or the second set of holes to secure the first cutting guide to the cutting base.

A method includes coupling a cutting base to a resected surface of a first bone. The cutting base includes a body defining a slot, a slit within the slot, a first set of holes, and a second set of holes. The first set of holes being positioned along a first flange extending away from the slot in a first direction, and the second set of holes being positioned along a second flange extending from the slot in a second direction that is opposite the first direction. A chamfer cut of the first bone is made by inserting a saw into the slit. A first cutting guide is coupled to the cutting guide base by inserting inferiorly extending pegs into the first set of holes. The first cutting guide has a body defining a plurality of holes that overlap one another to form a slot having a width that is smaller than a width of the slot defined by the cutting base. A reamer is plunged into each of the plurality of holes defined by the first cutting guide to form a first flat. The first cutting guide is rotated relative to the cutting guide base and is coupled to the cutting guide base by inserting the inferiorly extending pegs into the second set of holes. A reamer is plunged into each of the plurality of holes defined by the first cutting guide to form a second flat.

In some embodiments, a surgical device includes a body including a handle disposed at a first end and a locking protrusion extending a direction away from a longitudinal direction of the body. The locking protrusion defines an opening that is sized and configured to receive a locking tab therein and defining a hole that extends parallel to the longitudinal direction of the body. The locking tab defines an aperture having first and second portions in which the first portion is narrower than the second portion. A pair of spaced apart rails are configured to be disposed along a length of the body. A plunger rod is sized and configured to be received slidably within a threaded hole defined by the handle, the aperture defined by the locking tab, and the hole defined by the locking protrusion. The surgical device is configured to be coupled releasably to a first implant component and to guide a second implant component into position with respect to the first implant component.

In some embodiments, a method includes coupling an insertion device to a first implant component disposed within a joint, pushing a plunger rod of the insertion device axially to advance a second implant component along a body of the insertion device between a pair of spaced apart rails until a threaded portion of the plunger rod contacts a threaded hole defined by a handle of the insertion device, and rotating a handle of the plunger rod relative to the body of the insertion device such that the threads of the threaded portion of the plunger rod engage threads of the threaded hole to advance the second implant component into engagement with the first implant component.

A method includes placing a guide having a patient-specific surface on a first bone. The guide includes a pin holder that engages a pin that extends in a direction that is parallel to an axis of the first bone. A plurality of pins are inserted into the guide. The guide is slid along the plurality of pins to remove the guide from contacting the first bone. A conversion instrument is slid over a first subset of the plurality of pins, and a sizing and drill guide is slid over a second subset of the plurality of pins. The conversion instrument is coupled to the sizing and drill guide by inserting a dovetail extension of the sizing and drill guide into a cavity of a dovetail joint of the conversion instrument.

In some embodiments, a surgical system includes a trial and a spacer. The trial is configured to be received within a resected first bone. The trial includes a plate having a bottom surface defining a channel. The spacer has an elongate body and an extension disposed at one end thereof. The elongate body is sized and configured to be received within channel defined by the trial. The extension defining at least first and second holes that are configured to receive first and second pins positioned within a second bone.

In some embodiments, a method includes inserting an elongate body of a spacer into a channel defined by a trial positioned within a resected first bone, inserting first and second pins through first and second holes defined by an extension of the spacer that extends superiorly from the elongate body; and removing the spacer and the trial while leaving the first and second pins positioned within the second bone. A cutting guide is slid over the first and second pins.

DETAILED DESCRIPTION

Figure 1A:
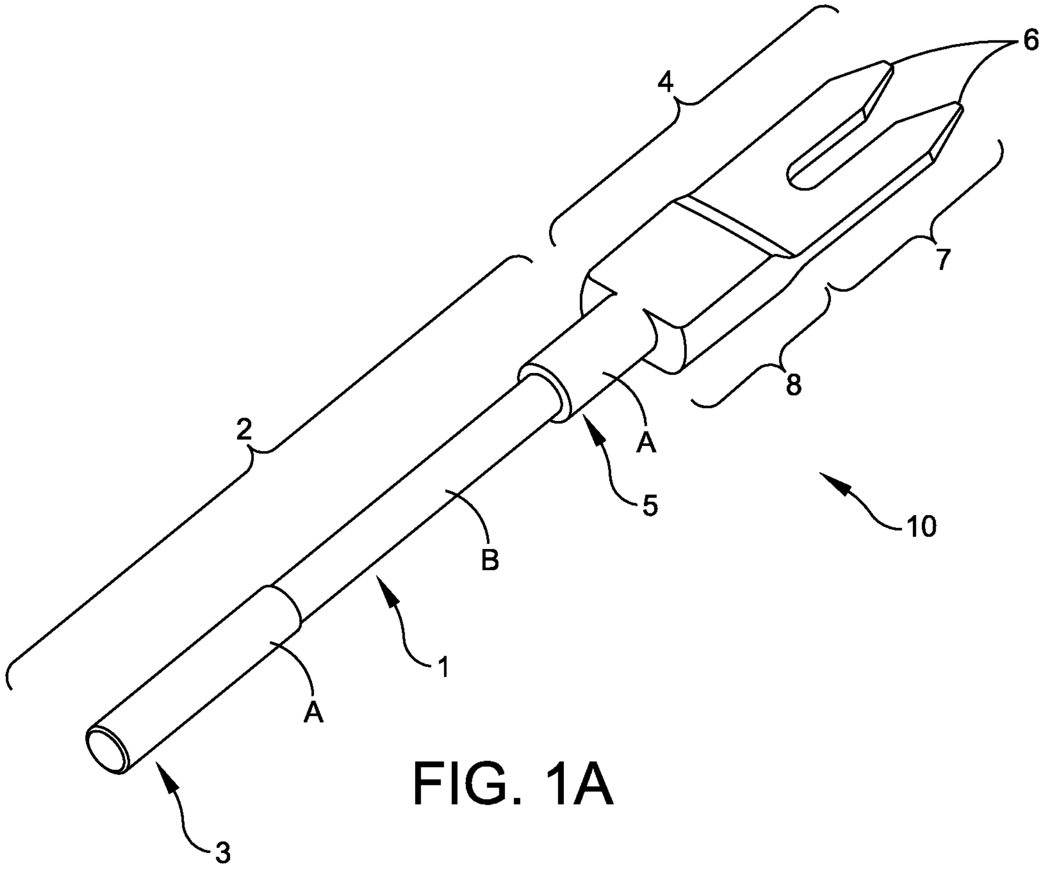
FIGS. 1A and 1B are isometric views of a medial gutter fork in accordance with some embodiments.

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

Rotation Guide Assembly

Figure 1B:
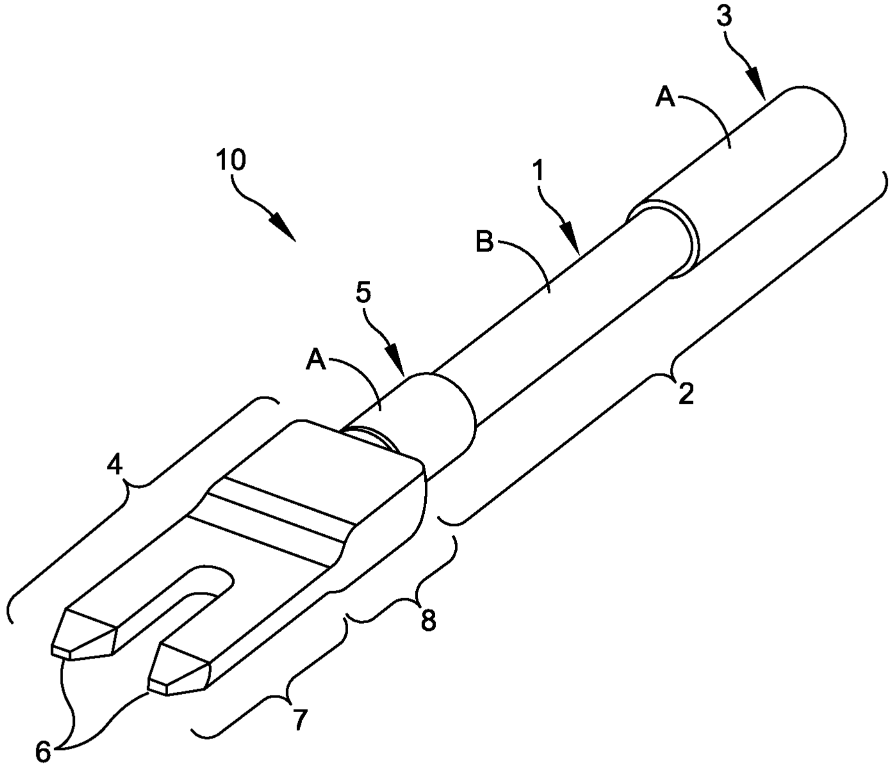

FIGS. 1-3 illustrate the one example of a rotation guide assembly 40 in accordance with some embodiments. In some embodiments, rotation guide assembly 40 includes a medial gutter fork 10, a rotation guide slide 20, and a rotation guide pointer 30. FIGS. 4A and 4B illustrate the rotation guide assembly 40 assembled together in accordance with some embodiments. The rotation guide assembly 40 assists in the accurate placement of a first guide pin 50 which serves as a guide for alignment frame assembly 140 discussed in greater detail below.

Figure 2A:
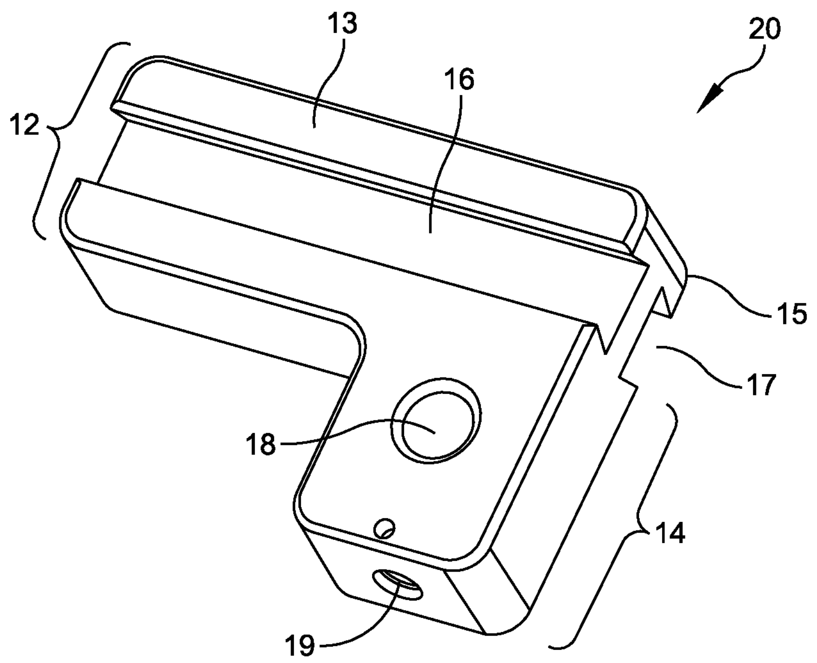
FIGS. 2A and 2B are isometric views of a rotation guide slide in accordance with some embodiments.
Figure 2B:
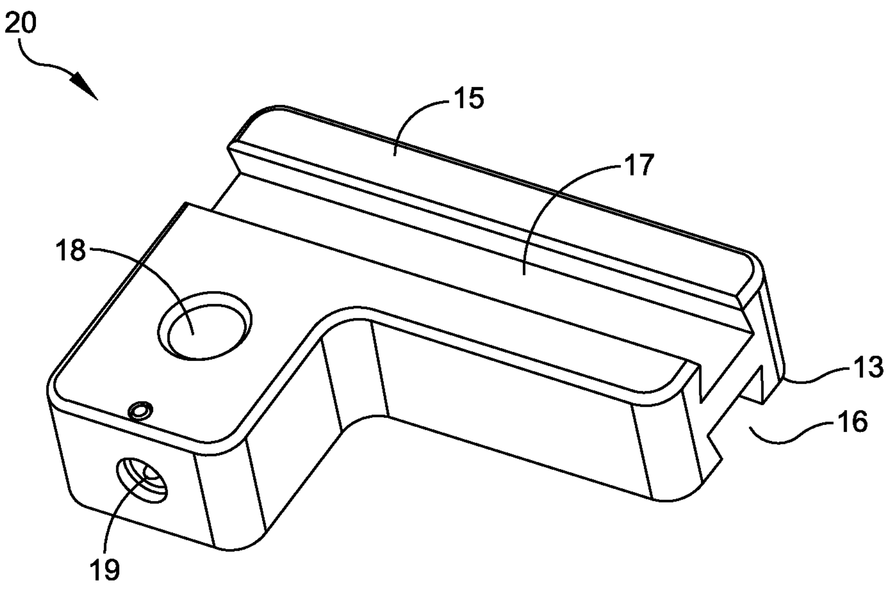

Referring again to FIGS. 1A and 1B, medial gutter fork 10 includes a shaft 2 and a head 4. In some embodiments, shaft 2 has a cylindrical geometry and includes a proximal end 3 and a distal end 5 each being of a first diameter A, and an inner section 1 disposed between proximal end 3 and distal end 5 and having a second diameter B. In some embodiments, the first diameter A is greater than second diameter B. Head 4 has a transitional portion 8, which is connected to the distal end 5 of shaft 2, and a forked portion 7 including a pair of prongs 6. As described in greater detail below, medial gutter fork 10 is configured to be inserted into the medial gutter of an ankle joint to serve as a reference point to the additional elements of the rotation guide assembly 40. In some embodiments, the head 4 does not have a forked shape FIGS. 2A and 2B are isometric views of a rotation guide slide 20. In some embodiments, rotation guide slide 20 has an "L" shaped body including a first portion 12 extending longitudinally in a first direction and a second portion 14 extending laterally from the first portion 12 in a second direction. In some embodiments, first portion 12 is longer than second portion 14 and the first and second directions are perpendicular with respect to one another. First portion 12 defines a first channel 16 that runs the length of first portion 12 on a first side 13 and defines a second channel 17 on second side 15, which is disposed opposite the first side 13. Second portion 14 defines a guide hole 18 which is configured to engage the shaft 2 of medial gutter fork 10. In some embodiments, hole 18 is located at the approximate center of second portion 14; however, hole 18 can be located at other positions of second portion 14. Another hole 19 is defined by the side of second portion 14 and is sized and configured to receive a set screw (not shown) for locking the position of rotation guide slide 20 relative gutter fork 10.

Figure 2C:
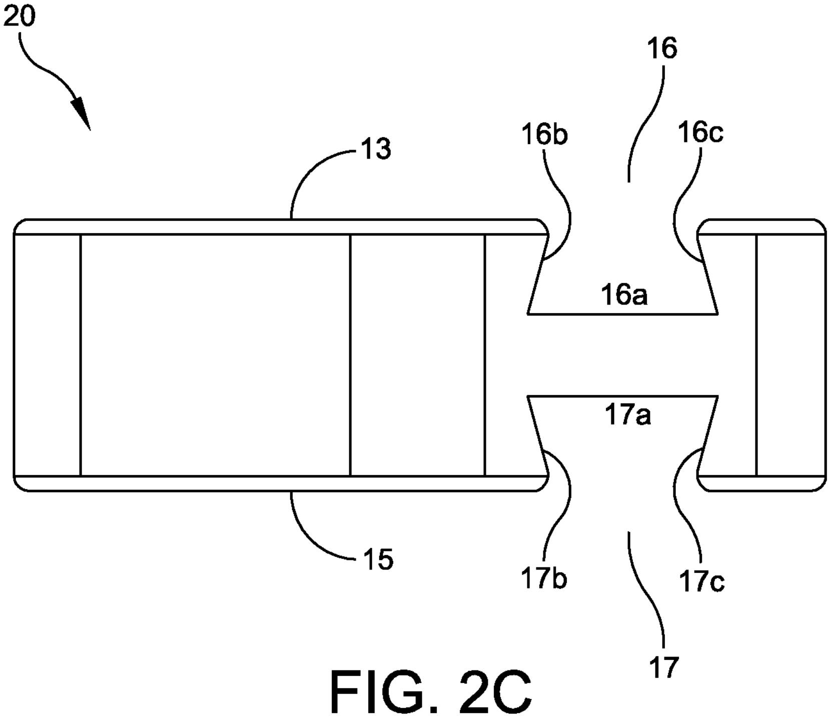
FIGS. 2C and 2D are side profile views of a rotation slide guide in accordance with some embodiments.

FIG. 2C illustrates one example of a configuration of channel 16 in accordance with some embodiments. Channel 16 is illustrated as having a flat bottom surface 16*a* and angled side walls 16*b* and 16*c* that taper inwardly such that the top of channel 16 is narrower than the bottom. Second channel 17 is aligned along the same longitudinal axis as first channel 16 and is shaped identical to first channel 16 with a flat bottom surface 17*a* and angled side walls 17*b* and 17*c* that taper inwardly such that the top of channel 17 is narrower than the bottom.

Figure 2D:
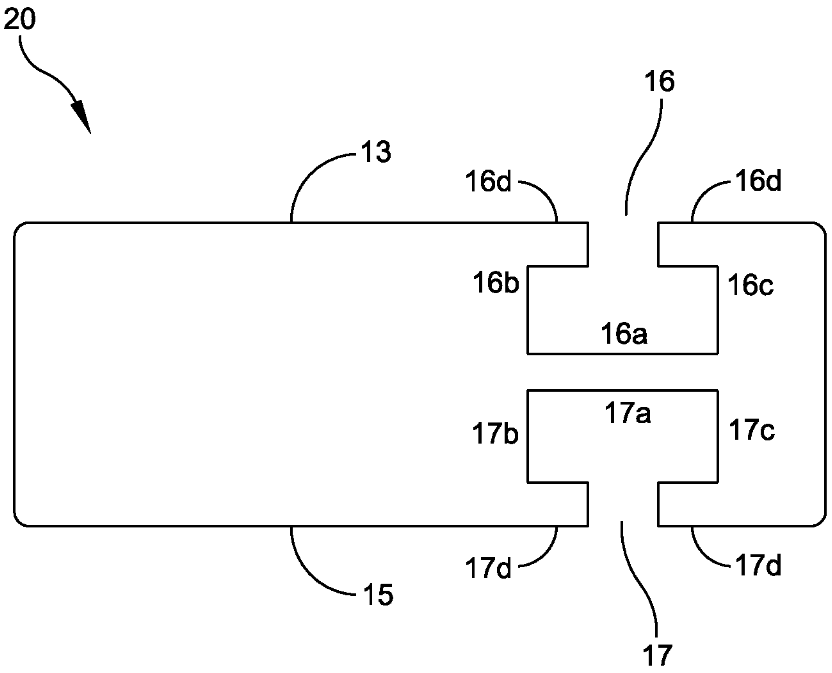

FIG. 2D illustrates another example of a configuration of channel 16. As shown in FIG. 2D, side walls 16*b* and 16*c* perpendicularly extend from bottom surface 16*a*. Like first channel 16, second channel 17 can also be configured such that side walls 17*b* and 17*c* perpendicularly extend from bottom wall 17*a*. In some embodiments, side walls 16*b*, 16*c* and 17*b*, 17*c* include internal extending rails 16*d*, 17*d* that perpendicularly extend inwardly from side walls 16*b*, 16*c* and 17*b*, 17*c*, respectively.

Regardless of the configuration of channels 16 and 17, either first channel 16 or second channel 17 faces away from the ankle and will engage with rotation guide pointer 30 as described in greater detail below. This configuration enables rotation guide slide 20 to be used during an ankle replacement procedure for either the right ankle or left ankle.

Figure 3A:
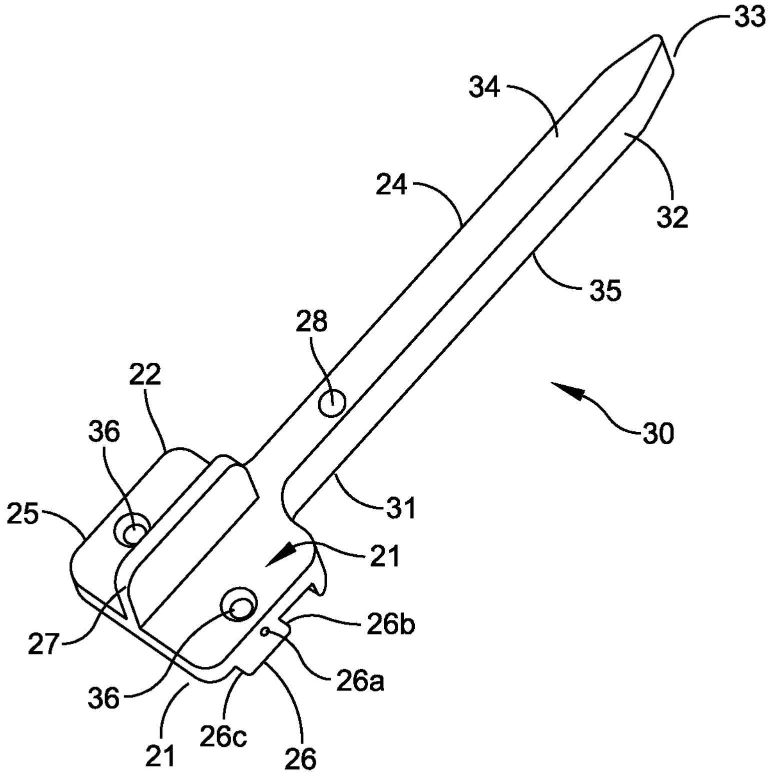
FIGS. 3A and 3B are isometric views of a rotation guide pointer in accordance with some embodiments.
Figure 3B:
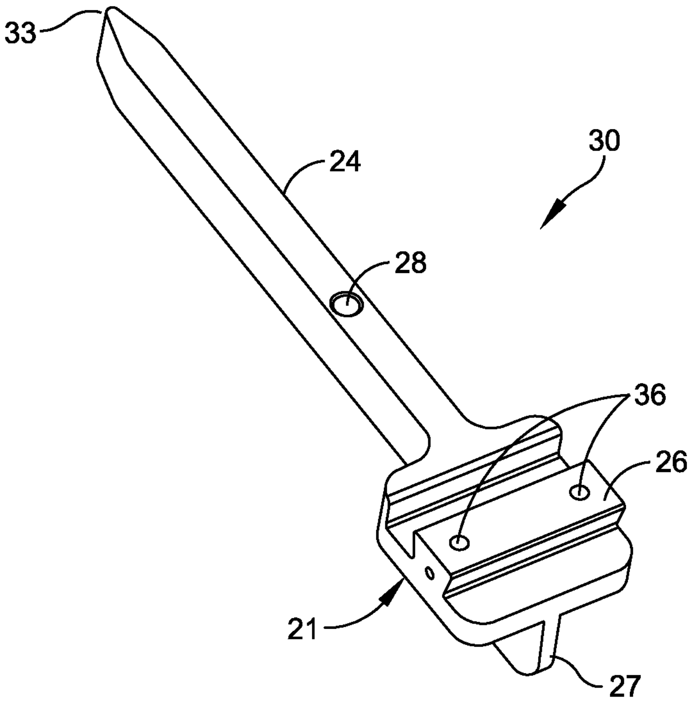
Figure 3C:
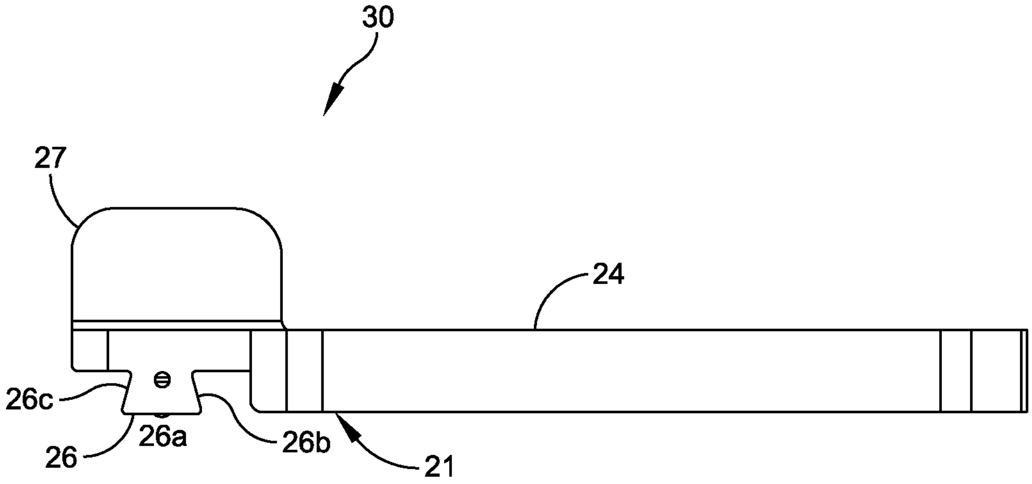
FIG. 3C is a side profile view of a rotation guide pointer in accordance with some embodiments.
Figure 4A:
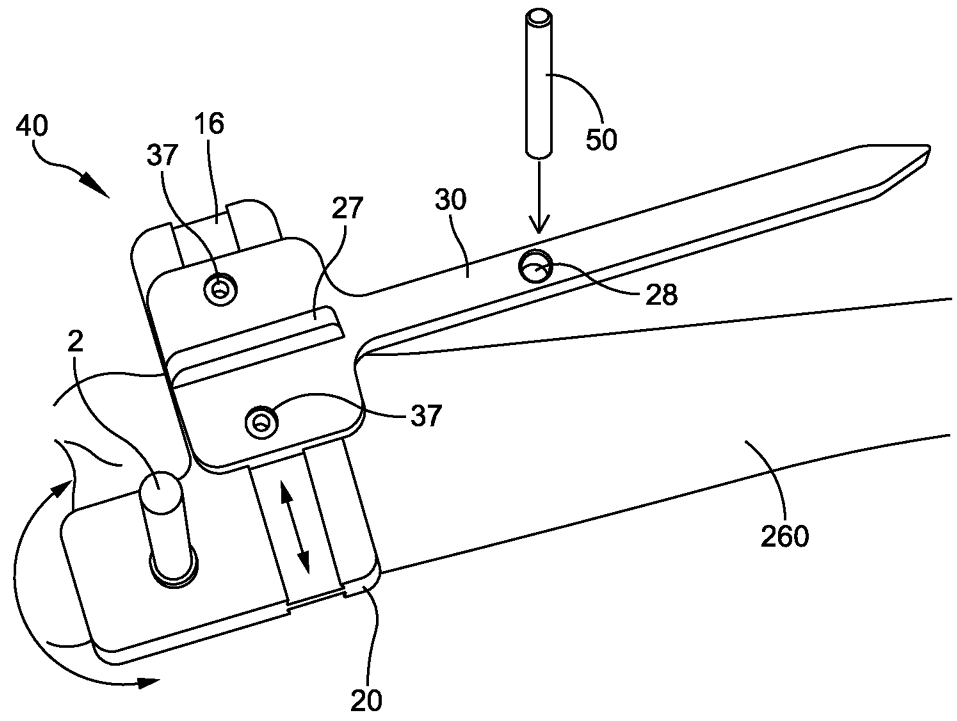
FIG. 4A is an isometric view of an assembled rotation guide assembly comprising a medial gutter fork, rotation guide slide, and rotation guide pointer in accordance with some embodiments.
Figure 4B:
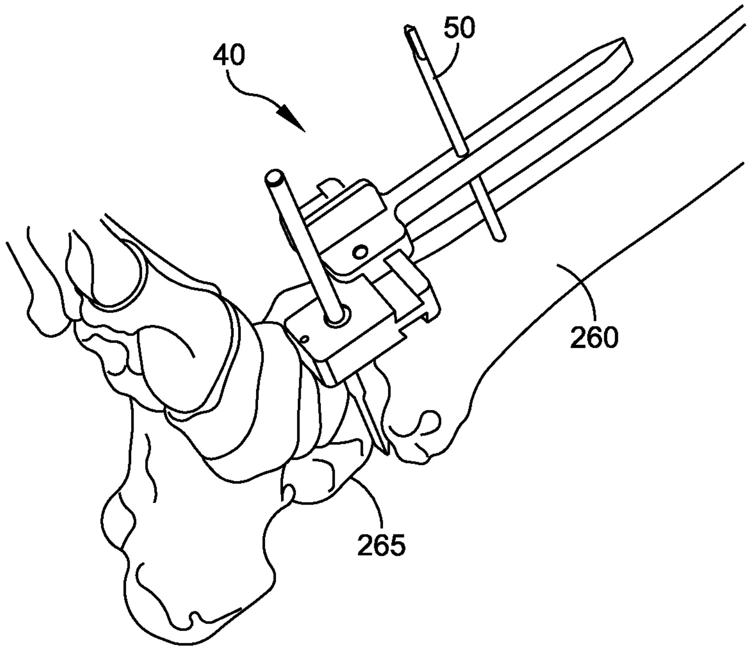
FIG. 4B is an isometric view of an assembled rotation guide assembly with first guide pin inserted in accordance with some embodiments.

FIGS. 3A and 3B are isometric views of one example of a rotation guide pointer 30 in accordance with some embodiment, and FIG. 3C is a side profile view rotation guide pointer 30. Rotation guide pointer 30 comprises a wide, rectangular base 22 and a narrow, elongated pointer extension 24 that extends from base 22. As best seen in FIG. 3C, the underside 21 of base 22 includes a protrusion 26 configured to engage first channel 16 or second channel 17 of rotation guide slide 20. Protrusion 26 extends longitudinally across base 22 (i.e., in a direction that is perpendicular with respect to the longitudinal length of elongated pointer extension 24). As best seen in FIG. 3C and has a flat bottom surface 26*a* and angled sides 26*b* and 26*c* such that the top portion of protrusion 26 is narrower than the bottom surface such that protrusion 26 has a complementary shape to channels 16 and 17 of rotation guide slide 20. In some embodiments, sides 26*b* and 26*c* of protrusion 26 perpendicularly extend from bottom surface 26*a* of protrusion 26.

Referring again to FIG. 3A, the top side 25 of base 22 includes a finger tab 27 extending perpendicularly from the top side 25 of base 22 and running along a lateral axis perpendicular to the longitudinal axis of protrusion 26. Put another way, finger tab 27 extends from top side 25 and extends parallel to the longitudinal direction of the elongated pointer extension 24. Finger tab 27 can be used to approximately align pointer extension 24 with the mechanical axis of the tibia 260 as described in greater detail below.

Still referring to FIG. 3A, top side 25 of base 22 defines a pair of screw holes 36, with one hole being located on either side of finger tab 27. Each screw hole 36 is configured to receive a screw 37 (FIG. 4A) to affix rotation guide pointer 30 to rotation guide slide 20. In some embodiments, screw 37 extends through protrusion 26, exiting bottom surface 26*a* and penetrating bottom surface 16*a* on the rotation guide slide 20. In other embodiments, screws 37 do not exit the rotation guide pointer 30; rather, screws 37 are configured to expand side walls 26*b* and 26*c*, causing protrusion 26 to expand within channel 16 and creating a friction connection between rotation guide pointer and rotation guide slide.

Pointer extension 24 extends from base 22 at a first end 31 and tapers at a second end 32 to form a rounded point 33. Pointer extension 24 defines a pin hole 28 along its length that extends from a top side 34 to a bottom side 35. The pin hole 28 is positioned at a distance from the base 22 that is sufficient to allow the appropriate travel of other components, e.g., adjustment block 100, which is described in greater detail below.

The use of rotation guide assembly 40 is now briefly described with reference to FIGS. 4A and 4B, which is used once access is gained to the tibia 260 and talus 265. In some embodiments, such access is gained by making an anterior incision lateral of the tibialis, with care taken to avoid the anterior tendons, to expose the tibia 260, talus 265, and a portion of the midfoot. In some embodiments, the incision is approximately 125 mm long; however, one of ordinary skill in the art will understand that the incision can be greater or less than 125 mm.

Gutter fork 10 is inserted into the medial gutter of the ankle joint, and rotation guide slide 20 is operationally connected to medial gutter fork 10 by placing guide hole 18 over shaft 2 as illustrated in FIG. 4A. Rotation guide slide 20 is positioned with either first channel 16 or second channel 17 facing away from the tibia 260. Rotation guide pointer 30 is operationally connected to rotation guide slide 20 by sliding protrusion 26 into either first channel 16 or second channel 17, whichever is facing away from the tibia 260. Thus assembled, an operator uses finger tab 27 to rotate the combined rotation guide slide 20 and rotation guide pointer 30 about an axis defined by shaft 2. A surgeon or other profession can also use finger tab 27 to slide rotation guide pointer 30 along an axis defined by first channel 16 or second channel 17. The operator thus uses finger tab 27 to rotate the combined rotation guide slide 20 and rotation guide pointer 30 and slide rotation guide pointer 30 until pointer extension 24 is approximately aligned with the mechanical axis of the tibia 260.

Figure 5:
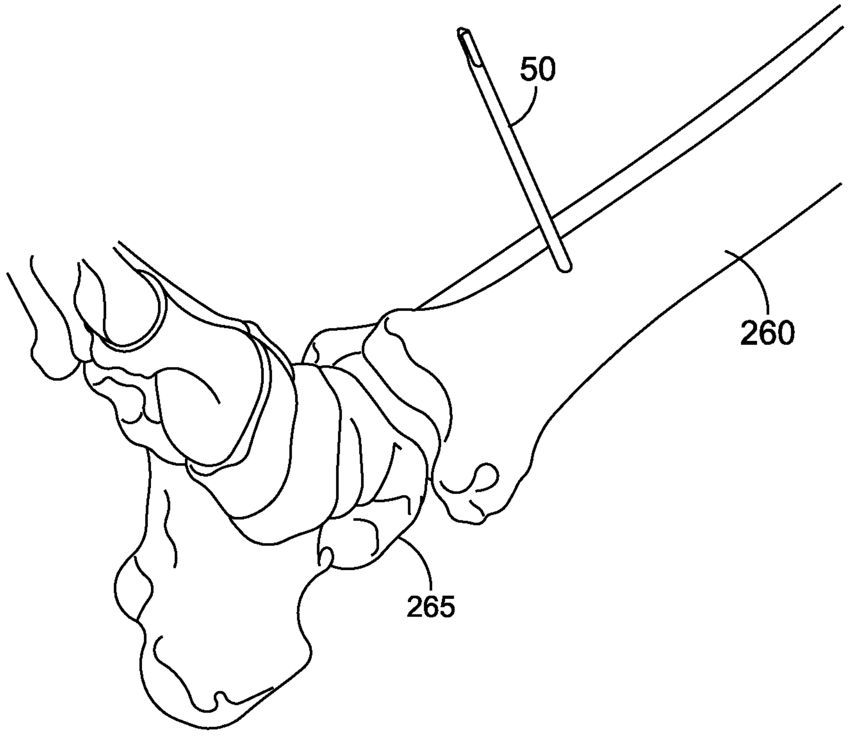
FIG. 5 is an isometric view of a tibia with first guide pin inserted in accordance with some embodiments.

The position of rotation guide slide 20 can be fixed relative to gutter fork 10 by inserting a set screw (not shown) into hole 19 defined by rotation guide slide 20, and the position of the rotation guide pointer 30 relative to the rotation guide slide 20 can be fixed by tightening screws 37. A first guide pin 50 is inserted through pin hole 28 and into the tibia either percutaneously or directly into the tibial shaft. With first guide pin 50 thus inserted, the entire rotation guide assembly 40 is removed, leaving first guide pin 50 in place. FIG. 5 is an isometric view of a tibia 260 with first guide pin 50 inserted and the rotation guide assembly 40 removed.

In some embodiments, the placement of guide 50 is accomplished using patient-specific guides. Examples of such patient-specific guides and methods of making such patient-specific guides are described in commonly assigned U.S. patent application Ser. No. 12/711,307, entitled "Method for Forming a Patient Specific Surgical Guide Mount, U.S. patent application Ser. No. 13/330,091, entitled "Orthopedic Surgical Guide," and U.S. patent application Ser. No. 13/464,175, entitled "Orthopedic Surgical Guide," the entireties of which are incorporated by reference herein. A conversion instrument for interfacing with patient specific guides is described in greater detail below.

Alignment Frame Assembly and Related Components

Figure 6:
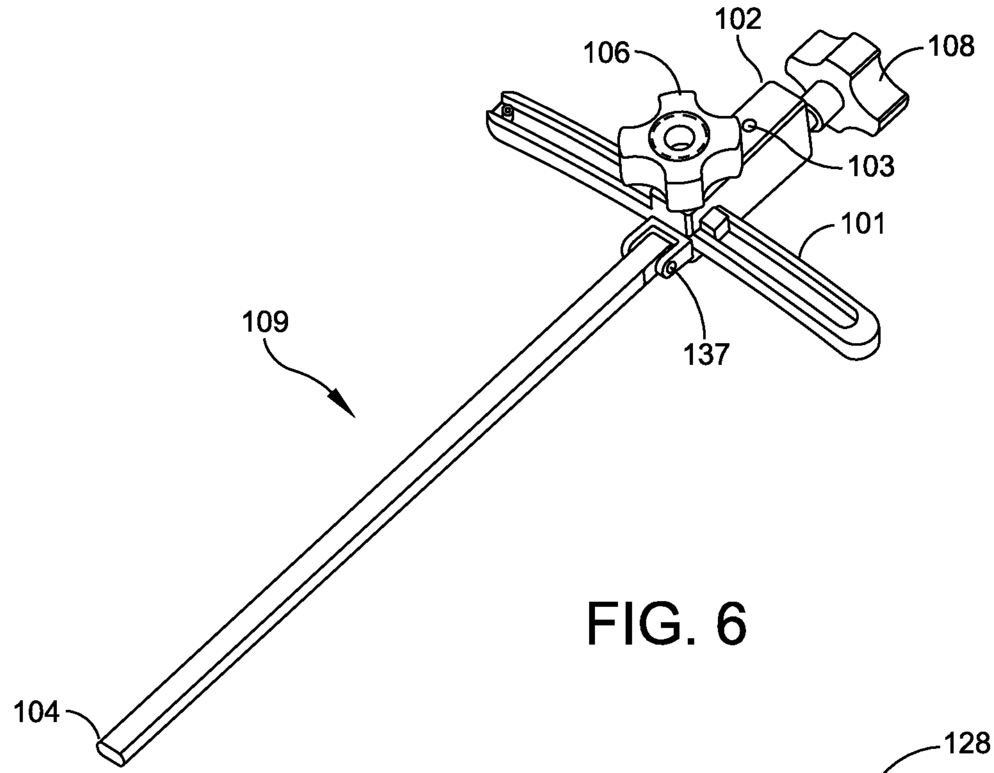
FIG. 6 is an isometric view of one example of a proximal alignment frame sub-assembly in accordance with some embodiments.
Figure 7:
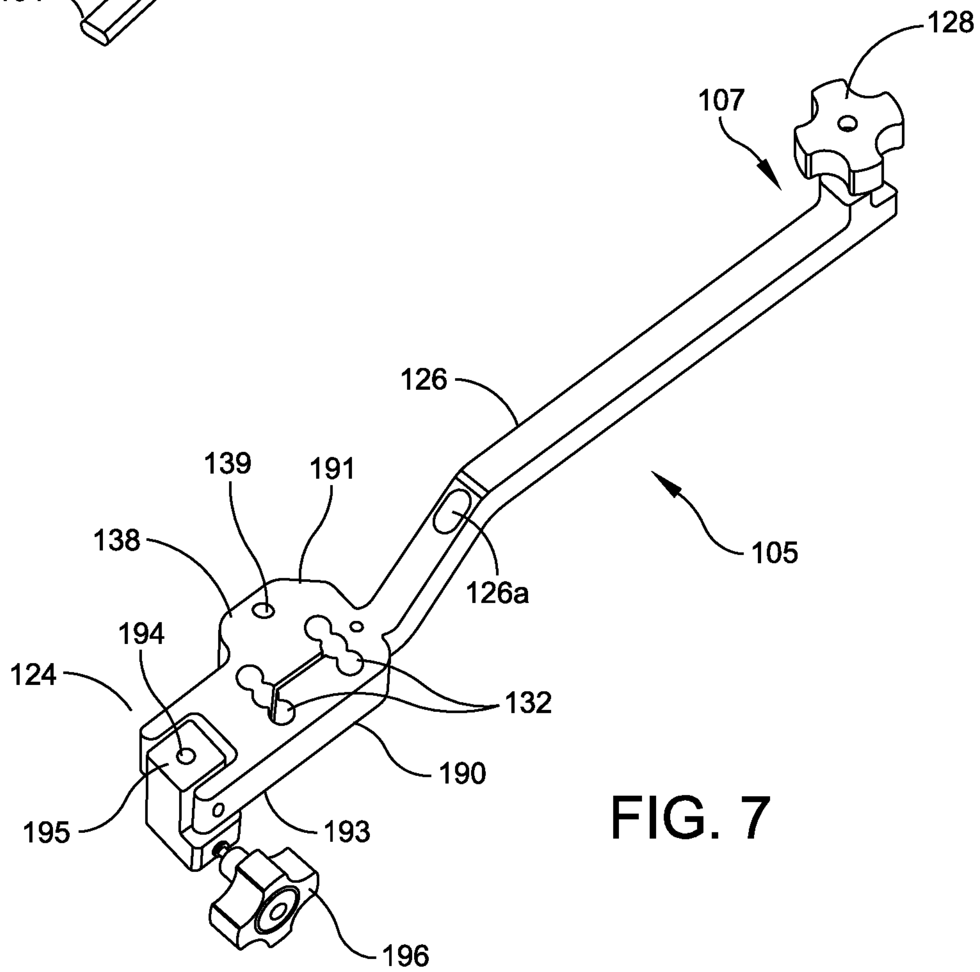
FIG. 7 is an isometric view of one example of a distal alignment frame sub-assembly in accordance with some embodiments.

FIGS. 6 and 7 illustrate one example of an alignment frame assembly 140 in accordance with some embodiments. Alignment frame assembly 140 can be used to place pins 150 (FIG. 28) in a patient's tibial. In some embodiments, alignment frame 140 includes a proximal alignment frame 109 as illustrated in FIG. 6 and a distal alignment frame 105 as illustrated in FIG. 7.

Referring first to FIG. 6, proximal alignment frame subassembly 109 includes an elongate body with a first end 102 and a second end 104. In some embodiments, proximal alignment frame 109 includes two knobs 106, 108 at end 102. Knob 106 can be selectively loosened and tightened to allow for coronal rotation adjustment and for locking the adjustment of the angle between an axis defined by the end 102 and an axis defined by the end 104 by locking the proximal end 102 at a particular location along perpendicular slot 101 for coronal rotation adjustment. Knob 108 allows for sagittal rotation adjustment and connecting end 102 to a proximal tibial pin 154, which is received within hole 103, or to a knee bracket 142 as described in greater detail below. Hinge 137 allows for end 102 to pivot relative to end 104.

Turning now to FIG. 7, distal alignment frame subassembly 105 extends between a first end 107 and a second end 124. At end 107, the distal alignment frame 105 includes an elongate body 126 defining a central channel 126*a*, which extends the length of body 126 and is configured to receive end 104 of the proximal alignment frame 109 therein. A knob 128 is provided at end 107 and is configured to allow adjustment and fixation of the length of the proximal alignment frame 109. For example, knob 128 can be loosened to enable end 104 of proximal alignment frame 109 to be slid within channel 126*a*, and knob 128 can be tightened to prevent relative movement between proximal alignment frame 109 and distal alignment frame subassembly 105.

At end 124, the distal alignment frame 105 includes a rectangular body or structure 190 defining a plurality of holes 132. Holes 132 extend from a top surface 191 to a bottom surface 193 of structure 190 and are sized and configured to receive pin sleeves 176 (FIG. 24A) for installing pins 150 into the tibia 260. Although six holes 132 are shown in FIG. 7, fewer or more holes are provided in some embodiments. As described in greater detail below, pins 150 are inserted into the tibia 260 and are used for positioning other devices during a total ankle replacement surgery in accordance with some embodiments.

Still referring to FIG. 7, a hole 194 is defined in a structure 195, which is disposed in a distal-most portion of distal alignment frame 105. Structure 195 is hingedly connected to rectangular structure 190 and is sized and configured to receive a guide pin 50 within hole 194, which is inserted into the tibia 260 using rotation guide assembly 40 as described above. A knob 196 is configured to lock frame 105 to pin 50 received within hole 194.

Figure 17:
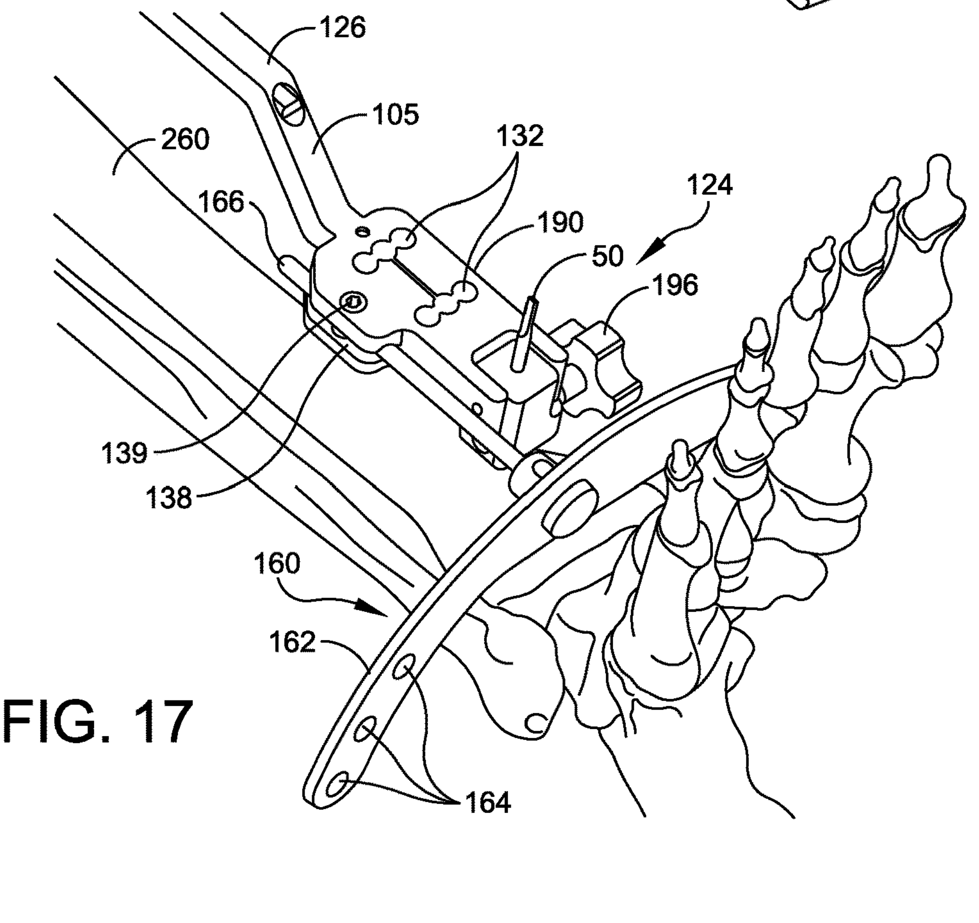
FIG. 17 is an isometric view of one example of the angel wing alignment guide attached to the distal end of the distal alignment frame, which is connected to the bone via the distal tibial pin in accordance with some embodiments.

As best seen in FIG. 17, structure 190 defines a longitudinal slot 138 that extends parallel to the longitudinal direction of distal alignment frame 105 (i.e., in a distal to proximal direction). Longitudinal slot 138 is configured to receive a shaft of an angel wing alignment guide 160. Structure 190 also defines a hole 139 that extends from top surface 191 and intersects slot 138. Hole 139 is configured to receive a set screw (not shown) to secure the angel wing alignment guide 160 in place as described in greater detail below.

Figure 8:
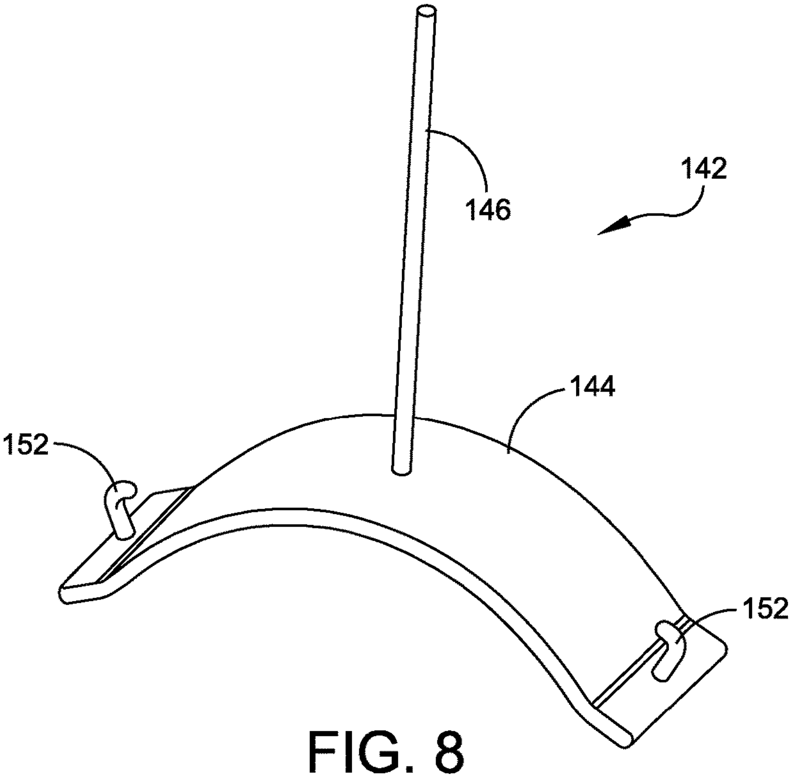
FIG. 8 is an isometric view of one example of a knee bracket in accordance with some embodiments.
Figure 9:
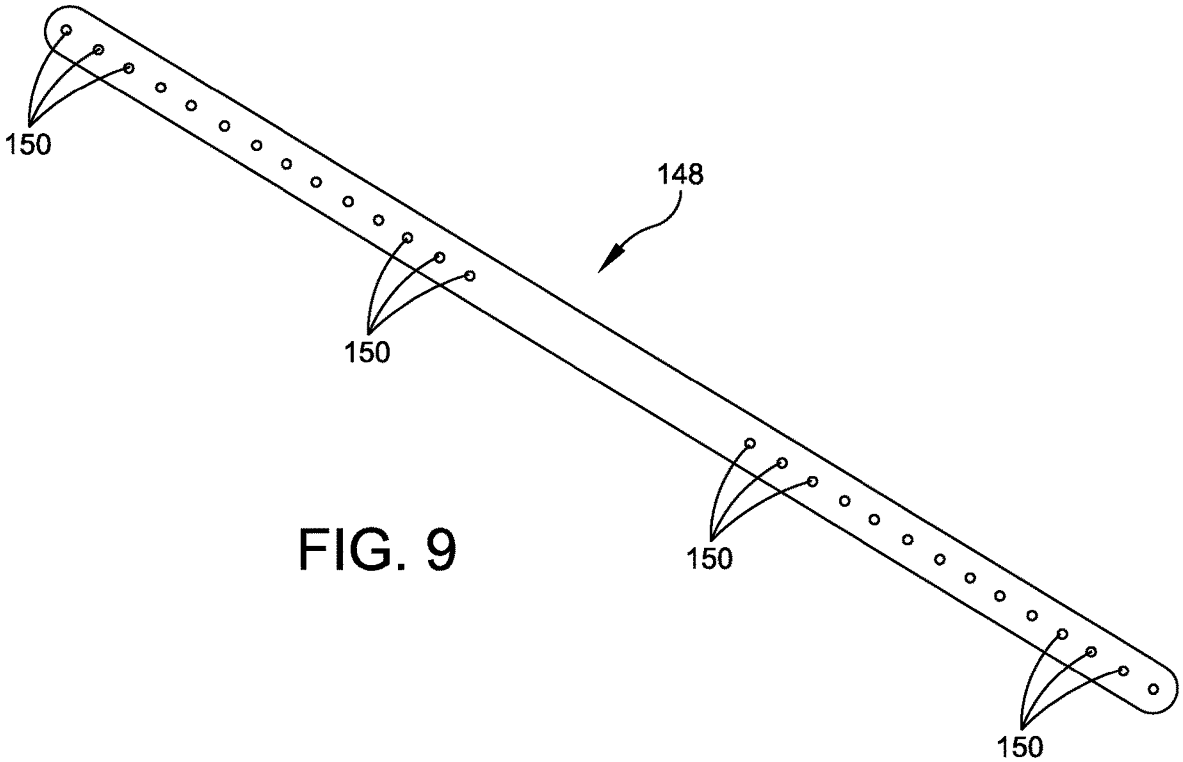
FIG. 9 is an isometric view of one example of a rubber strap in accordance with some embodiments.

FIG. 8 illustrates one example of a knee bracket 142 in accordance with some embodiments. Knee bracket 142 includes a base 144 that is curved to be positioned over the proximal end of the tibia 260 and a post 146 configured to be received within the hole 103 of the proximal end 102 of the proximal alignment frame 109. A hook 152 extends from an upper surface of each end of knee bracket 142. Hooks 152 are provided to secure a strap, such as strap 148 illustrated in FIG. 9, to knee bracket 142. In some embodiments, strap 148 is formed from rubber, but strap 148 can be provided from other materials as will be understood by one of ordinary skill in the art. Strap 148 defines a plurality of holes 150 that are sized and configured to receive hooks 152 of knee bracket 142.

Figure 10:
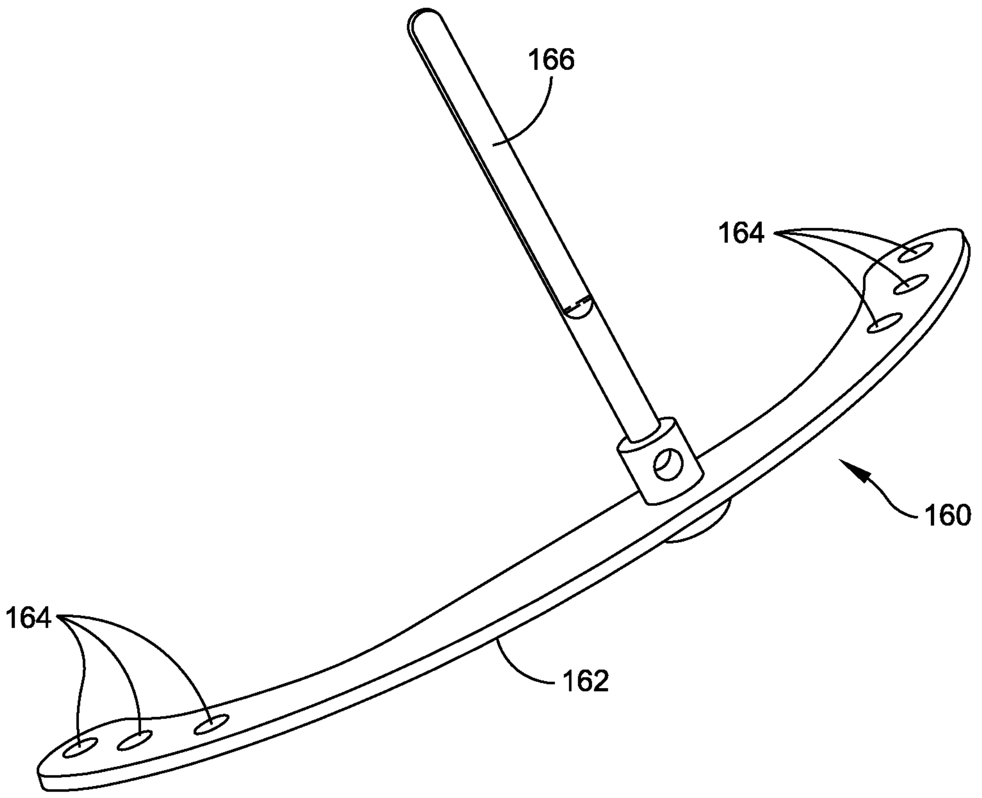
FIG. 10 is an isometric view of one example of an angel wing alignment guide in accordance with some embodiments.
Figure 11:
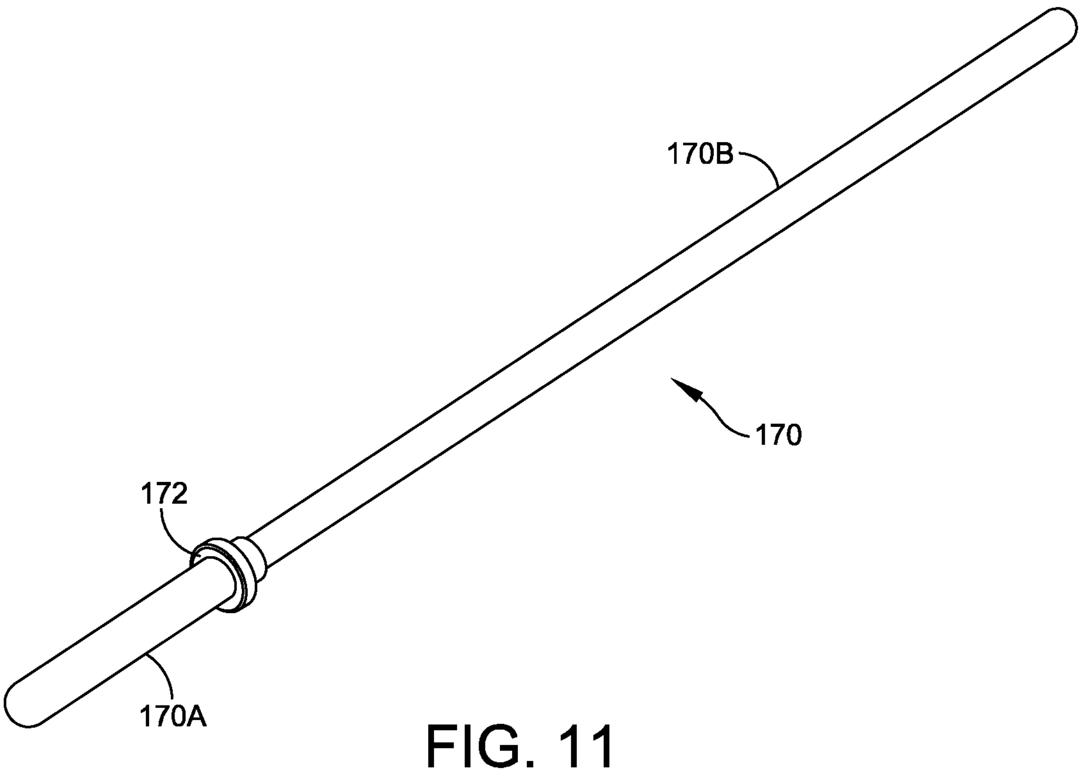
FIG. 11 is an isometric view of one example of an alignment rod in accordance with some embodiments.

FIG. 10 is an isometric view of one example of an angel wing alignment guide 160 in accordance with some embodiments. Angel wing alignment guide 160 includes a hippocrepiform base 162 defining a plurality of holes 164 at both ends. A post 166 extends perpendicularly from the base 162 and is configured to be received within the slot 138 at end 124 of the distal alignment frame 105 as best seen in FIG. 17. Holes 164 are sized and configured to receive an alignment rod, such as alignment rod 170 illustrated in FIG. 11. In some embodiments, alignment rod 170 has an elongate body that includes a stop collar 172 disposed along its length to divide alignment rod 170 into unequal portions 170A and 170B. As shown in FIG. 11, portion 170A is shorter than portion 170B.

Figure 12:
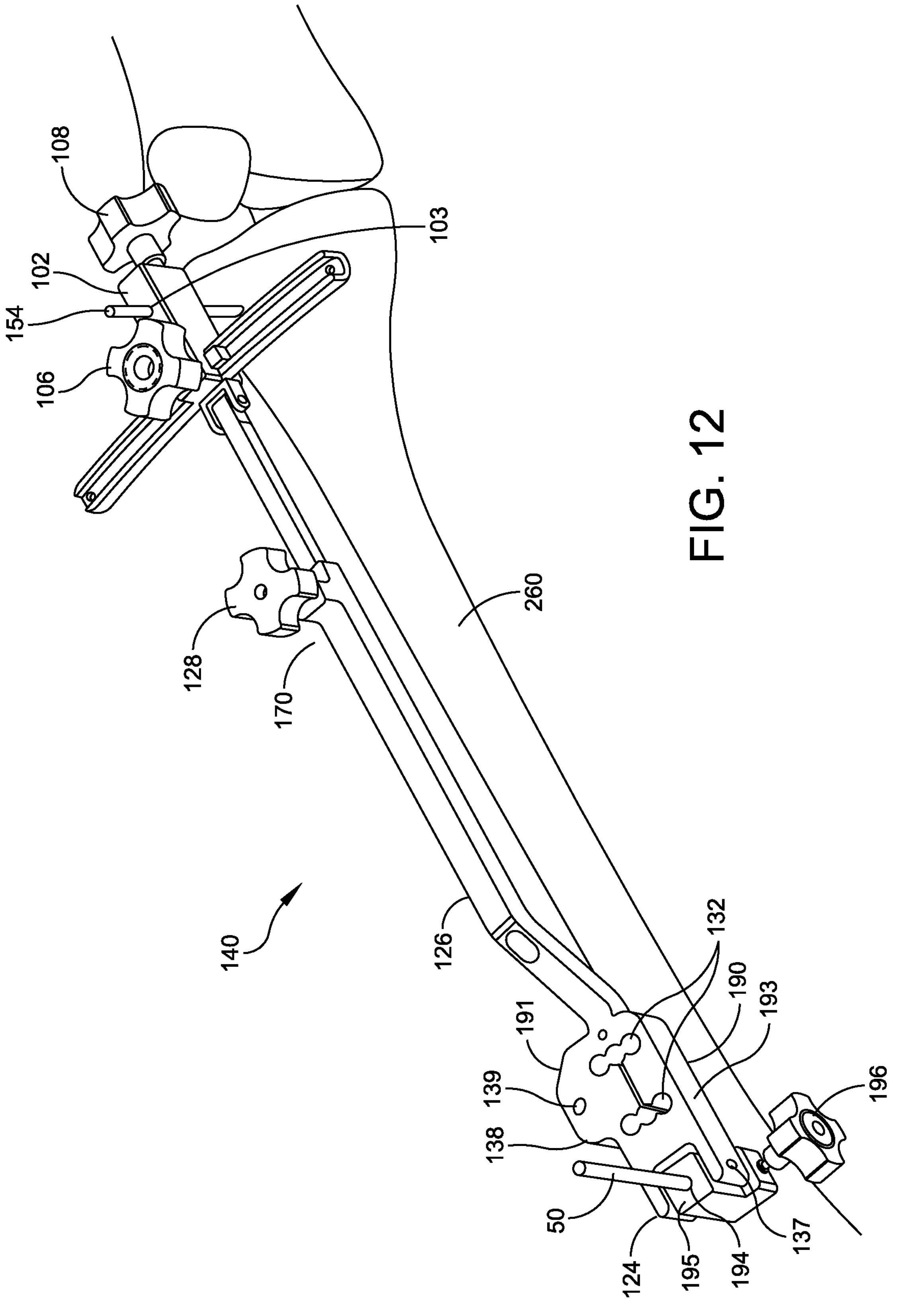
FIG. 12 is an isometric view of one example of an alignment frame assembly comprising the proximal alignment frame and the distal alignment frame attached to a bone via distal and proximal tibial pins in accordance with some embodiments.

The installation of alignment frame assembly 140 is described briefly with reference to FIGS. 12-28. FIG. 12 illustrates one example of alignment frame assembly 140 in its assembled form. In some embodiments, alignment frame assembly 140 is assembled by inserting end 104 of the proximal alignment frame 109 into end 107 of distal alignment frame 105. Alignment frame assembly 140 is connected to the tibia by sliding the hole 194 at end 124 of the distal alignment frame 105 over the first guide pin 50 that is positioned in tibia 260 as shown in FIG. 12. A pin 154 is installed percutaneously through the hole 103 at the proximal end 102 of the proximal alignment frame 109 into a tibial tuberosity.

Figure 13A:
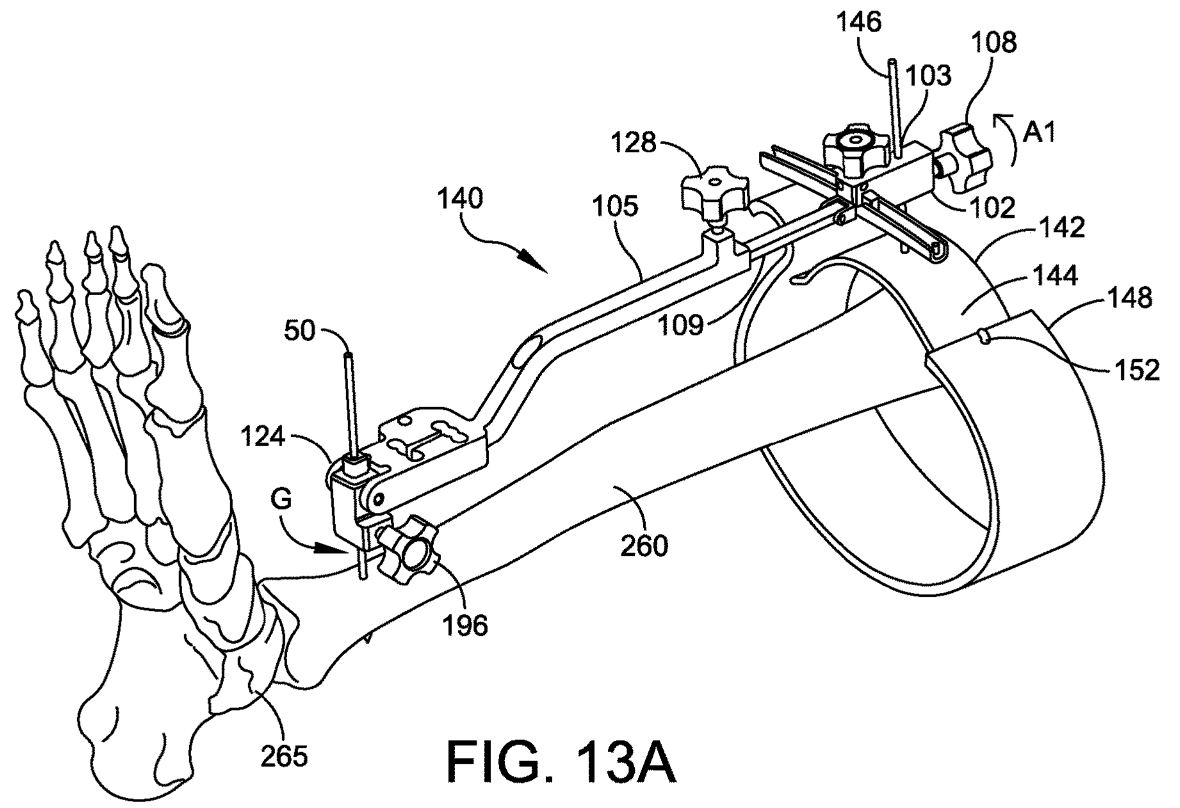
FIGS. 13A, 13B, and 13C are isometric views of some examples of an alternative alignment frame assembly comprising the proximal alignment frame and the distal alignment frame attached to a bone via first guide pin on a distal end of the distal alignment frame and attached to the knee bracket on a proximal end of the proximal alignment frame.
Figure 13B:
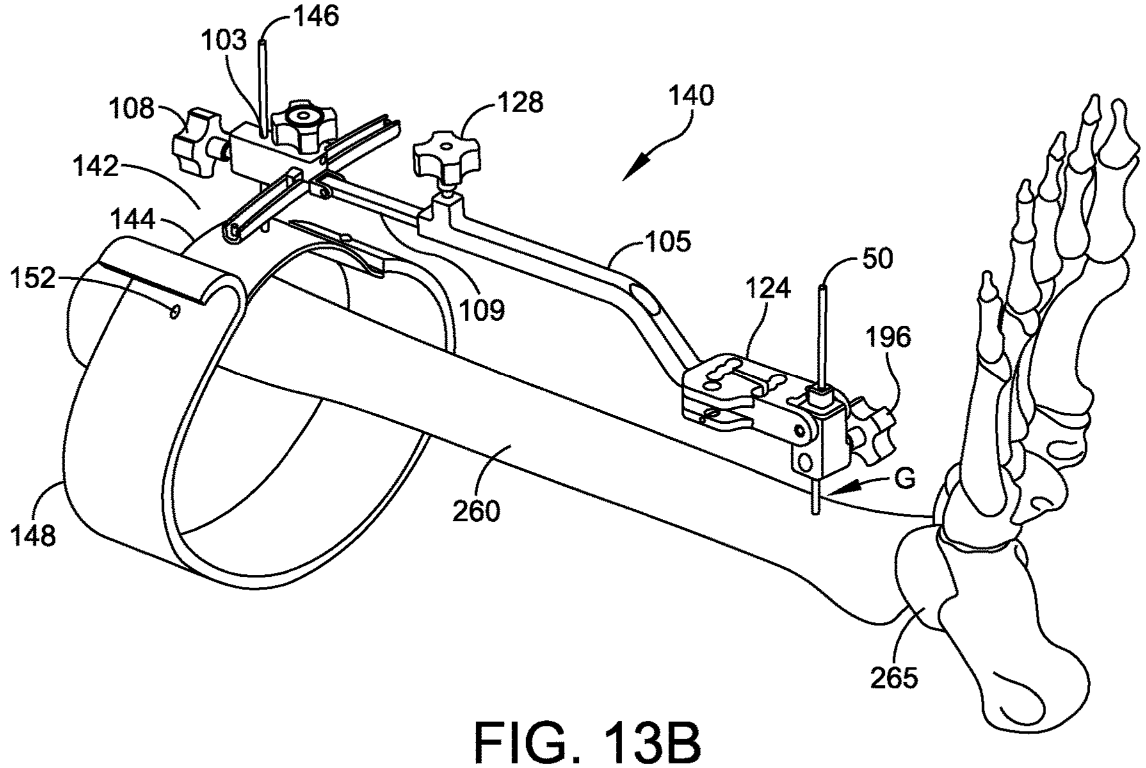
Figure 13C:
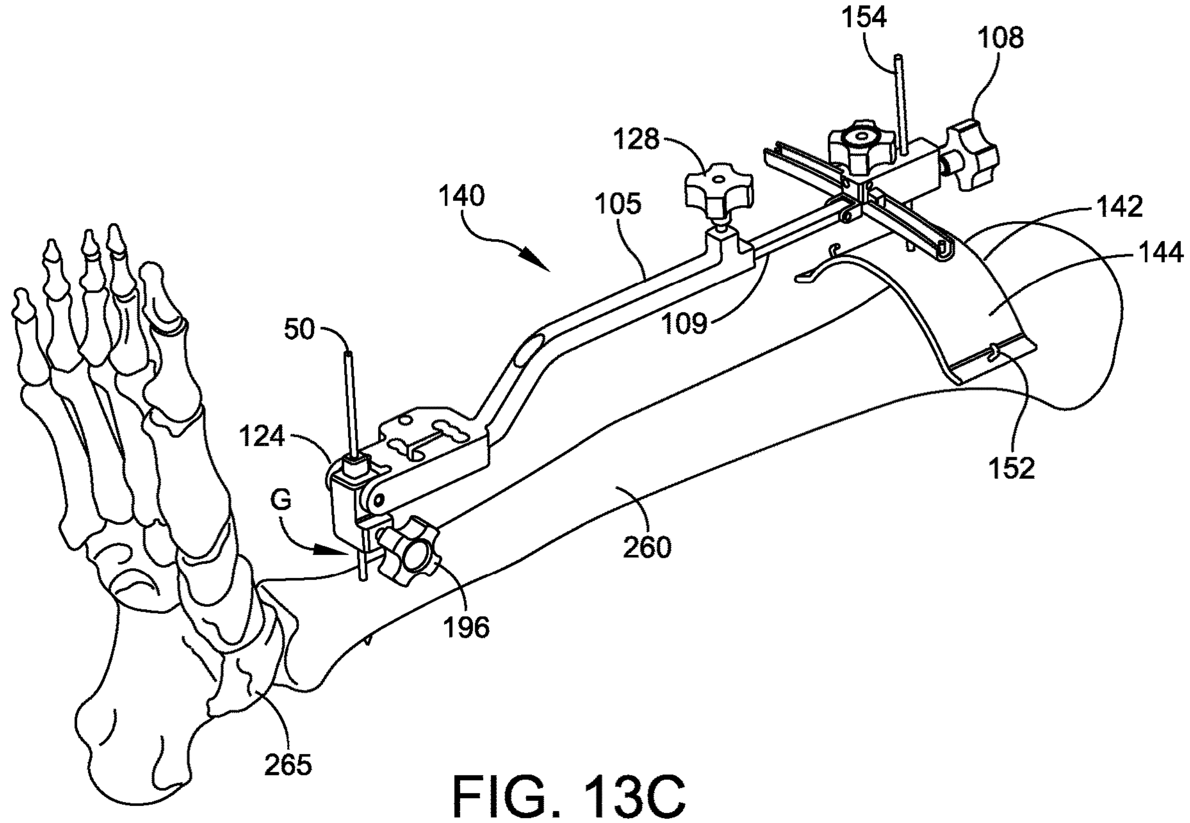

Alternatively, as shown in FIGS. 13A-13C, the knee bracket 142 and rubber strap 148 can be used to secure the alignment frame assembly 140 to the proximal end of the tibia 260. For example, knee bracket post 146 is inserted into the hole 103 defined at end 102 of the proximal alignment frame 109 such that knee bracket base 144 is positioned over the proximal end of the tibia 260. Rubber strap 148 is used to secure the patient's leg to knee bracket 142. For example, rubber strap 148 is wrapped laterally around the tibia 260, and hooks 152 of the knee bracket base 144 are inserted into the holes 151 of the rubber strap 148.

Figure 14:
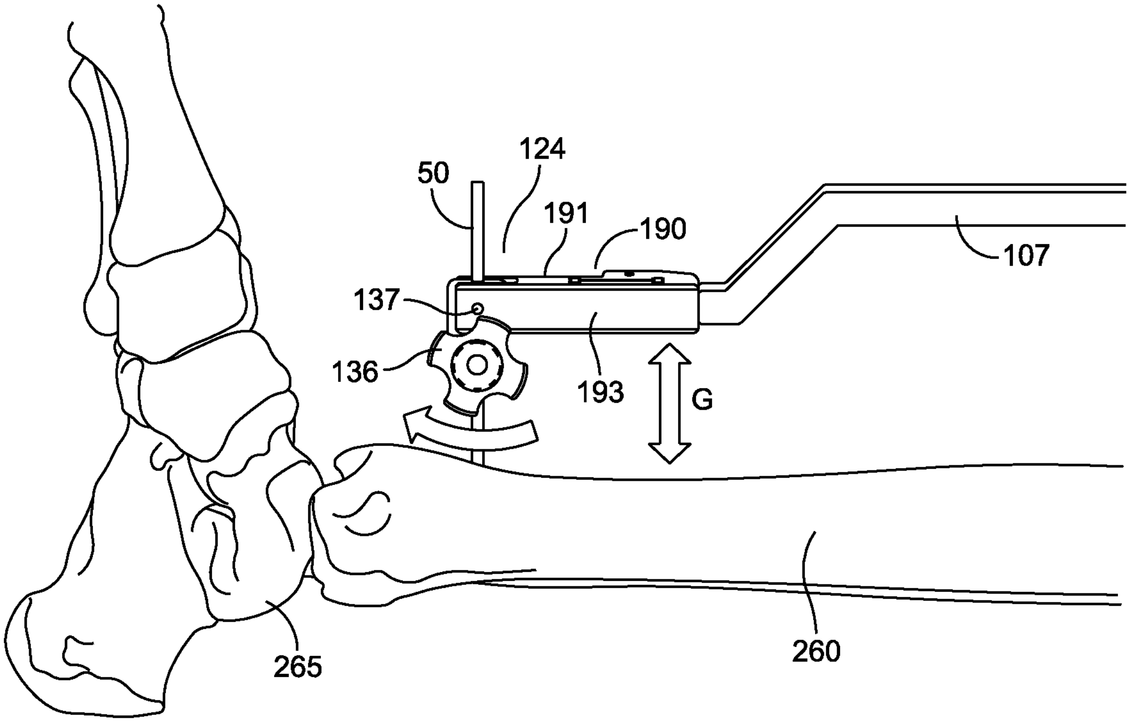
FIG. 14 is an isometric view of one example of an adjustment mechanism to lock the distal end of the distal alignment frame to the distal tibial pin in accordance with some embodiments.

The distal end 124 of the distal alignment frame 105 is placed above the tibia such that a gap, G, is provided between the distal alignment frame 105 and the tibia as shown in FIG. 14. In some embodiments, the gap is approximately 20-25 mm from the frame 105 to the tibia 260; however, gap, G, can have other dimensions that are greater than or less than 20-25 mm. Once the desired gap is achieved, distal knob 196 is turned to lock the distal end 124 of the distal alignment frame 105 to the first guide pin 50, as illustrated in FIG. 14.

Figure 15:
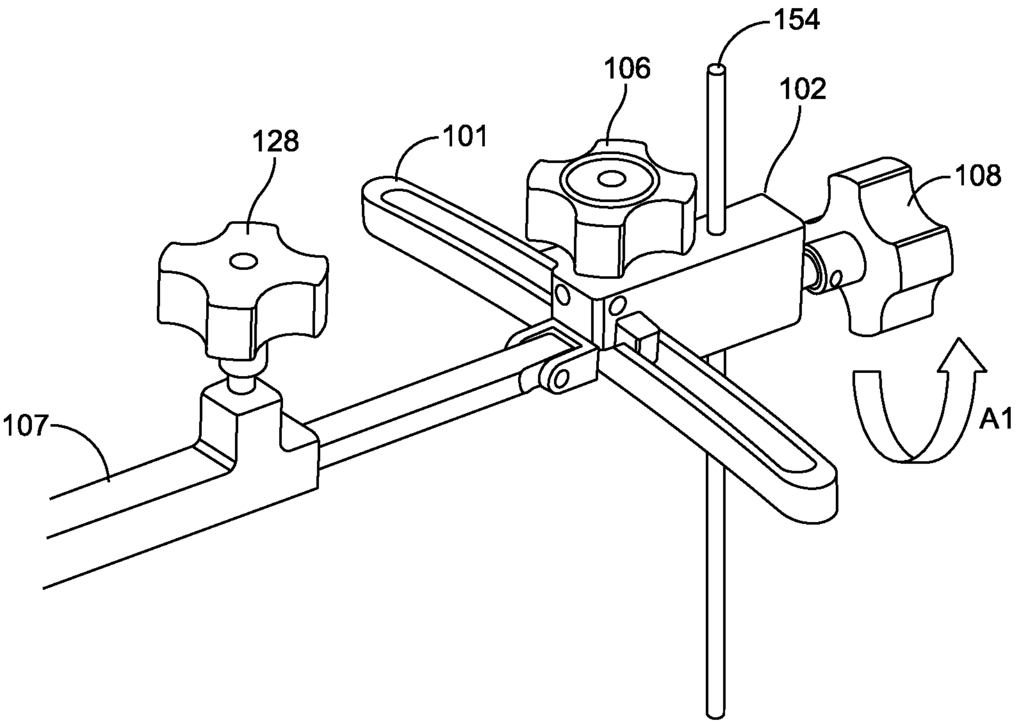
FIG. 15 is an isometric view of one example of an adjustment mechanism to lock the proximal end of the proximal alignment frame to the proximal tibial pin in accordance with some embodiments.
Figure 16:
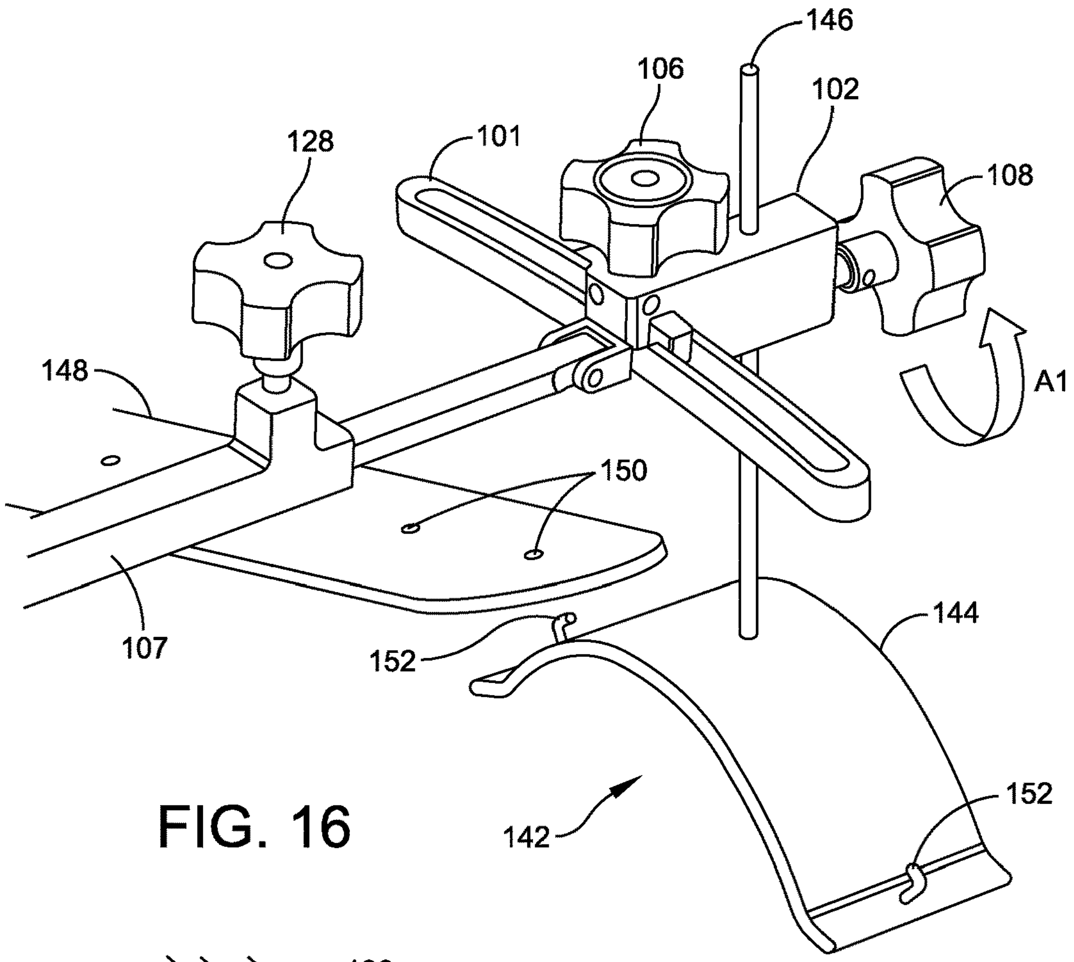
FIG. 16 is an isometric view of one example of an adjustment mechanism to lock the proximal end of the proximal alignment frame to the knee bracket in accordance with some embodiments.
Figure 18:
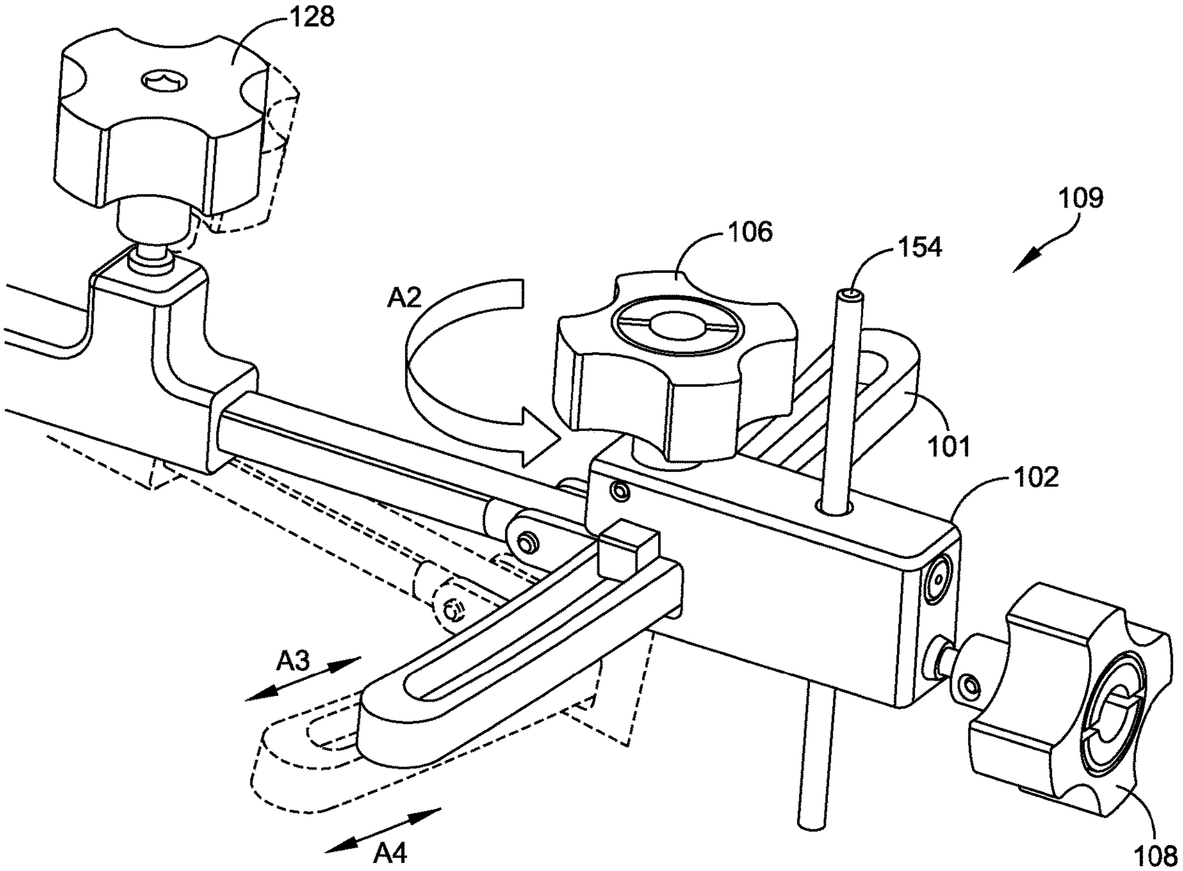
FIG. 18 is an isometric view of one example of an adjustment mechanism for coronal rotation in accordance with some embodiments.

As described above, the proximal alignment frame 109 is adjustable in length and can be fixed at a particular length by turning knob 128 of the distal alignment frame 105 as shown in FIG. 18. First knob 106 at the proximal end 102 of the proximal alignment frame 109 can be turned as indicated by arrow A2 to allow adjustment of the angle of a perpendicular slot 101 at the proximal end 102 of the proximal alignment frame 109 for coronal rotation adjustment as indicated by arrows A3 and A4. As shown in FIGS. 15 and 16, knob 108 of the proximal alignment frame 109 is turned as indicated by arrow A1 to lock the alignment frame assembly 140 to the pin 154 and/or knee bracket post 146.

Figure 19:
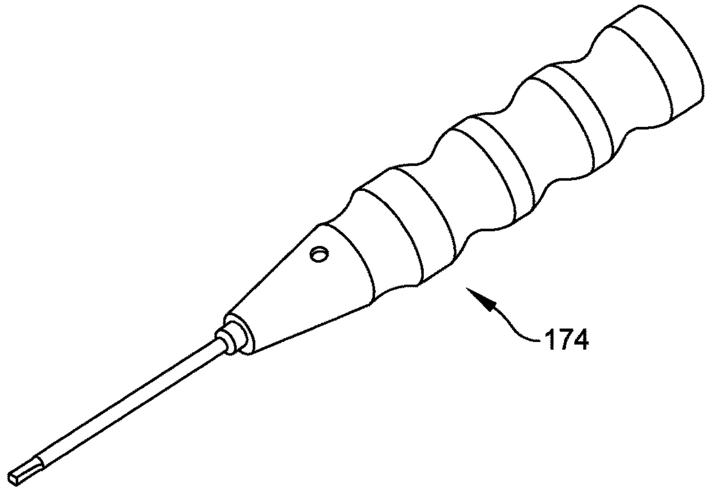
FIG. 19 is an isometric view of one example of a hex driver in accordance with some embodiments.
Figure 20:
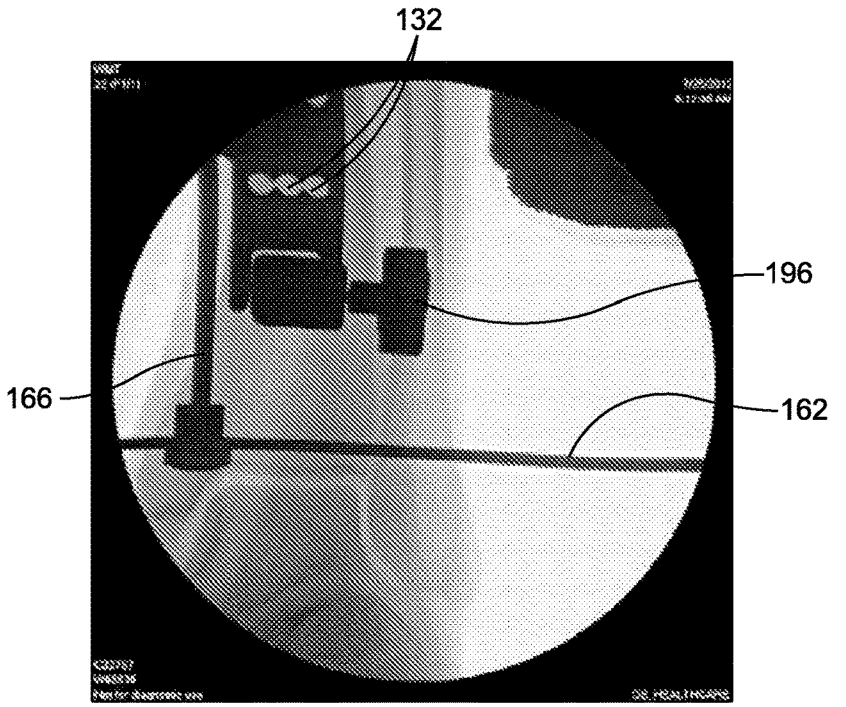
FIG. 20 is one example of a fluoroscopic image of the angel wing alignment guide attached to the distal end of the distal alignment frame, which is connected to the bone via the distal tibial pin in accordance with some embodiments.

FIG. 17 is an isometric view of the angel wing alignment guide 160 attached to the distal end 124 of the distal alignment frame 105, which is connected to the tibia via the first guide pin 50. In some embodiments, the angel wing alignment guide 160 is attached to the alignment frame assembly 140 by inserting the angel wing alignment guide post 166 into the slot 138 at the distal end 124 of the distal alignment frame 105. A set screw (not shown) is inserted through hole 139 that intersects the slot 138 and secured with a hex driver 174 (FIG. 19). The set screw (not shown) can be loosened to allow proximal/distal adjustment of the angel wing alignment guide 160. In some embodiments, the position of the angel wing alignment guide 160 is viewed under A/P fluoroscopy to establish coronal alignment, which is typically parallel to the natural joint line, as illustrated in FIG. 20.

Figure 21:
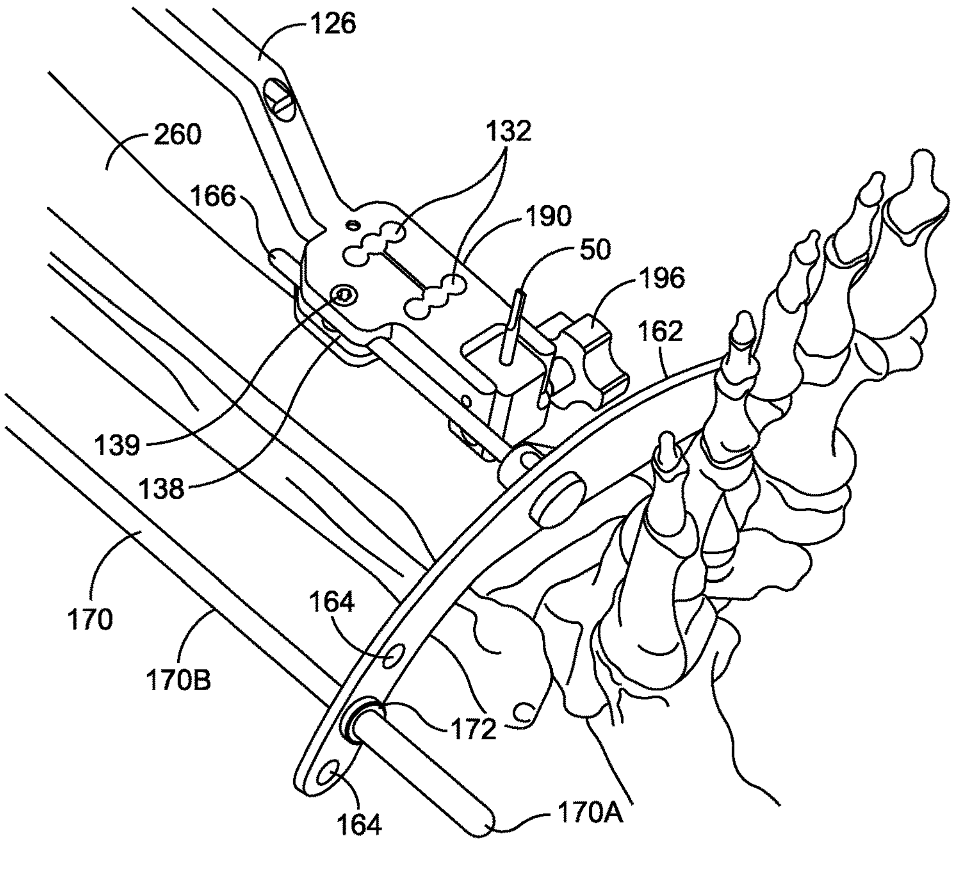
FIG. 21 is an isometric view of one example of an alignment guide assembly comprising the angel wing alignment guide, alignment rod and alignment frame assembly in accordance with some embodiments.
Figure 22:
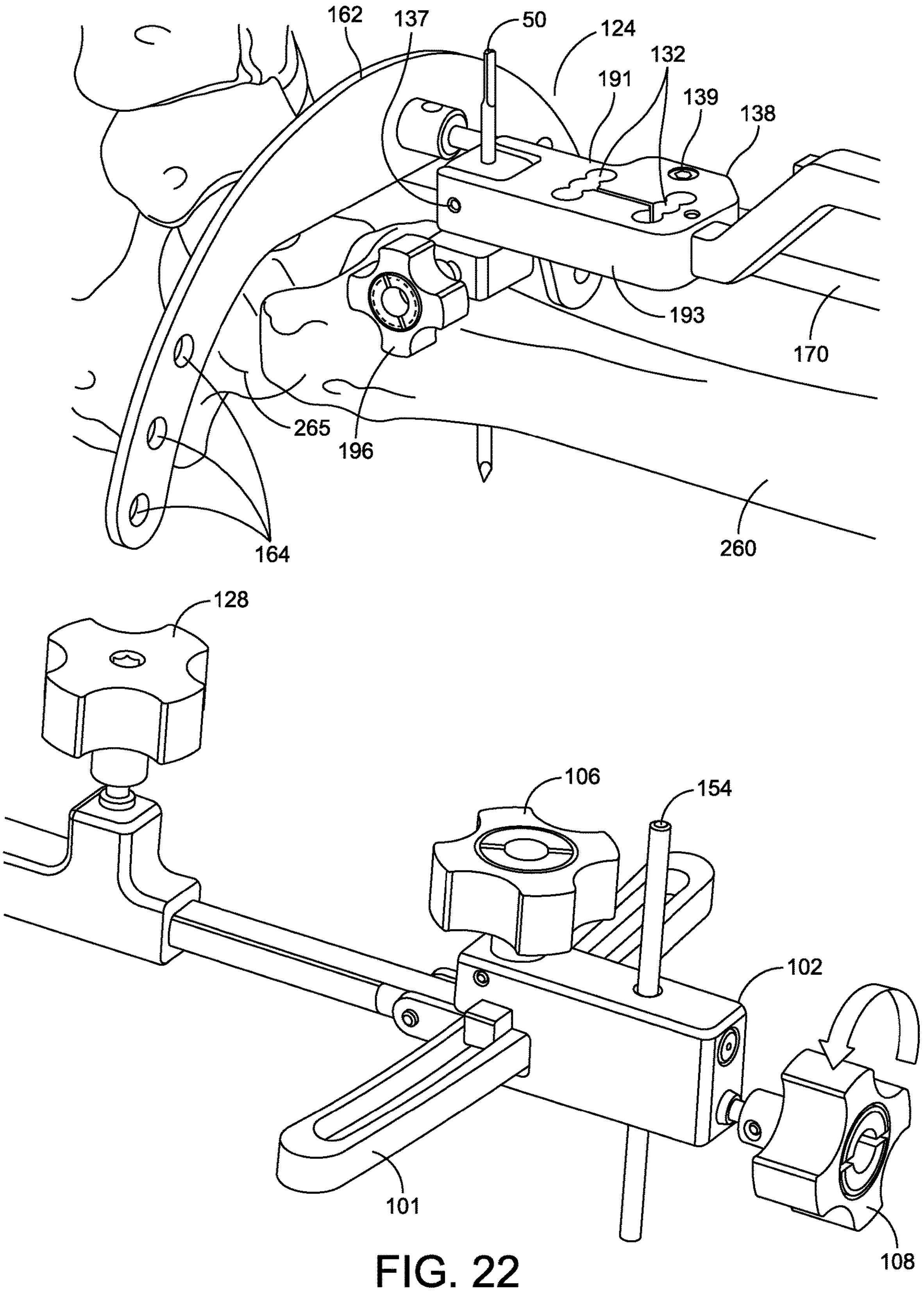
FIG. 22 is an isometric view of one example an adjustment mechanism for sagittal rotation in accordance with some embodiments.
Figure 23:
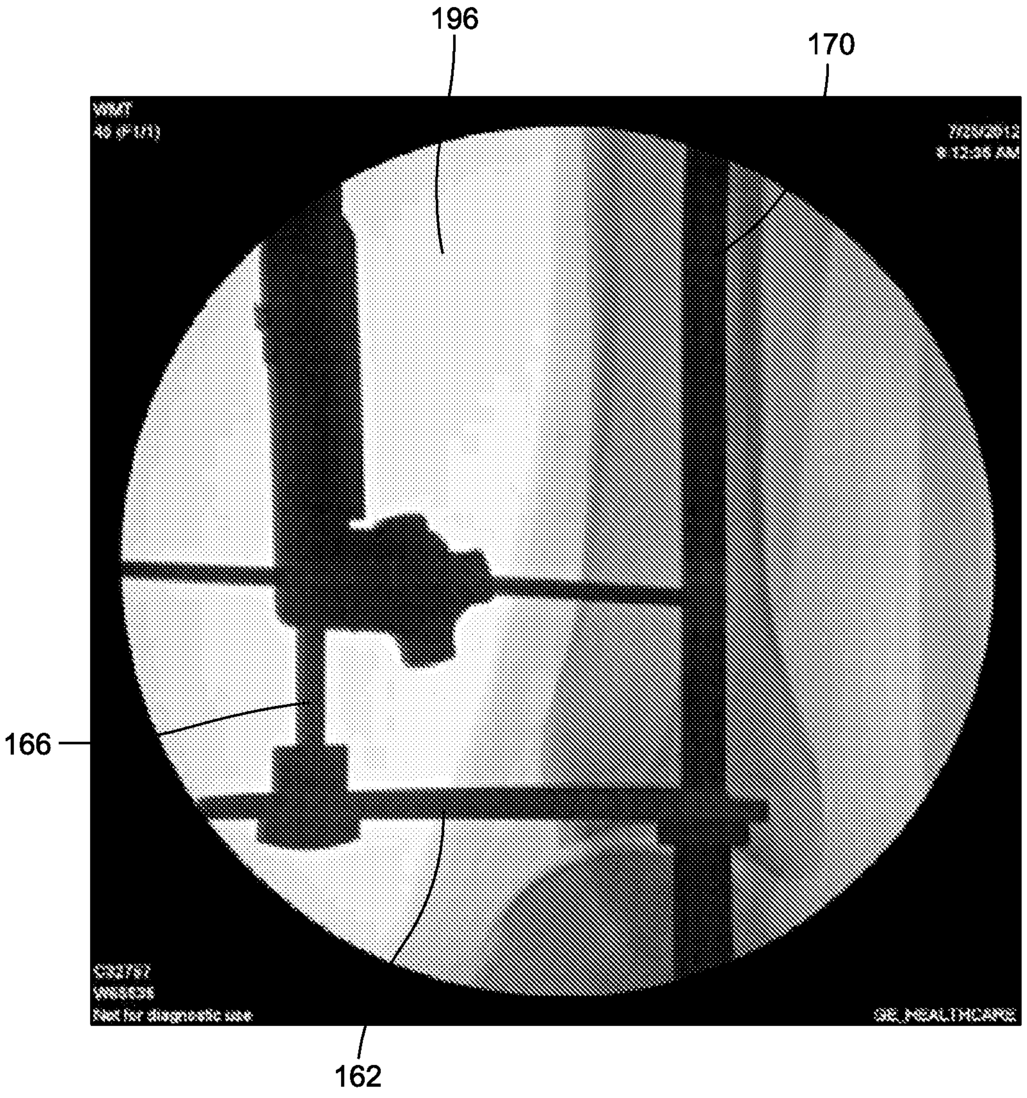
FIG. 23 is one example of a fluoroscopic image of the alignment guide assembly comprising the angel wing alignment guide, alignment rod and alignment frame assembly in accordance with some embodiments.

As illustrated in FIG. 21, the portion 170B of alignment rod 170 is inserted through one of the holes 164 in either side of the angel wing alignment guide base 162, and alignment rod 170 is inserted into one of the holes 164 until stop collar 172 abuts angle wing alignment guide base 162. Second knob 108 and/or the distal knob 196 of the alignment frame assembly 140 can be turned to allow sagittal rotation adjustment, as illustrated in FIG. 22. The position of the alignment rod 170 can be viewed under lateral fluoroscopy to establish sagittal rotation, which is typically parallel to a shaft of the tibia 260, as illustrated in FIG. 23.

Figure 24A:
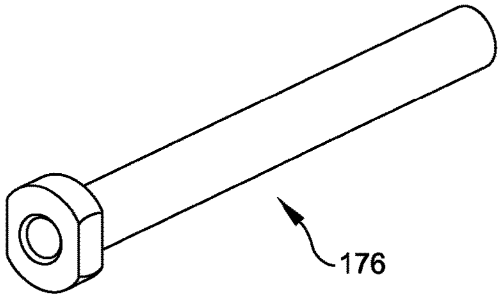
FIGS. 24A and 24B are isometric views of one example of a pin sleeve and trocar in accordance with some embodiments.
Figure 24B:
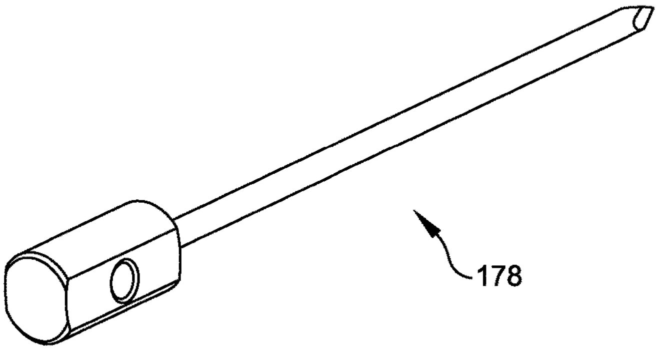
Figure 25:
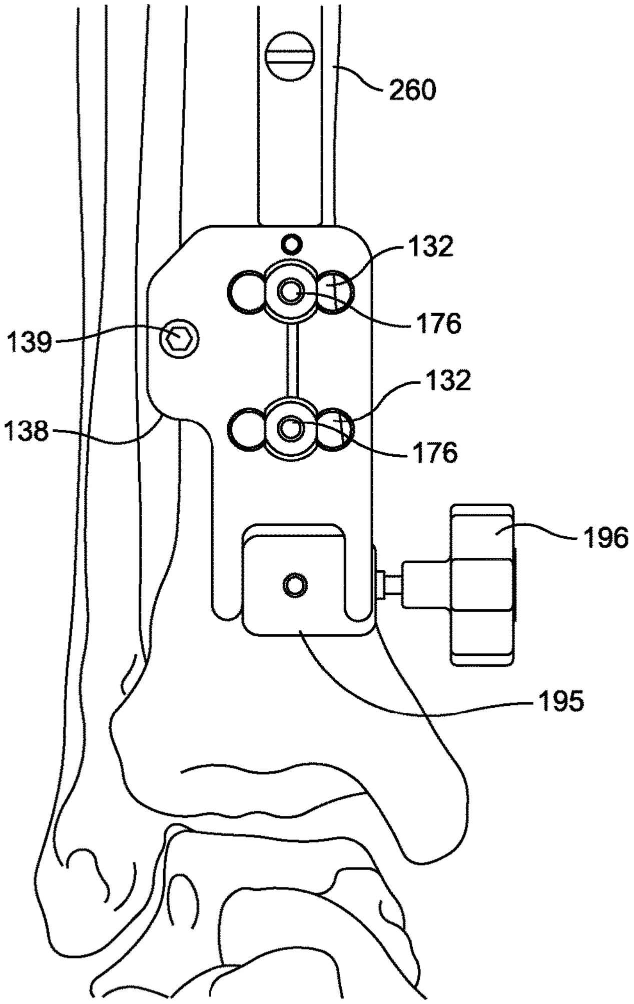
FIG. 25 is an isometric view of two pin sleeves inserted into the distal end of the distal alignment frame in accordance with some embodiments.
Figure 26:
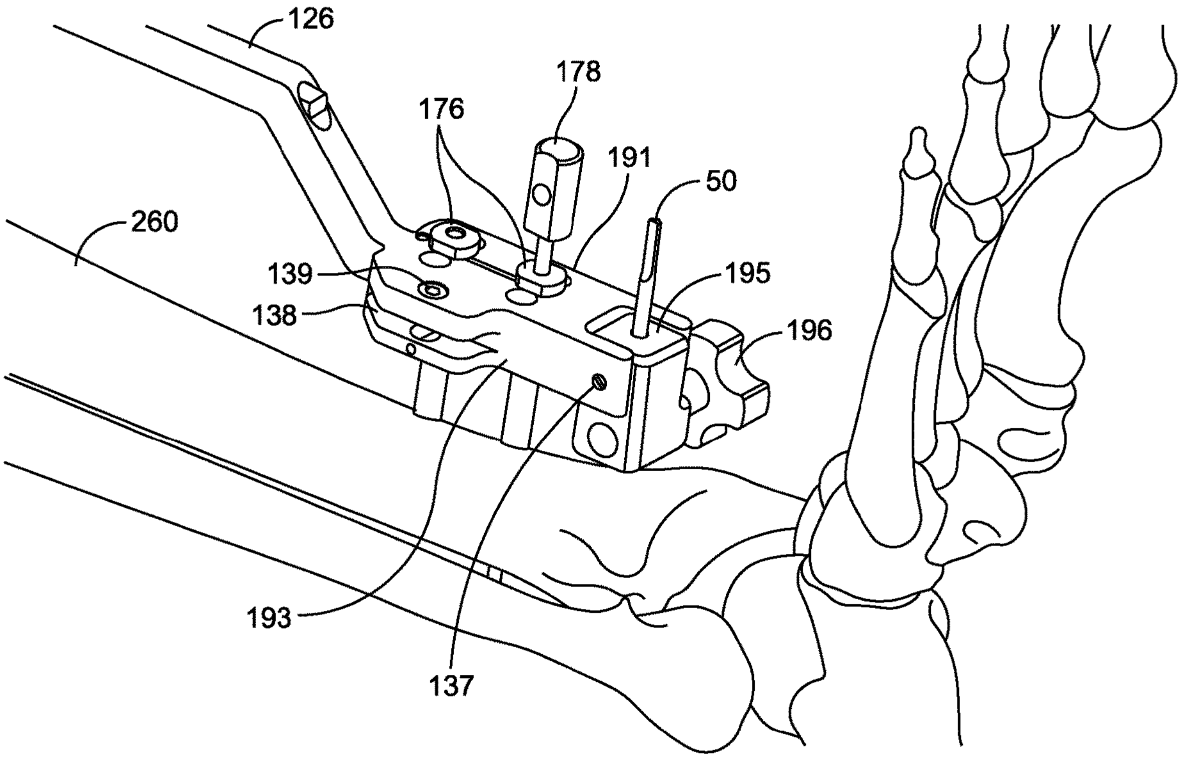
FIG. 26 is an isometric view of one example of the trocar inserted into one of the pin sleeves that is inserted into the distal end of the distal alignment frame in accordance with some embodiments.

After the adjustments are made, the angel wing alignment guide 160 and alignment rod 170 are removed. As illustrated in FIGS. 24A and 25, pin sleeves 176 are inserted into a pair of aligned holes 132 of the plurality of holes 132 at the distal end 124 of the distal alignment frame 105 that provide the optimal bone purchase. As illustrated in FIG. 25, this position is shown as the two center holes 132 in the superior and inferior rows of holes; however, the optimal bone purchase position could be the medial or lateral holes 132. A trocar, such as trocar 178 illustrated in FIG. 24B, is inserted into each of the pin sleeves 176 to create "stab wounds" for percutaneous pins, as illustrated in FIG. 26. The trocar 178 is then removed.

Figure 27:
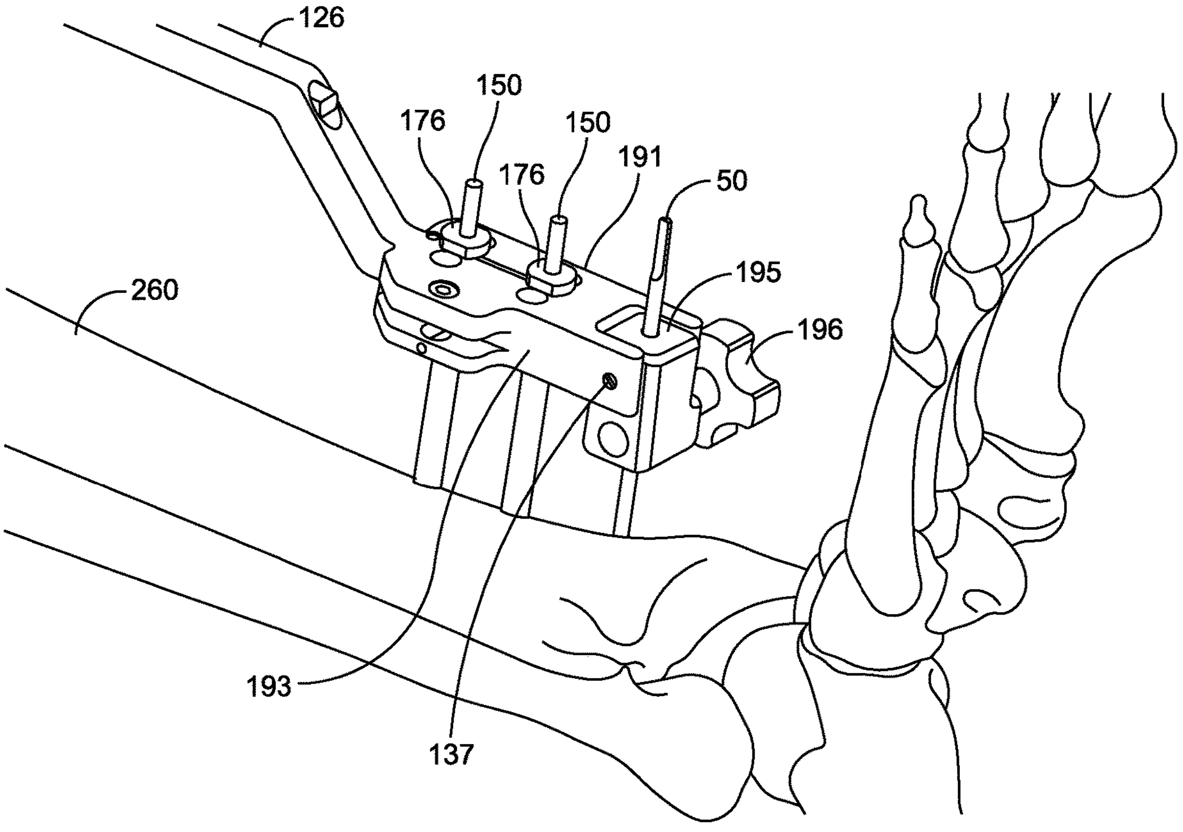
FIG. 27 is an isometric view of two pins inserted into the pin sleeves that are inserted into the distal end of the distal alignment frame in accordance with some embodiments.
Figure 28:
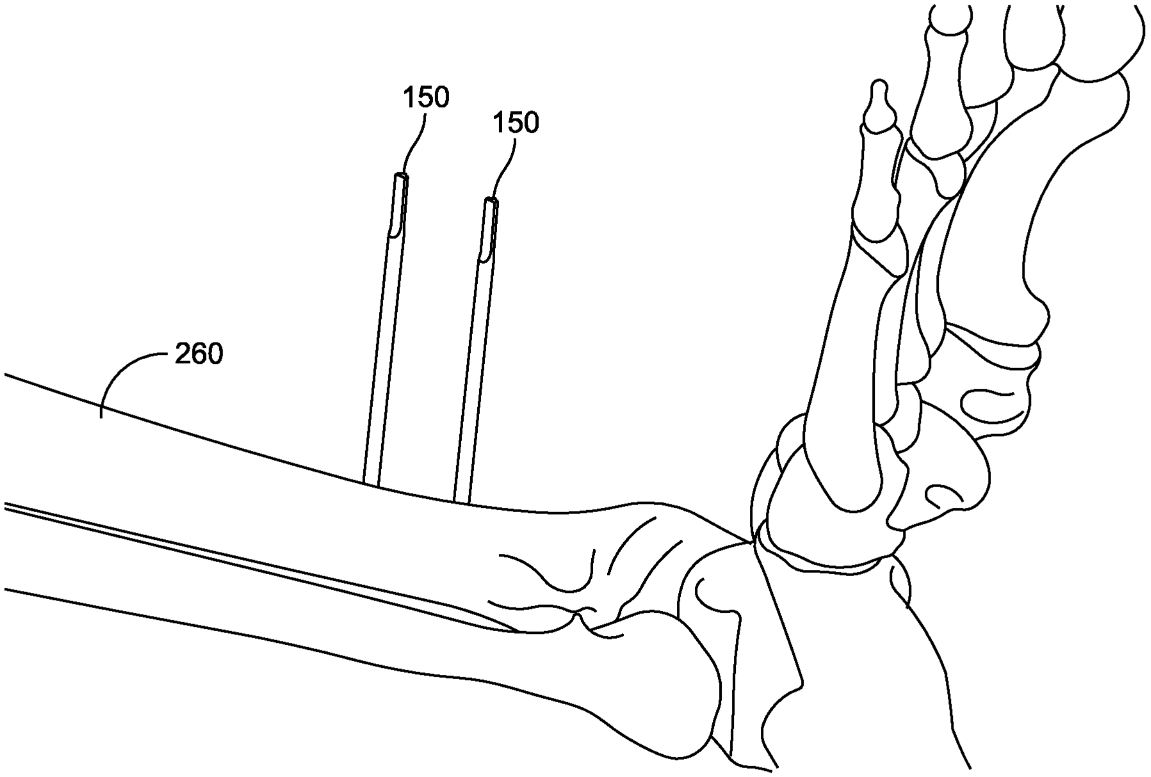
FIG. 28 is an isometric view of the two pins attached to the bone after the pin sleeves, alignment frame assembly, distal tibial pin, and proximal tibial pin or knee bracket and rubber strap are removed in accordance with some embodiments.

As illustrated in FIG. 27, a pin 150 is inserted into each of the pin sleeves 176 and through both cortices of the tibia 260, which is used for positioning of other structures of the total ankle replacement system as described in greater detail below. Once the pins 150 are placed, the pin sleeves 176 are removed and the second knob 108 and distal knob 196 are loosened to remove the alignment frame assembly 140. The proximal tibial pin 154 or knee bracket 142 and the first guide pin 50 are then removed, leaving pins 150 in the tibia 260, as illustrated in FIG. 28.

Position Adjustment Guide and Related Components

Figure 29:
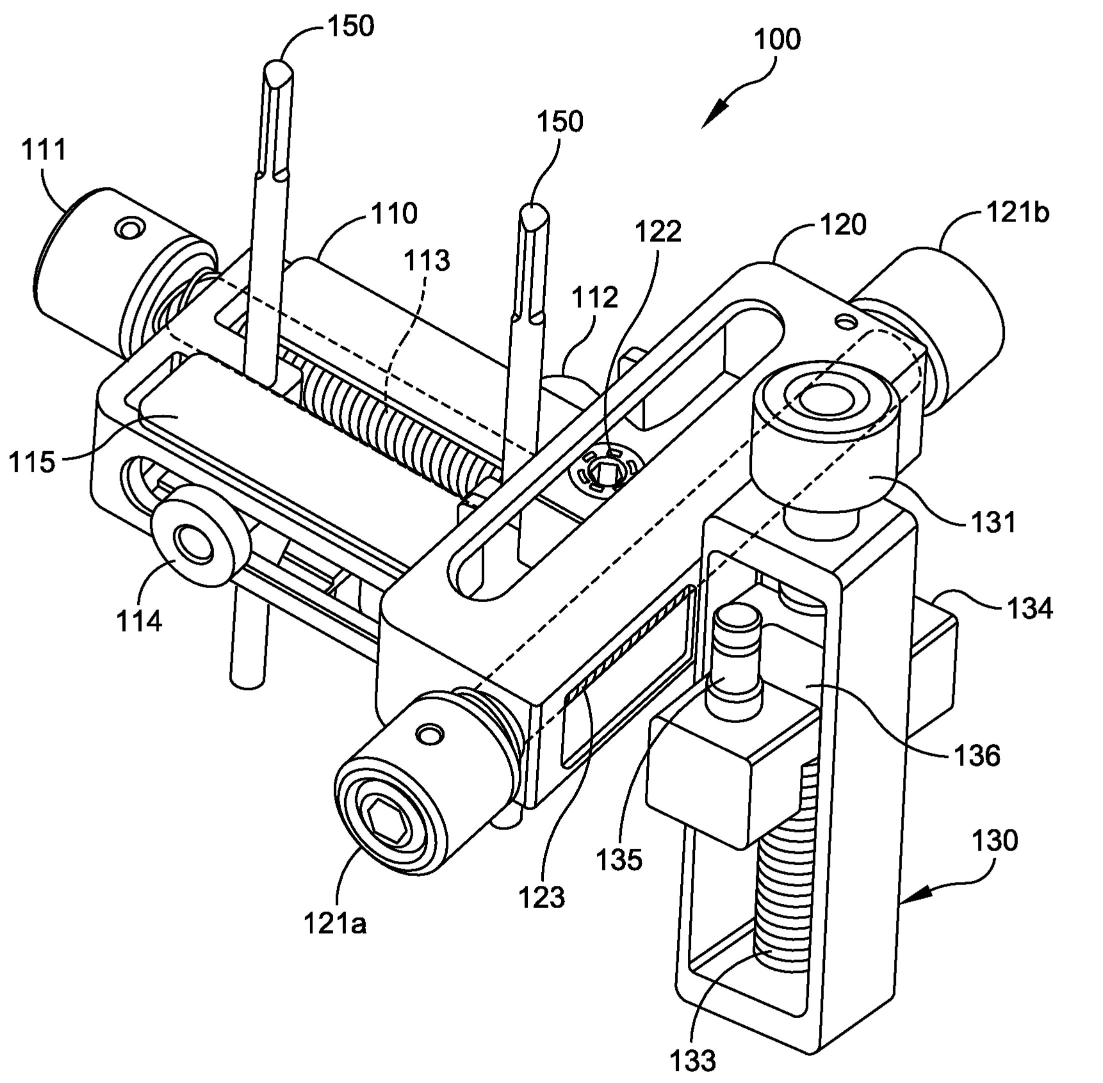
FIG. 29 is an isometric view of a position adjustment device, or adjustment block suitable for sizing and trialing an implant.

FIG. 29 is an isometric diagram of a position adjustment device 100 (also referred to below as an "adjustment block") for positioning of drilling and cutting tools for tibia resectioning and for tibia trial insertion in accordance with some embodiments. Adjustment block 100 provides a common reference location for locating tools and the tibia trial components throughout sizing, resectioning, and trialing procedures. In some embodiments, the adjustment block 100 is small enough in profile to position a cut guide into the wound space close to the tibia bone without applying excess skin tension. The physician can use the adjustment block to position a drill guide and/or cut guide closer to the tibia bone, to make more accurate cuts with less chance of the blade or pins flexing.

The adjustment block 100 has three independently positionable frames 110, 120, and 130 for precisely positioning a tool holder 134 adjacent the joint to be replaced.

The first frame 110 is configured to be attached to two fixation pins 150, which have been inserted in the anterior surface of the tibia, near the distal end of the tibia using the instrumentation as described above. A locking screw 112 actuates a locking plate (not shown), which bears against the fixation pins 150 to secure the adjustment block 100 relative to the pins. The first frame has a proximal-distal adjustment knob 111 coaxially connected to a screw 113. The screw 113 can have an Acme thread, trapezoidal thread, square thread or other suitable thread for leadscrew use. The second frame 120 is fixedly attached or unitarily formed with a leadscrew nut (not shown), which the screw 113 drives. Rotation of the proximal-distal adjustment knob 111 rotates screw 113 to advance or retract the second frame 120 in the proximal-distal direction. When the second frame 120 is at the desired proximal-distal coordinate, the physician advances the locking screw 114 to lock the second frame 120 to the first frame 110 in place.

The second frame 120 has at least one medial-lateral adjustment knob 121*a*, 121*b* coaxially connected to a screw 123. The screw 123 can have an Acme thread, trapezoidal thread, square thread or other suitable thread for leadscrew use. The screw 123 drives a leadscrew nut (not shown), to which the third frame 130 is fixedly attached or unitarily formed. Rotation of the medial-lateral adjustment knob 121*a* or 121*b* rotates screw 123 to move the third frame 130 in the medial-lateral direction. When the third frame 130 is at the desired medial-lateral coordinate, the physician advances the locking screw 122 to lock the leadscrew 123 of the second frame 120 in place.

The third frame 130 has an anterior-posterior adjustment knob 131 coaxially connected to a screw 133. The screw 133 can have an Acme thread, trapezoidal thread, square thread or other suitable thread for leadscrew use. The screw 133 drives a leadscrew nut 136, to which a tool holder 134 is fixedly attached or with which tool holder 134 is unitarily formed. Rotation of the anterior-posterior adjustment knob 131 rotates screw 133 to move the tool holder 134 in the anterior-posterior direction. The tool holder 134 is adapted to hold a drilling tool, a cutting tool, or a tibia trial 210.

Figure 30:
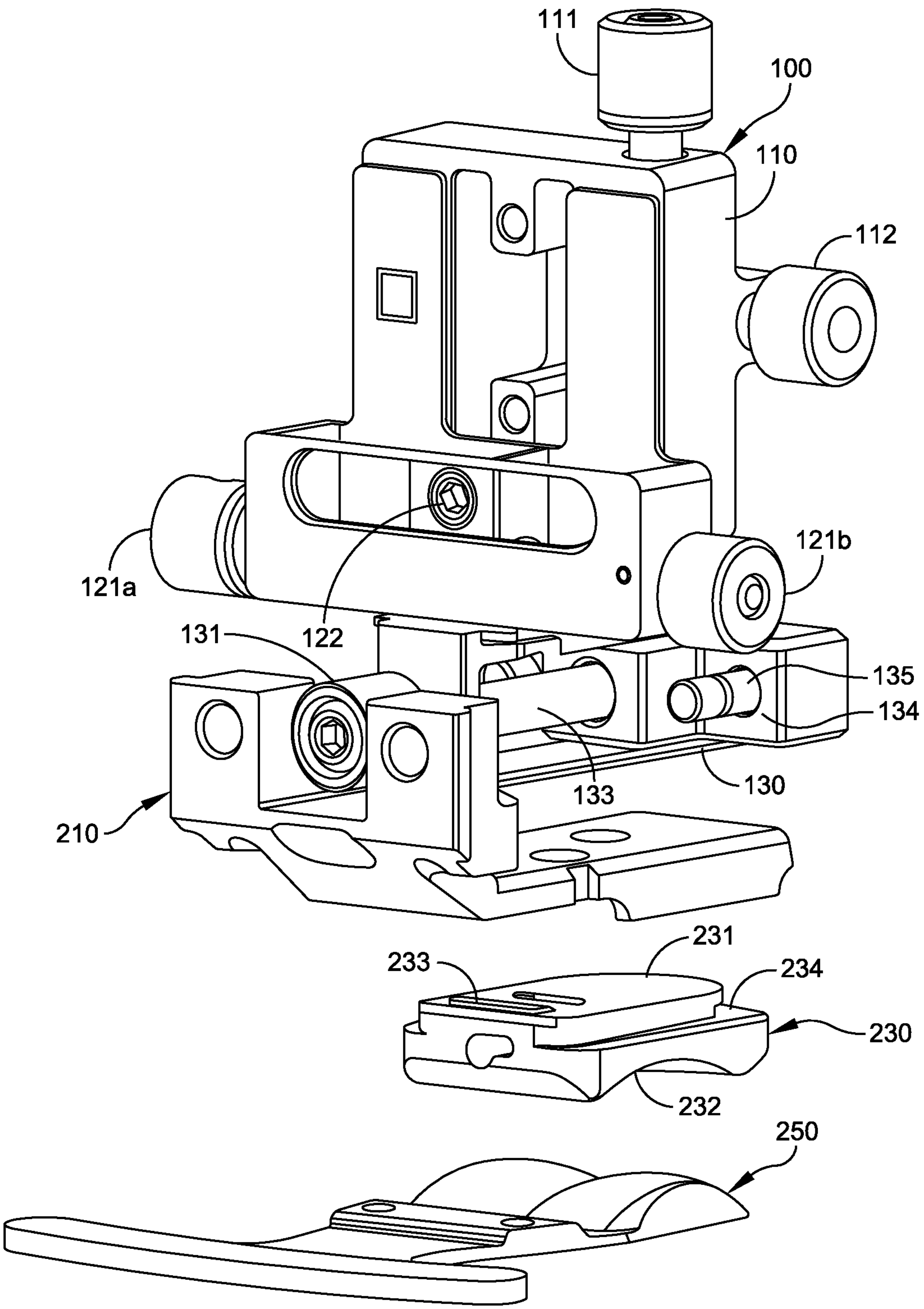
FIG. 30 is an exploded view showing the adjustment block, tibial trial, poly trial insert, and floating trial.
Figure 31:
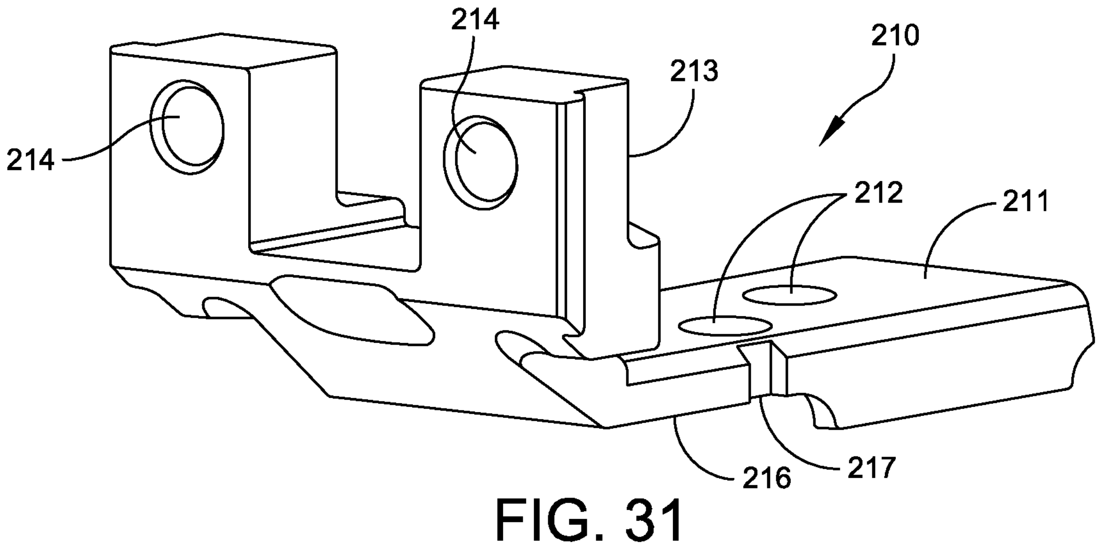
FIG. 31 is an isometric view of the tibia trial of FIG. 30.
Figure 32:
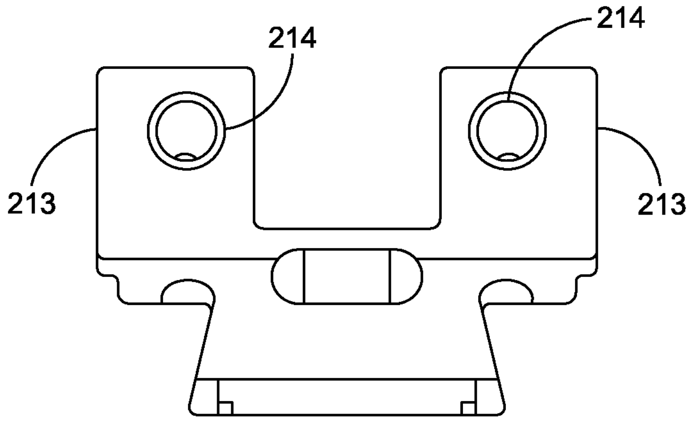
FIG. 32 is an anterior elevation view of the tibia trial of FIG. 31.
Figure 33:
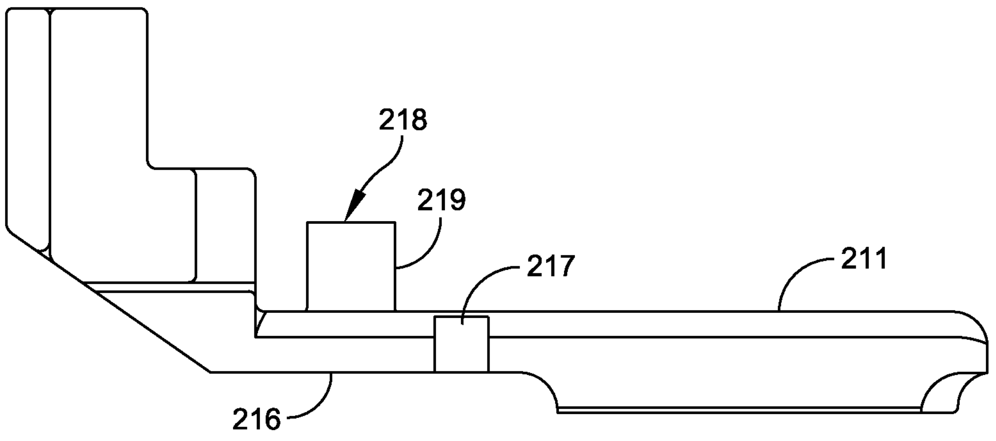
FIG. 33 is a lateral elevation view of the tibia trial of FIG. 31.

FIG. 30 is an exploded view showing the adjustment block 100, tibia trial 210, poly trial insert 230, and floating trial 250. FIG. 31 is an isometric view of the tibia trial 210. FIG. 32 is an anterior (front) elevation view of the tibia trial 210. FIG. 33 is a sagittal (side) elevation view of the tibia trial 210.

Figure 41:
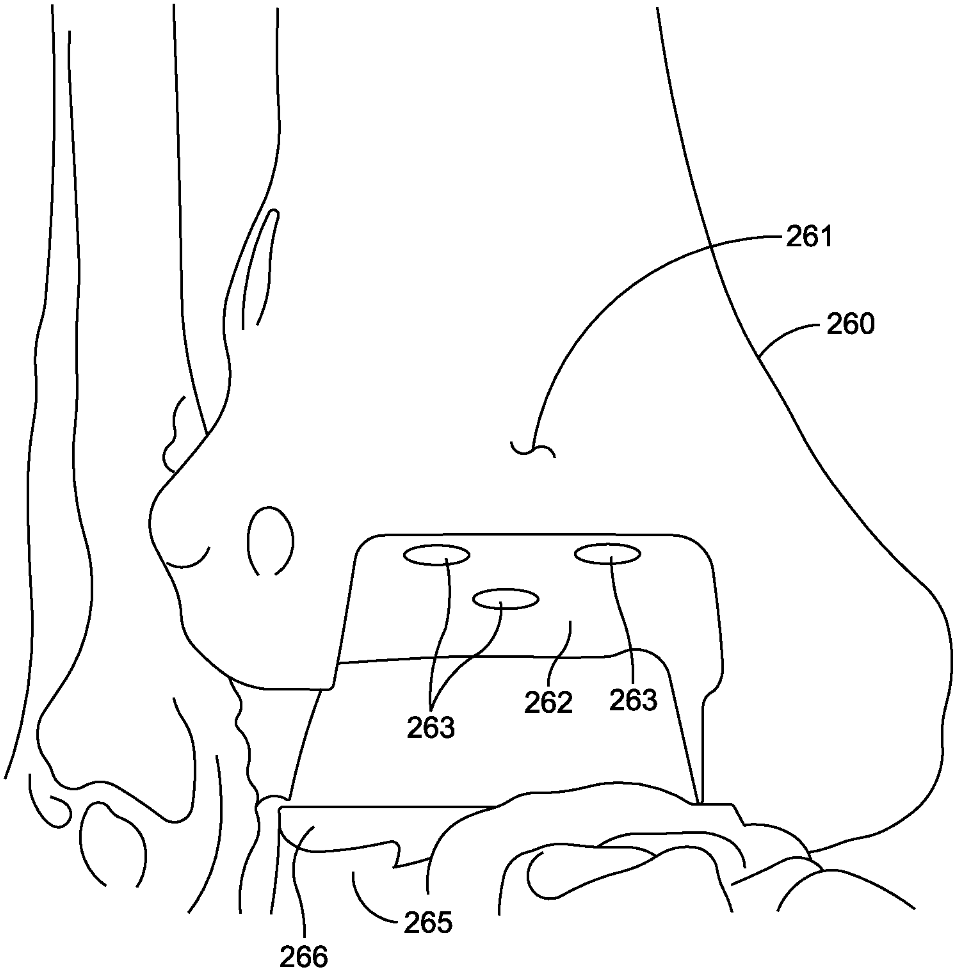
FIG. 41 shows the tibia and talus after resectioning.

The tibia trial 210 provides the profile of the tibia tray portion of an ankle replacement system. The tibia trial 210 comprises a plate 211 with a top surface adapted to fit against a distal surface 262 of the resectioned tibia 260 (FIG. 41). The plate 211 has a plurality of holes 212 (FIG. 31) to be used to locate peg holes 263 in the resectioned tibia 260 (FIG. 41). The plate 211 has a bottom surface 216 including a channel adapted to receive a trial insert, such as a poly trial insert 230. An anterior tibia reference member 218 extends from the plate 211 as best seen in FIG. 33. The anterior tibia reference member 218 has a posterior surface 219 adapted to contact an anterior surface 261 of the tibia 260 (FIG. 41) when the tibia trial 210 is positioned properly. The tibia trial 210 has an anterior mounting portion 213, which defines holes 214, that is sized and shaped to be mounted to the tool holder 134 of the adjustment block 100. In some embodiments, the tibia trial 210 has a notch 217 for aligning an anterior surface of the poly trial insert 230 with the tibia trial 210. Alignment (or misalignment is readily visible by checking whether the notch 217 is aligned with an edge of the poly trial insert 230). In some embodiments, the tibia trial 210 is formed of a strong, corrosion resistant material such as stainless steel or a titanium alloy.

Referring again to FIG. 30, poly trial insert 230 is configured to provide the profile of the poly insert of an ankle replacement system. The poly trial insert 230 comprises a top surface 231 adapted to be detachably mounted to the bottom surface 216 of the plate 211 of the tibia trial 210 (FIG. 31). The poly insert 230 has a concave bottom surface 232 with a size and shape of a prosthetic tibia joint surface of the ankle replacement system. The thickness of the poly trial insert 230 matches the poly insert of the ankle replacement system to which the poly trial insert 230 corresponds, allowing verification of the size and thickness of the poly insert using the poly trial insert 230. In some embodiments, the poly insert of the ankle replacement system has a locking tab to prevent release from the talar tray after surgery; but the poly trial insert 230 has a non-locking tab 233 with a ramped surface, to be detachably inserted in the tibia trial 210 and removed after sizing and resectioning is completed. The non-locking tab 233 fits in a corresponding recess (not shown) in the bottom surface 216 of the tibia trial 210. The posterior end of the poly trial insert 230 has an undercut 234. In some embodiments, the poly trial insert 230 is made from the same type of material used in the poly insert of an ankle replacement system. In some embodiments, the poly trial insert 230 is made of a chemical-resistant material such as polyphenylsulfone, which is also referred to as RadelR.

Figure 34:
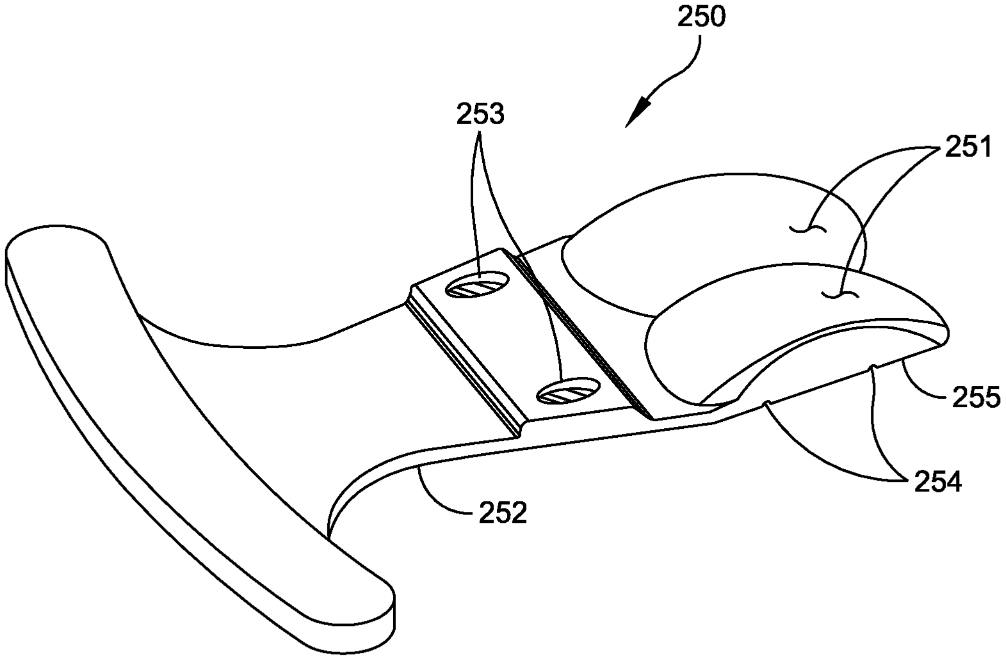
FIG. 34 is an isometric view of the floating trial of FIG. 30.

FIG. 34 is an isometric view of the floating trial 250. The floating trial 250 is configured to provide a contour that matches the contour of the talar dome of the ankle replacement system, which is described in greater detail below. The floating trial 250 is configured to be inserted beneath the poly trial insert 230 to contact the concave bottom surface 232 of insert 230. The floating trial 250 comprises a member 251 having at least one convex anterior surface with a size and shape of a prosthetic talar dome of the ankle replacement system, to permit articulation with the concave surface 232 of the insert. The posterior surface 255 of the member 251 is shaped to match the contour of the resectioned talus. In some embodiments, the floating trial 250 has two convex surfaces 251 as shown in FIG. 34. The floating trial 250 further includes a handle portion 252, which is sized to project from the resection site, so the physician can easily optimize the position of the floating trial for smooth articulation with the poly trial insert 230. The handle 252 of the floating trial 250 has a plurality of pin holes 253 for receiving fixation pins to be used for locating a talar cut guide (not shown). Once the position is optimized, the pins are inserted through the pin holes 253 before completing the resectioning of the talus. In some embodiments, the floating trial 250 is formed of a strong, corrosion resistant material such as stainless steel or a titanium alloy. In some embodiments, the floating trial 250 also has one or more anterior chamfers 254 for reference and alignment.

FIGS. 35-45 show various stages of a method of resectioning and trialing, using the adjustment block 100, optional drill guide 280, optional cut guide 290, tibia trial 210, poly trial insert 230 and floating trial 250. This is one example of a use of the devices, but is not limiting.

Figure 35:
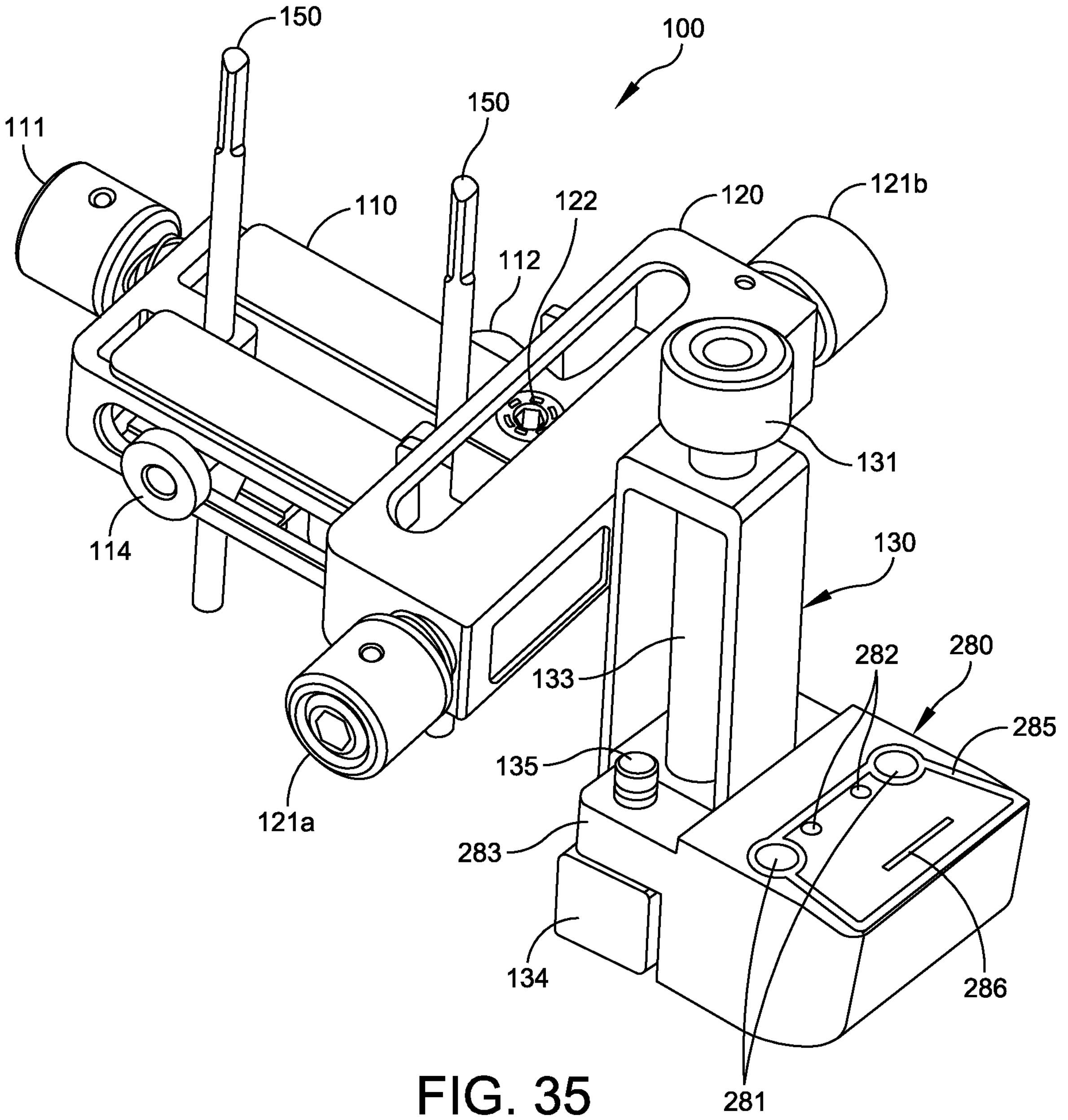
FIG. 35 is an isometric view of an adjustment block of FIG. 29, holding a drilling guide.

FIG. 35 shows the adjustment block 100 fixed to the fixation pins 150 (e.g., 3.2 mm pins), which have been inserted in the anterior surface of the tibia 260 near the distal end 261 of the tibia (not shown). Also shown in FIG. 35 is a drill guide 280 attached to the tool holder 134 of the adjustment block 100, with the first frame 110 slightly above the anterior surface of the tibia 260. In some embodiments, the tool holder 134 includes a stage with a pair of pins 135, and the drill guide 280 has a corresponding pair of mounting ears 283 with holes adapted to snap onto the pins 135. This tool holder design is just exemplary in nature, and other embodiments include other suitable mounting structures as described in greater detail below.

In the embodiment of FIG. 35, the drill guide 280 is a small profile device sized and shaped to be inserted beneath the retracted skin (not shown) in the ankle region. The drill guide 280 has at least two guide holes 281 to be used to drill pilot holes in the tibia 260. The drill guide also has pin holes 282 that can be used to pin the drill guide to the bone, for position fixation. In some embodiments, the drill guide 280 has sizing patterns 285 showing the size and location of one or more resectioning cuts corresponding to the holes to be drilled using the drill guide 280. In some embodiments, the drill guide 280 has one or more reference lines 286 that the physician optionally can use to position the drill guide 280 (by adjusting the proximal-distal knob 111, the medial-lateral knob 121*a* or 121*b*, and the anterior-posterior knob. In some embodiments, the lines 285, 286 are visible under a fluoroscope, so the physician can view the position and size of the lines 285, 286 in situ, relative to the patient's bones.

The physician sizes the tibial tray component of the ankle replacement system by mounting a drill guide 280 on the tool holder and adjusting its position as described above. The position adjustment device (adjustment block) 100 is locked with the tool holder 134 at first coordinates in the proximal-distal and medial-lateral directions.

The physician views the X-ray of the tibia bone 260 and drill guide 280 and determines whether it is the optimum size and position for the patient. The position can be adjusted based on the X-ray, using knobs 111, 121, 131. If the size of the resectioning cut corresponding to the drill guide 280 is too large or too small, the physician removes the drill guide, selects a different size drill guide, and snaps the new drill guide onto the tool holder 134 of the adjustment block 100. The drill guide is then repositioned against the tibia, imaged by fluoroscope, and the size is again checked. To facilitate fluoroscopic X-ray imaging, the drill guide 280 can be made of plastic, while the circles surrounding holes 281 and the patterns 285, 286 can be made of metal. Thus, only the circles surrounding holes 281 and the patterns 285, 286 appear on the X-ray, superimposed against the tibia 260 and talus 265.

Although some embodiments use a single drill guide 280 for sizing, location of fixation pins by holes 282 and drilling corners 281, other embodiments described below use a first guide with holes 282 and patterns 285, 286 for sizing the tibia trial 210 and locating the fixation pins, and a second guide (e.g., a drilling guide) with holes 281 and 282 for performing the drilling. Because the adjustment block 100 and the pins in holes 282 provide common references, the holes 281 can still be drilled with proper location relative to the pin holes 282 and patterns 285, 286.

Figure 36:
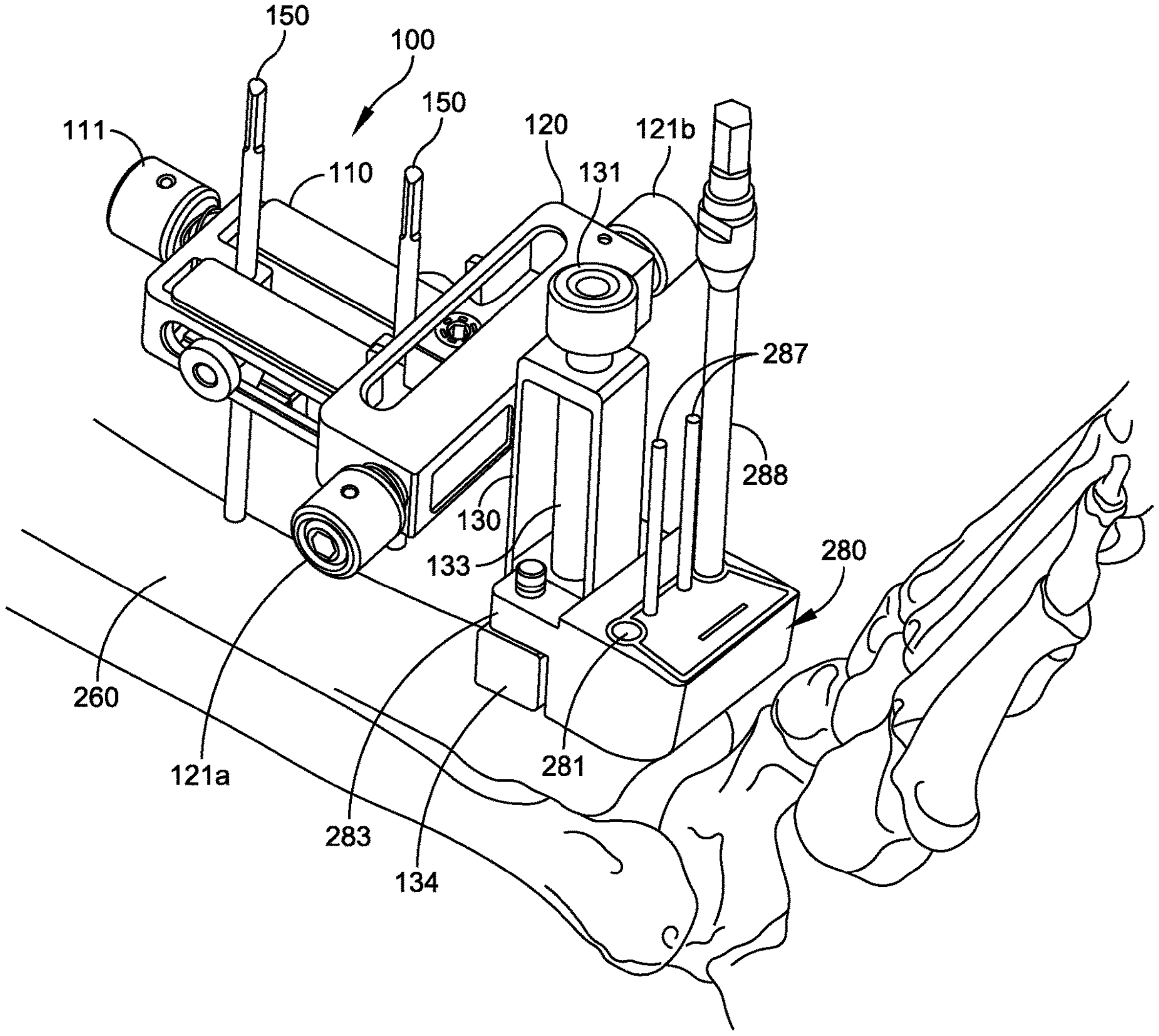
FIG. 36 is an isometric view of the adjustment block and drilling guide of FIG. 35, during the drilling operation.

FIG. 36 shows the tibia 260 with adjustment block 100 and drill guide 280. Soft tissue is omitted for ease of viewing. When the physician has verified that the optimum size of drill guide 280 has been selected, the physician pins the drill guide 280 to the tibia 260 using (e.g., 2.4 mm) fixation pins 287 inserted through the pin holes 282 and trimmed such that pins 287 extend slightly above the drill guide 280. Then the physician drills holes in the tibia 260 through the guides holes 281 using the drill guide 280 and drill 288. The holes thus drilled in the bone 260 define corners of a resectioning cut to be performed in the tibia. The physician then removes the drill guide 280, while leaving the pins 287 in place (in the distal portion of the tibia 260 to be removed by the resectioning). While removing the drill guide 280, the adjustment block can remain locked in the first coordinates with the first frame 110 adjusted to the same proximal-distal coordinate and the second frame 120 adjusted to the same medial-lateral coordinate.

Figure 37:
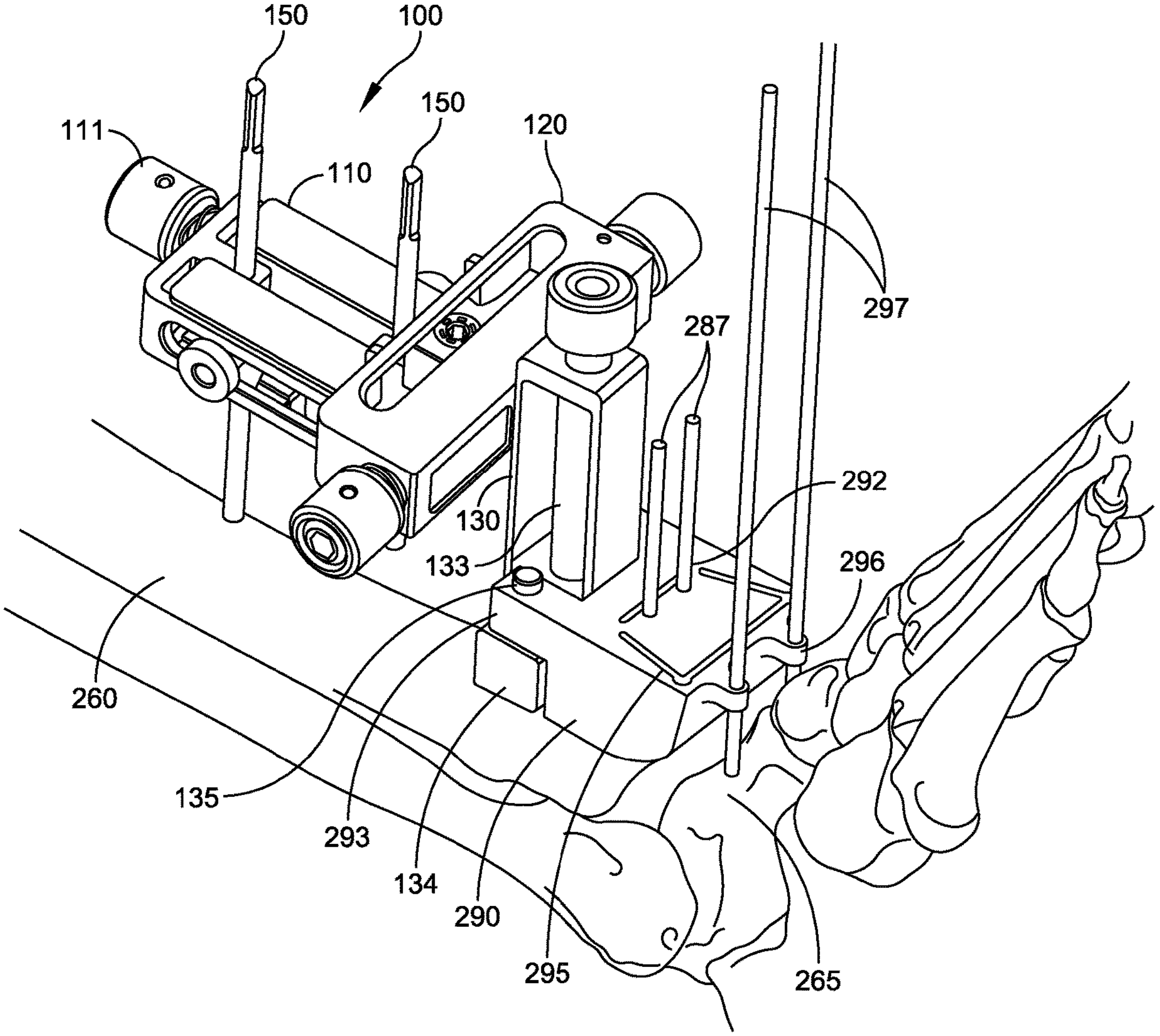
FIG. 37 is an isometric view of the adjustment block of FIG. 29, holding a cut guide.

FIG. 37 shows the adjustment block 100 still fixed to the fixation pins 150 in the same position, with a cut guide 290 mounted to the tool holder 134 of the adjustment block 100. The cut guide 290 has a plurality of slots 295, sized and located to connect the corner holes drilled with the drill guide 280. The cut guide 290 is sized and shaped to match the drill guide 280. Thus, the physician has a set of drill guides 280 and a corresponding set of cut guides 290. The selection of a drill guide size automatically selects the corresponding cut guide size to make cuts which are sized and located to connect the corner holes drilled with the drill guide 280, as described above. The cut guide 290 has a corresponding pair of mounting ears 293 with holes adapted to snap onto the pins 135. The cut guide 290 also has pin holes 292 which are sized and located to receive the fixation pins 287. This aligns the position of the cut guide 290 with the position previously occupied by the drill guide 280, to ensure alignment of the resectioning cuts with the previously drilled corner holes. In some embodiments, the cut guide 290 includes additional ears 296 with pin holes for receiving additional fixation pins 297.

To mount the cut guide 290, the physician slides the holes 292 of cut guide 290 over the fixation pins 287 and snaps the cut guide into place on the tool holder 134. For stability, the physician can then insert two more fixation pins 297 through the pin holes of ears 296 and into the talus bone 265. With the cut guide 290 securely pinned to bones 260, 265, the physician performs the resectioning cuts through the guide slots 295, cutting the bone to connect the previously drilled holes. In some embodiments, such as the embodiment illustrated in FIG. 37, one cut guide 290 is used for both the tibia resection and the first cut of the talar resection. The cut guide 290 is then removed from the surgery site, and detached from the adjustment block 100. The sections of the tibia 260 and talus 265 that have been cut are removed, along with the fixation pins 287 and 297. In other embodiments (not shown), the tibia cut guide is only used to resection the tibia, and a separate cut guide is used to resection the talus after removal of the tibia cut guide.

The use of the adjustment block 100 permits the holes 281 to be drilled first with a first tool, and the cuts to be performed afterwards with a second tool, while maintaining accurate alignment between the holes and the cuts. Drilling the holes first avoids stress concentrations at the corners of the resectioned distal tibia.

Although some embodiments described herein use a drill guide 280 and a cut guide 290 commonly fixed using the adjustment block 100 and fixation pins 287, other embodiments attach different tools to the tool holder 134 for purpose of resectioning the tibia and talus. For example, some embodiments include a cut guide without using a separate drill guide.

Following the initial resectioning of tibia 260, which is described in greater detail below, the physician inserts the tibia trial 210, poly trial insert 230 and floating trial 250, while the adjustment block 100 is still locked to the two fixation pins 150, and the tool holder 134 is in the first coordinates in the proximal-distal and medial-lateral directions. Should the physician choose to temporarily remove the adjustment block from the surgery site (e.g., for inspection, cleaning or suctioning), the physician returns the adjustment block to the same coordinates to locate the tool holder 134 at the same position to complete the procedure. Because the fixation pins 150 are excluded from the distal portion of the tibia removed by the resection, the fixation pins 150 are available throughout the procedure for use in adjusting or correcting the resection cuts.

Figure 38:
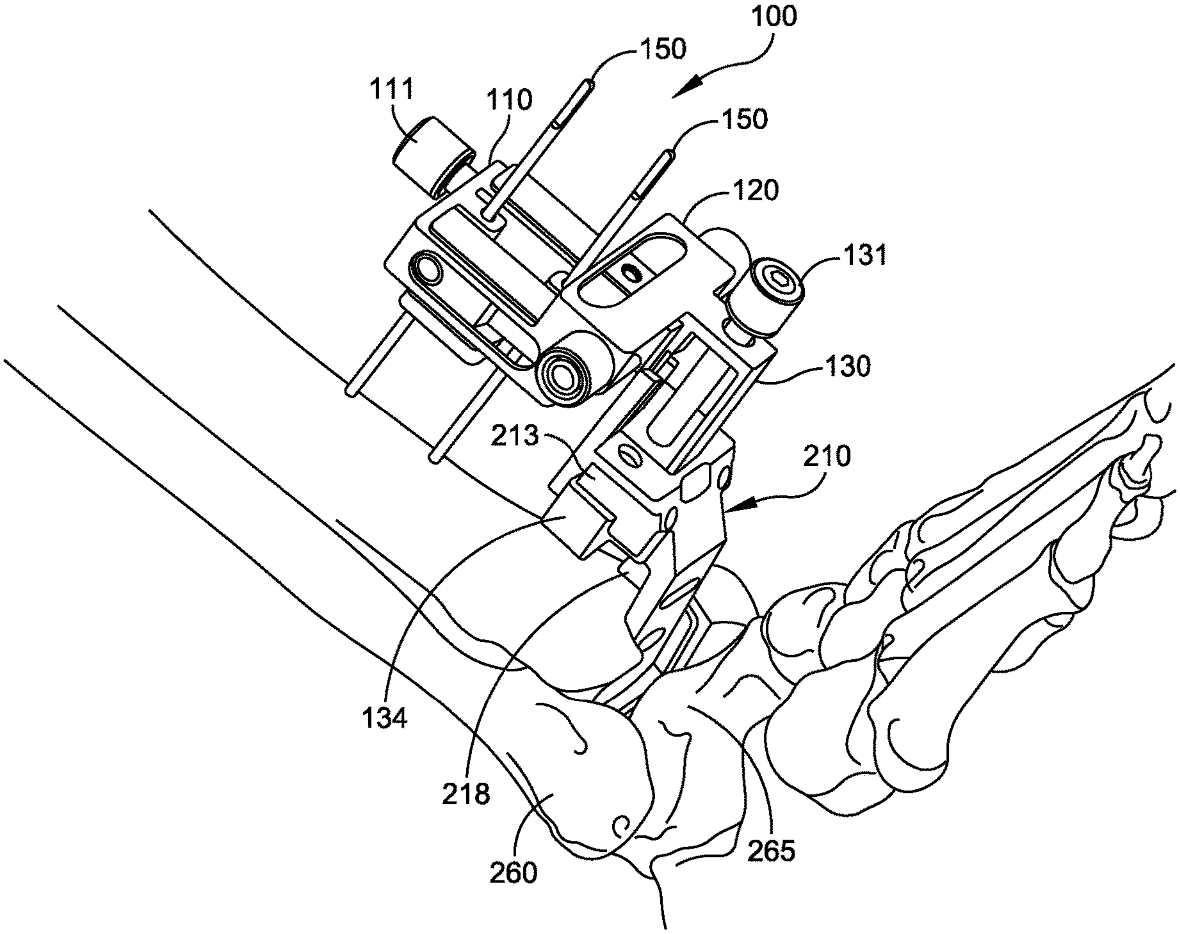
FIG. 38 is an isometric view showing the adjustment block and tibial trial during trial insertion.
Figure 39:
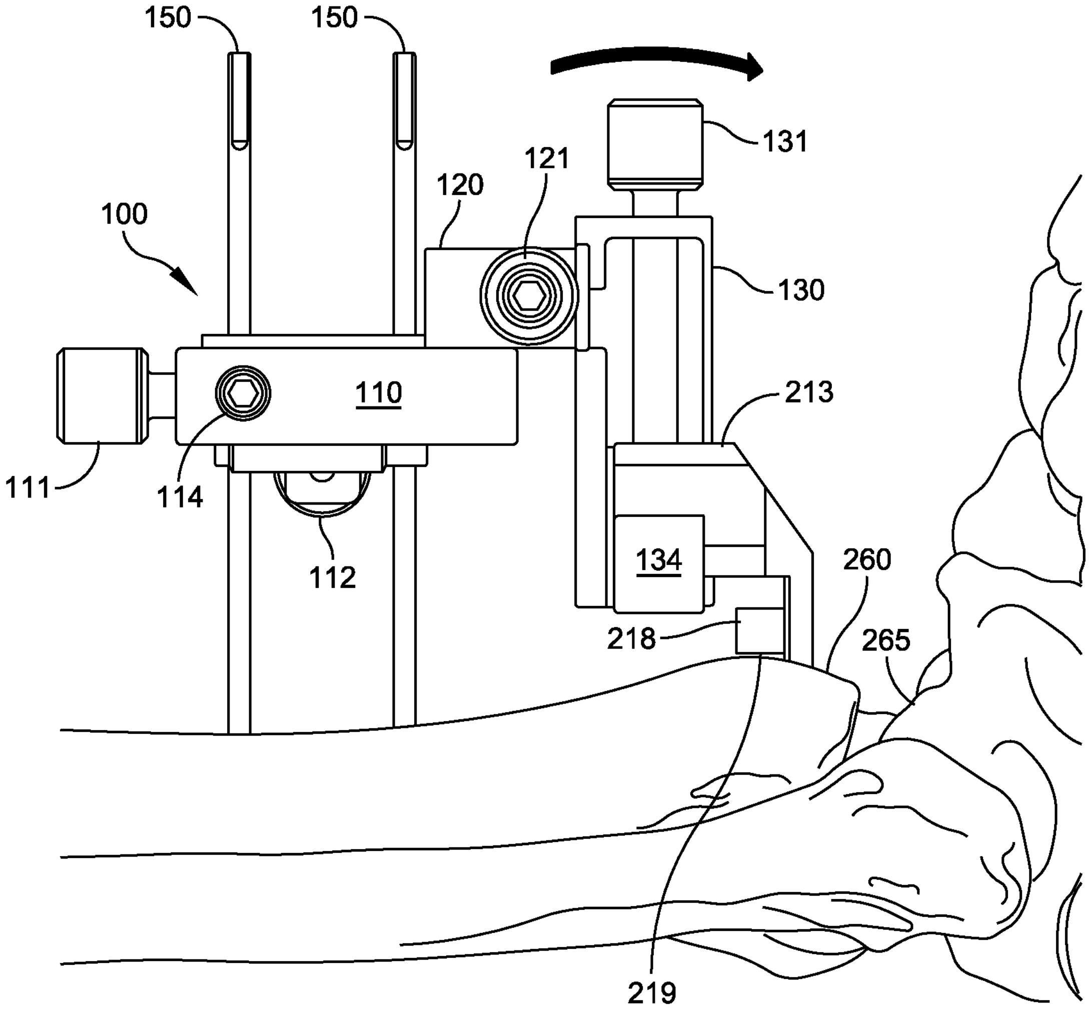
FIG. 39 is a lateral side elevation view of the adjustment block and tibial trial during trial insertion.

The physician snaps the tibia trial 210 onto the tool holder 134. FIGS. 38 and 39 show the adjustment block in position with the tibia trial 210 attached. The adjustment block 100 is adjusted to position the tool holder in an anterior-posterior direction, while the tool holder is at the first coordinates in the proximal-distal and medial-lateral directions. The tibia trial 210 is repositioned in the posterior direction until a predetermined portion of the tibia trail contacts an anterior cortex of the tibia. In some embodiments, the position of the third frame 130 is adjusted until the posterior surface 219 of anterior tibia reference member 218 extending from the plate 211 contacts the anterior cortex of the tibia 260.

Figure 39A:
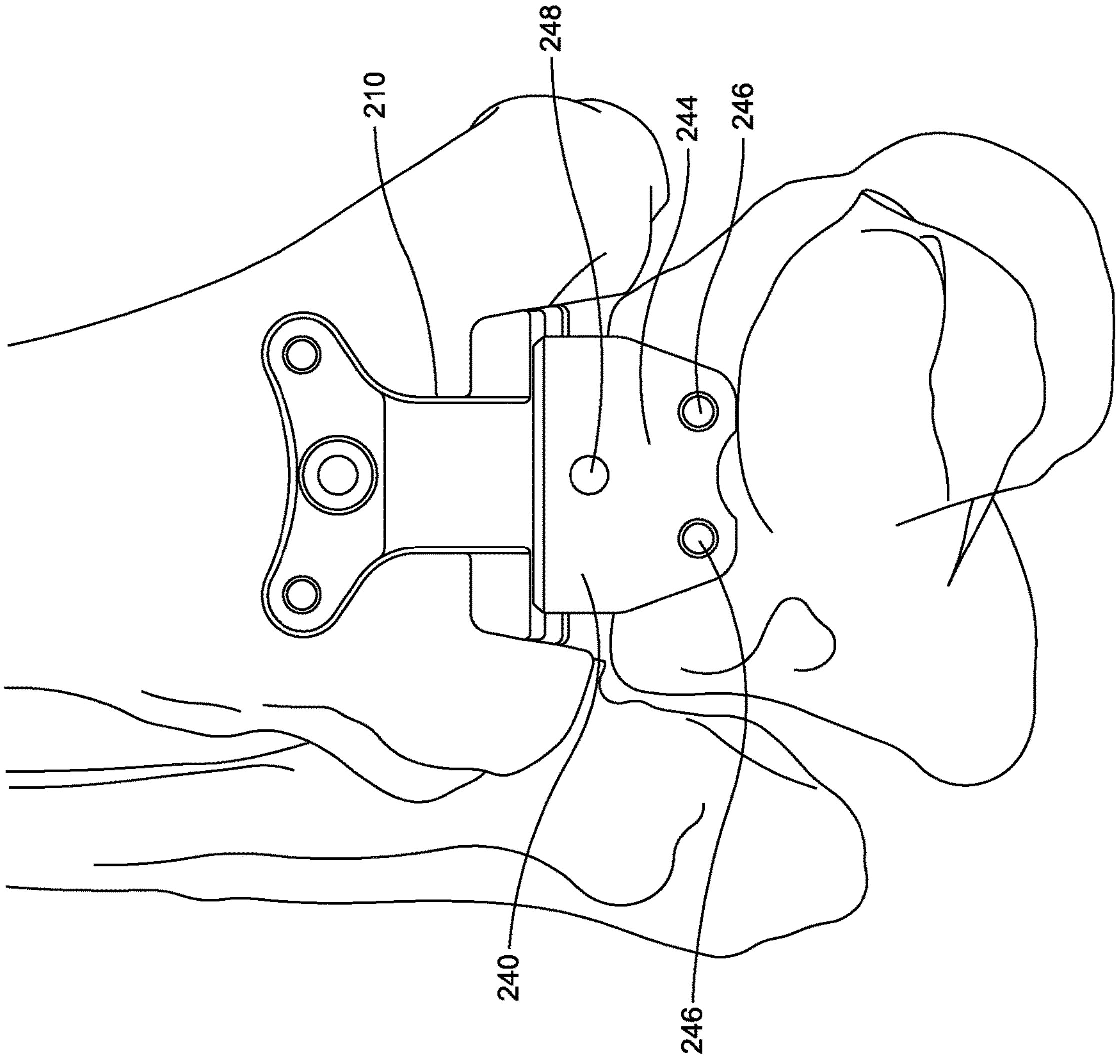
FIG. 39A is a front side view of a spacer coupled to a tibial trial in accordance with some embodiments.
Figure 39B:
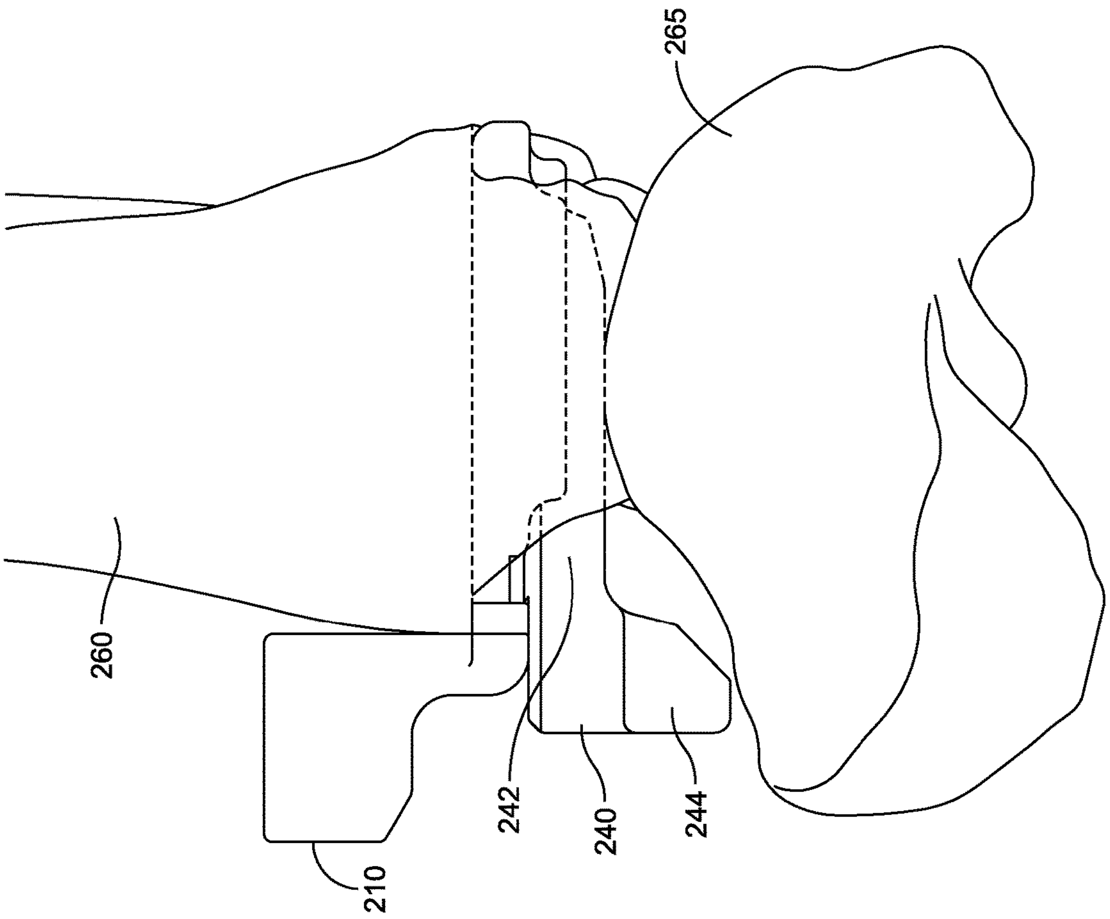
FIG. 39B is a side view of the spacer coupled to the tibial trial in accordance with some embodiments.

In some embodiments, the tibial trial 210 is used in connection with a spacer 240 to assess the ligament laxity of the ankle joint as shown in FIGS. 39A and 39B. Spacer 240 can be provided in a variety of thicknesses including, but not limited to 4 mm, 5 mm, and 6 mm to list only a few possibilities. As shown in FIGS. 33A and 33B, spacer 240 includes an elongate body 242 including an extension 244 at one end. Extension 244 defines spaced apart holes 246 that are sized and configured to receive fixation pins 297 therein. A blind hole 248 that is at least partially threaded is also defined by spacer 240 and is configured for aiding the removal of spacer 240 from its engagement with tibial trial 210. In some embodiments, spacer 240 is fabricated from a radiolucent material.

Figure 39C:
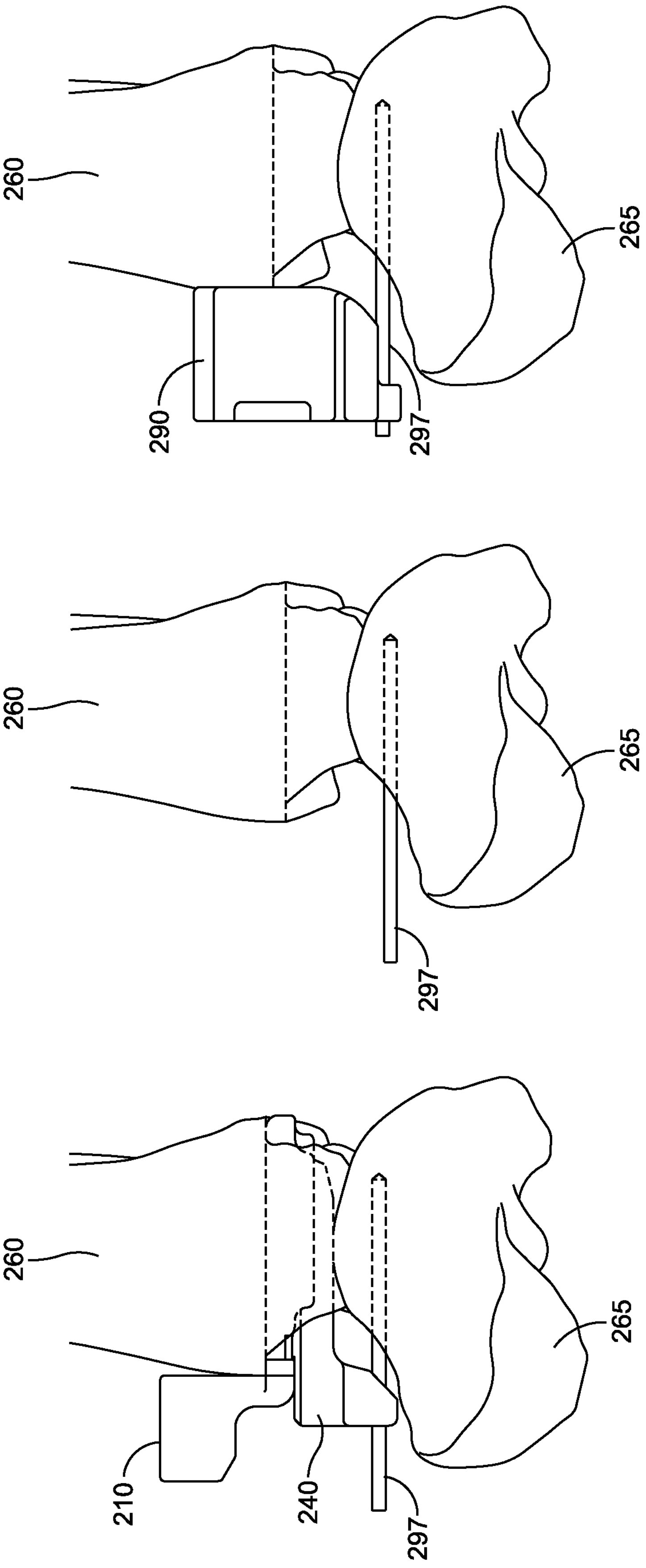
FIG. 39C illustrates the spacer and tibial trial being removed and replaced with a cutting guide in accordance with some embodiments.

Once tibia 260 is resectioned using the superior and angled medial and lateral slots of cutting guide 290 shown in FIG. 37, the resected portion of the tibia 260 is removed. Tibia trial 210 is inserted as described above, and spacer 240 is inserted into engagement with tibia trial 210 as shown in FIGS. 39A and 39B. The combination of tibia trial 210 and spacer 240 are used to assess the ligament laxity prior to resection of the upper talus. Once the ligament laxity has been assessed, spacer 240 can be removed and cutting guide 290 can be placed back over pins 297 and the inferior slot can be used to resect to the top of talus 265 as shown in FIG. 39C.

Figure 39E:
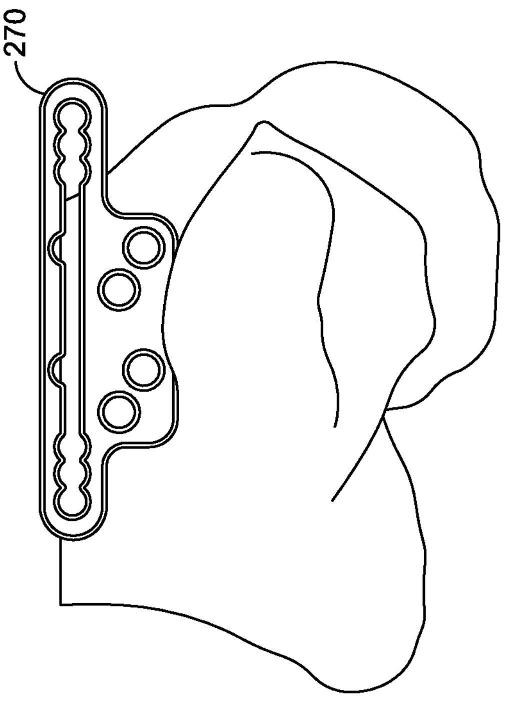
FIGS. 39D and 39E illustrate another example of a cutting guide positioned over fixation pins placed using the tibial trial and spacer in accordance with some embodiments.
Figure 39D:
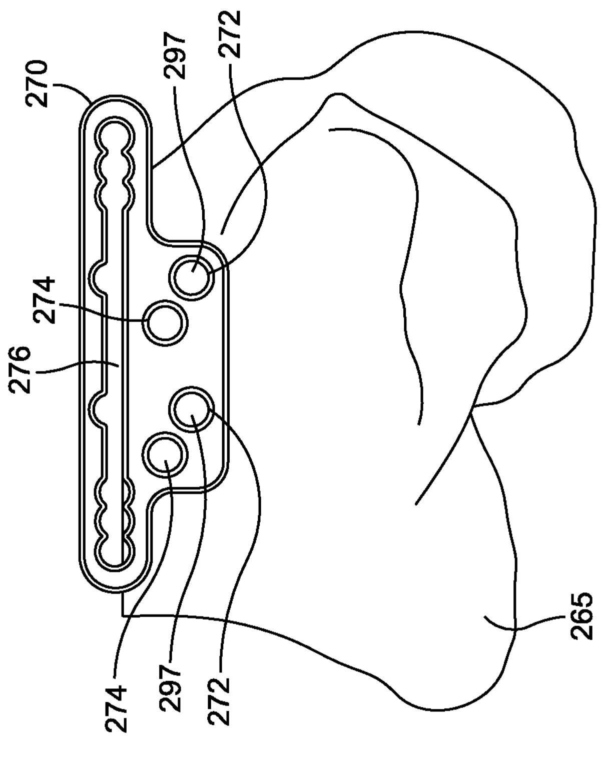

In some embodiments, an additional talar cutting guide, such as talar cutting guide 270 illustrated in FIGS. 39D and 39E, can be used to provide an initial talar resection or to further resect the talus beyond the resection provided by cutting guide 290. As shown in FIGS. 39D and 39E, illustrate one example of a cutting guide 270 coupled to a resected talus 265 by fixation pins 297, which are disposed within distal holes 272. A set of proximal holes 274, which are offset from distal holes 272, and an elongate cutting slot 276 slot also are defined by cutting guide 270. As can be seen by comparing FIGS. 39D and 39E, proximal holes 274 are offset from distal holes 272 by a distance to provide a surgeon with the options of resecting different amounts of the talus bone. In some embodiments, the vertical difference between the position of holes 272 and holes 274 is 2 mm. However, one of ordinary skill in the art will understand that the vertical distance between the center of holes 272 and 274 can be greater or less than 2 mm.

Figure 40:
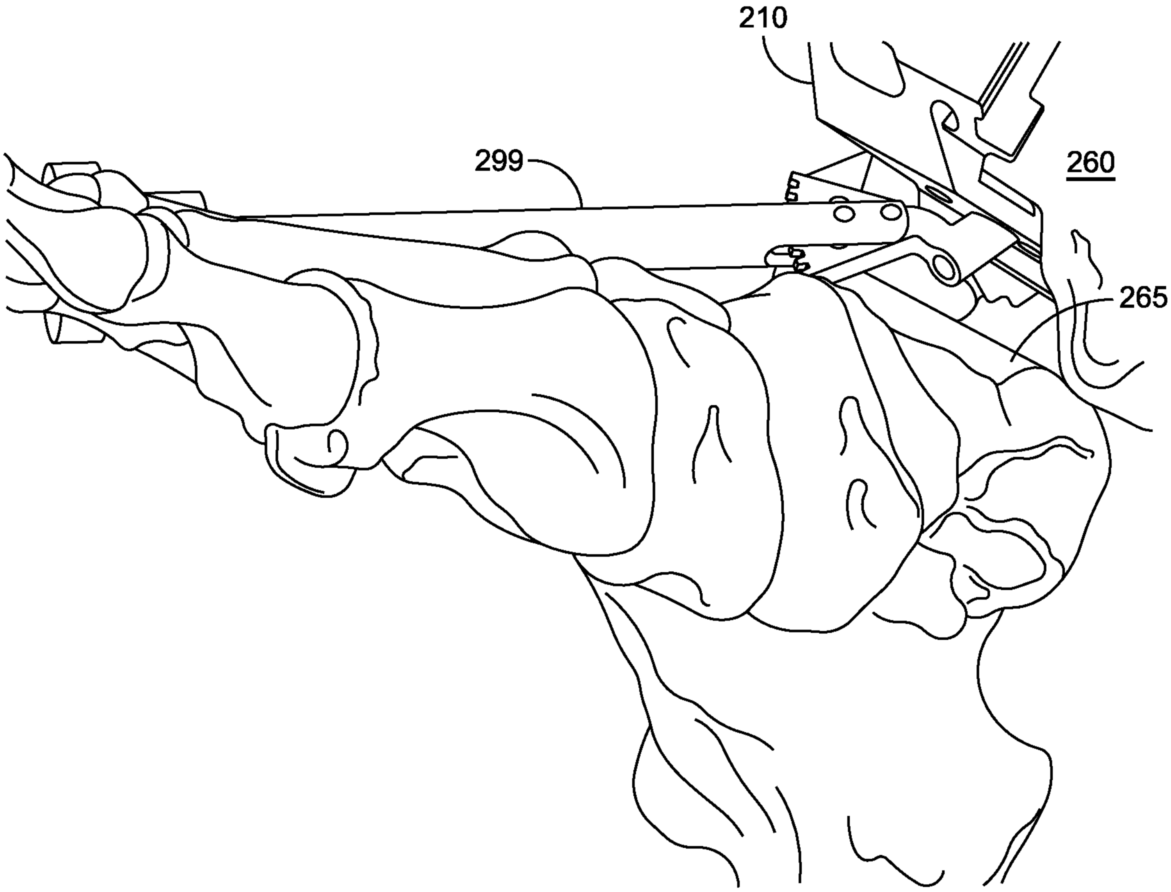
FIG. 40 is an isometric view showing drilling using the tibia trial to locate peg holes in the distal surface of the tibia.

FIG. 40 shows the tibia 260 and talus 265 with the tibia trial 210 in position. The tibia peg drill (not shown) is placed in the head of a tibia peg drill guide 299, and is inserted in the holes 212 (FIG. 31) of the tibia trial 210. The physician drills a plurality (e.g., 3) peg holes 263 in the distal surface 262 of the resectioned tibia 260 using the tibia peg drill 299. The holes 212 (FIG. 31) of the tibia trial 210 are used to locate these holes 263. FIG. 41 shows the distal end 261 of the tibia 260 at the completion of the peg drilling, with the three peg holes 263 in the resectioned surface 262 of the tibia.

The tibia trial 210 is used to verify size and shape of the resectioning using the tibia trial, prior to implanting the ankle replacement system. Advantageously, the steps of attaching the tibia trial 210 to the tool holder 134, adjusting the position adjustment device 100 to position the tool holder 134 in an anterior-posterior direction, and placing the tibia trial 210 on the resectioned tibia 260 using the tool holder 134, can be formed without inserting any additional location fixing pins into the tibia, while the tool holder is locked in the first coordinates in the proximal-distal and medial-lateral directions.

Figure 42:
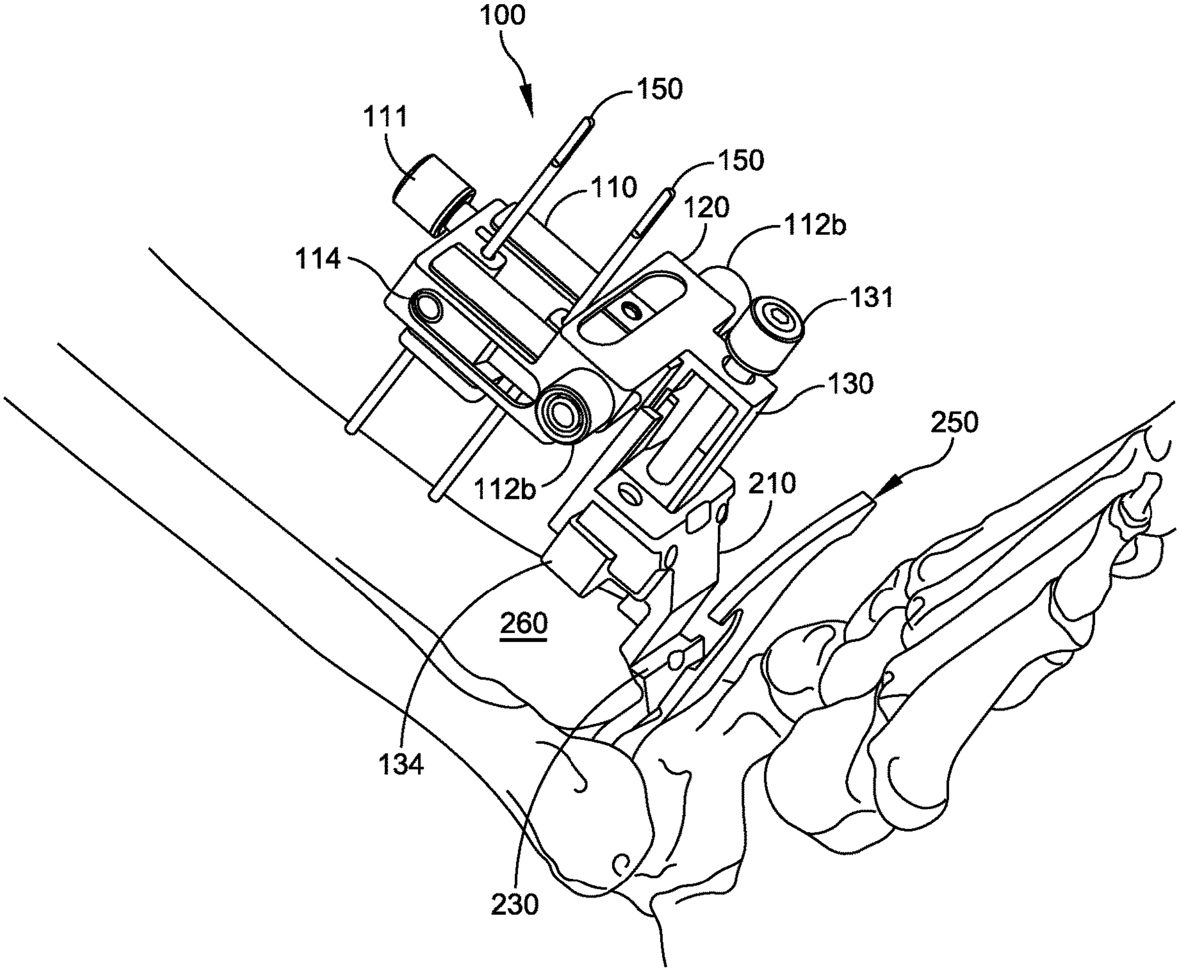
FIG. 42 is an isometric view showing the adjustment block, tibial trial, poly trial insert, and floating trial inserted in the surgical window.
Figure 43:
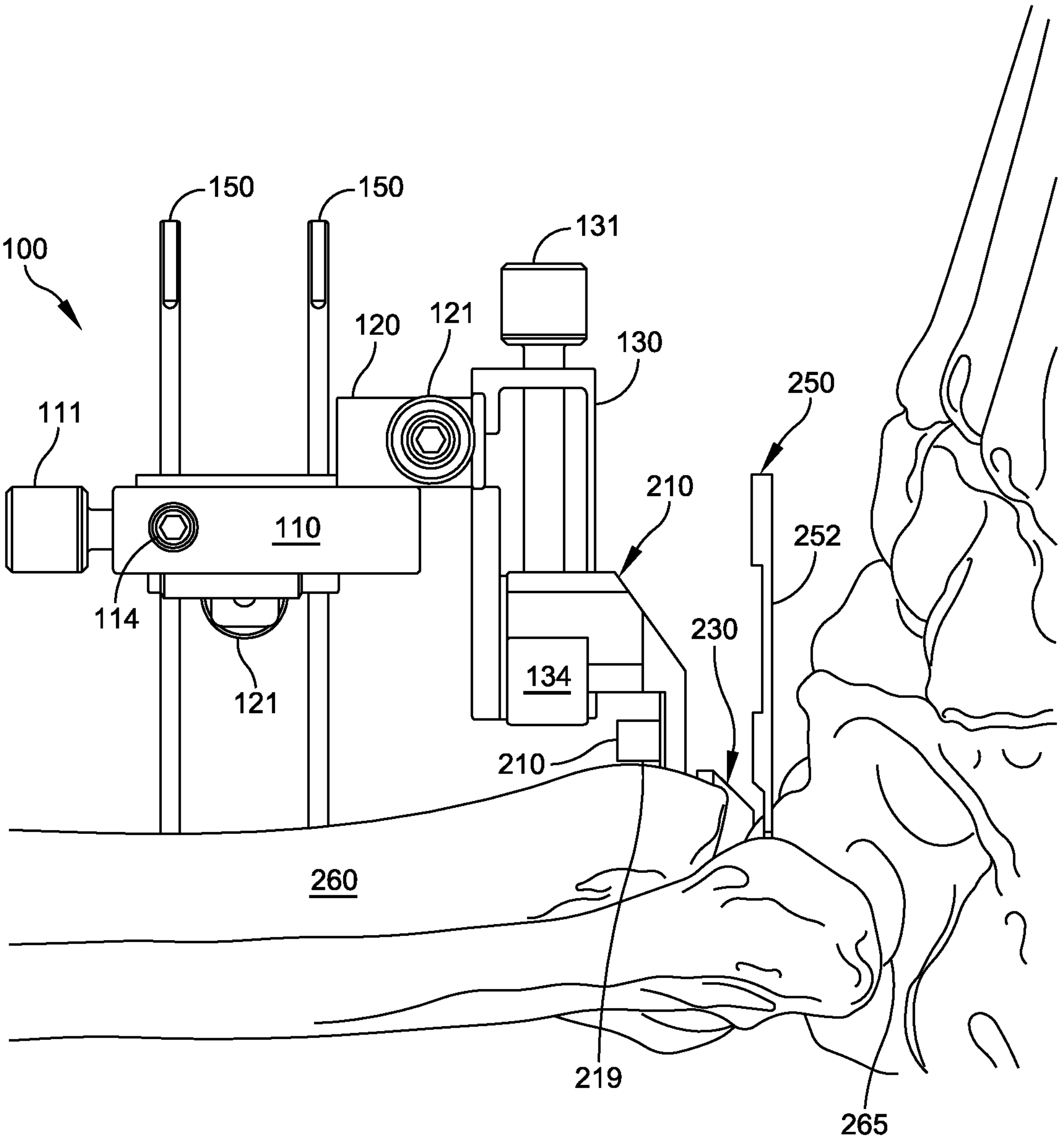
FIG. 43 is a lateral side elevation view of the adjustment block, tibial trial, poly trial insert, and floating trial inserted in the surgical window.

FIGS. 42 and 43 show the adjustment block 100 and tibia trial 210, after installing the poly trial insert 230 into the tibia trial 210 and positioning the floating trial 250 between the talus 265 and the poly insert trial 230, to permit articulation with the concave surface 232 of the poly insert trial 230 while the tool holder is in the first coordinates in the proximal-distal and medial-lateral directions. The physician can now assess the fit of the ankle replacement system, including size, anterior-posterior position, and whether the tibia has been sized, drilled and cut optimally. If any adjustments are deemed appropriate to the tibia resectioning, the physician can reapply the cut guide with the adjustment block set to the same proximal-distal and medial-lateral coordinates used before.

Figure 44:
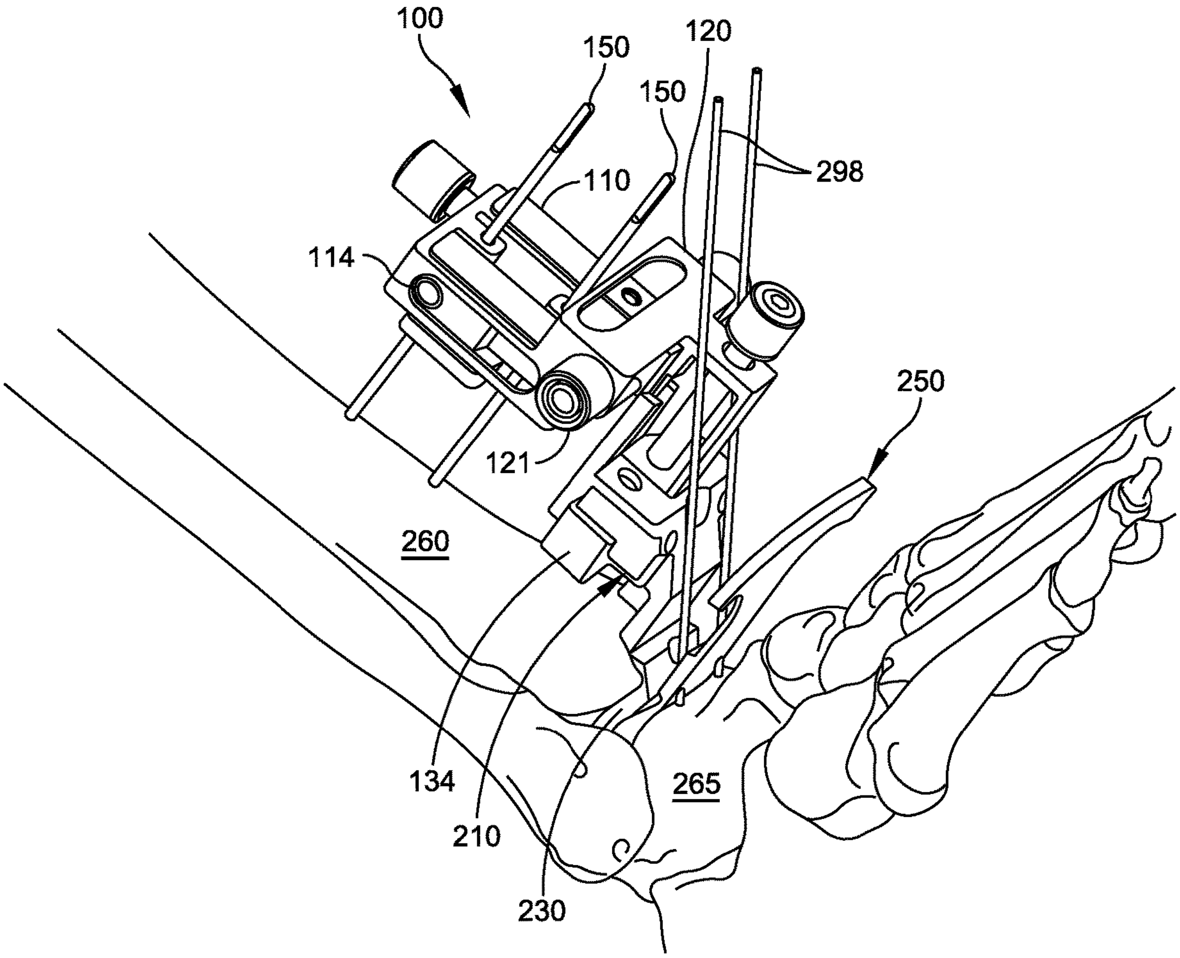
FIGS. 44 and 45 are isometric and lateral side elevation views showing the adjustment block, tibial trial, poly trial insert, and floating trial inserted while the floating trial is being pinned to the talus.
Figure 45:
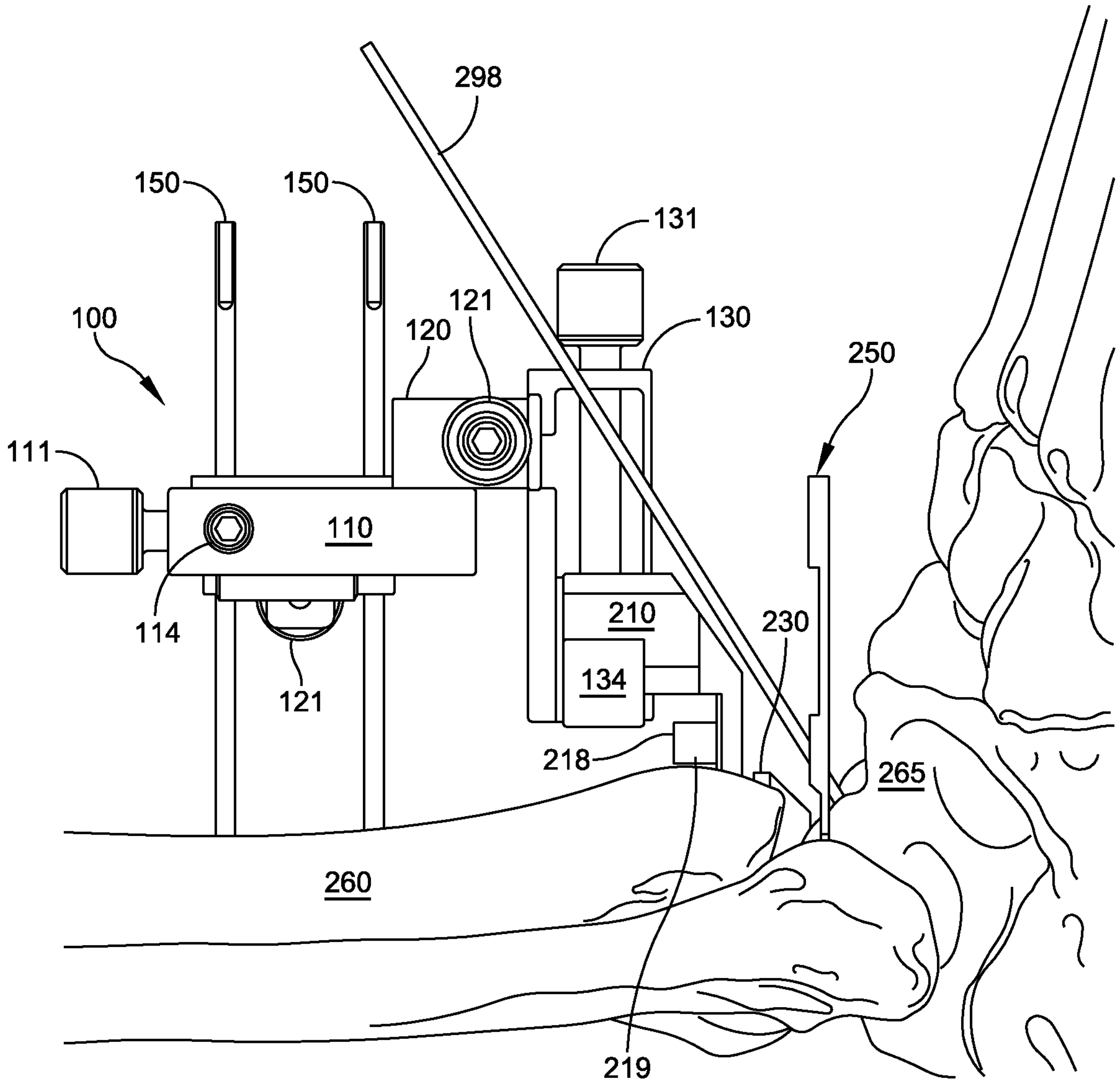

Referring to FIGS. 44 and 45, the physician now performs a trial reduction to ensure the correct poly insert height and talus dome position. The talar implant anterior-posterior coordinate is determined by moving the floating trial 250 to the location where it best articulates with the concave surface 232 of the poly trial insert 230. Two additional fixation pins 298 are inserted through the pin holes 253 of the floating trial 250 using a K-wire, such as a 2 mm K-wire, for example. Additional resection guides, described in greater detail below can be positioned by sliding pin holes in the resection guide(s) over the fixation pins 298. The remaining talar cuts are then performed to match the geometry of the talar dome implant of the ankle replacement system as described below.

A position adjustment device (or adjustment block) 100 as described above provides a fixed point of reference that facilitates the AP position of the tibial and talar implants of an ankle replacement system. The adjustment block 100 is capable of fixing a tibial trial 210 via a modular connection 134 to avoid insertion of additional pins in the distal tibia. The tibial trial 210, while attached to the adjustment block 100, allows the user to set the tibial implant anterior-posterior position by abutting the anterior post 218 against the tibial bone. The tibial trial 210 also serves as a drill guide to prepare the tibial pegs on the tibial implant.

The tibial trial 210 while rigidly fixed to the adjustment block 100 then translates the anterior-posterior position to the talar trial 250 by using the poly trial insert 230 to articulate with the talar (dome) trial 250. The talar trial 250 also has chamfer indicators 254 to help the user determine the optimal talar anterior-posterior position.

Advantageously, the system and method described above uses the adjustment block 100 as a fixed reference to associate all other instruments used for trial sizing and trials related to tibial side of the ankle replacement. Thus, a tibial sizer (e.g., drill guide 280), tibial resection guide (e.g., cut guide 290), and tibial trial 210 can all be anchored at the same position defined by the adjustment block 100. This method preserves the distal layer of the tibia to avoid excess pin holes from fixation pins and devices.

The compact size of the adjustment block allows the tools to be fixed and placed close to the surgery site, for more accurate cuts, with reduced chance of components flexing. Sizing guides (e.g., drill guide 280) and resection guides (e.g. cut guide 290) can all be placed in the surgical window. The position of the tools and trials can be accurately adjusted by turning the adjustment knobs 111, 121, 131 in a small area.

Figure 46:
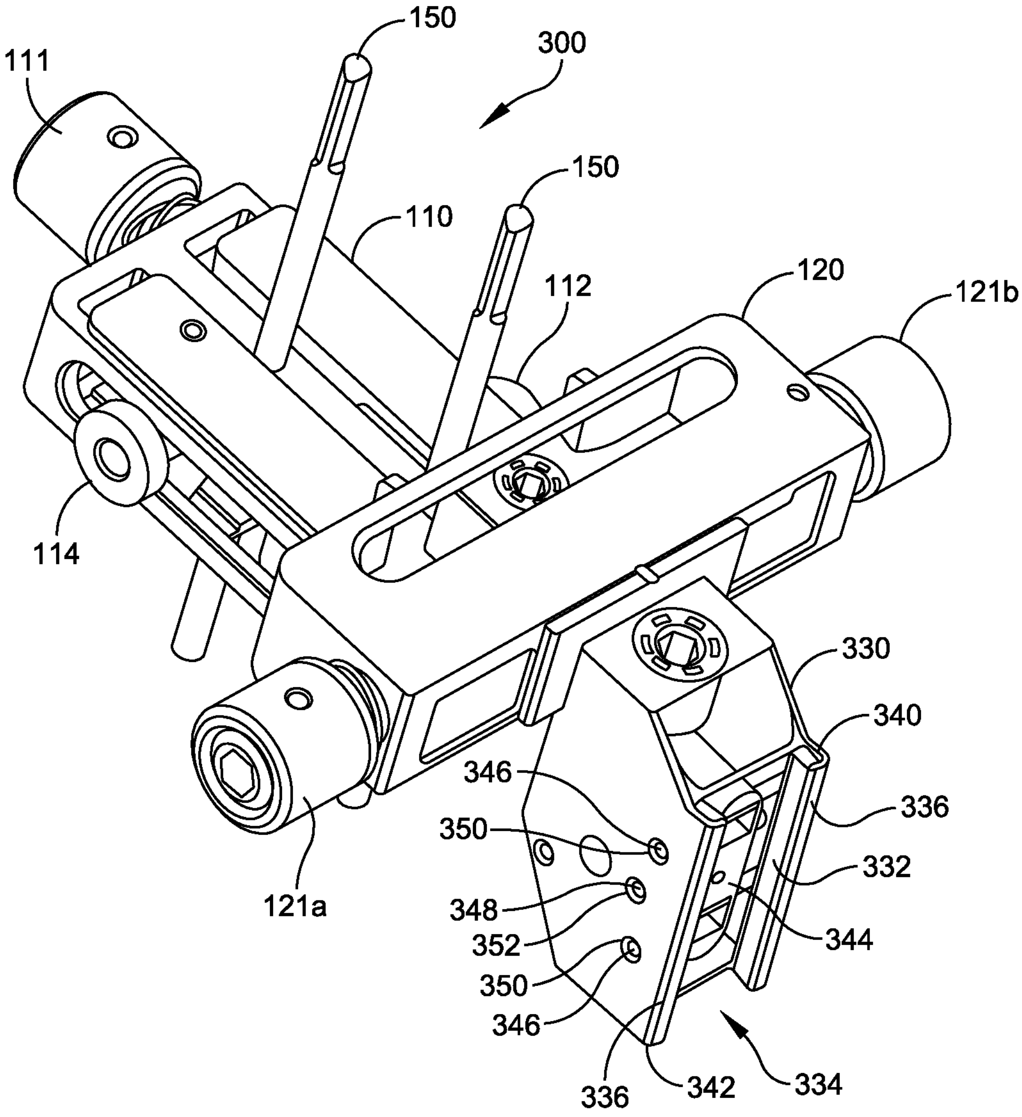
FIG. 46 is an isometric view of an embodiment of the adjustment block providing proximal-distal and medial-lateral adjustments.
Figure 47:
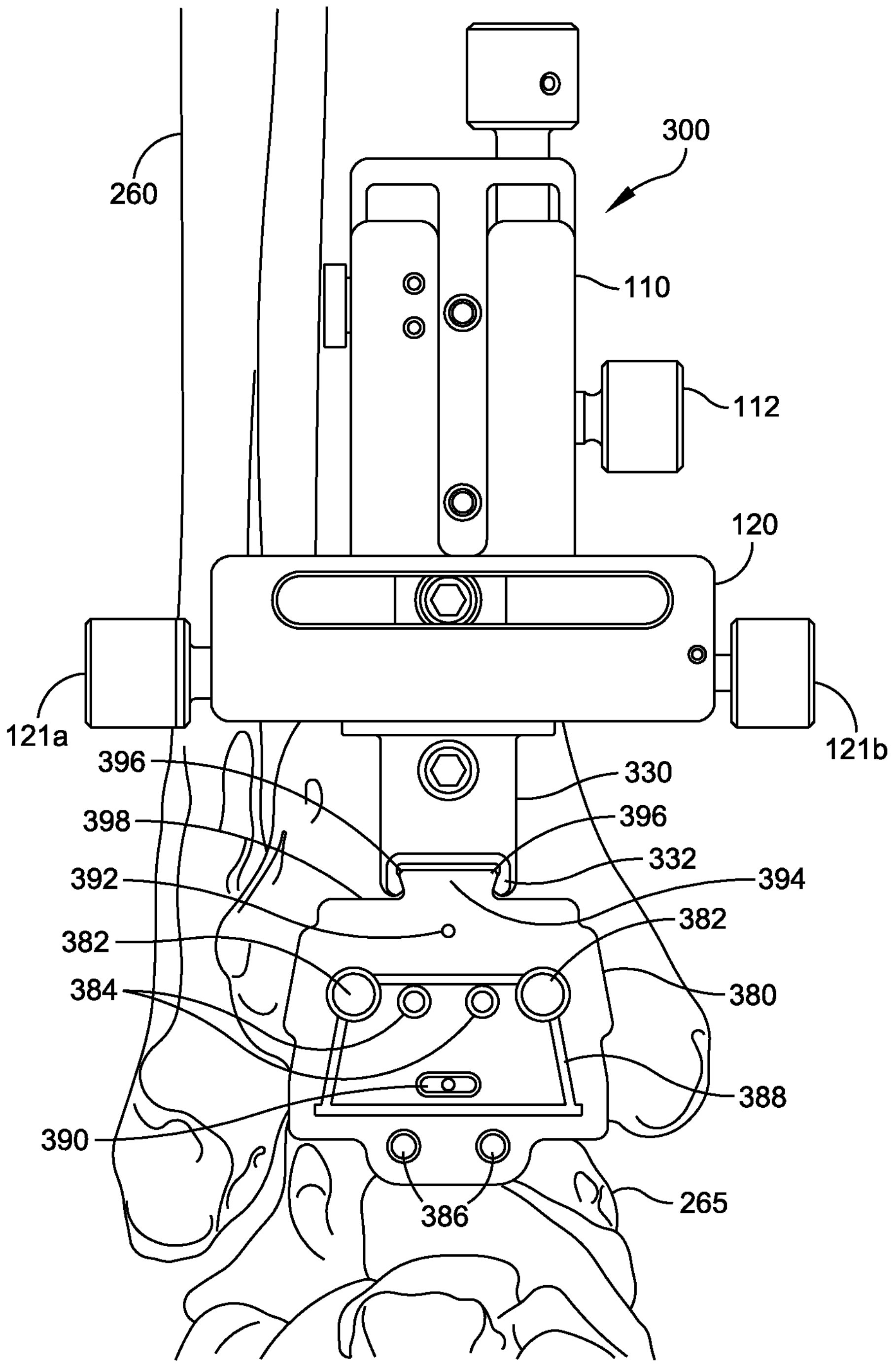
FIG. 47 is an anterior top plan view of the adjustment block of FIG. 46, with a drill guide attached to its tool holder.

FIGS. 46 and 47 show another embodiment of the adjustment block 300 configured with a tool holder 330. The adjustment block 300 has two independently positionable frames 110, 120 for precisely positioning a tool holder 330 in the proximal-distal and medial-lateral directions, adjacent the joint to be replaced.

The first frame 110 is configured to be attached to two fixation pins 150 which have been inserted in the anterior surface of the tibia, near the distal end of the tibia as described above. A locking screw 112 actuates a locking plate (not shown), which bears against the fixation pins 150 to secure the adjustment block 100 relative to the pins. The first frame has a proximal-distal adjustment knob 111 coaxially connected to a screw 113. The screw 113 can have an Acme thread, trapezoidal thread, square thread or other suitable thread for leadscrew use. The second frame 120 is fixedly attached or unitarily formed with a leadscrew nut (not shown), which the screw 113 drives. Rotation of the proximal-distal adjustment knob 111 rotates screw 113 to advance or retract the second frame 120 in the proximal-distal direction. When the second frame 120 is at the desired proximal-distal coordinate, the physician advances the locking screw 114 to lock the second frame 120 to the first frame 110 in place.

The second frame 120 has at least one medial-lateral adjustment knob 121*a*, 121*b* coaxially connected to a screw 123. The screw 123 can have an Acme thread, trapezoidal thread, square thread or other suitable thread for leadscrew use. The screw 123 drives a leadscrew nut (not shown), to which the tool holder 330 is fixedly attached or unitarily formed with. Rotation of the medial-lateral adjustment knob 121*a* or 121*b* rotates screw 123 to move the tool holder 330 in the medial-lateral direction. When the tool holder 330 is at the desired medial-lateral coordinate, the physician advances the locking screw 122 to lock the leadscrew 123 of the second frame 120 in place.

The position of the tool holder 330 in the anterior-posterior direction is determined by location of the first frame 110 relative to the pins 150. The tool holder 330 can have any of a variety of configurations for easily attaching a tool or trial. One example of a tool holder 330 is illustrated in FIG. 46. As shown in FIG. 46, tool holder 330 includes a dovetail joint 332 and defines a cavity 334 between rails 336 of dovetail joint 332. Tool holder 330 also defines a hole 338 extending in a direction parallel to the direction in which rails 336 of dovetail joint 332 extend from a first side 340 to a second side 342.

Cavity 334 is sized and configured to receive a locking wedge 344 therein. As best seen in FIG. 46, locking wedge 344 is cross-pinned in cavity 334 by the combination of pins 346, 348, which are respectively received in holes 350, 352 (see also FIG. 52). For example, a pair of pins 346 are received within holes 350, and a pin 348 is received within hole 352. Locking wedge 344 includes a pair of spaced apart notches 354 (FIG. 52) each being sized and configured to receive a biasing member 356. Biasing members 356, which may take the form of compression springs, are disposed within notches 354 and urge locking wedge 344 towards hole 338. A slot 358 (FIG. 52) is defined in locking wedge 344 and is sized and configured to receive pin 348 (FIG. 46) therein to prevent locking wedge 344 from being separated from tool holder 330.

Referring again to FIG. 52, the upper surface 360 of locking wedge 344 includes a pair of chamfered or angles 362, which facilitate engagement with a locking screw 364 and the displacement and movement of locking wedge 344 relative to tool holder 330. For example, hole 338 defined by tool holder 330 is sized and configured to receive locking screw 364 and is in communication with cavity 334 such that shoulders 366 and 368 of locking screw 364 are in abutment with chamfers 362 of locking wedge 344. In addition to shoulders 366, 368, locking screw includes an enlarged head 370 and threads or other engagement feature 372 at a distal end for engaging a corresponding structure defined by locking wedge 344 for maintaining locking wedge 344 in a locked position such that locking wedge is pressed against biasing members 356 and engages a tool disposed within dovetail joint 332. A pin 374 is disposed within hole 376 defined by tool holder 330 at a position in which pin 374 is configured to contact shoulder 368 when locking screw 364 is in an unlocked position to maintain locking screw 364 in engagement with tool holder 330.

FIG. 47 illustrates an example of a coronal sizing and drill guide 380, which is similar to drill guide 280 described above, that is configured to be mated to tool holder 330. One of ordinary skill in the art will understand that other tools (e.g., a cut guide) and trials (e.g., tibia trial) can be adapted to fit the tool holder 330.

Coronal sizing and drill guide 380 includes corner drill holes 382, fixation holes 384, 386, sizing pattern 388, a slot 390, and a coronal parallax cue pin 392. Corner drill holes 382 are sized and configured to receive a drill or reamer therein as described above and in greater detail below. Fixation holes 384, 386 are sized and configured to receive a pin (e.g., fixation pin 297) therein for pinning the coronal sizing and drill guide 380 to the tibia and talus, respectively. Coronal sizing guide 380 can be formed from plastic or other material that is translucent under a fluoroscope.

Figure 48:
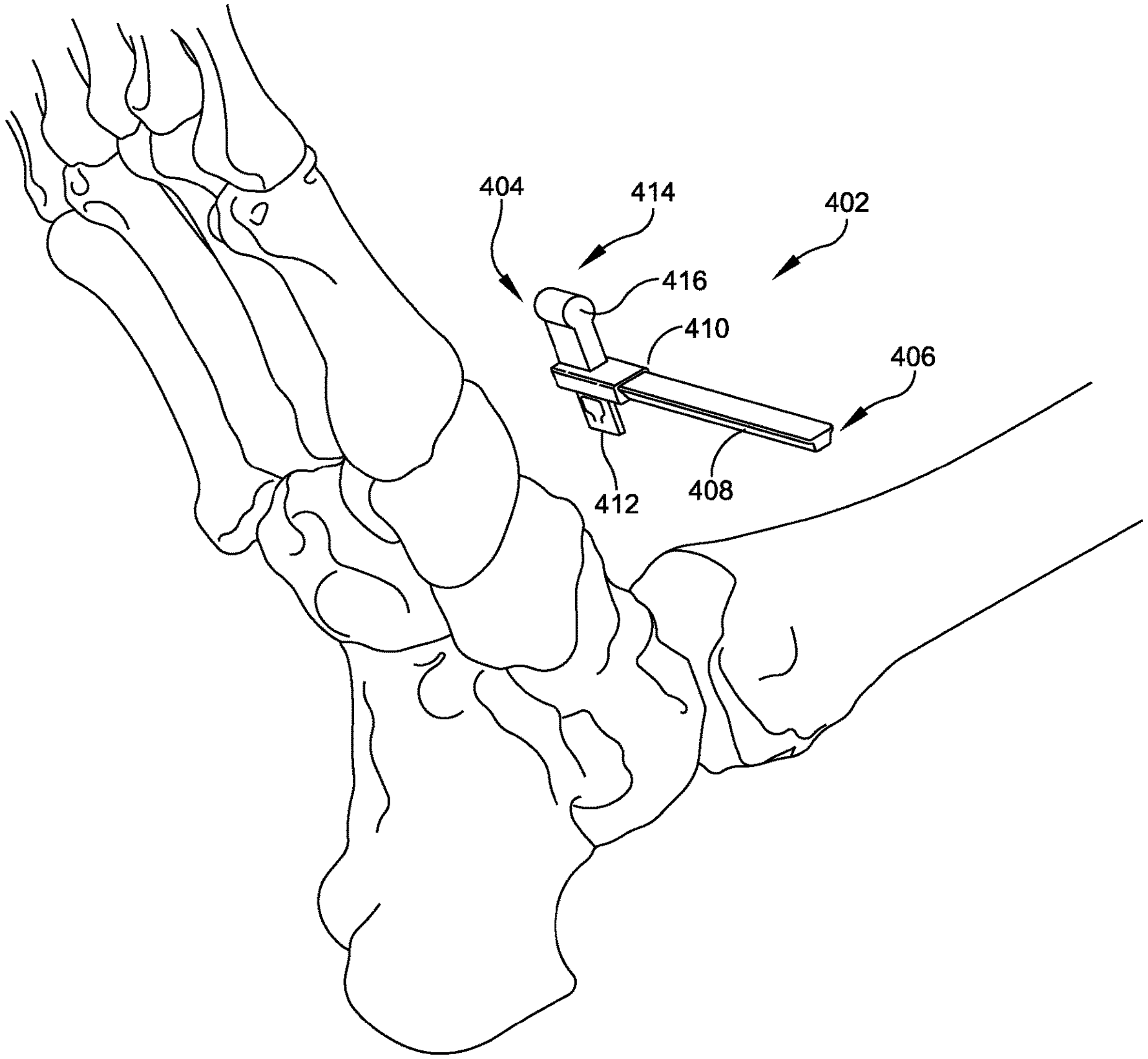
FIG. 48 is an isometric view of a guide arm of a sagittal sizing guide assembly disposed above an ankle joint in accordance with some embodiments.

Slot 390 is sized and configured to receive a mating extension 412 of a guide arm 402 for supporting a sagittal sizing guide assembly 400 as shown in FIG. 48 and described in greater detail below. Sizing patterns 388 have a shape that corresponds to the outer dimensions of a tibial implant 1100 (FIG. 84) of an ankle replacement system and is formed from a material that is opaque under a fluoroscope. Examples of such material include, but are not limited to, a metallic material. Still referring to FIG. 47, coronal parallax cue pin 392 is located in coronal sizing and drill guide 380 provides for coronal parallax adjustment as it is aligned with a pair of pins (not shown) disposed on either side of cue pin 392.

Coronal sizing and drill guide 380 also includes a dovetail extension 394 including a pair of opposed rails 396 which extend from an upper surface 398 of coronal sizing and drill guide 380. Rails 396 are sized and configured to be complementary to rails 336 of dovetail joint 332 of tool holder 330.

Adjustment block 100, tool holder 330, and drill guide 380 are configured to support a sagittal sizing guide assembly 400 as illustrated in FIGS. 48-56. As best seen FIG. 50, sagittal sizing guide assembly 400 includes a guide arm 402, a ratchet arm frame 420, and a sagittal sizing guide body 460.

Figure 49:
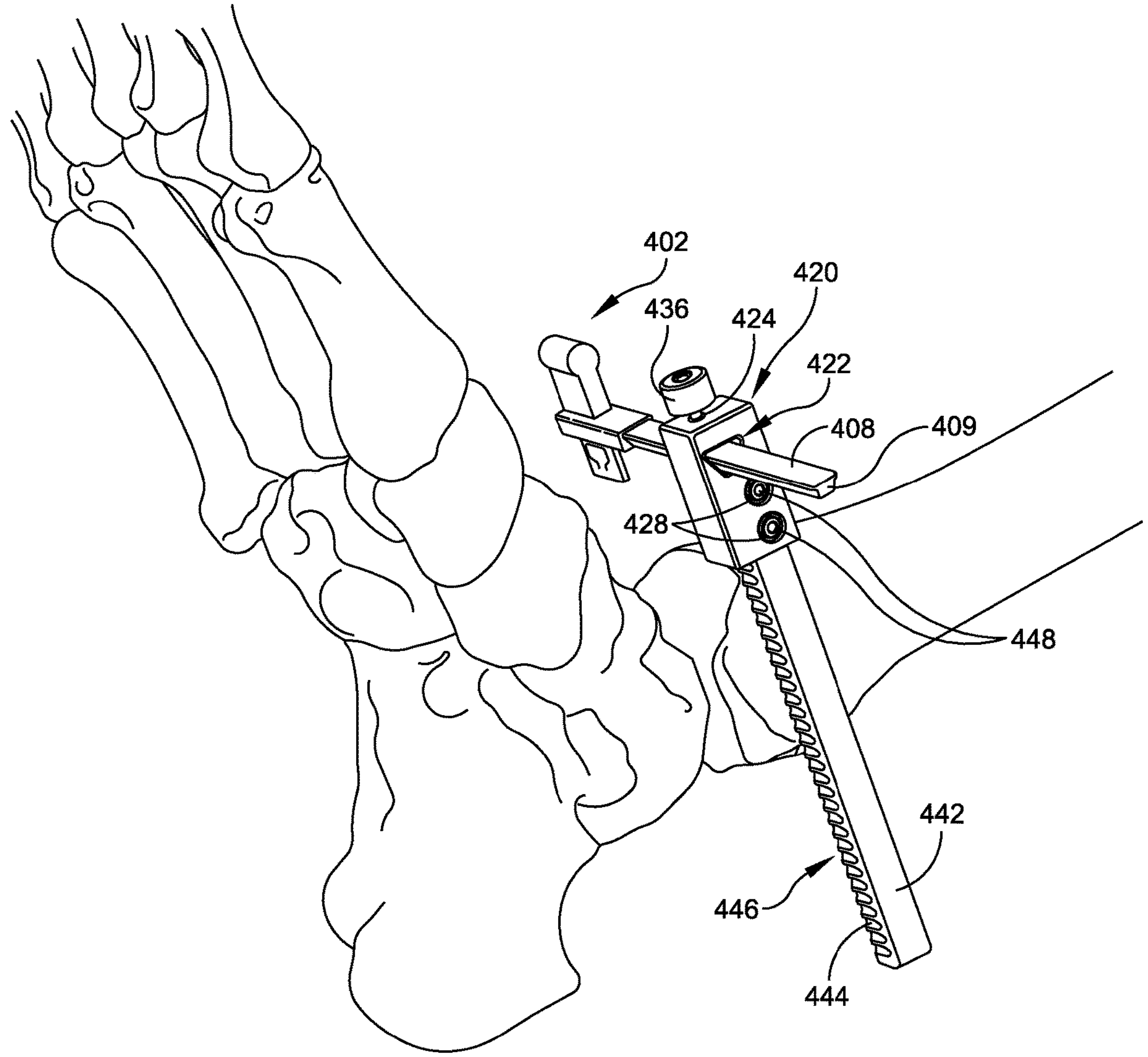
FIG. 49 is an isometric view of a guide arm received within a ratchet arm frame of a sagittal sizing guide assembly in accordance with some embodiments.
Figure 50:
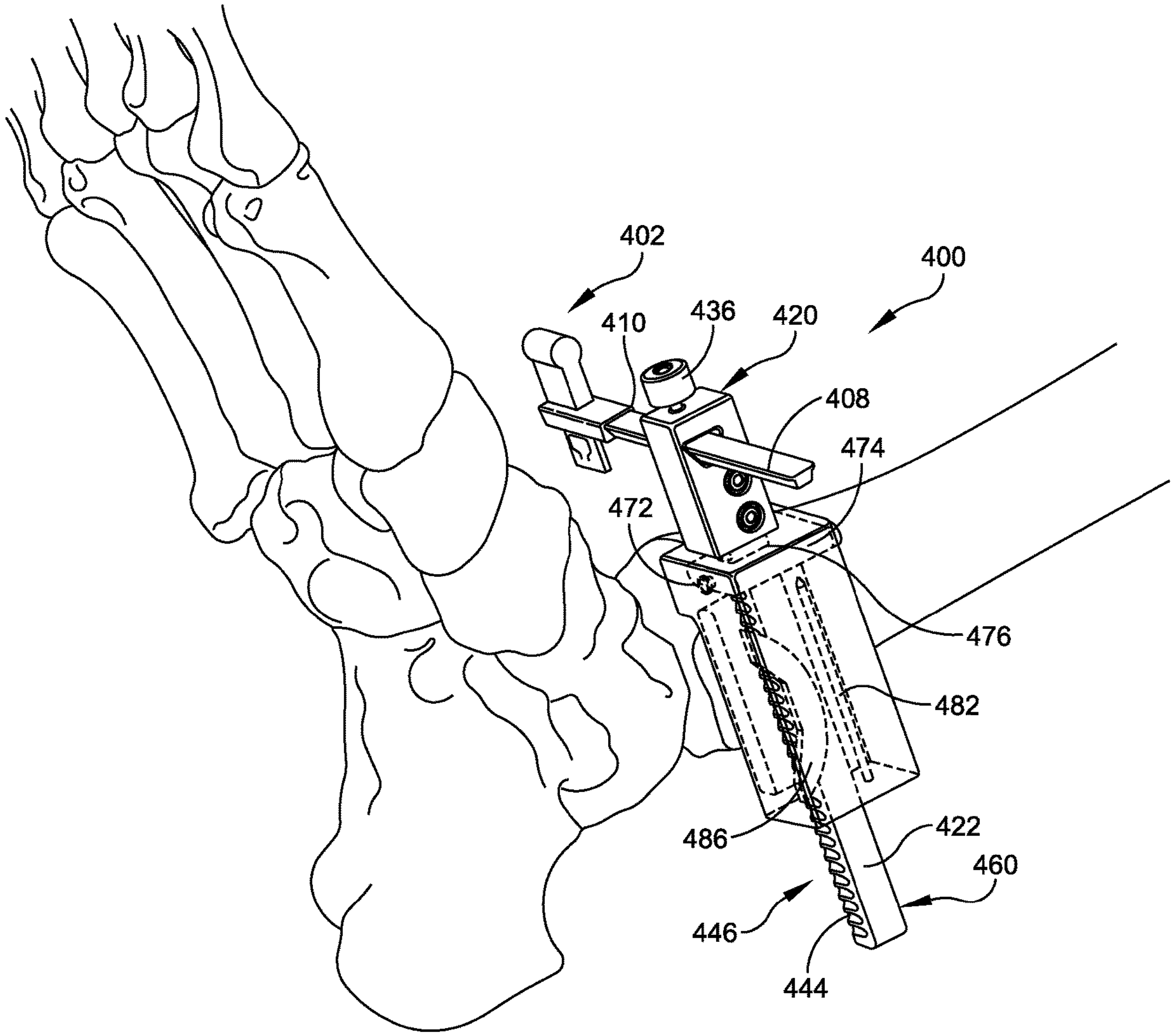
FIG. 50 is an isometric view of a sagittal sizing guide assembly disposed adjacent to an ankle joint in accordance with some embodiments.
Figure 51:
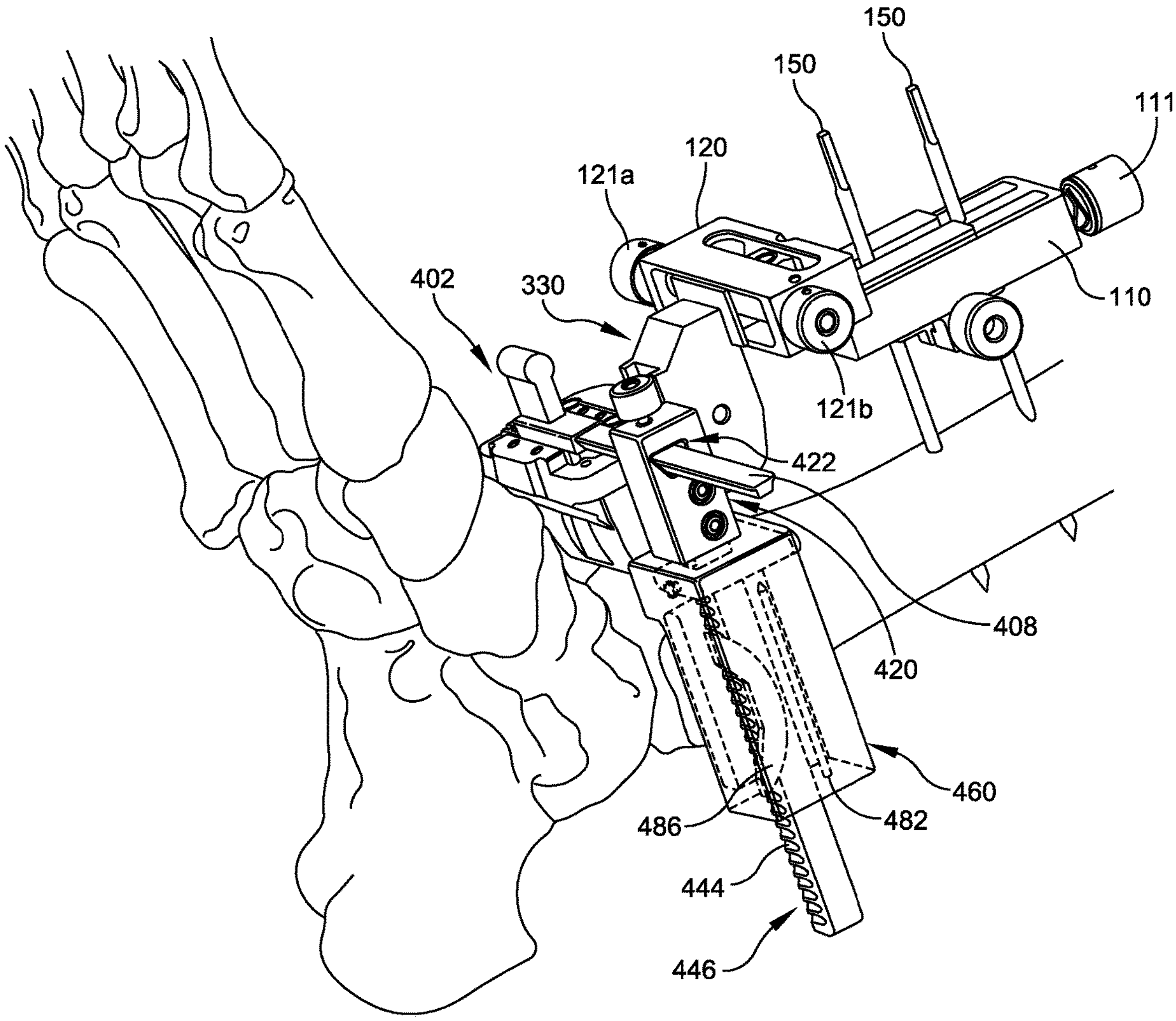
FIG. 51 is an isometric view of a sagittal sizing guide assembly coupled to a coronal sizing guide supported by an adjustment block in accordance with some embodiments.

Turning now to FIGS. 48 and 49, guide arm 402 extends from a first attachment end 404 to a second end 406, which is disposed at a distance from end 404. Attachment end 404 has an enlarged cross-sectional area relative to the sliding area 408 such that one or more shoulders 410 sized and configured to providing a stop for ratchet arm frame 420. A mating extension 412 extends from attachment end 404 and has an elongate shape that is sized and configured to be received within reference line 286 (FIG. 35) defined by drill guide 280 described above. A second extension 414 extends from attachment end 404 in a direction opposite of mating extension 412 and provides an area for grasping or otherwise being manipulated. In some embodiments, extension 414 terminates at region 416 having a cylindrical shape, although one of ordinary skill in the art will understand that region 416 can have other geometric shapes to facilitate manipulation.

Sliding area 408 and second end 406 are elongate and have a cross-sectional shape that facilitates sliding while at the same time preventing rotation by ratchet arm frame 420. In some embodiments, for example, sliding area 408 and second end 406 have a trapezoidal cross sectional area such that ratchet arm frame 420 can slide along the length of guide arm 402 without rotationally pivoting. One of ordinary skill in the art will understand that sliding area 408 and second end 406 can have other cross-sectional geometries.

Figure 52:
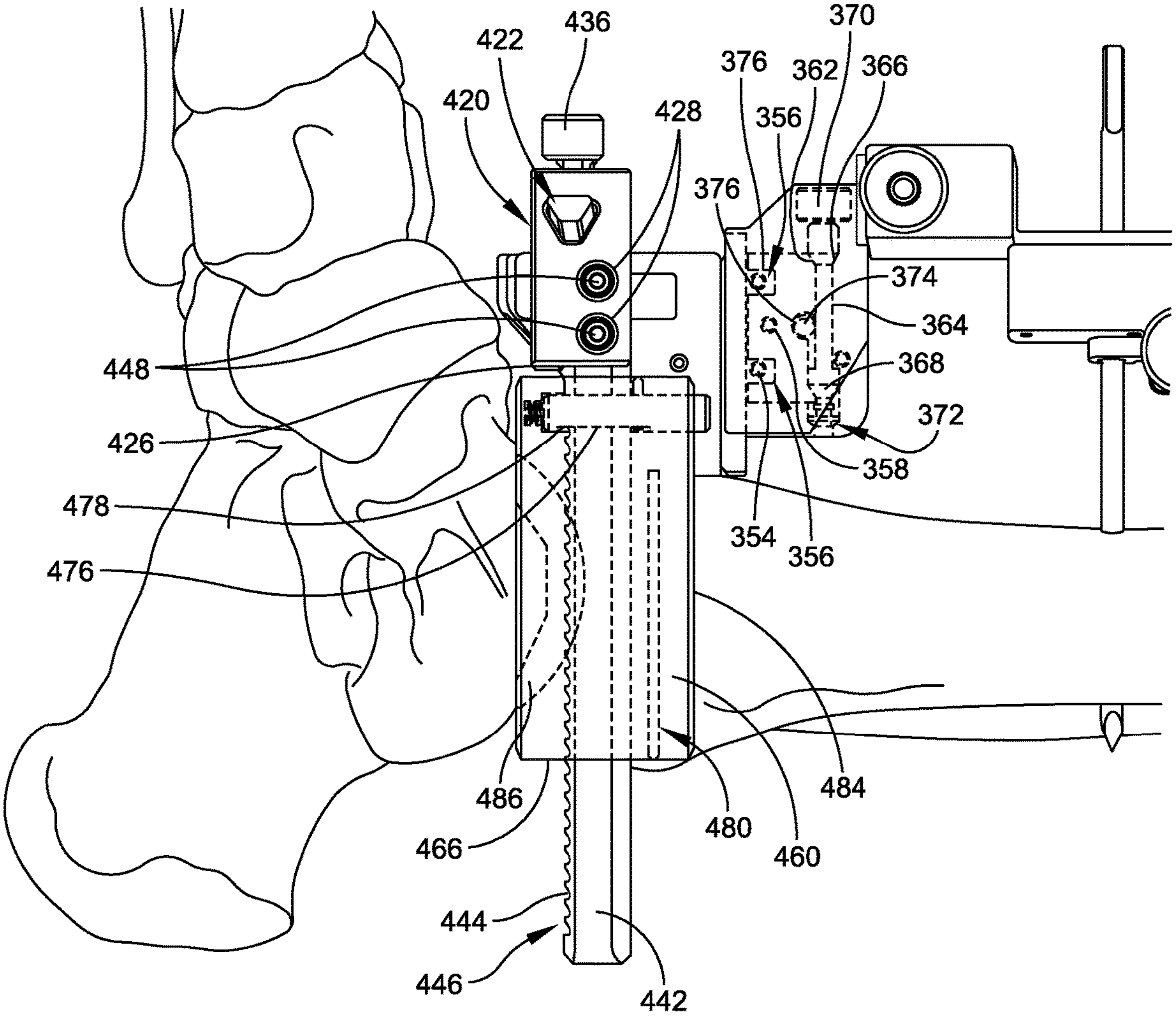
FIG. 52 is a side view of a sagittal sizing guide assembly coupled to a coronal sizing guide supported by an adjustment block in accordance with some embodiments.
Figure 53:
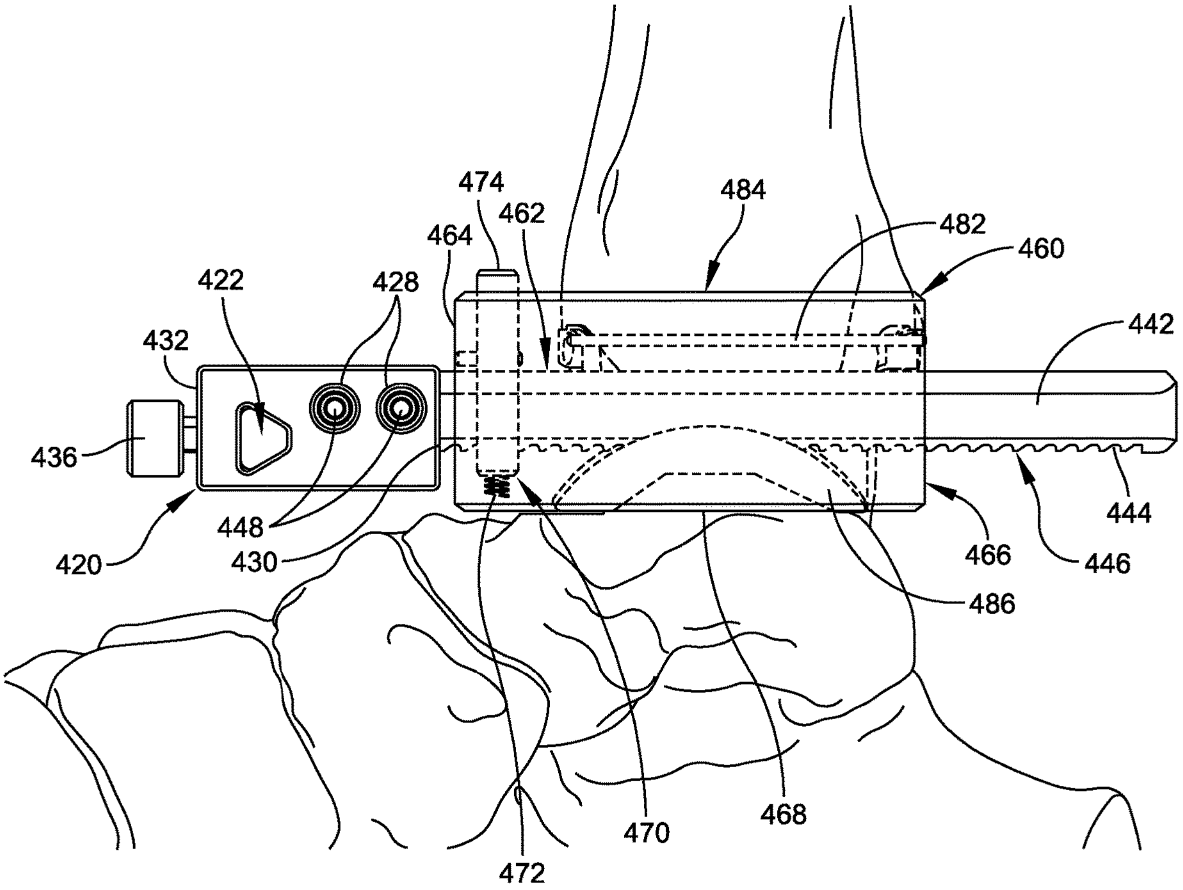
FIG. 53 is a side view of select components of the sagittal sizing guide assembly in accordance with some embodiments.
Figure 54:
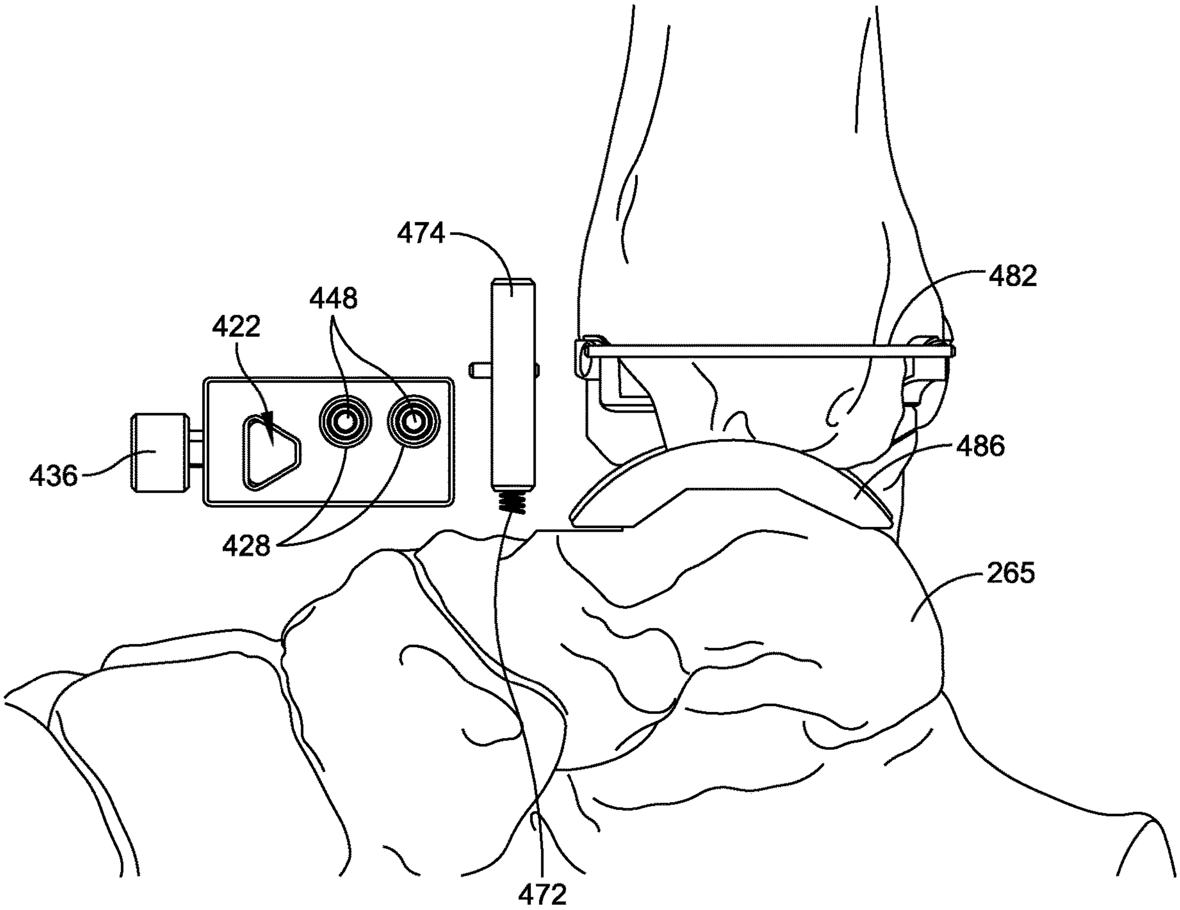
FIG. 54 is a side view of select components of the sagittal sizing guide assembly in accordance with some embodiments.
Figure 55A:
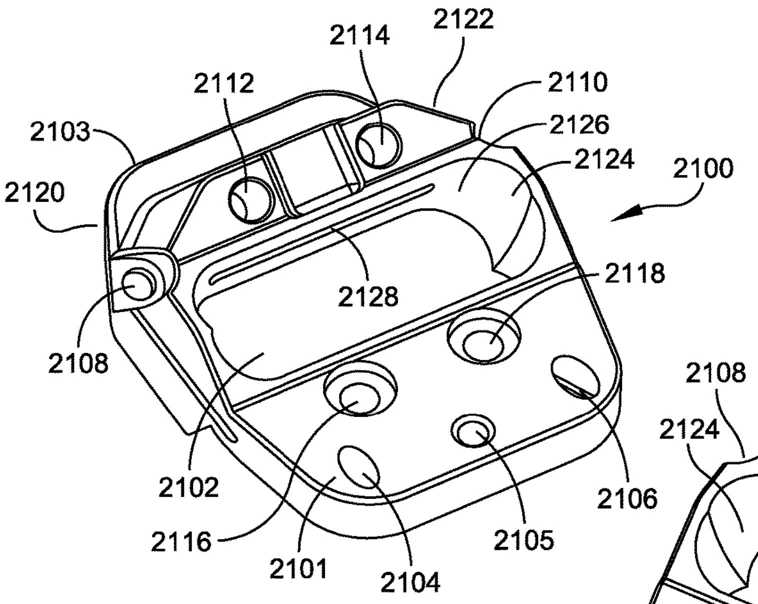
FIGS. 55A, 55B, 55C, 55D, 55E, and 55F are various isometric views of one example of a talar resection guide base in accordance with some embodiments.
Figure 55B:
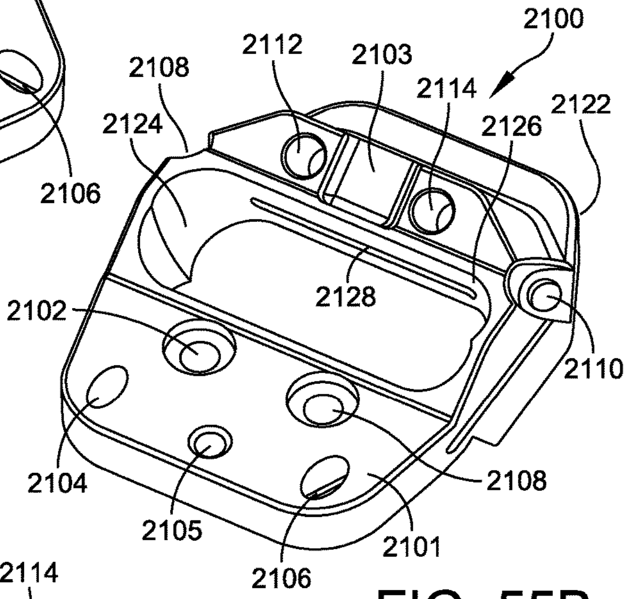
Figure 55C:
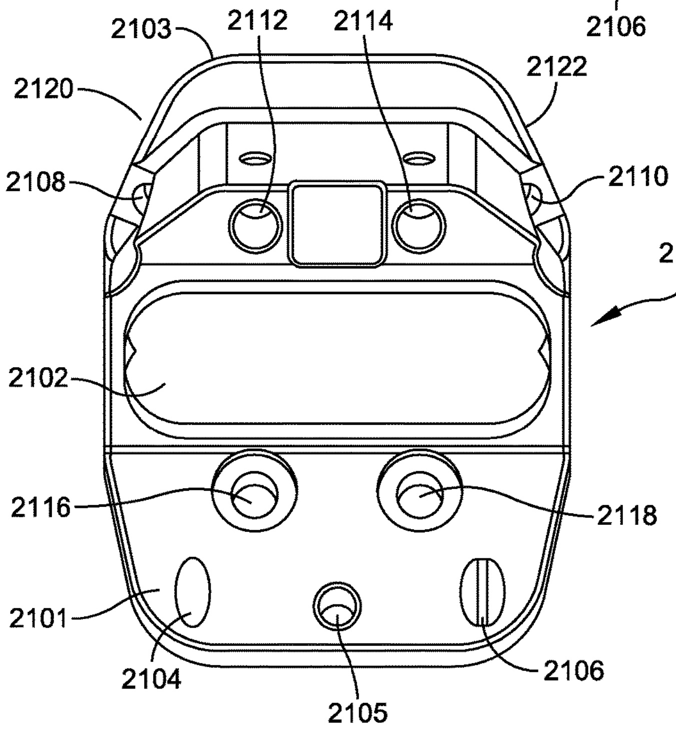
Figure 55D:
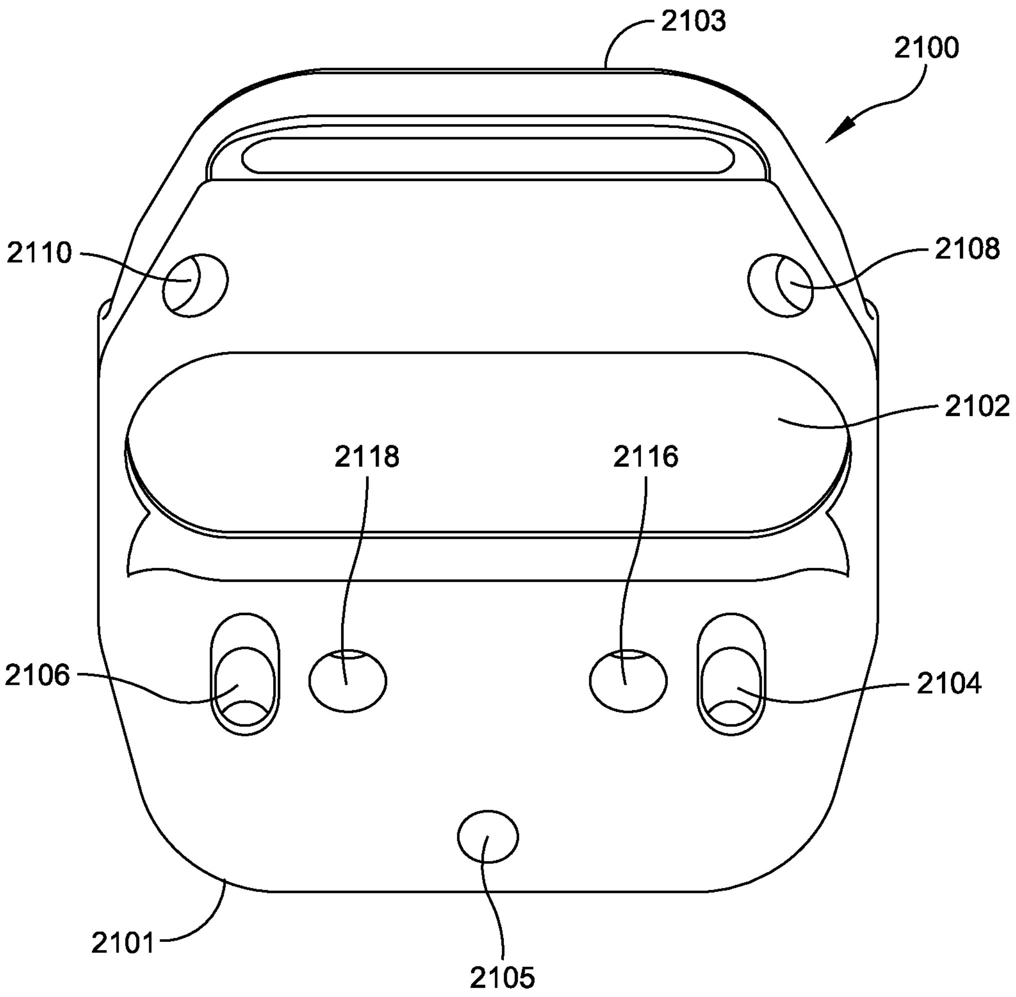
Figure 55E:
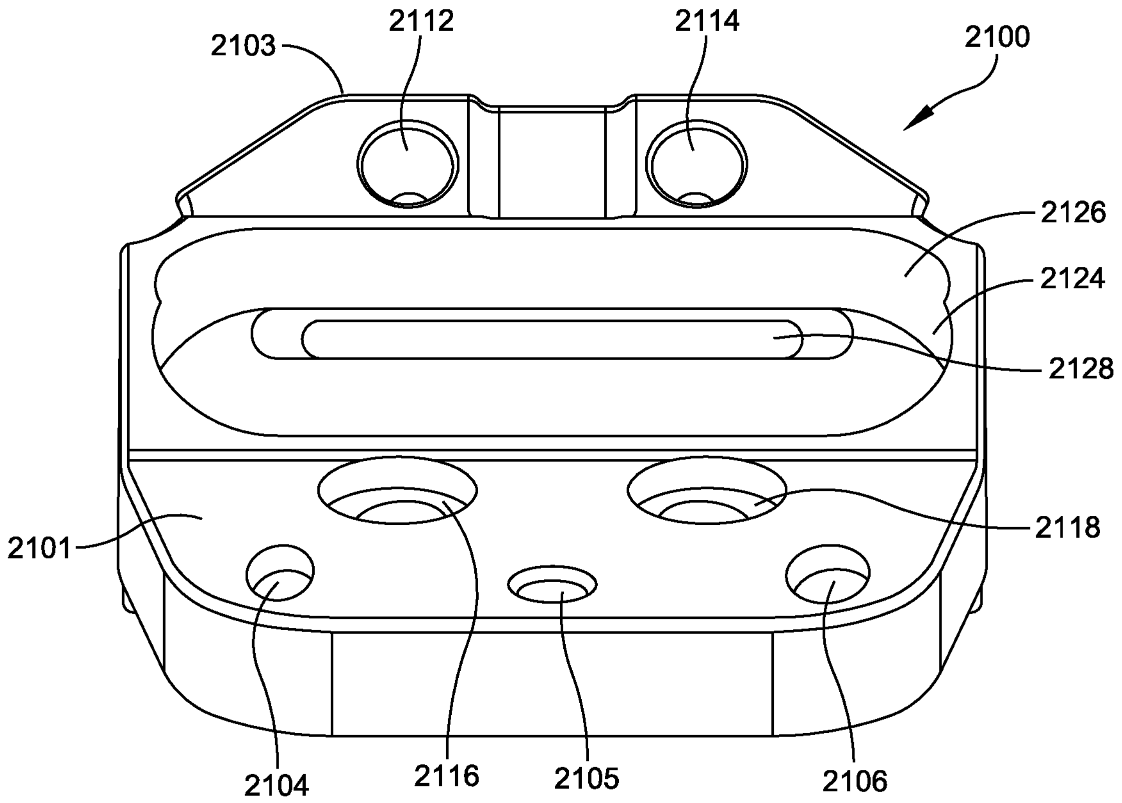
Figure 55F:
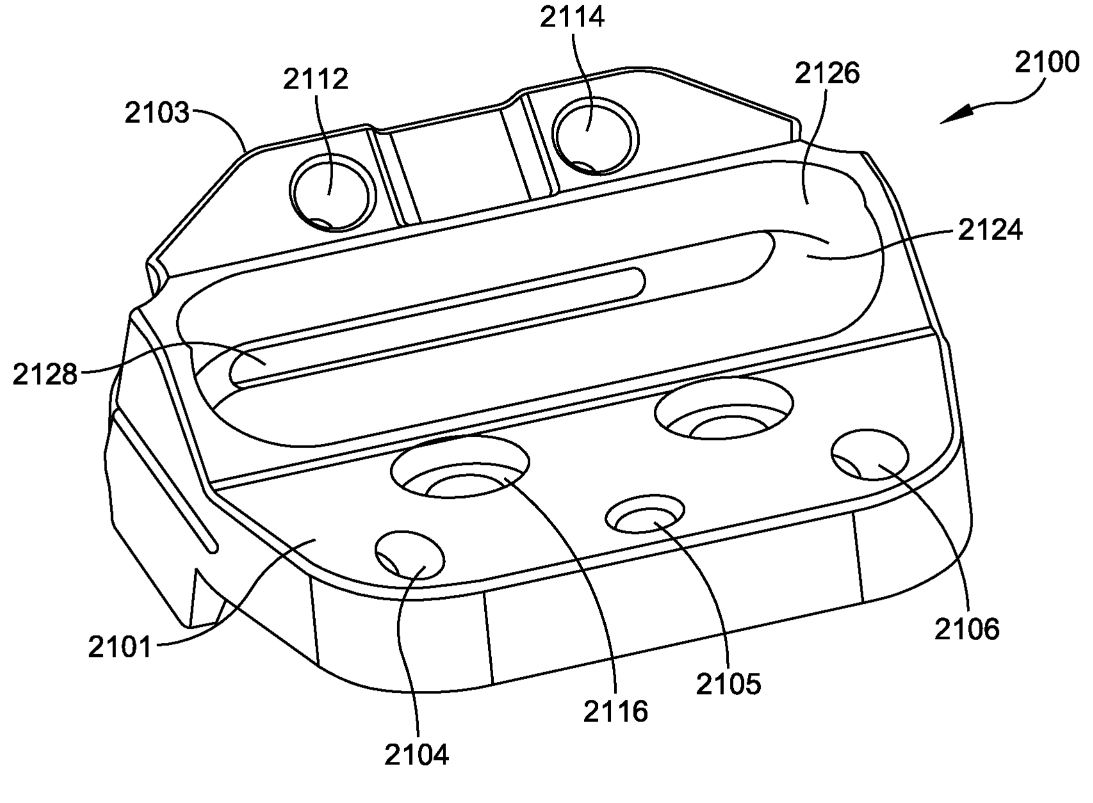

Turning now to FIGS. 49-53, ratchet arm frame 420 defines an opening 422 (FIGS. 49 and 52) sized and configured to receive sliding area 408 and second end 406 slidably therein as shown in FIG. 49. A second hole 424 illustrated in FIG. 49 is defined by ratchet arm frame 420 orthogonal to opening 422 such that the second hole 424 intersects opening 422. Ratchet arm frame 420 also defines a blind opening 426 and one or more pin or screw holes 428. Blind opening 426 extends inwardly from the side 430 that is disposed opposite the side 432 in which the second hole 424 is defined as best seen in FIG. 53. One or more pin or screw holes 428 inwardly extend from side 434 and intersect with blind opening 426.

A locking knob 436 is sized and configured to be received within opening 422 and lock the position of ratchet arm frame 420 along the length of guide arm 402. In some embodiments, locking knob 436 is biased by a biasing member (not show), such as a compression spring, such that an abutment portion (not shown) of locking knob engages and frictionally locks a portion of the sliding area 408 of guide arm 402. Blind opening 426 is sized and configured to receive a portion of a ratchet arm 442 therein. As best seen in FIGS. 52-53, ratchet arm 442 includes a plurality of ridges 444 or notches along at least one side 446. Ratchet arm 442 is coupled to ratchet arm frame 420 by pins or screws 448 that are received within pin or screw holes 428.

Referring now to FIG. 53, sagittal sizing guide body 460 is shown as a rectangular cuboid defining a channel 462 that extends through the length of sagittal sizing guide body 460 from a first side 464 to a second side 466. A third side 468 defines a chamber 470 sized and configured to receive a biasing member 472 and push button 474 therein. Push button 474 defines a window 476 (FIGS. 50 and 52) that is sized and configured to receive ratchet arm 442 therein. The bottom ledge 478 of window 476 (FIG. 52) has a width that is sized and configured to be received within the ridges 444 defined in the side 446 of ratchet arm 442.

As shown in FIGS. 52 and 53, a dowel hole 480 inwardly extends from side 466 and is sized and configured to receive a dowel 482 that is formed from a material that is opaque to fluoroscopy. Dowel hole 480 is disposed at distance from side 484 of sagittal sizing guide body 460 that corresponds to a location at which the tibia is resected, and dowel hole 480 has a length that corresponds to a length of tibial implant 1100 of ankle replacement prosthesis 1000, which is described in greater detail below. Sagittal sizing guide body 460 also includes a fluoro-opaque profile 486 having a size and shape that corresponds to the profile of talar implant 1200 of ankle replacement prosthesis 1000. In some embodiments, the fluoro-opaque profile 486 is disposed within a recess defined by sagittal sizing guide body 460, and, in some embodiments, fluoro-opaque profile 486 is coupled to an exterior surface of sagittal sizing guide body 460 using an adhesive or mechanical coupling as will be understood by one of ordinary skill in the art.

The combination of dowel 482 and fluoro-opaque profile 486 advantageously enable the sizing of a talar implant 1200 and the appropriate height of the talar resection to be check using fluoroscopy prior to resecting the talus. The resection height can be adjusted and locked in by adjusting knob 111 of adjustment block 100. A number of sagittal sizing guide bodies 460 can be available such that a surgeon or other health care professional can select the appropriate size based on the actual anatomy of the patient. The differently sized sagittal sizing guide bodies 460 can be swapped for one another until the appropriate sagittal sizing guide body 460 is identified.

Talar Resection Guide and Related Components

Figure 56:
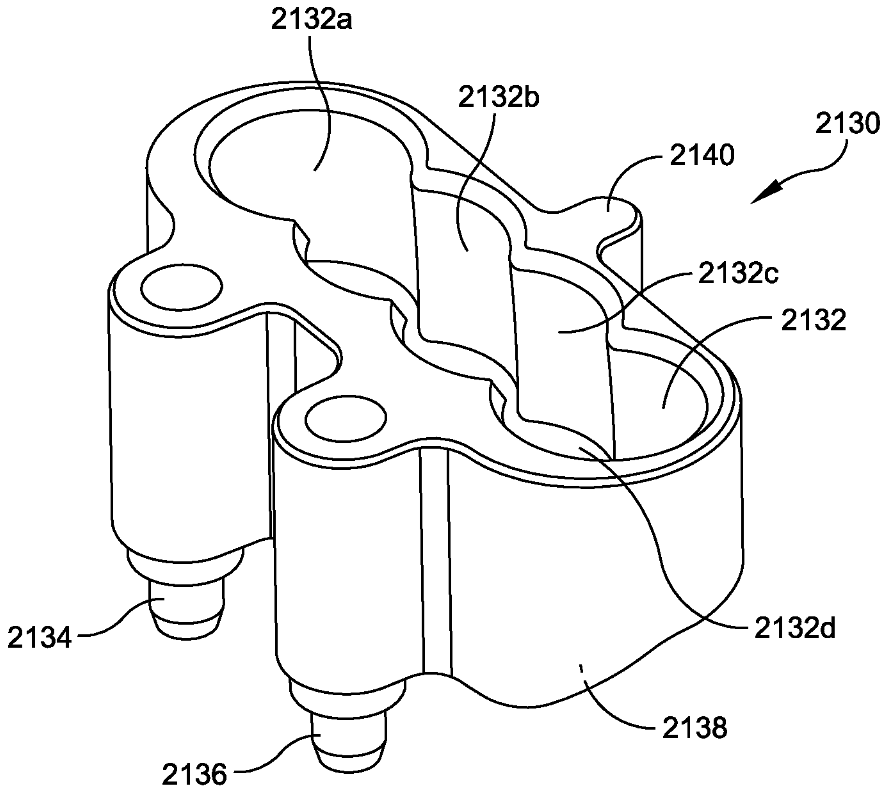
FIG. 56 is an isometric view of one example of an anterior talar pilot guide in accordance with some embodiments.
Figure 58:
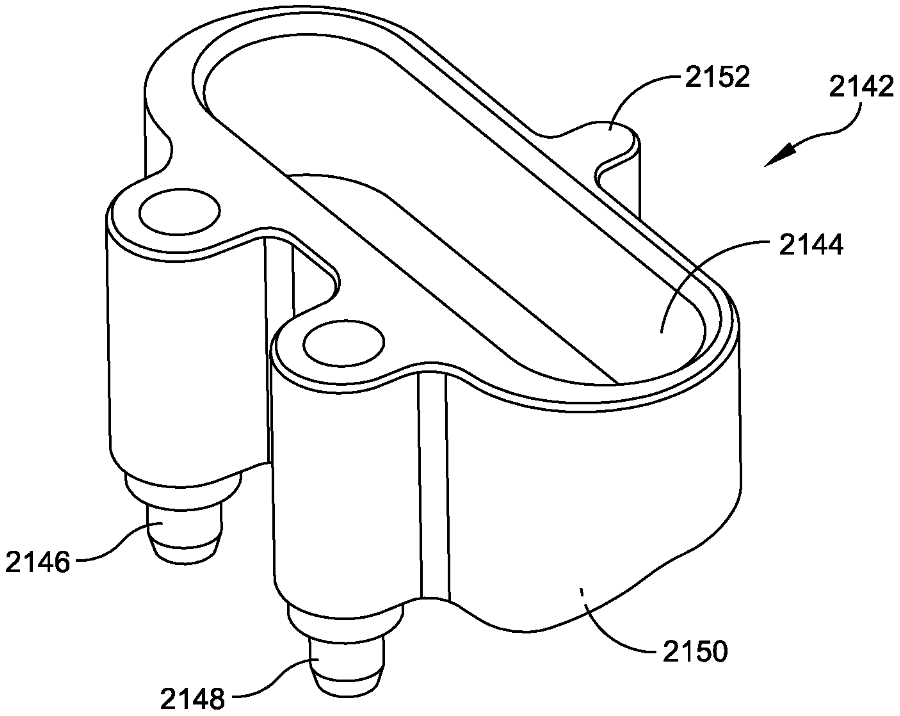
FIG. 58 is an isometric view of one example of an anterior talar finish guide in accordance with some embodiments.

FIGS. 55A-55F illustrate one example of a talar resection guide base 2100 in accordance with some embodiments. The talar resection guide base 2100 is configured for use as a base for an anterior talar pilot guide 2130, which is illustrated in FIG. 56, and an anterior talar finish guide 2142, which is illustrated in FIG. 58, in resecting a talus 265.

Figure 59:
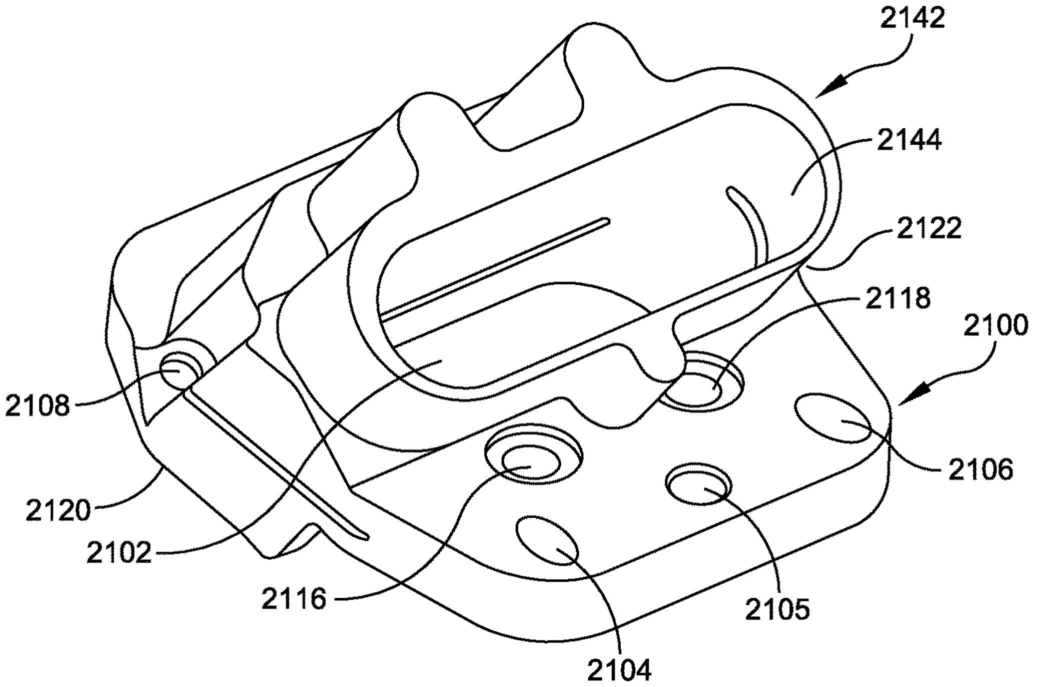
FIG. 59 is an isometric view of one example the talar resection guide base and the anterior talar finish guide attached to one another in accordance with some embodiments.
Figure 62A:
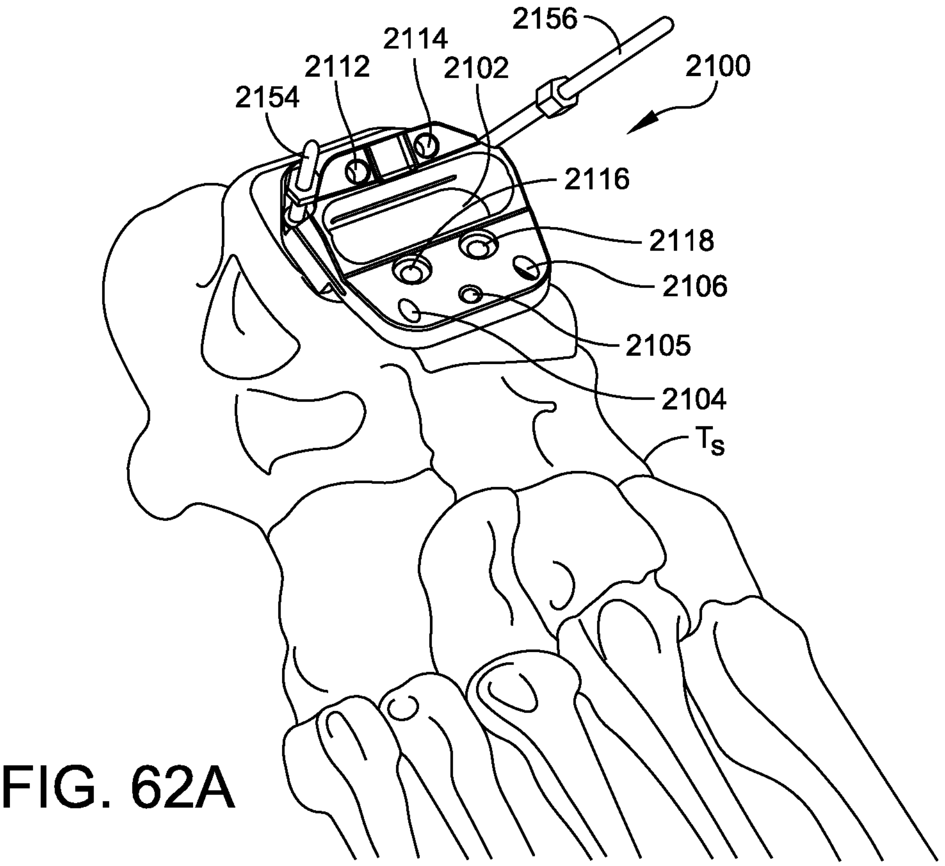
FIG. 62A is an isometric view of one example of the talar resection guide base attached to the bone via two temporary fixation screws or pins in accordance with some embodiments.
Figure 62B:
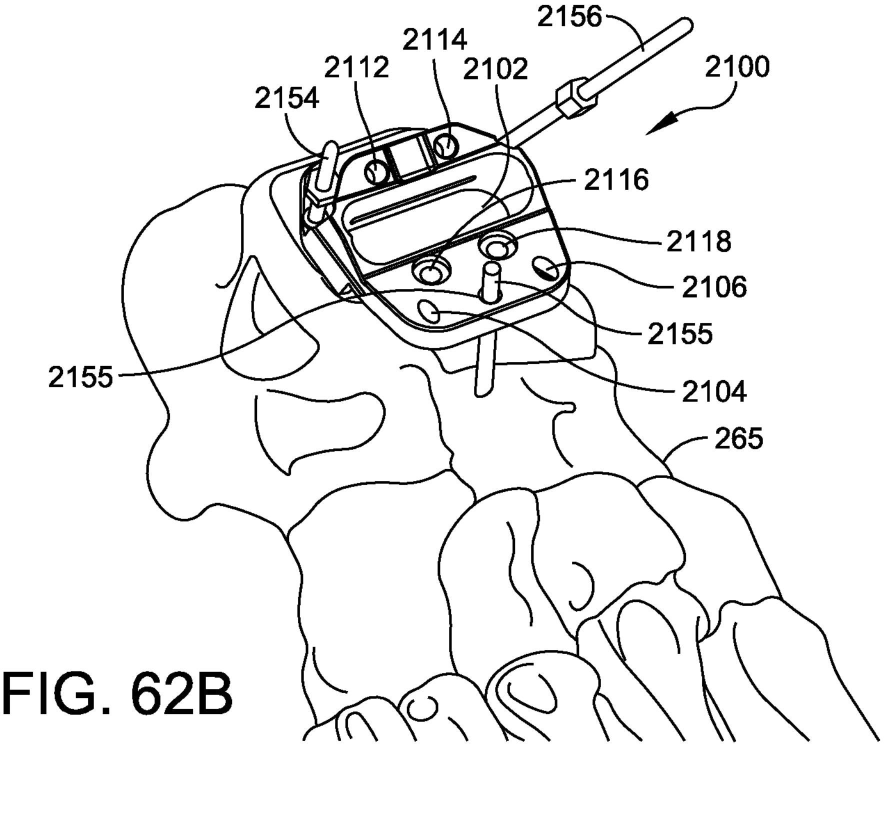
FIG. 62B is an isometric view of one example of the talar resection guide base attached to the bone via three temporary fixation screws or pins in accordance with some embodiments.

Talar resection guide base 2100 defines a slot 2102 that extends transversely across the base 2100. As described in greater detail below, slot 2102 is arranged and configured to align with the interconnecting holes 2132 defined by anterior talar pilot guide 2130 (FIG. 57) and slot 2144 defined by the anterior talar finish guide 2142 (FIG. 59). The talar resection guide base 2100 also includes a plurality of holes 2104-2110 each being sized and configured to receive a pin or other surgical instrument therein. For example, two inferior holes 2104, 2106 are defined on medial and lateral sides 2120, 2122 of lower flange 2101 of the base 2100 that extends away from slot 2102. Holes 2104, 2106 are configured to receive fixation pins 298, and Inferior hole 2105, which is defined between the two inferior holes 2104, 2106, is configured to receive a pin 2155 (FIG. 62B).

Holes 2108, 2110 are defined on medial and lateral sides 2120, 2122 of the upper flange 2103 of base 2100, and each hole is configured to receive a respective pin 2154, 2156 (FIG. 63) or other surgical device. Although there are five holes 2104-2110 configured to receive pins described, fewer or more holes are provided in some embodiments.

The talar resection guide base 2100 includes holes 2112-2118 disposed near the slot 2102. Holes 2112, 2114 are defined by upper flange 2103 above the slot 2102, and holes 2116, 2118 are defined by lower flange 2101 below the slot 2102. Slot 2102 includes a shoulder 2124 that extends along the circumference of slot 2102. The superior side 2126 of the shoulder 2124 includes a narrow lateral slit 2128 extending parallel to the longitudinal axis of slot 2012 and being sized and configured to receive a saw blade or bone saw therein. Slit 2128 is configured to aid in creating a posterior talar chamfer resection 2170 as described below.

Figure 57:
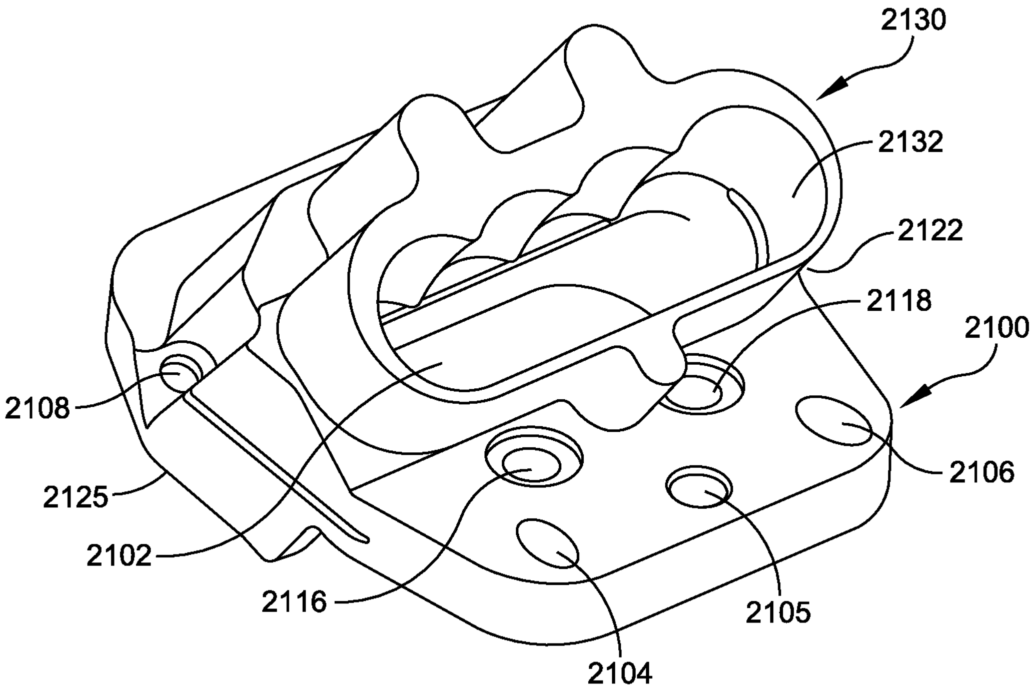
FIG. 57 is an isometric view of one example of the talar resection guide base and the anterior talar pilot guide attached to one another in accordance with some embodiments.
Figure 66:
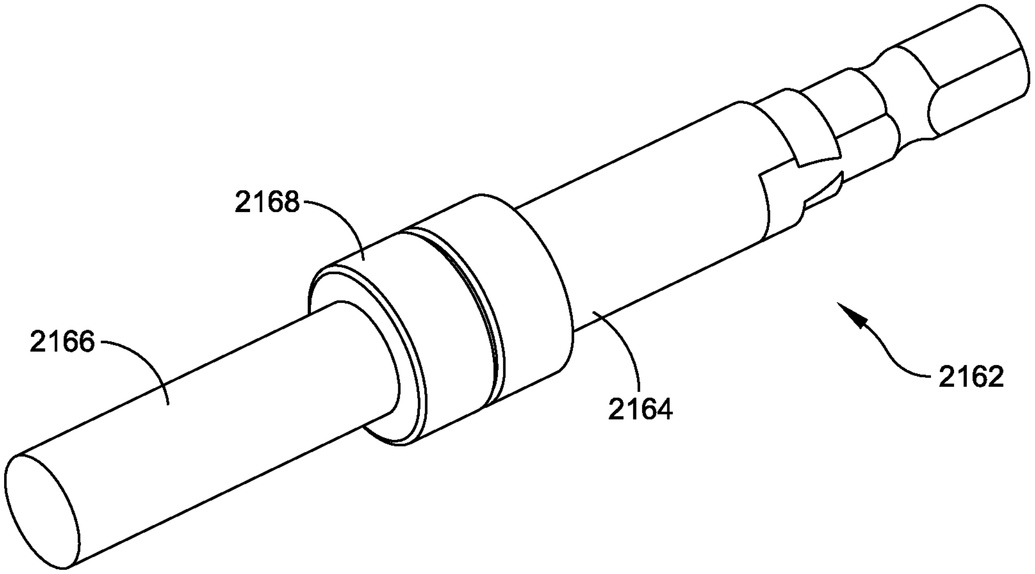
FIG. 66 is an isometric view of one example of the talar reamer in accordance with some embodiments.
Figure 67:
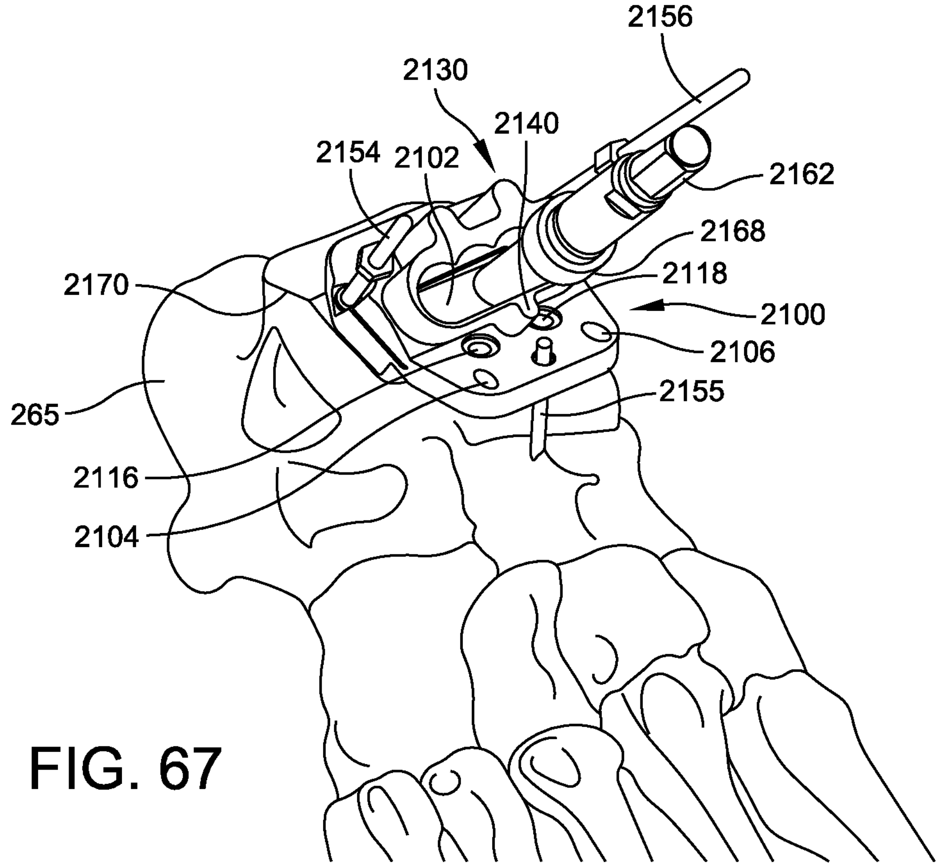
FIG. 67 is an isometric view of one example of the talar reamer inserted through the interconnecting holes of the talar resection guide base and the slot of the anterior talar pilot guide attached to the bone via temporary fixation screws or pins in accordance with some embodiments.

Turning now to FIG. 56, an isometric view of one example of the anterior talar pilot guide 2130 is illustrated in accordance with some embodiments. The anterior talar pilot guide 2130 includes a plurality of interconnecting holes 2132*a*, 2132*b*, 2132*c*, 2132*d* that cooperate to define a slot 2132 that extends parallel to the longitudinal axis of the anterior talar pilot guide 2130. Each hole of slot 2132 is configured to receive a talar reamer 2162 (FIGS. 66-67). The anterior talar pilot guide 2130 also includes pegs 2134, 2136 on its posterior side 2138. Each peg 2134, 2136 is sized and configured to be received in holes 2112-2118 adjacent to slot 2102 of the talar resection guide base 2100 such that the anterior talar pilot guide 2130 can be coupled to the talar resection guide base 2100 as illustrated in FIG. 57. The anterior talar pilot guide 2130 further includes an inferior tab 2140 for ease of assembly and disassembly.

Figure 70:
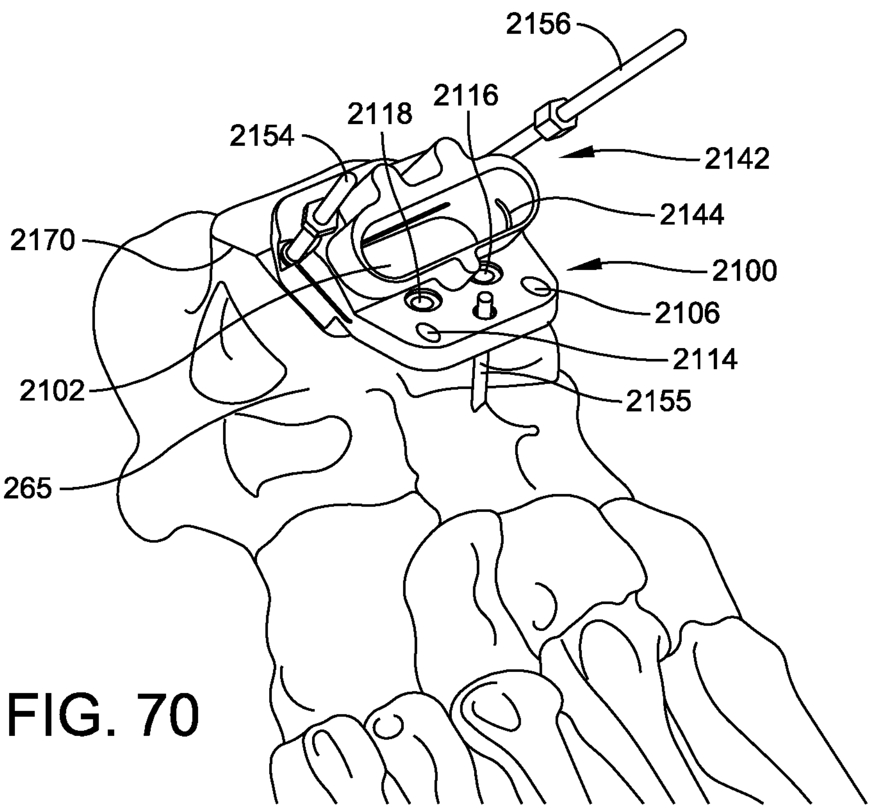
FIG. 70 is an isometric view of one example of the talar resection guide base and the anterior talar finish guide attached to the bone via temporary fixation screws or pins in accordance with some embodiments.
Figure 71:
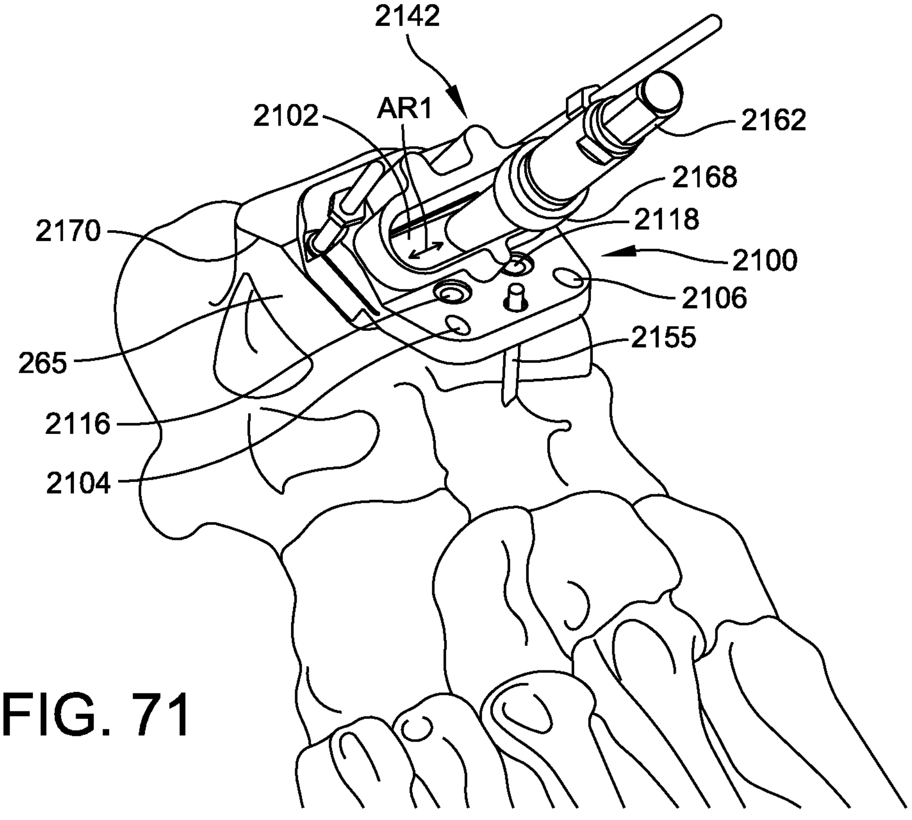
FIG. 71 is an isometric view of one example of the talar reamer inserted through the slots of the talar resection guide base and the anterior talar finish guide attached to the bone via temporary fixation screws or pins in accordance with some embodiments.

FIG. 58 is anisometric view of one example of the anterior talar finish guide 2142 in accordance with some embodiments. The anterior talar finish guide 2142 includes a slot 2144 extending parallel to the longitudinal axis of finish guide 2142. Slot 2144 is configured to receive the talar reamer 2162 (FIGS. 66, 70-71). Anterior talar finish guide 2142 also includes pegs 2146, 2148, which extend inferiorly from the posterior side 2150 of finish guide 2142 and are configured to be received in holes 2112-2118 near the slot 2102 of the talar resection guide base 2100 such that anterior talar finish guide 2142 can be coupled to talar resection guide base 2100 as shown in FIG. 59. The anterior talar finish guide 2142 also includes an inferior tab 2152 for ease of assembly and disassembly.

Figure 60:
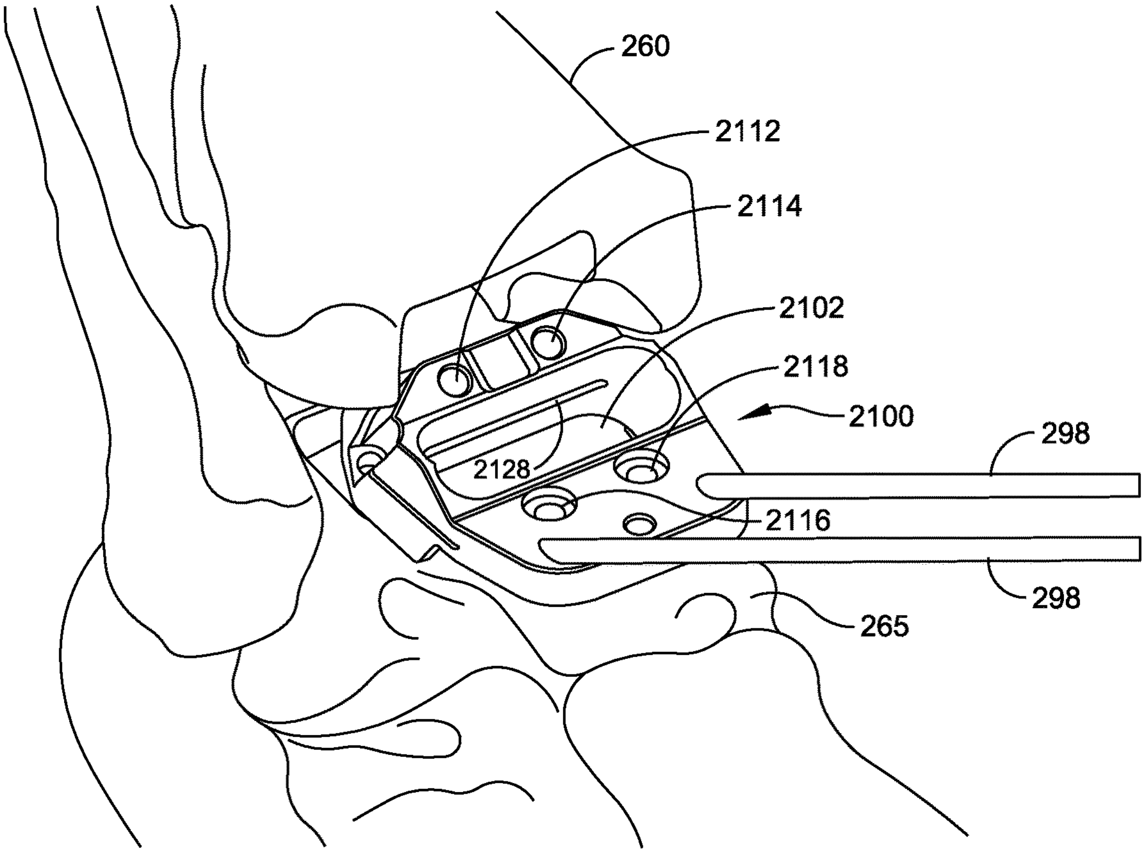
FIG. 60 is an isometric view of one example of the talar resection guide base attached to a bone via pins previously inserted in a talus in accordance with some embodiments.
Figure 61:
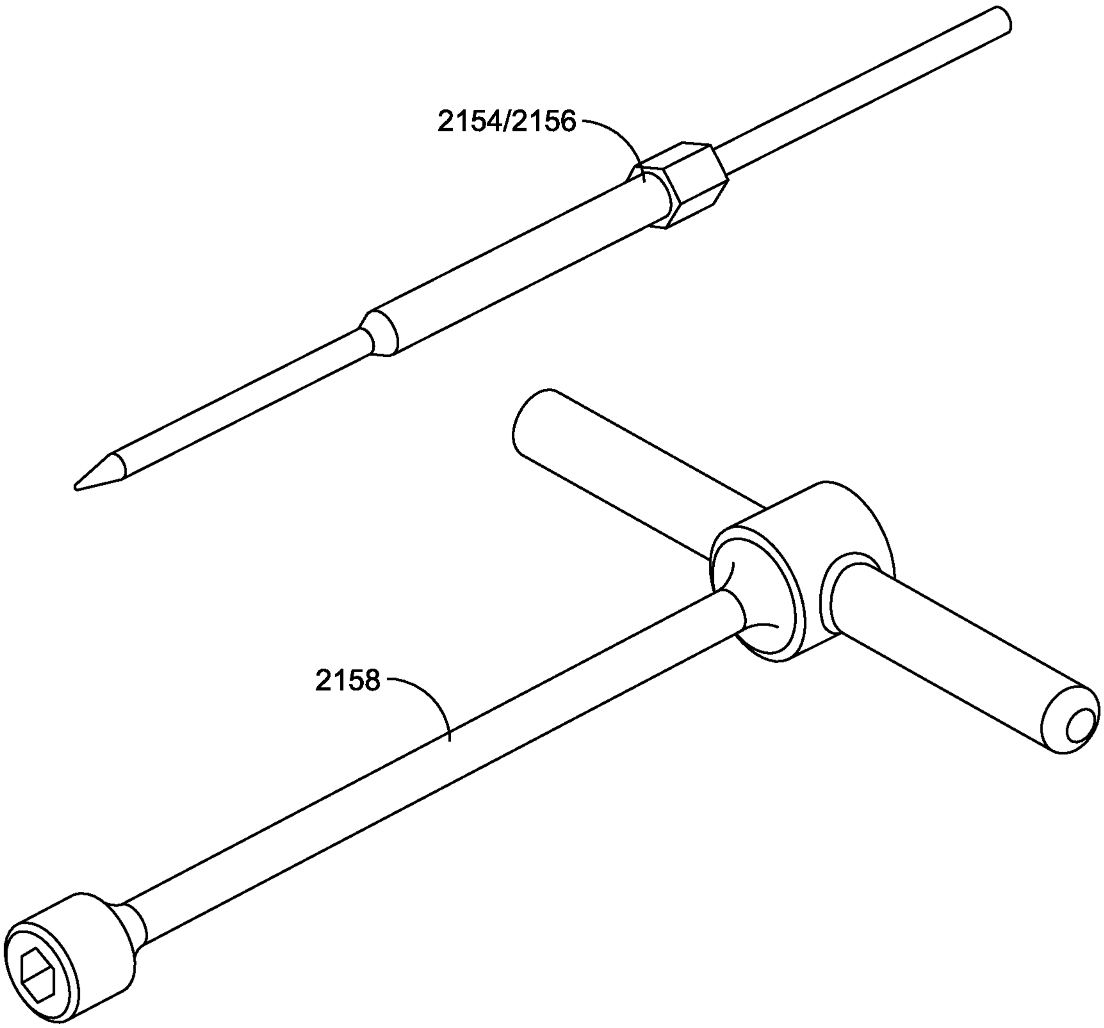
FIG. 61 is an isometric view of one example of a temporary fixation screw or pin and a T-handle pin driver in accordance with some embodiments.

The use of the talar resection guide base 2100 in combination with the anterior talar pilot guide 2130 and anterior talar finish guide 2142 is described with reference to FIGS. 60-74. FIG. 60 is an isometric view of one example of the talar resection guide base 2100 attached to a talus 265 via fixation pins 298 in accordance with some embodiments. The talar resection guide base 2100 is connected to a talus 265 by sliding the holes 2104, 2106 of the talar resection guide base 2100 over fixation pins 298, which can be previously installed having been guided using a talar dome trial device, such as floating trial 250 shown in FIG. 30 and described above. In some embodiments, the talar resection guide base 2100 is seated flush to the previously resected talar surface. As illustrated in FIGS. 61 and 62A, temporary fixation screws or pins 2154, 2156 are inserted into the two holes 2108, 2110 on either side of the base 2100 using a T-handle pin driver 2158, which is illustrated in FIG. 61. As illustrated in FIG. 62B, pin 2155 can be inserted through inferior hole 2105 for additional stability. Pin 2155 can be cut flush to the surface of the talar resection guide base 2100 to prevent interference with any saw blades and reamers.

Figure 63:
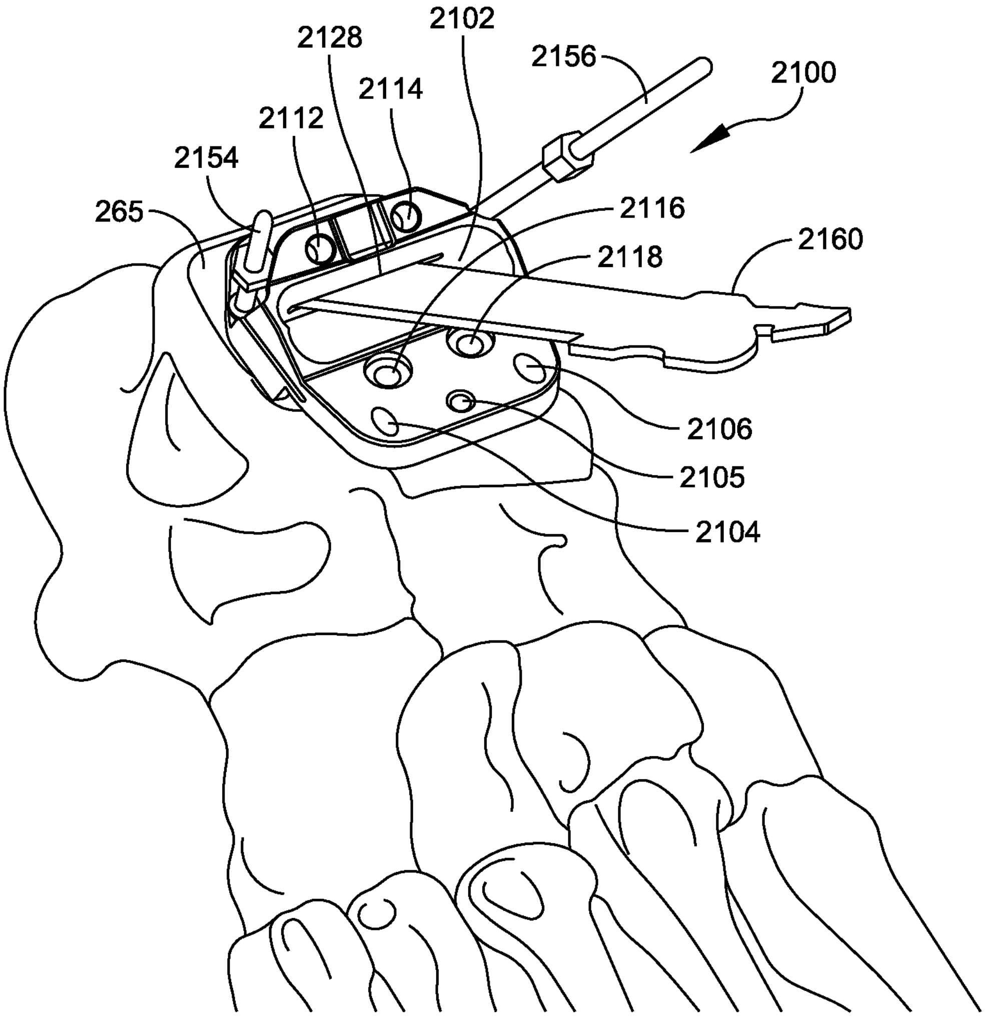
FIG. 63 is an isometric view of one example of a saw blade or bone saw inserted into the slit of one example of the talar resection guide base attached to the bone via temporary fixation screws or pins in accordance with some embodiments.
Figure 64:
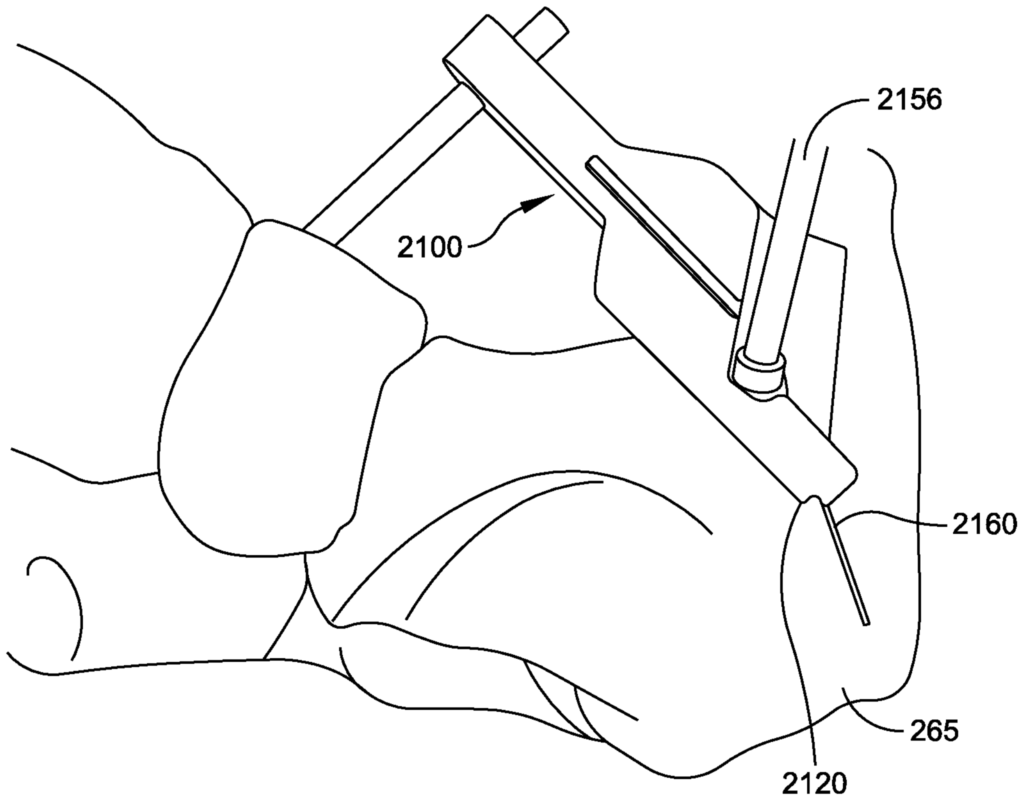
FIG. 64 is an exploded lateral side view of one example of a saw blade or bone saw inserted into the slit of one example of the talar resection guide base attached to the bone via temporary fixation screws or pins in accordance with some embodiments.

Turning now to FIGS. 63 and 64, an appropriately sized saw blade or bone saw 2160 is inserted through the lateral slit 2128 in the shoulder 2124 of the slot 2102 of the talar resection guide base 2100. The saw blade or bone saw 2160 is used to resect the talus 265 to create the posterior talar chamfer 2170, as best in FIG. 74. Once the area is resected, the saw blade or bone saw 2160 is removed.

Figure 65:
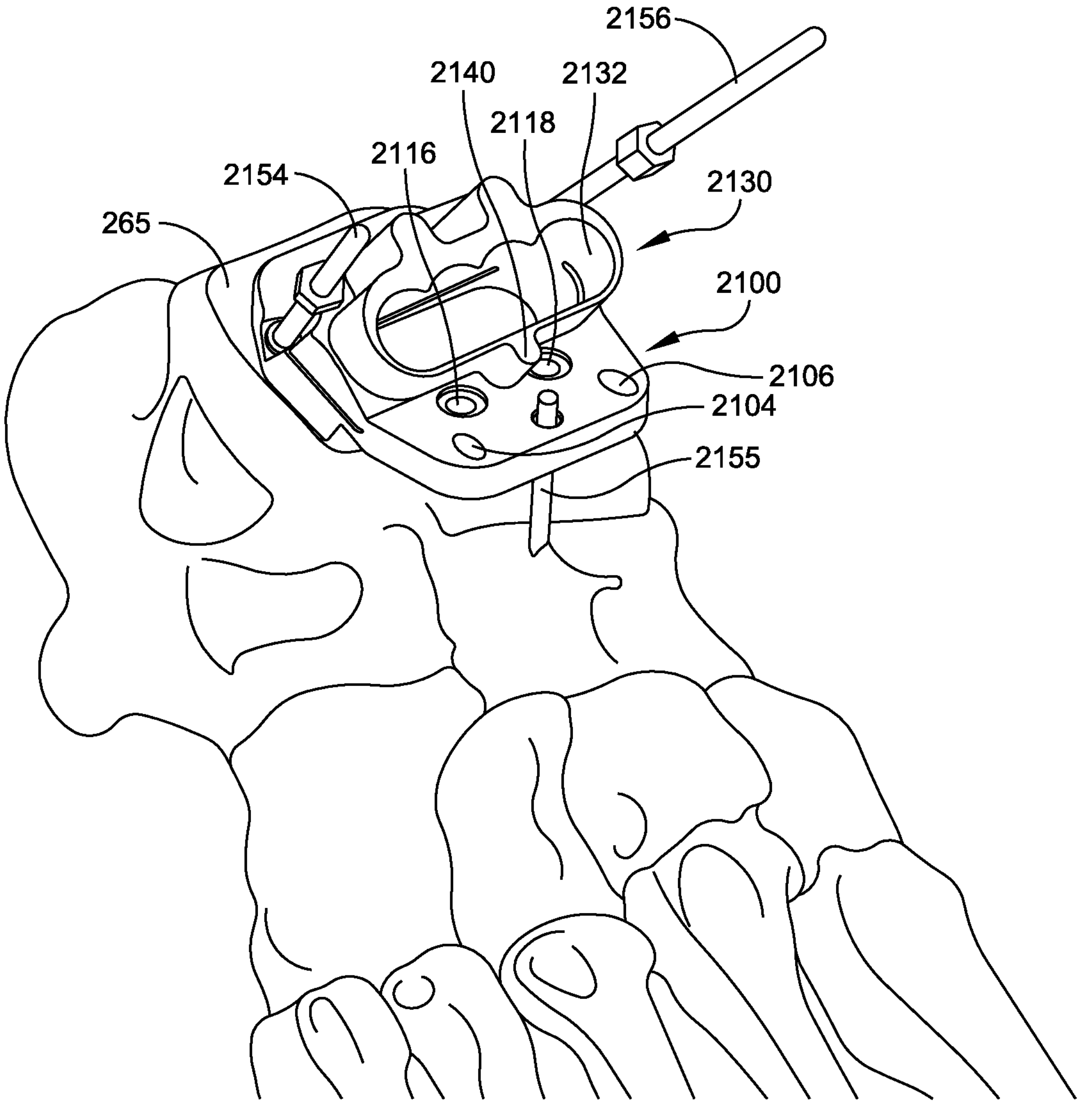
FIG. 65 is an isometric view of one example of the talar resection guide base and the anterior talar pilot guide attached to the bone via temporary fixation screws or pins in accordance with some embodiments.

As illustrated in FIG. 65, the anterior talar pilot guide 2130 is coupled to the talar resection guide base 2100 by inserting the pegs 2134, 2136 of the anterior talar pilot guide 2130 into holes 2112, 2114 located in the upper flange 2103 above the slot 2102 of the talar resection guide base 2100. An appropriate size talar reamer, such as talar reamer 2162 illustrated in FIG. 66, is used to make plunge cuts through the interconnecting holes that form slot 2132 of the anterior talar pilot guide 2130. In some embodiments, the talar reamer 2162 has a solid elongate body 2164 with one end 2166 configured to be received in the holes 2132 of the anterior talar pilot guide 2130 as a means to make plunge cuts in the talus 265. The talar reamer 2162 includes a collar 2168 on its end 2166 that serves as a stop for reaming depth.

Figure 68:
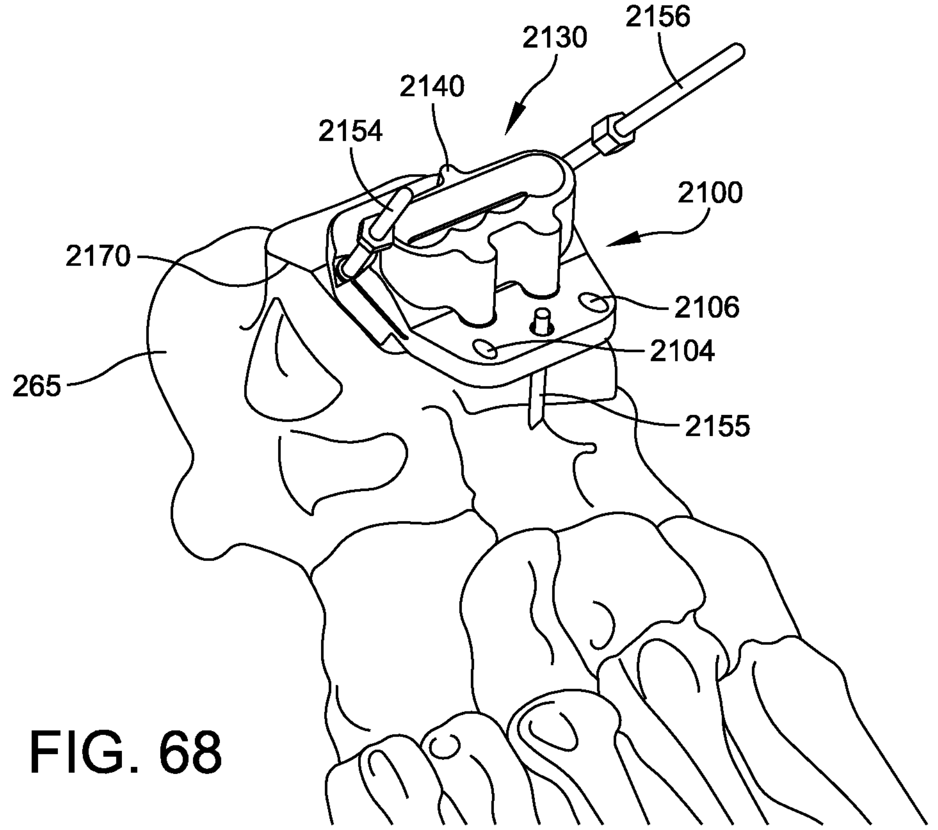
FIG. 68 is an isometric view of one example of the talar resection guide base and the anterior talar pilot guide attached to the bone via temporary fixation screws or pins following a 180° rotation of the anterior talar pilot guide in accordance with some embodiments.
Figure 74:
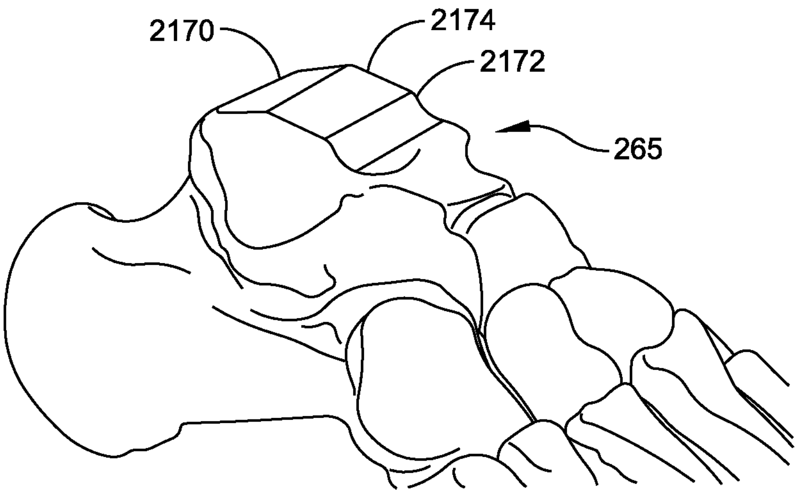
FIG. 74 is an isometric view of the talus bone following resection of the posterior and anterior talar chamfer and the anterior talar flat in accordance with some embodiments.

Turning now to FIG. 67, plunge cuts are made to prepare the talar surface for making an anterior chamfer 2172, which is best seen in FIG. 74. Once the plunge cuts have been made, the anterior talar pilot guide 2130 is removed from the talar resection guide base 2100 and is rotated 180° as shown in FIG. 68. Pegs 2134, 2136 of the anterior talar pilot guide 2130 are inserted into two holes 2116, 2118 below the slot 2102 of the talar resection guide base 2100.

Figure 69:
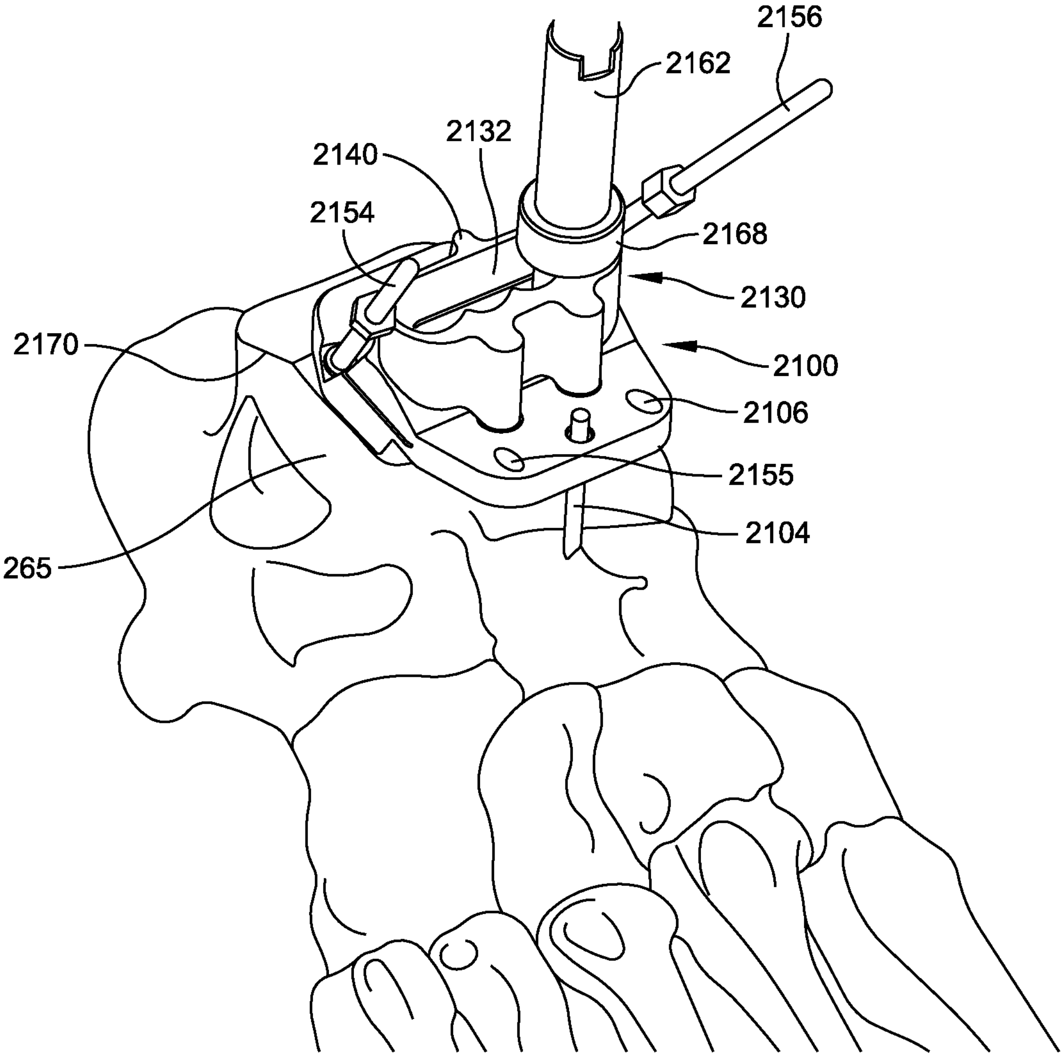
FIG. 69 is an isometric view of one example of the talar reamer inserted through the interconnecting holes of the talar resection guide base and slot of the anterior talar pilot guide attached to the bone via temporary fixation screws or pins following a 180° rotation of the anterior talar pilot guide in accordance with some embodiments.

As illustrated in FIG. 69, the talar reamer 2160 is used to plunge cut through the interconnecting holes that collectively define slot 2132 of the anterior talar pilot guide 2130 to prepare the talar surface for an anterior flat 2174, which is best seen in FIG. 74. The anterior talar pilot guide 2130 is removed from the talar resection guide base 2100 once the plunge cuts have been made.

FIG. 70 illustrates the anterior talar finish guide 2142 coupled to talar resection guide base 2100, which is accomplished by inserting the pegs 2146, 2148 of the anterior talar finish guide 2142 into two holes 2112, 2114 defined in the upper flange 2103 of the talar resection guide base 2100. With finish guide 2142 coupled to talar resection guide base 2100, the talar reamer 2162 is used to perform the finishing cuts for the anterior chamfer 2172 by sliding the talar reamer 2162 from side to side within the slot 2144 of the finish guide 2142, as indicated by arrow AR1 in FIG. 71. In some embodiments, the talar reamer 2162 is positioned flush against the anterior talar finish guide 2142 for each reaming step to ensure that the bone cuts are at the proper depth.

Figure 72:
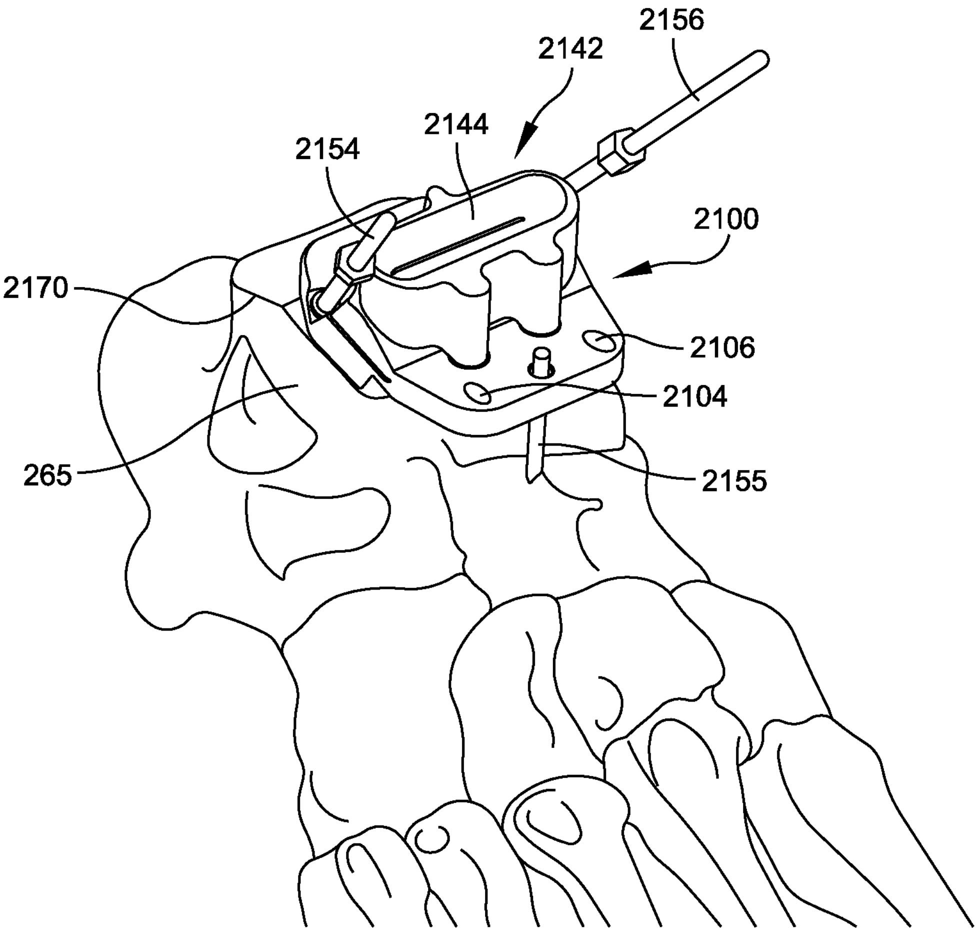
FIG. 72 is an isometric view of one example of the talar resection guide base and the anterior talar finish guide attached to the bone via temporary fixation screws or pins following a 180° rotation of the anterior talar finish guide in accordance with some embodiments.
Figure 73:
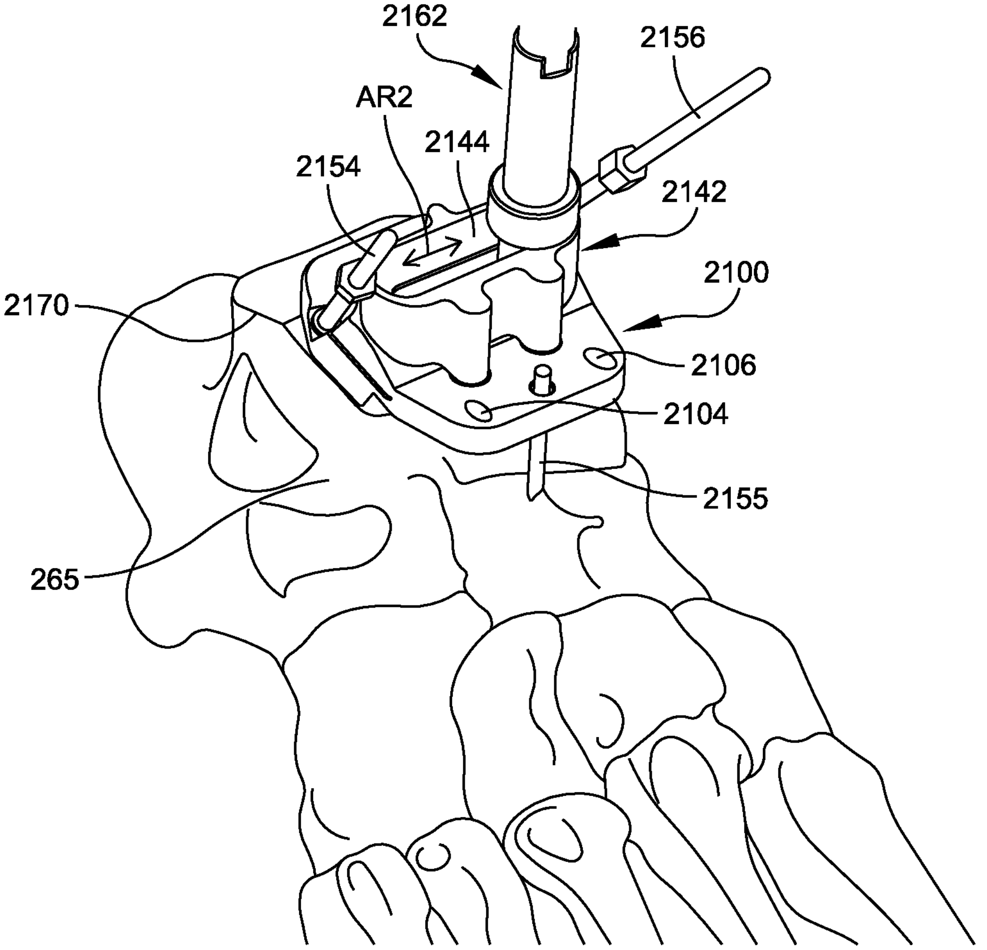
FIG. 73 is an isometric view of one example of the talar reamer inserted through the slots of the talar resection guide base and the anterior talar finish guide attached to the bone via temporary fixation screws or pins following a 180° rotation of the anterior talar finish guide in accordance with some embodiments.

Once the finishing cuts for the anterior chamfer 2172 have been made, the anterior talar finish guide 2142 is removed from the talar resection guide base 2100 and is rotated 180° as illustrated in FIG. 72. The pegs 2146, 2148 of the anterior talar finish guide 2142 are inserted into holes 2116, 2118 defined by the lower flange 2101 of the talar resection guide base 2100. As shown in FIG. 73, the talar reamer 2162 is used to perform the finishing cuts for the anterior talar flat 2174 by sliding the talar reamer 2162 from side to side within the slot 2144 of the finish guide 2142, as indicated by arrow AR2. FIG. 74 illustrates the talus 265 once the anterior talar finish guide 2142, talar resection guide base 2100, and pins 2154, 2156 have been removed. The edges of the residual bone can be cleaned up as will be understood by one of ordinary skill in the art.

Figure 75:
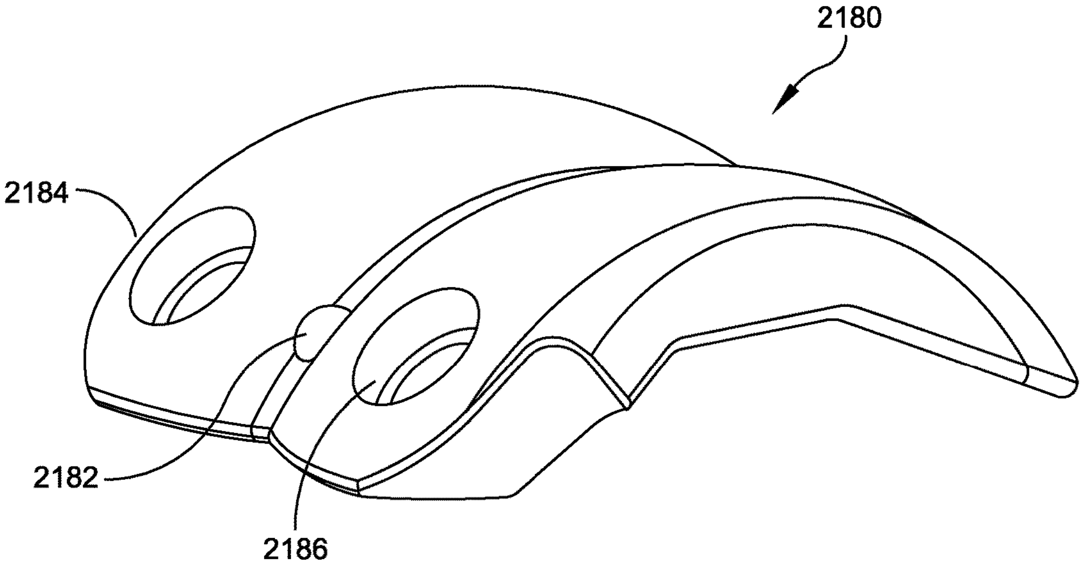
FIG. 75 is an isometric view of one example of a talar peg drill guide in accordance with some embodiments
Figure 79:
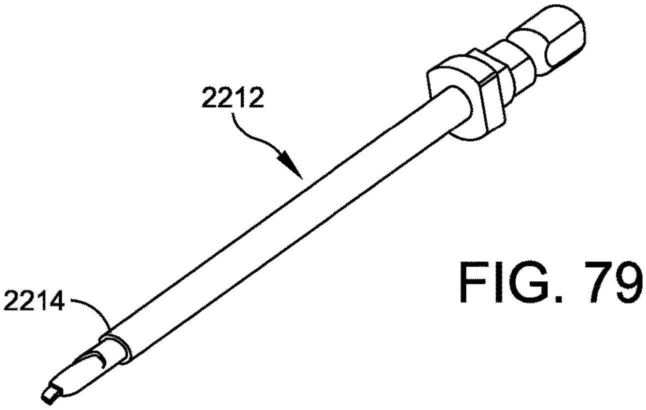
FIG. 79 is an isometric view of one example of an anterior peg drill in accordance with some embodiments.

FIG. 75 is an isometric views of one example of a talar peg drill guide 2180 in accordance with some embodiments. The talar peg drill guide 2180 has an arcuate body configured to be placed on a joint space of the resected talus 265. In the embodiment illustrated in FIG. 75, talar peg drill guide 2180 includes holes 2182, 2184, 2186 on its anterior side. One smaller hole 2182 is disposed between holes 2184, 2186 and is configured to receive a pin 2210. Holes 2184, 2186, which are disposed on either side of hole 2182, are configured to receive an anterior peg drill 2212 (FIG. 79). In some embodiments, the superior surface of talar peg drill guide 2180 has a contour that is similar to the contour of the articulating surface of the ankle replacement prosthesis as shown in FIG. 75.

Figure 76:
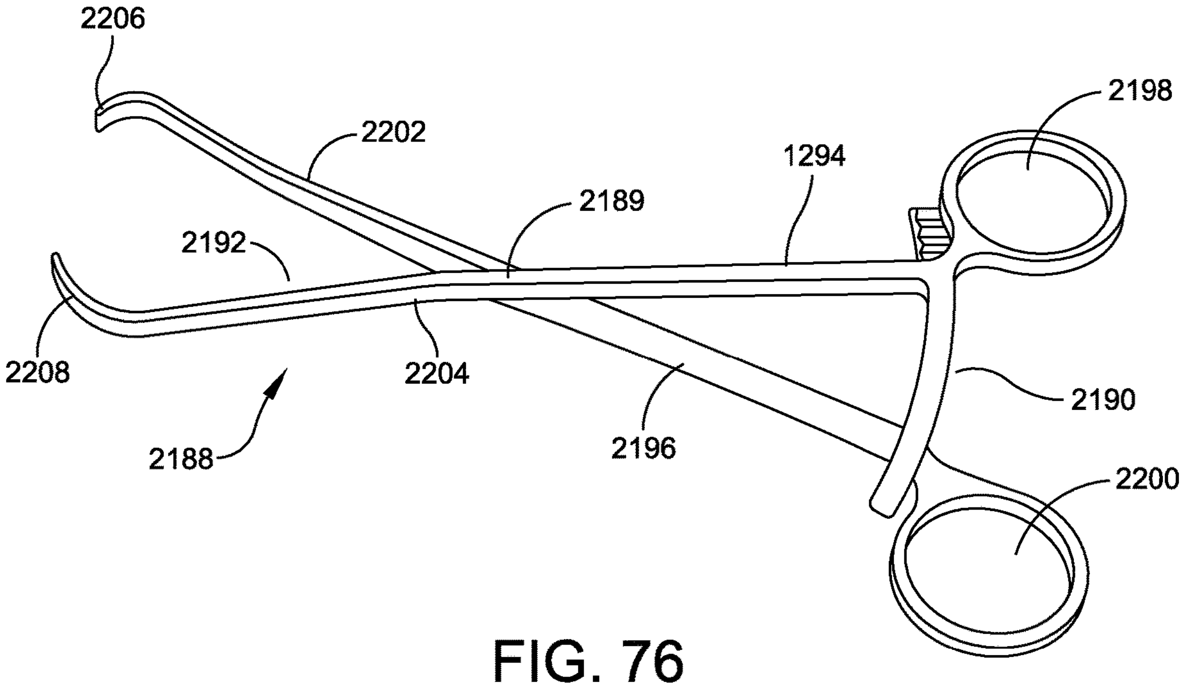
FIG. 76 is an isometric view of one example of a talar implant holder in accordance with some embodiments.

FIG. 76 illustrates one example of a talar implant holder 2188 in accordance with some embodiments. As shown in FIG. 76, talar implant holder 76 can be a scissor-shaped tool having a first end 2190 and a second end 2192, which are attached at an approximate center 2189. End 2190 includes two arms 2194, 2196 with each arm 2194, 2196 defining a respective hole 2198, 2200 at its detached end. Holes 2198, 2200 are sized and configured to receive a surgeon's finger as a means to grasp the talar implant holder 2188. End 2192 defines two legs 2202, 2204 with each leg 2202, 2204 being curved inwardly at its detached end 2206, 2208 as a means to grasp a talar implant such as the talar peg drill guide 2180.

Figure 77:
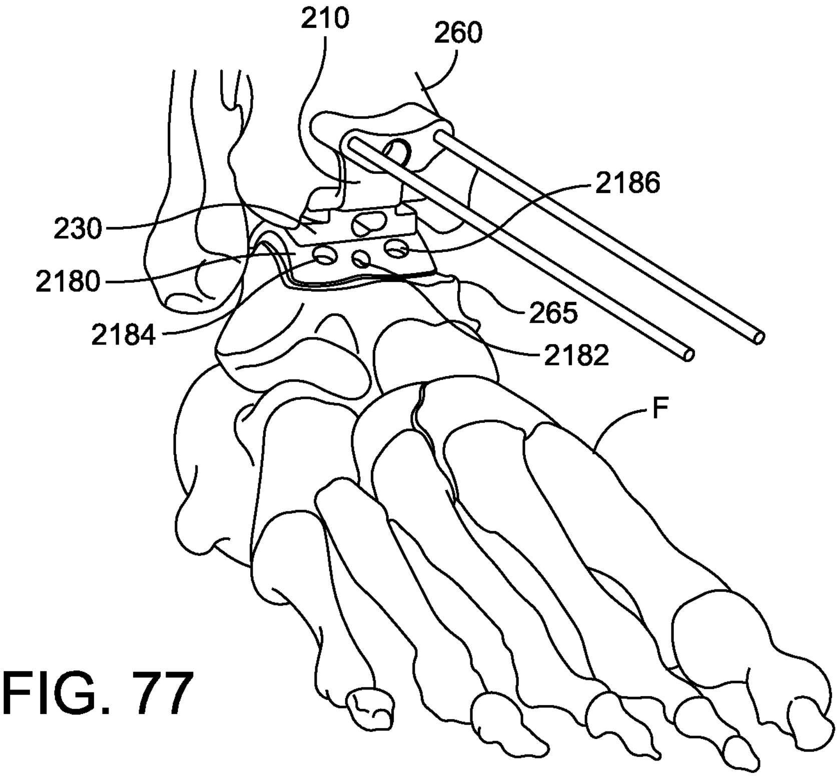
FIG. 77 is an isometric view of one example of the talar peg drill guide, the tibial tray trial, and poly insert trial inserted into a resected area of the bone in accordance with some embodiments.
Figure 78:
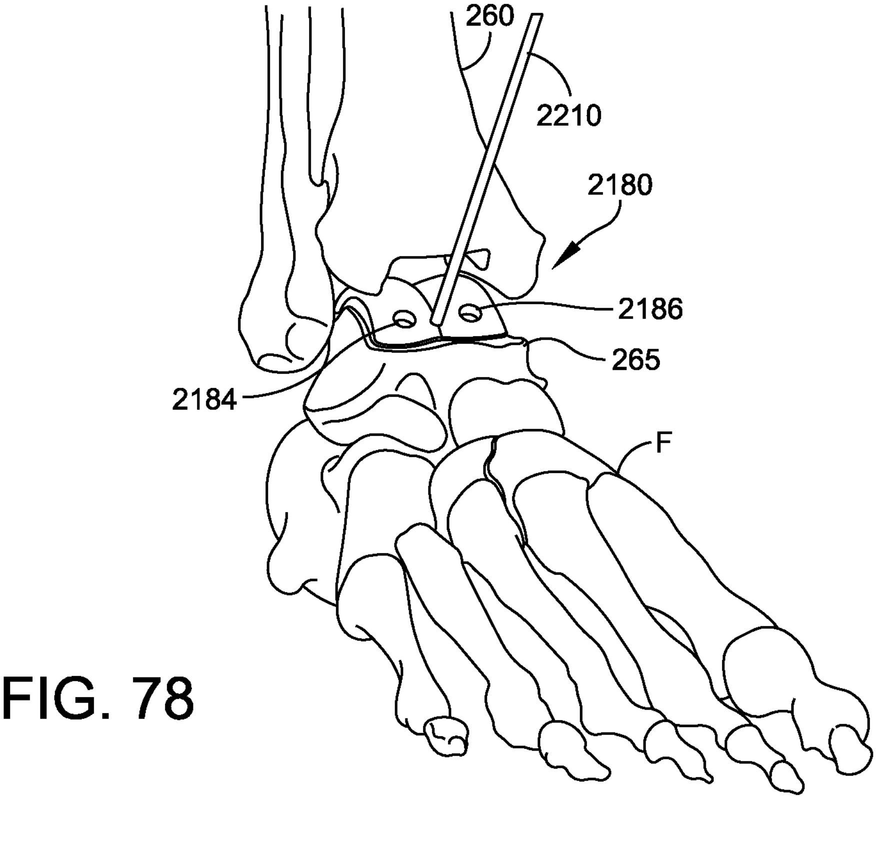
FIG. 78 is an isometric view of one example of the talar peg drill guide attached to the bone via a pin in accordance with some embodiments.

Turning now to FIG. 77, the previously described tibial tray trial 210 is inserted into the resected joint space between tibia 260 and talus 265. The talar implant holder 2188 (FIG. 76) is used to insert the talar peg drill guide 2180 into the joint space below tibial tray trial 210. The previously described poly trial insert 230 is inserted into the tibial trial 210. A trial reduction is performed to establish optimal talar medial/lateral positioning. The foot F is slightly plantar-flexed and a pin 2210 is inserted through the small hole 2182 in the center of the talar peg drill guide 2180 as a means to temporarily hold the talar peg drill guide 2180 in position, as illustrated in FIG. 78.

Figure 80:
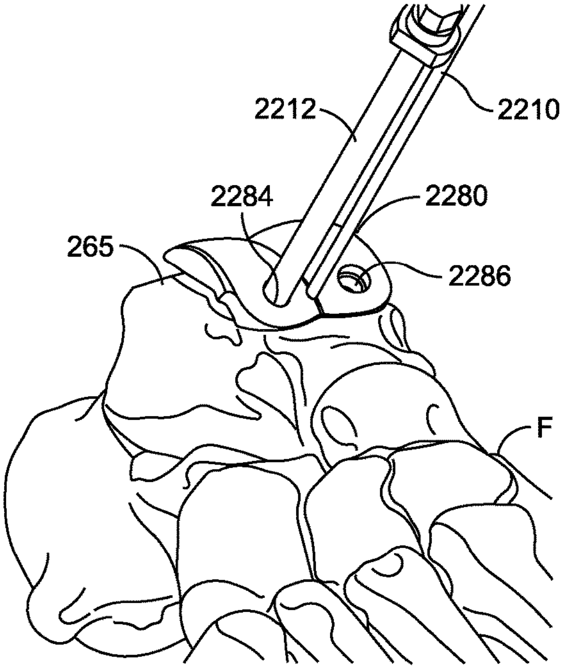
FIG. 80 is an isometric view of one example of an anterior peg drill inserted into a hole of the talar peg drill guide attached to the bone via a pin in accordance with some embodiments.
Figure 81:
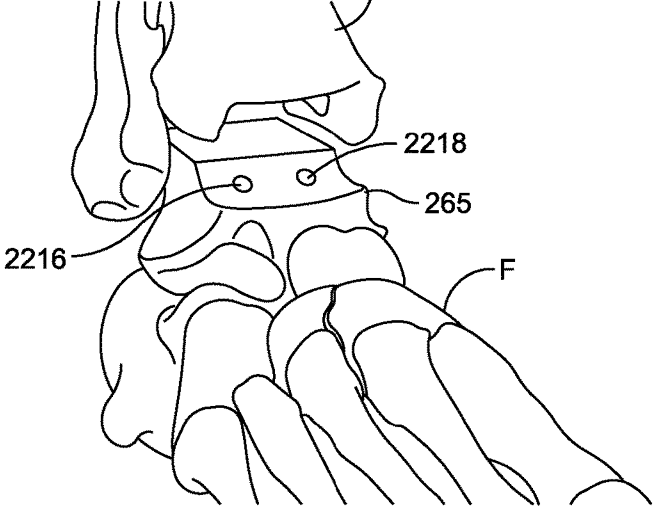
FIG. 81 is an isometric view of the tibia and talus bone following creation of two holes using the anterior peg drill and talar peg drill guide in accordance with some embodiments.

FIG. 79 illustrates one example of an anterior peg drill 2212 in accordance with some embodiments. Peg drill 2212 includes a stop 2214 that is configured to limit the depth to which the peg drill 2212 is inserted into a bone. FIG. 80 illustrates anterior peg drill 2212 being inserted into holes 2184, 2186 to drill holes 2216, 2218 shown in FIG. 81. Holes 2216, 2218 formed by anterior peg drill 2212 being inserted into holes 2284, 2286 are sized and configured to receive anterior pegs 1202 for securing the talar dome 1200 to talus 265 (FIG. 99) as described in greater detail below. FIG. 81 illustrates the holes 2216, 2218 formed in talus 265 and the resected joint space once pins 2210 are removed from in the tibia 260 and talus 265 as are the talar peg drill guide 2180, poly trial insert 230, and tibial trial 210.

Figure 82:
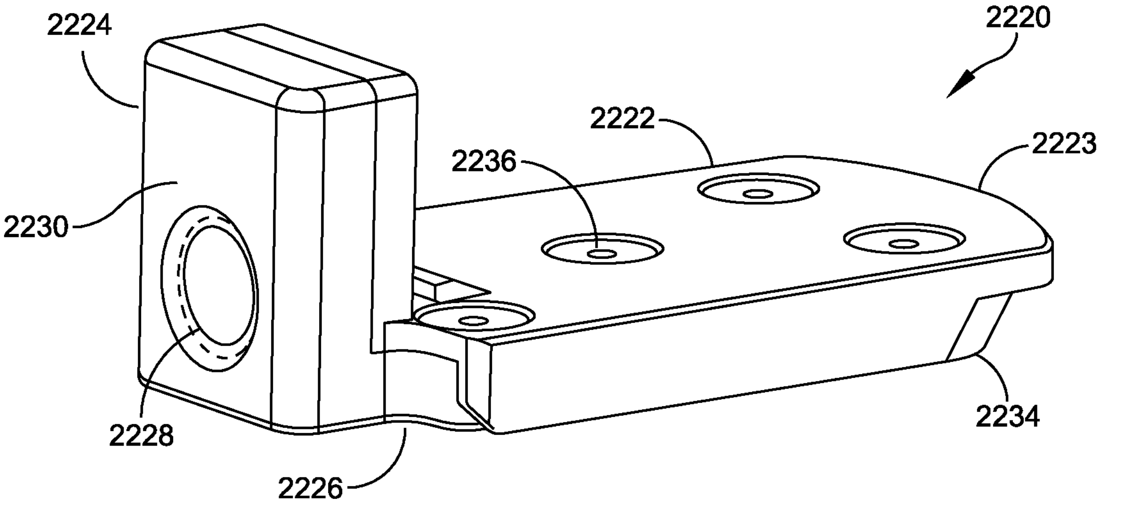
FIG. 82 is an isometric view of one example of a tibial tray impaction insert in accordance with some embodiments.
Figure 83:
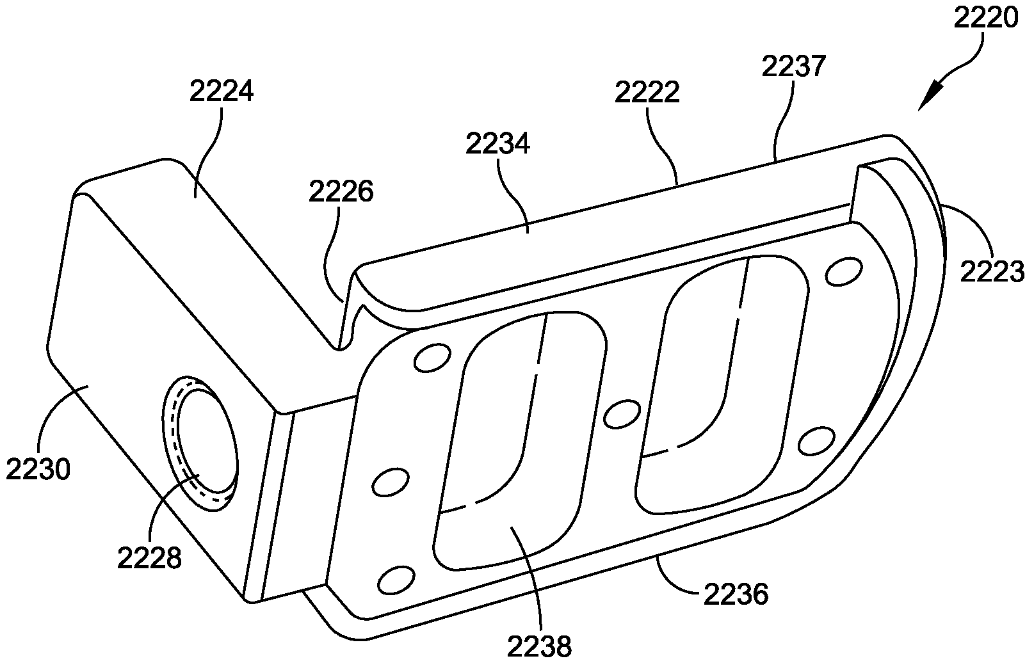
FIG. 83 is an inferior side view of one example of a tibial tray impaction insert in accordance with some embodiments.

FIGS. 82 and 83 illustrate one example of a tibial tray impaction insert 2220 in accordance with some embodiments. As shown in FIGS. 82 and 83, the tibial tray impaction insert 2220 has a body 2222 having a rectangular cuboid shape with curved insertion edge 2223 configured to be received in tibial implant 1100 (FIGS. 84, 86) as described in greater detail below. More particularly, body 2222 includes two opposed longer sides 2234, 2236 that are separated from one another by curved insertion edge 2223 and end 2226 from which extension 2224 is disposed. Body 2222 also includes a superior side 2237 and an inferior side 2238.

The tibial tray impaction insert 2220 includes an extension 2224 extending perpendicularly from end 2226 of tibial tray impaction insert 2220. Extension 2224 also has a shape of a rectangular cuboid and defines a hole 2228 on its anterior face 2230 that is sized and configured to receive an end 2266 of insertion handle 2264, which is shown in FIG. 87.

Figure 84:
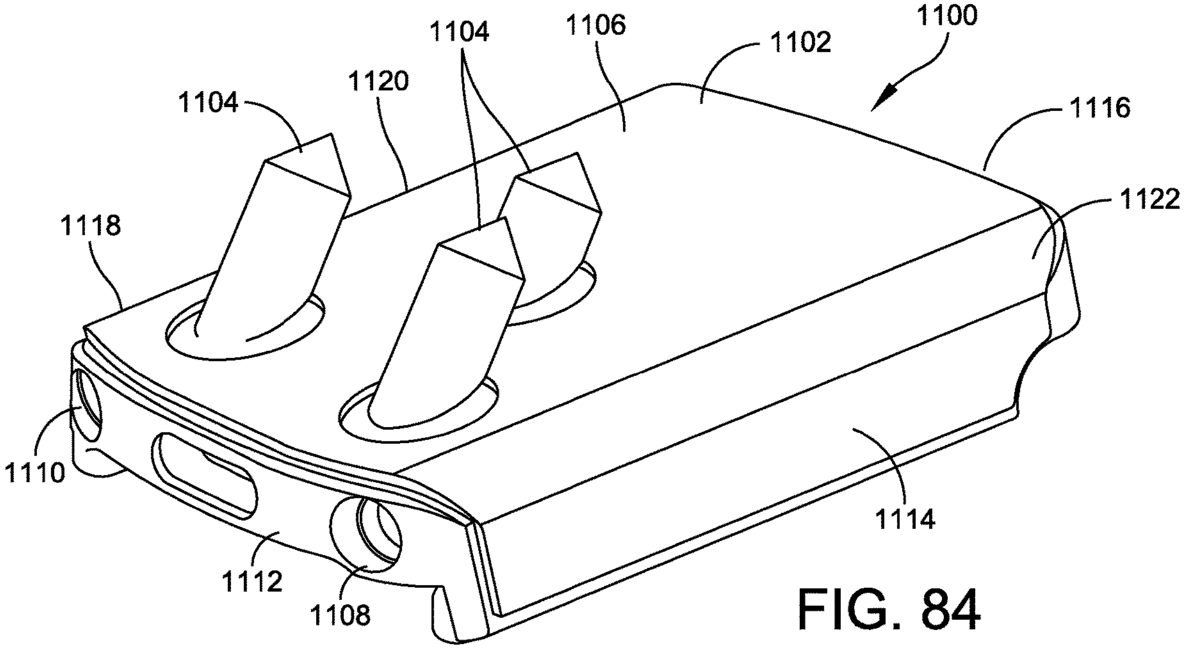
FIG. 84 is an isometric view of one example of a tibial tray in accordance with some embodiments.
Figure 85:
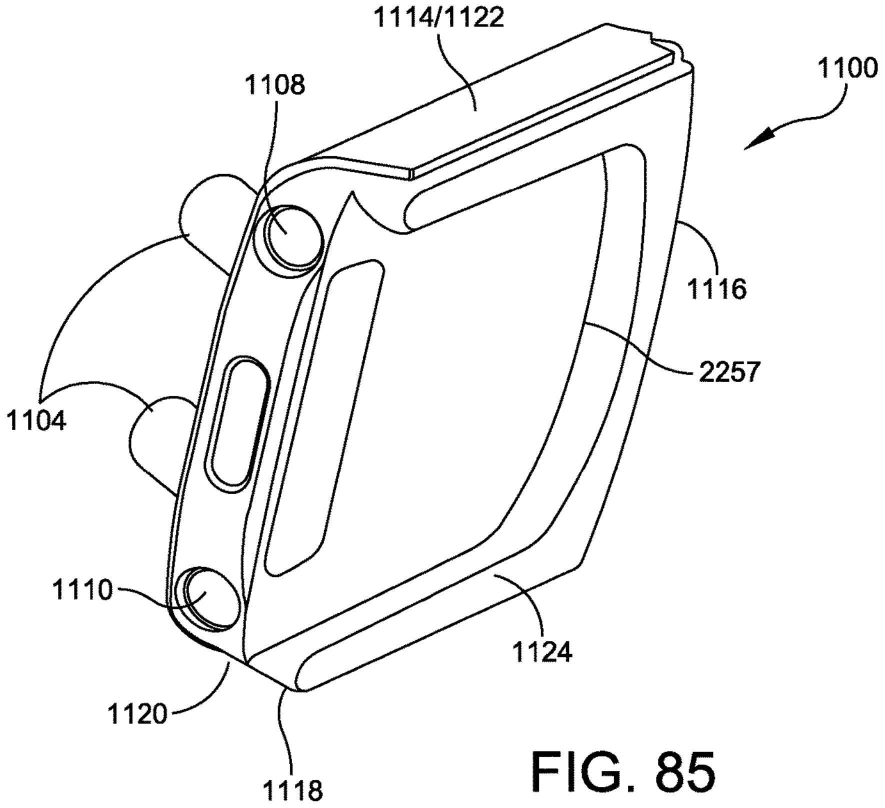
FIG. 85 is an inferior side view of one example of a tibial tray in accordance with some embodiments.

One example of a tibial implant 1100 is illustrated in FIGS. 84 and 85. Tibial implant 1100 has a rectangular cuboid body 1102 with a plurality (three in this example) pegs 1104 protruding out of the superior side 1106 of body 1102. Pegs 1104 are configured to be received holes 263 formed in the tibia 260 (FIG. 41) as described above. Holes 1108, 1110 are defined by the anterior face 1112 of tibial implant 1100 with each hole 1108, 1110 being sized and configured to receive two attachment screws 3500 (FIGS. 93A, 93B) for use with a poly inserter as described in greater detail below. Tibial implant 1100 also includes opposed shoulders 1114, 1118 that are curved or chamfered relative to superior side 1102 and sides 1120, 1122 of body 1102. A recessed area or recess 2257 extends posteriorly from anterior face 1112 to insertion end (or posterior end) 1116 along the inferior side 1124 of implant 1100.

Figure 86:
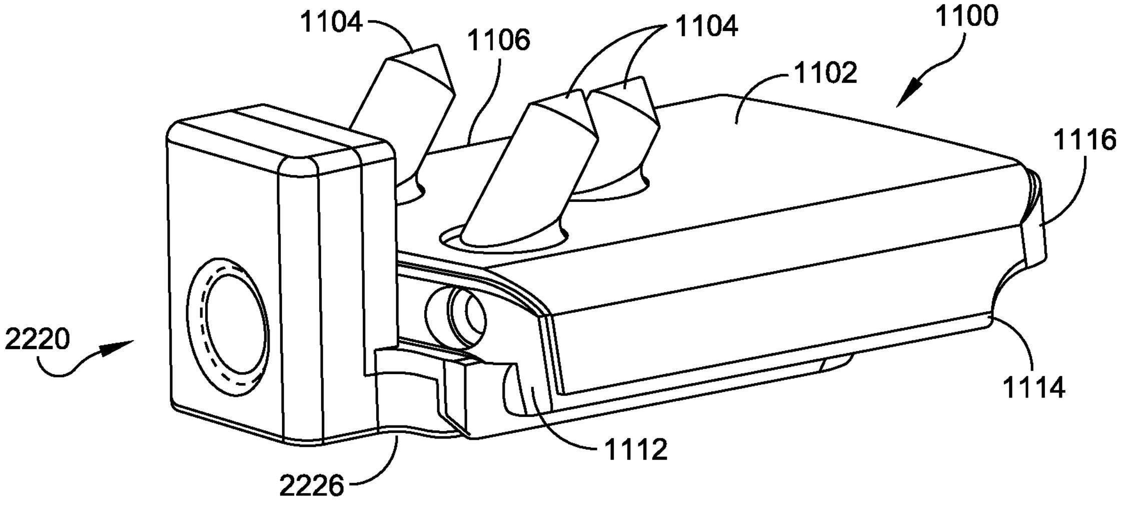
FIG. 86 is an isometric view of one example of the tibial tray impaction insert attached to a tibial tray in accordance with some embodiments.

Recess 2257 is sized and configured to receive the sides 2234, 2236 and curved edge 2223 of the tibial tray impaction insert 2220 as a means for holding the tibial tray impaction insert 2220 in place in the tibial implant 1100 as shown in FIG. 86. The coupling between tibial tray impaction insert 2220 and implant 1100 is achieved by sliding the tibial tray impaction insert 2220 into the tibial implant 1100. Bone cement (not shown) can be applied to the superior 1106, medial 1120, and lateral sides 1122 of the rectangular body 1102 of the tibial implant 1100 while the anterior face 1112 of the tibial tray 1100 and inferior side 2238 of the tibial implant impaction insert 2220 remains free of any cement.

Figure 87:
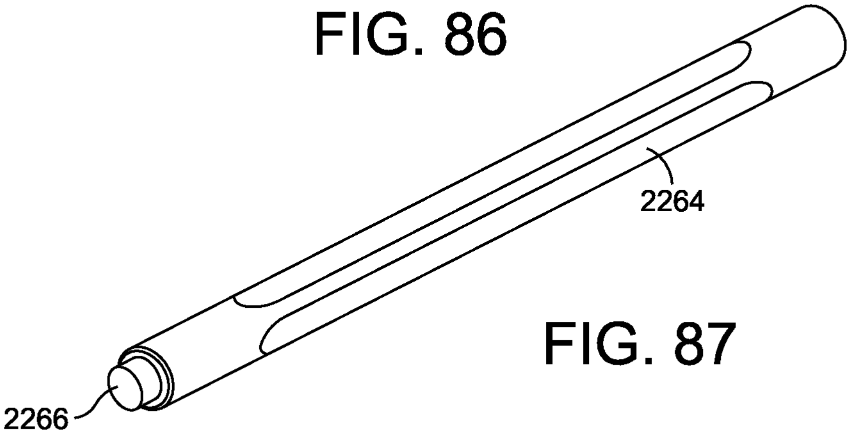
FIG. 87 is an isometric view of one example of an insertion handle in accordance with some embodiments.
Figure 88:
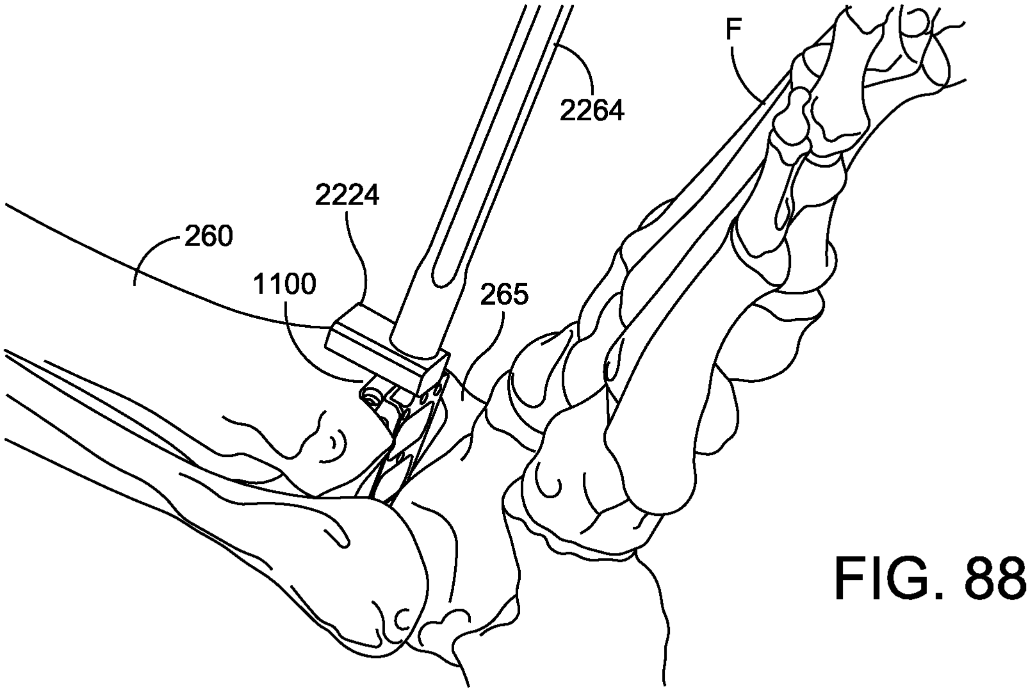
FIG. 88 is an isometric view of one example of the insertion handle attached to the tibial tray impaction insert and tibial tray which is being inserted into the bone in accordance with some embodiments.

Turning now to FIG. 88, the assemblage of tibial tray implant 1100 and tibial tray impaction insert 2220 are shown being inserted into the resected joint space between tibia 260 and talus 265 using insertion handle 2264, which is illustrated in FIG. 87. Insertion handle 2264 is coupled to hole 2228 of tibial tray impaction insert 2220 and moves three pegs 1104 of the tibial implant 1100 into alignment with holes 263 formed in the tibia 260 (FIG. 41). The insertion handle 2264 is then removed from the hole 2228 of the rectangular extension 2224 of the tibial tray impaction insert 2220. A mallet or other impaction device can be used to strike extension 2230 of tibial impaction insert 2220 as will be understood by one of ordinary skill in the art. The tibial impaction insert 2220 can be slid out of engagement with tibial tray implant 2220, which is configured to receive a poly implant/insert 1300 using a poly insertion device 3100, 3300.

Poly Inserter and Related Components

FIGS. 89 through 95 illustrate the construction and operation of one example of a poly inserter 3100 and poly insert guide rail 3300 in accordance with some embodiments. The purpose of poly inserter 3100 and poly insert guide rail 3300 is to assist in the accurate placement of a poly implant 1300 as will be appreciated and understood after reading the following description and referencing the figures.

Figure 89:
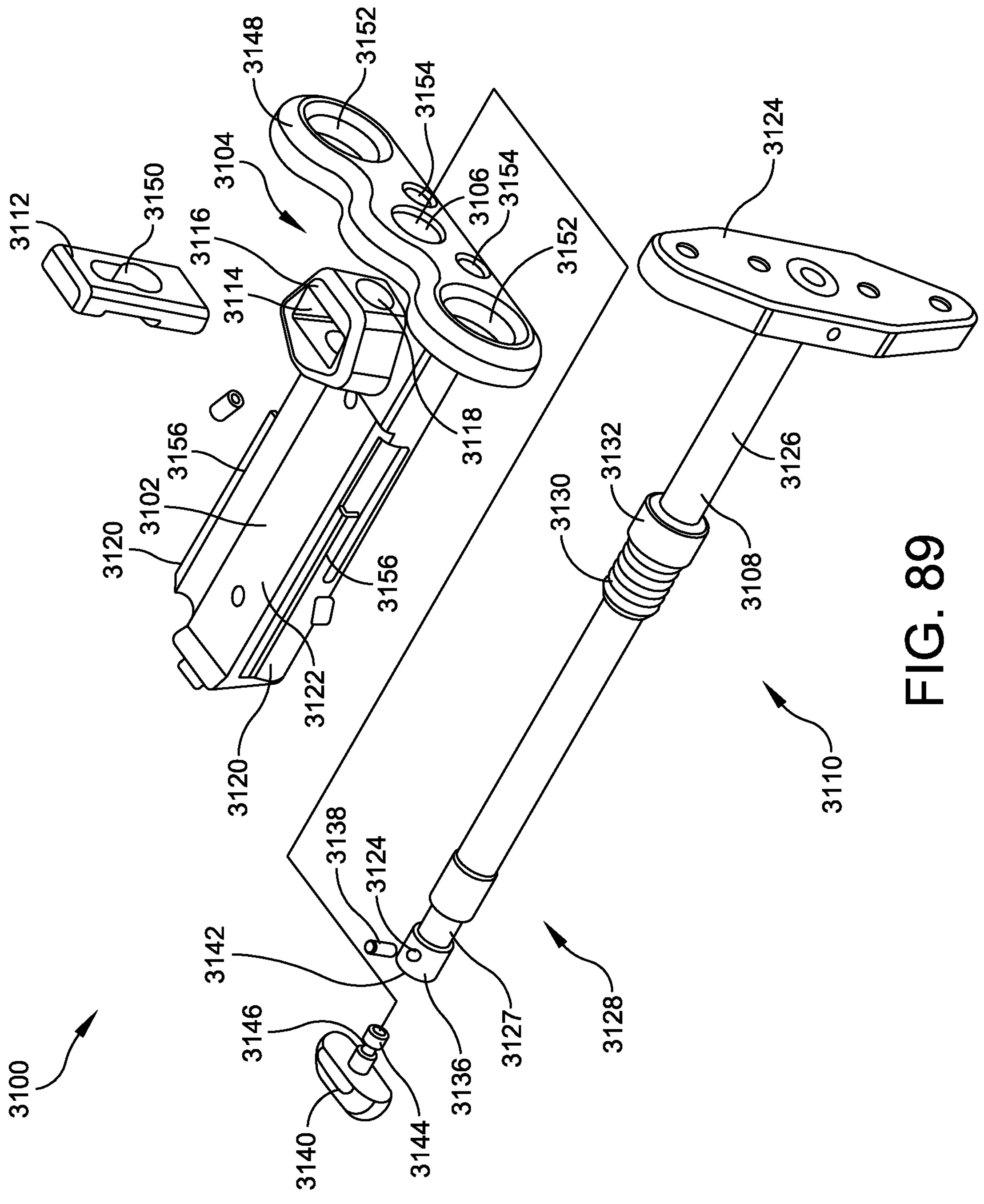
FIG. 89 is an isometric view of one example of a disassembled poly inserter in accordance with some embodiments.

FIG. 89 is an isometric view of a poly inserter 3100. Poly inserter 3100 comprises an elongate body 3102 having gripping handle 3148 defining an aperture 3106 that is at least partially threaded and has an internal diameter sized and configured to slidably receive a majority of a shaft 3108 of a plunger rod 3110. Gripping handle 3148 defines a pair of gripping holes 3152 and attachment screw receiving holes 3154.

A locking protrusion 3116 extends at an angle from the elongate body 3102 adjacent to the proximal end 3104. Locking protrusion 3116 defines a rectangular opening 3114 that is sized and configured to receive a locking tab 3112 and a cylindrical opening 3118 that aligns with threaded aperture 3106 for receiving plunger rod 3110 therethrough. Locking tab 3112 defines an aperture 3150 which is configured to receive plunger rod 3110. A pair of opposed channels 3120 extend proximally from the distal end 3122 of the elongate body 310. Channels 3120 are sized and configured to receive attachment screws 3500 (FIGS. 93A and 93B) and are.

Opposed channels 3120 are aligned with attachment screw receiving holes 3154 in gripping handle 3148.

Plunger rod 3110 includes a handle 3124 at its proximal end 3126. A shoulder 3132 is disposed adjacent to an enlarged threaded portion 3130 that is disposed between the proximal end 3126 and a distal end 3128 of plunger rod 3110. A push bar 3140 is connected to the distal end 3128 of plunger rod 3110 by inserting a push bar extension 3144 into a blind hole 3142 located at the distal-most end of plunger rod 3110. In some embodiments, push bar 3140 is cross-pinned to plunger rod 3110 using a pin 3138, which is inserted into hole 3134 located at distal end 3128. However, one of ordinary skill in the art will understand that other securement mechanisms can be used to couple push bar 3142 to plunger rod 3110. A circumferential recess 3146 is defined about the external surface of the push bar extension 3144 and is sized and configured to receive the pin 3138 therein for coupling the push bar 3140 to the distal end 3128 of the plunger rod 3110. Distal end 3128 of plunger rod 3100 further includes a distal notch 3127.

Figure 90:
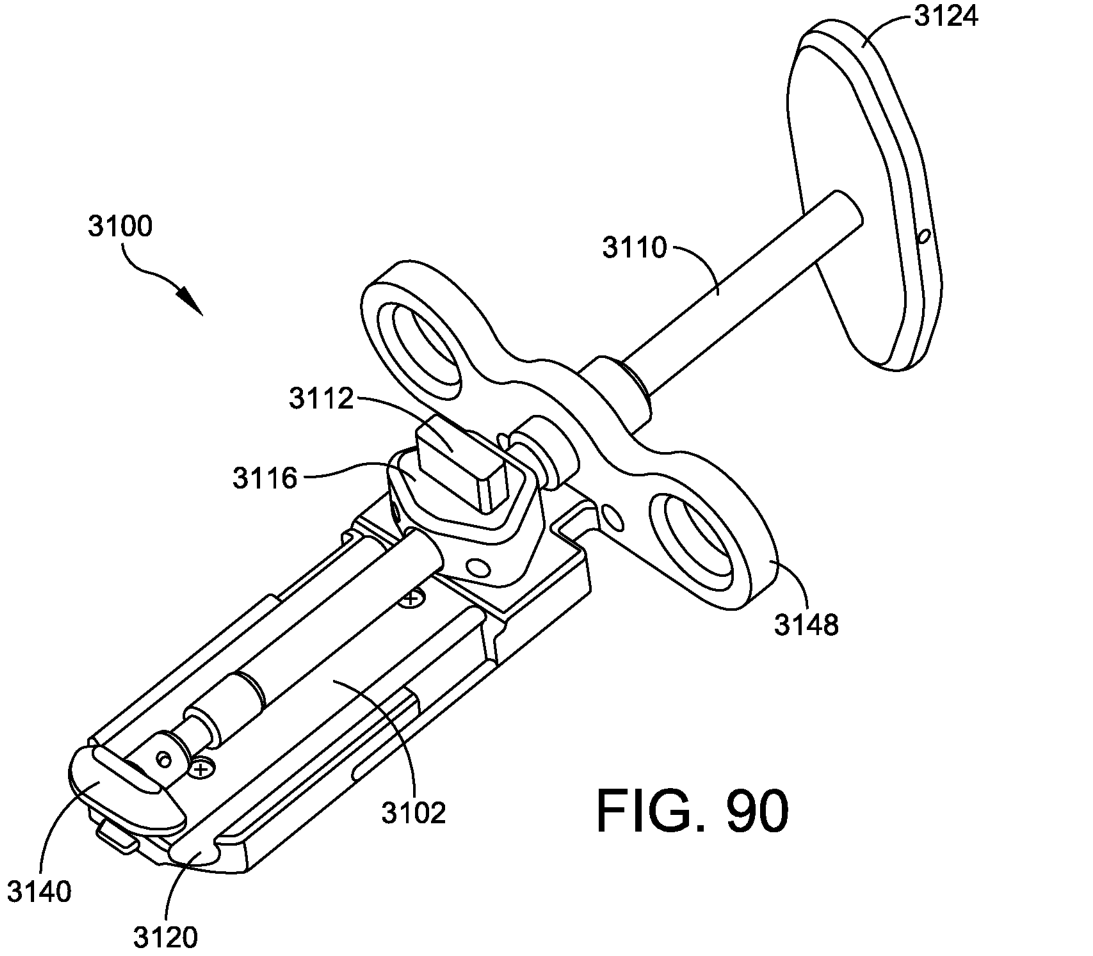
FIG. 90 is an isometric view of one example of an assembled poly inserter in accordance with some embodiments.

FIG. 90 is an isometric view of a poly inserter 3100 once assembled. Locking tab 3112 is inserted into rectangular opening 3114. Plunger rod 3110 is inserted through threaded aperture 3106 and cylindrical opening 3118. Push bar 3140 is then connected to the distal end 3128 of plunger rod 3110 as described above.

Figure 91:
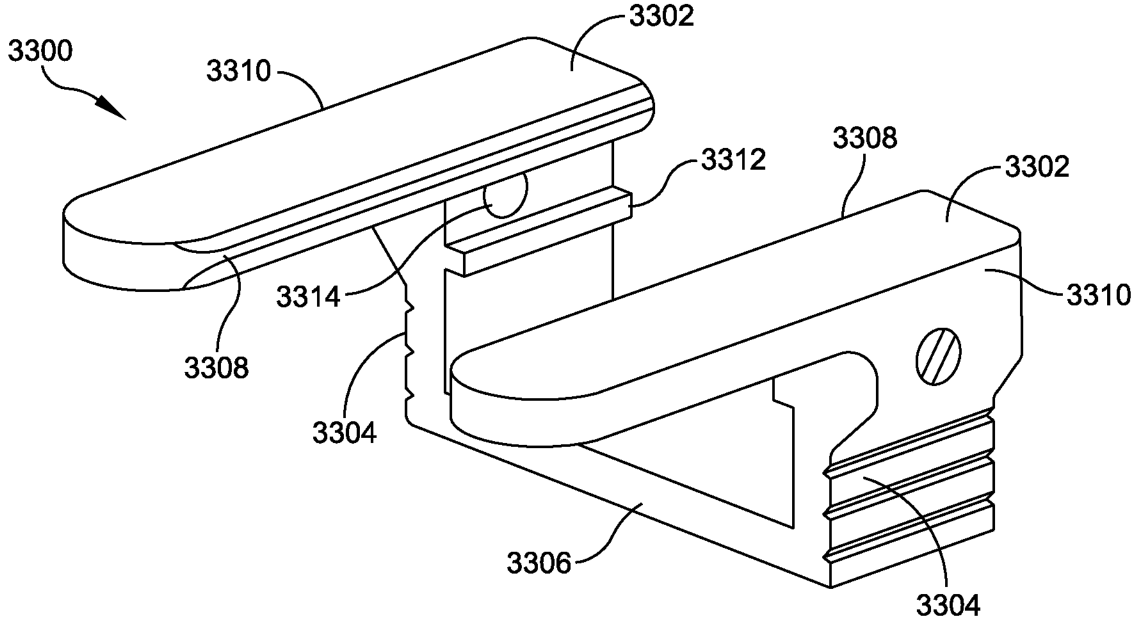
FIG. 91 is an isometric view of one example of a poly insert guide rail in accordance with some embodiments.

FIG. 91 is an isometric view of one example of a poly insert guide rail 3300 in accordance with some embodiments. Although shown as a separate component from poly inserter 3100, one of ordinary skill in the art will understand that guide rail 3300 can be integrally formed with poly inserter 3100. Guide rail 3300 includes a pair of spaced apart rails 3302 connected to a central portion 3306 by a pair of downconnectors 3304. Each rail 3302 has an interior edge 3308 and an exterior edge 3310. In some embodiments, interior edges 3308 are rounded while exterior edges 3310 are squared. Downconnectors 3304, which extend in a direction perpendicular to the direction in which rails extend and central portion 3306 extends, include a railing protrusion 3312 running parallel with the length of rails 3302. Together, the interior edges 3308 of rails 3302 and the railing protrusion 3312 define a pair of recesses 3314 configured to slide over the lateral edges 3156 of the elongate body 3102 of poly inserter 3100. Poly insert guide rail 3300 is coupled to poly inserter 3100 by sliding poly inserter guide rail 3300 over poly inserter 3100 such that recesses 3314 are aligned with lateral edges 3156 of elongate body 3102.

Figure 92:
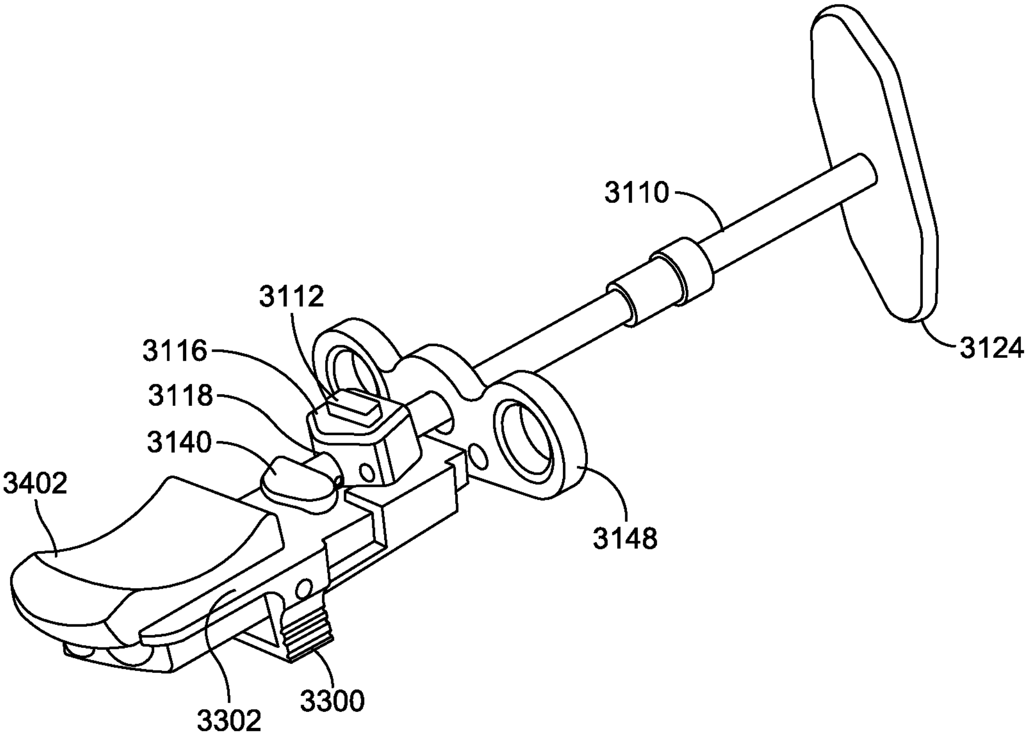
FIG. 92 is an isometric view of a poly inserter connected to a poly insert guide rail and a poly insert implant in accordance with some embodiments.

FIG. 92 is an isometric view of a poly inserter 3100 coupled with a poly inserter guide rail 3300 for guiding a poly insert 1300, which is shown disposed between rails 3302. In use, plunger rod 3110 is pulled proximally and locked in its proximal-most position by engaging locking tab 3112. For example, with plunger rod 3110 pulled to its proximal-most position, distal notch 3127 is aligned with locking tab 3112. Locking tab 3112 is depressed into rectangular opening 3114, causing the narrower top portion of aperture 3150 to engage distal notch 3127 and hold plunger rod 3110 in the proximal-most position. This engagement prevents plunger rod 3110 from prematurely implanting poly implant 1300. Plunger rod 3110 is prevented from being fully removed as push bar 3140 has a length that is larger than cylindrical opening 3118. With the plunger rod 3110 locked relative to the position of the poly inserter 3100, a poly implant 1300 is positioned between extending rails 3302 of poly inserter guide rail 3300 as shown in FIG. 92.

Figure 93A:
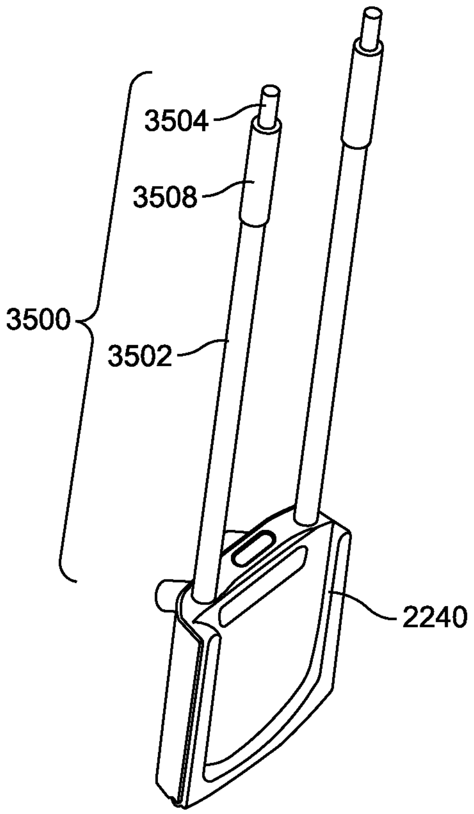
FIGS. 93A and 93B are isometric views of attachment screws installed in the tibial tray in accordance with some embodiments.
Figure 93B:
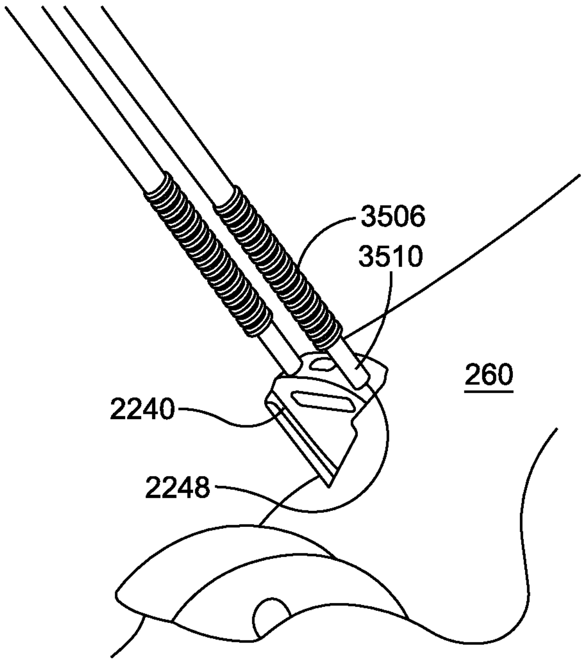

FIG. 93A is an isometric view of attachment screws 3500 installed in tibial implant 1100. Attachment screws 3500 comprise a threaded proximal end 3504, a shoulder portion 3508, a shaft 3502, and a threaded distal portion 3506, which is shown in FIG. 93B. Attachment screws 3500 are configured to be threadably inserted into tibial implant 1100 using threaded distal end 3506. Attachment screws 3500 are additionally configured, once threadably inserted into tibial implant 1100, to be inserted into opposed channels 3120 of poly inserter 3100.

FIG. 93B is an isometric view of attachment screws 3500 as they are being installed in tibial implant 1100. In some embodiments, as illustrated in FIG. 93B, attachment screw 3500 has a non-threaded tip 3510 disposed adjacent to threaded distal portion 3506, which engages threaded holes 1108, 1110 of tibial implant 1100.

Figure 94:
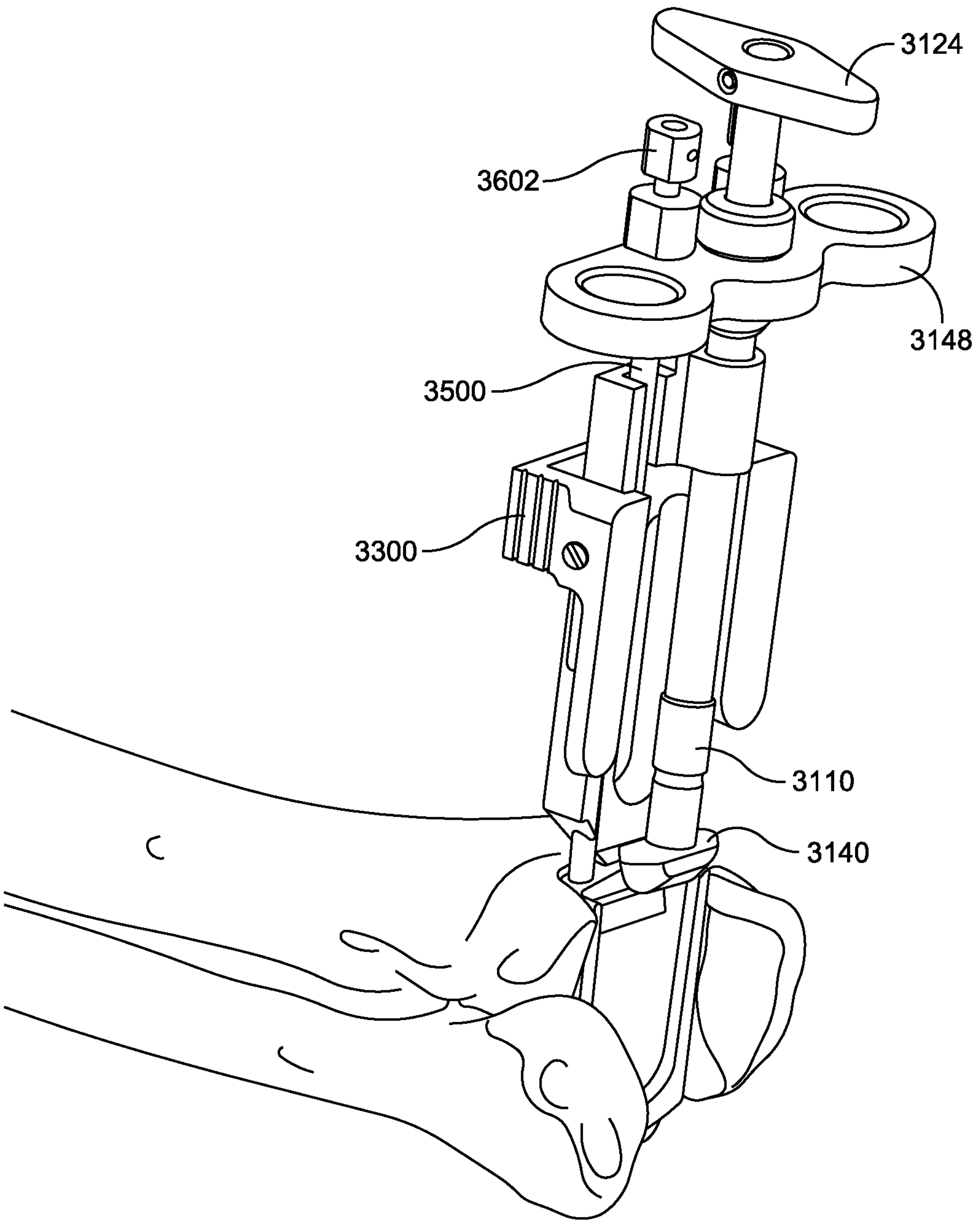
FIG. 94 is an isometric view of a poly inserter connected to attachment screws installed in the tibial tray in accordance with some embodiments.

FIG. 94 is an isometric view of a poly inserter 3100 connected to attachment screws 3500 installed in the tibial tray 1100 with the poly insert removed for simplifying the view. With attachment screws 3500 threadably inserted into threaded holes 1108, 1110 of tibial implant 1100, the assembled poly inserter 3100 is lowered onto attachment screws 3500 such that attachment screws 3500 are disposed within opposed channels 3120. An attachment nut 3602 is threadably connected to the threaded proximal end 3504 of each attachment screw 3500 to secure poly inserter to the anterior face 1112 of the tibial implant 1100.

Figure 95A:
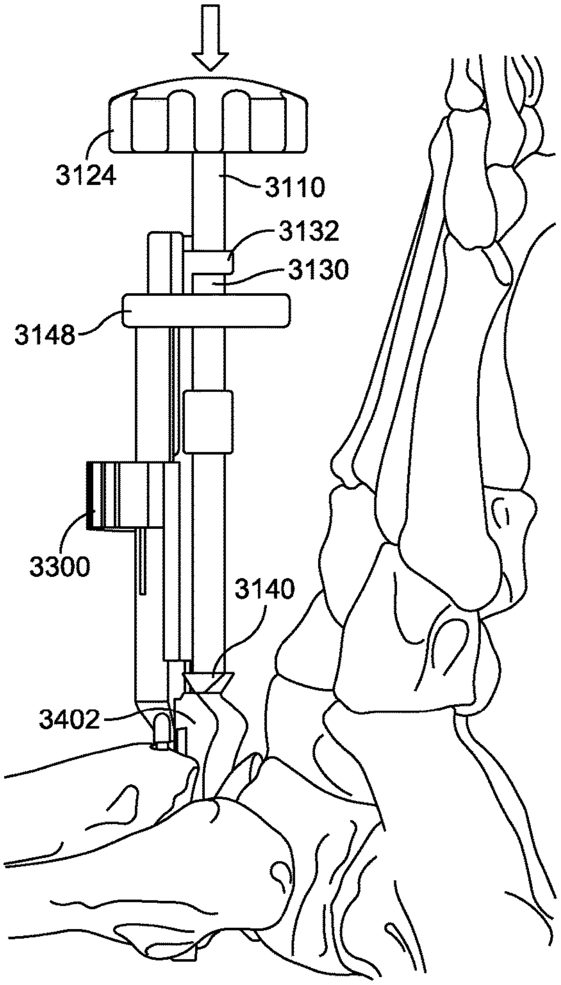
FIGS. 95A and 95B are lateral side elevation views of the poly inserter inserting a poly insert implant in accordance with some embodiments.
Figure 95B:
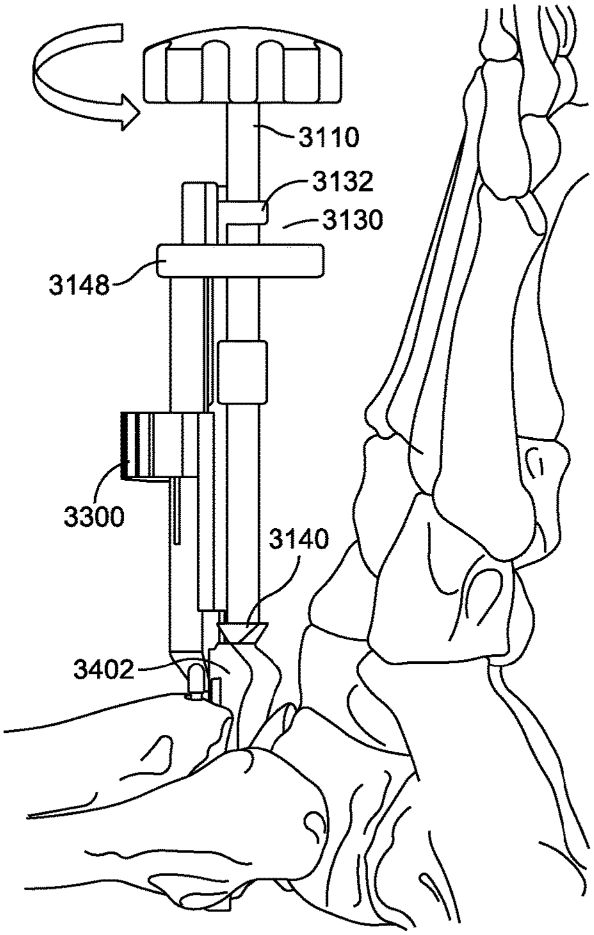

FIGS. 95A and 95B are lateral side views of the operation of poly inserter 3100 once secured to tibial implant 1100 in accordance with some embodiments. Locking tab 3112 (not shown in FIGS. 95A and 95B) is pulled in a direction away from elongate body 3102 such that the wider diameter base of aperture 3150 is aligned with plunger rod 3110 to permit plunger rod 3110 to slide relative to the elongate body 3102 of poly inserter 3100. Handle 3124 is used to slide the plunger rod 3110 distally such that poly implant 1300, positioned between rails 3302 of poly inserter guide rail 3300, is slid distally into the resected tibial bone space.

Plunger rod 3110 is moved distally until enlarged threaded portion 3130 abuts threaded hole 3106 of poly inserter 3100 at which point plunger rod 3110 is rotated about its longitudinal axis to facilitate distal (axial) translation of the plunger rod 3110 relative to elongate body 3102. Poly implant 1300 does not rotate as the plunger rod 3110 rotates since the plunger rod 3110 is allowed to spin relative to the push bar 3140 that is in abutting contact with the poly implant 1300 due to the pin 3138 that is received within the circumferential slot 3146 defined by push bar extension 3144. Shoulder 3132 prevents excessive downward motion of poly implant 1300 because its diameter is larger than threaded aperture 3106, arresting movement once the entire enlarged threaded portion 3130 has been threadably inserted into threaded aperture 3106.

When poly implant 1300 has been inserted into resected tibial bone space, poly inserter 3100 is removed from its engagement with poly implant 1300 by removing attachment nuts 3602 and pulling on handle 3124. Due to the threaded engagement between enlarged threaded portion 3130 and threaded aperture 3106, poly inserter 3100 is slid along the attachment screws 3500 until disengaged. As an alternative, poly inserter 3100 may be removed by pulling on gripping handle 3148. Attachment screws 3500 are then unscrewed from tibial implant 1100.

Ankle Replacement Prosthesis

Figure 96:
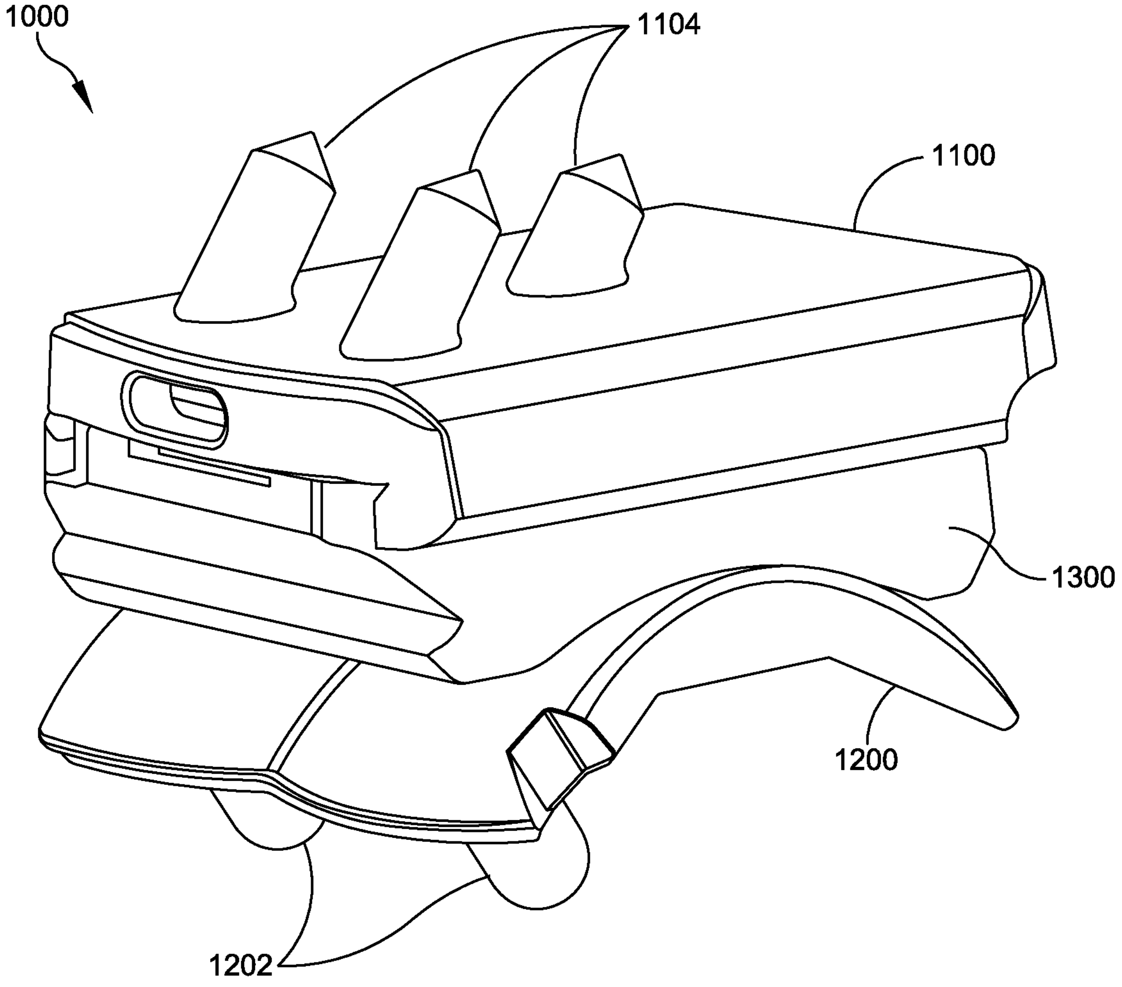
FIG. 96 is an isometric view of an ankle replacement prosthesis in accordance with some embodiments.
Figure 97:
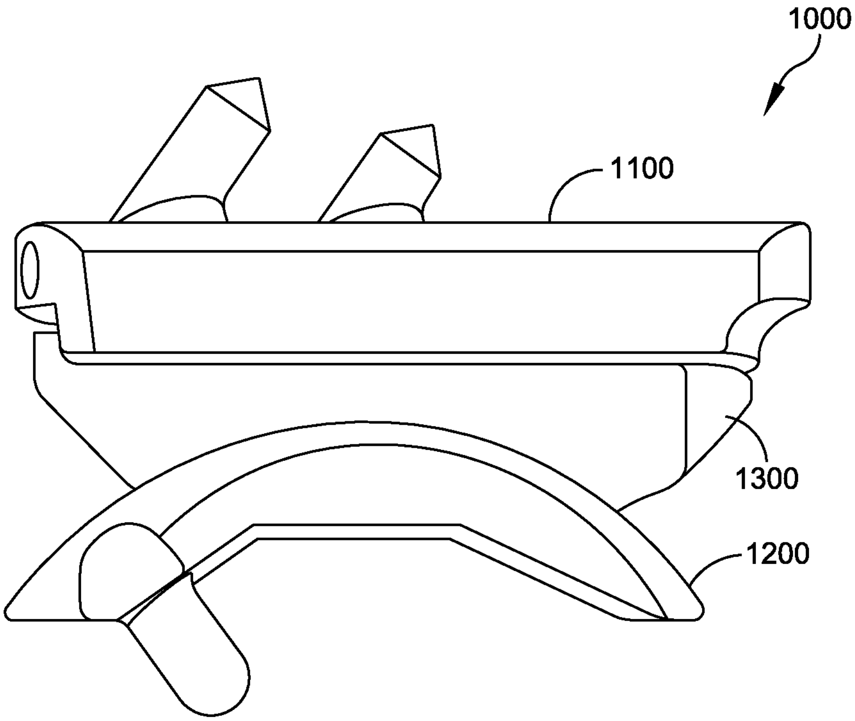
FIG. 97 is a side view of an ankle replacement prosthesis in accordance with some embodiments.
Figure 98:
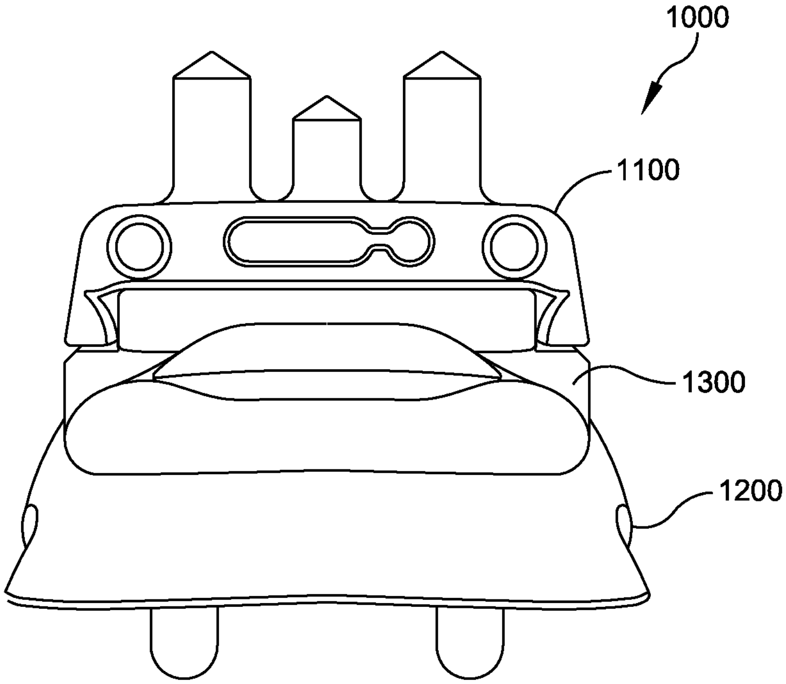
FIG. 98 is a front side view of an ankle replacement prosthesis in accordance with some embodiments.
Figure 99:
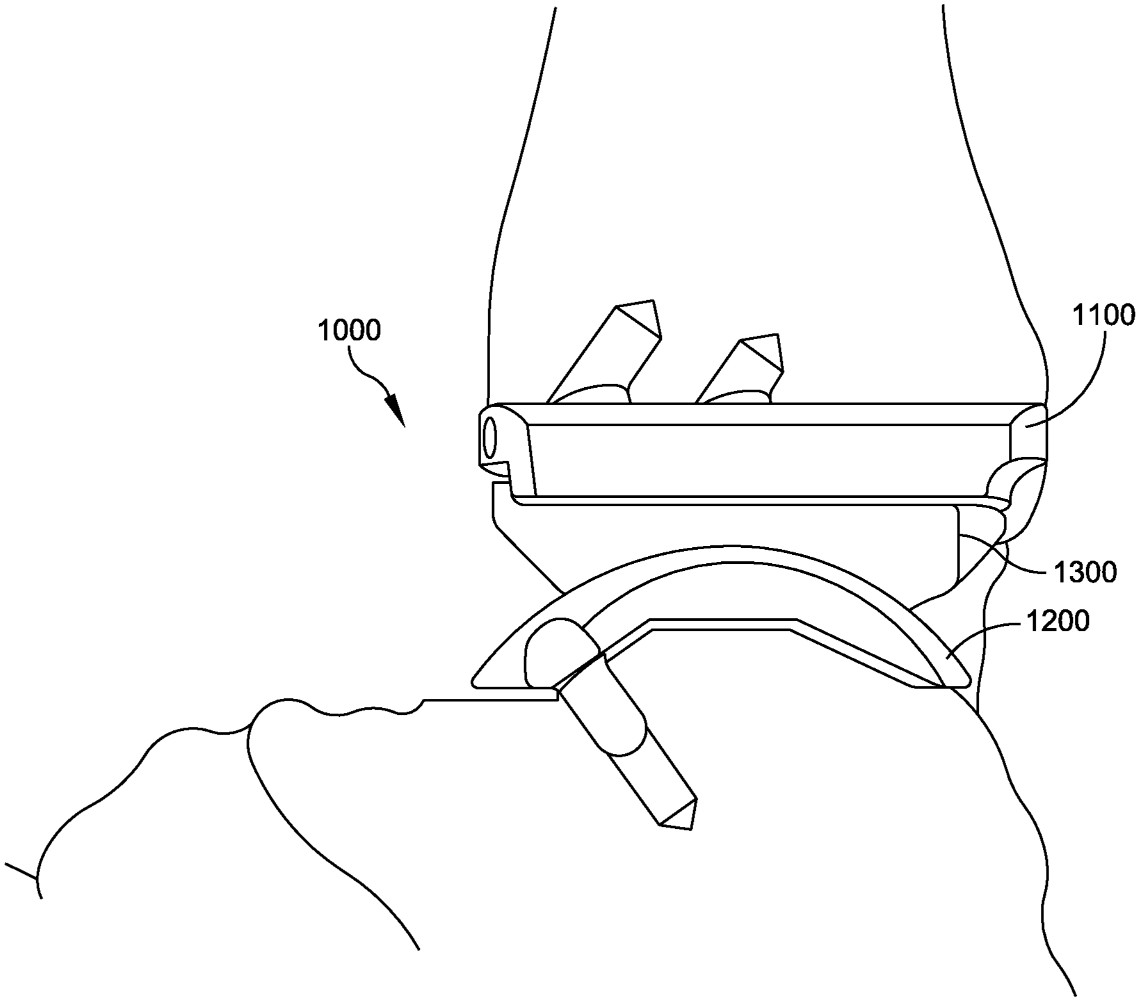
FIG. 99 is a side view of an ankle replacement prosthesis disposed within an ankle joint in accordance with some embodiments.

FIGS. 96-98 provide various views of the complete ankle replacement prosthesis 1000 in accordance with some embodiments, and FIG. 99 illustrates the position of the ankle replacement prosthesis 1000 upon completion of an ankle replacement procedure.

Ankle replacement prosthesis 1000 comprises tibial implant 1100, talar implant 1200, and poly implant 1300.

Upon completion of an ankle replacement procedure, tibial implant 1100 is connected to the tibia 260, with pegs 1104 disposed within peg holes 263 in the resectioned tibia 260. Talar implant 1200 is connected to the talus 265, with talar dome anterior pegs 1202 disposed within holes 2214 and 2216. Poly implant 1300 is inserted and disposed between tibial implant 1100 and talar implant 1200.

Method of Ankle Replacement

A method of performing an ankle replacement is disclosed using the above-described system.

An anterior incision is made lateral of the tibialis avoiding the anterior tendons and never bundle to expose the tibia 260, talus 265, and a portion of the midfoot. In some embodiments, the incision is approximately 125 mm long; however, one of ordinary skill in the art will understand that the incision can be greater or less than 125 mm. Gutter fork 10, illustrated in FIG. 1, is inserted into the medial gutter of the ankle joint.

Once medial gutter fork 10 is inserted into the medial gutter of the ankle joint, rotation guide slide 20 is operationally connected to medial gutter fork 10 by placing guide hole 18 over shaft 2 as illustrated in FIG. 4A. Rotation guide slide 20 is positioned with either first channel 16 or second channel 17 facing away from the tibia 260. Rotation guide pointer 30 is operationally connected to rotation guide slide 20 by sliding protrusion 26 into either first channel 16 or second channel 17, whichever is facing away from the tibia 260. Thus assembled, an operator uses finger tab 27 to rotate the combined rotation guide slide 20 and rotation guide pointer 30 about an axis defined by shaft 2. An operator may also use finger tab 27 to slide rotation guide pointer 30 along an axis defined by first channel 16 or second channel 17. The operator thus uses finger tab 27 to rotate the combined rotation guide slide 20 and rotation guide pointer 30 and slide rotation guide pointer 30 until pointer extension 24 is approximately aligned with the mechanical axis of the tibia 260.

Once the rotation guide assembly 40 is positioned as described above, the position of the rotation guide pointer 30 relative to the rotation guide slide 20 is fixed by tightening screws 37. A first guide pin 50 is inserted through pin hole 28 and into the tibia 260 as shown in FIG. 4B. With first guide pin 50 thus inserted, the entire rotation guide assembly 40 is removed, leaving first guide pin 50 in place as illustrated in FIG. 5.

With attention now to FIG. 12, the alignment frame assembly 140 is assembled by inserting the distal end 104 of the proximal alignment frame 109 into the distal alignment frame 105. The alignment frame assembly 140 is connected to the tibia 260 by sliding the hole 194 of the distal end 124 of the distal alignment frame 105 over the first guide pin 50. A pin 154 is installed percutaneously through the hole 103 at the proximal end 102 of the proximal alignment frame 109 into a tibial tuberosity.

Alternatively, the knee bracket 142 and rubber strap 148 can be used to secure the alignment frame assembly 140 to the proximal end of the tibia 260, as illustrated in FIGS. 13A and 13B. The knee bracket post 146 is inserted into the hole 103 at the proximal end 102 of the proximal alignment frame 109. The knee bracket base 144 is then positioned over the proximal end of the tibia 260 and secured in place using the rubber strap 148 by wrapping the rubber strap 148 laterally around the tibia 260 and attaching the hooks 152 of the knee bracket base 144 to the holes 151 of the rubber strap 148.

Turning now to FIG. 14, once the alignment frame assembly 140 is connected to the proximal end of the tibia 260, the distal end 124 of the distal alignment frame 105 is placed above the tibia 260 such that a gap, G, is provided between the distal alignment frame 105 and the tibia 260. In some embodiments, the gap G is approximately 20-25 mm from the frame 105 to the tibia 260; however, gap G can have other dimensions that are greater than or less than 20-25 mm. Once the desired gap is achieved, distal knob 196 is turned to loosely lock the distal end 124 of the distal alignment frame 105 to the first guide pin 50.

As illustrated in FIGS. 13A-16, the proximal alignment frame 109 is adjustable in length and is maintained at a fixed length by turning the most proximal knob 128 of the distal alignment frame 105. The second knob 108 of the proximal alignment frame 109 is then turned as indicated by arrow A1 to loosely lock the alignment frame assembly 140 to the pin 154 and/or knee bracket post 146.

The angel wing alignment guide 160 is then attached to the alignment frame assembly 140 by inserting the angel wing alignment guide post 166 into the slot 138 at the distal end 124 of the distal alignment frame 105, as illustrated in FIG. 17. A set screw (not shown) is then inserted through hole 139 that intersects the slot 138 and secured with a hex driver 174. The set screw (not shown) can be loosened to allow proximal/distal adjustment of the angel wing alignment guide 160.

As shown in FIG. 18, coronal rotation adjustments can be made to the proximal alignment frame 109. The first knob 106 at the proximal end 102 of the proximal alignment frame 109 can be turned as indicated by arrow A2 to allow adjustment of the angle of a perpendicular slot 101 at the proximal end 102 of the proximal alignment frame 109 for coronal rotation adjustment as indicated by arrows A3 and A4. The position of the angel wing alignment guide 160 can be viewed under A/P fluoroscopy to establish coronal alignment, which is typically parallel to the natural joint line, as illustrated in FIG. 20. Once coronal alignment is established, first knob 106 is turned in direction A2 to lock the relative positions of proximal alignment frame 109 and angel wing alignment guide 160.

Continuing now to FIG. 21, the alignment rod 170 is inserted through one of the holes 164 in either side of the angel wing alignment guide base 162 where it slides along the hole 164 until it reaches the stop collar 172. Either the second knob 108 or the distal knob 196 of the alignment frame assembly 140 can be turned to allow sagittal rotation adjustment, as illustrated in FIG. 22. The position of the alignment rod 170 can be viewed under lateral fluoroscopy to establish sagittal rotation, which is typically parallel to a shaft of the tibia 260, as illustrated in FIG. 23.

The angel wing alignment guide 160 and alignment rod 170 are removed once the desired position has been achieved. As illustrated in FIGS. 24 and 25, two pin sleeves 176 are inserted into two aligned holes 132 of the plurality of holes 132 at the distal end 124 of the distal alignment frame 105 that provide the optimal bone purchase, which is typically the two center holes 132. A trocar 178, as illustrated in FIG. 24B, is inserted into each of the pin sleeves 176 to create "stab wounds" for percutaneous pins, as illustrated in FIG. 26. The trocar 178 is then removed.

As illustrated in FIG. 27, a pin 150 is inserted into each of the pin sleeves 176 and through both cortices of the tibia 260. Once the pins 150 are placed, the pin sleeves 176 are removed and the second knob 108 and distal knob 196 are loosened to remove the alignment frame assembly 140. The proximal tibial pin 154 or knee bracket 142 and the first guide pin 50 are then removed, leaving pins 150 in the tibia 260, as illustrated in FIG. 28.

The adjustment block 100 of FIG. 29 is lowered onto pins 150 until first frame 110 is slightly above the anterior surface of the tibia 260. Locking screw 112 is then rotated to lock the position of adjustment block 100 relative to the tibia 260.

With attention now to FIG. 35, a drill guide 280 is connected to the adjustment block 100, lowered onto the anterior surface of the tibia 260, and locked into position using a set screw (not shown). Drill guide 280 is then translated to the center of the ankle joint using proximal-distal adjustment knob 111 and the medial-lateral adjustment knobs 121*a* and 121*b*. Once centered, the position of drill guide 280 is locked using set screws (not shown).

The operator sizes the tibial implant 1100 of the ankle replacement system by mounting a drill guide 280 on the tool holder and adjusting its position using knobs 111, 121, 131. The physician views an X-ray of the tibia bone 260 and drill guide 280 and determines whether it is the optimum size and position for the patient. The position can be adjusted based on the X-ray, using knobs 111, 121, 131. If the size of the resectioning cut corresponding to the drill guide 280 is too large or too small, the physician removes the drill guide, selects a different size drill guide, and snaps the new drill guide onto the tool holder 134 of the adjustment block 100. The drill guide is then repositioned against the tibia 260, imaged by fluoroscope, and the size is again checked.

With attention now to FIGS. 50-53, the sagittal sizing guide assembly 400 is then used to fluoroscopically identify the appropriate talar implant 1200 size and to set the appropriate height of talar resection. Sagittal sizing guide assembly 400 is connected to coronal sizing and drill guide 380 by lowering guide arm 402 such that mating extension 412 is engaged with slot 390. For minimal parallax distortion the sagittal sizing guide assembly 400 should be oriented to hang on the side of the ankle closest to the c-arm receiver and the sagittal sizing guide assembly 400 should be placed as close to the bones of the ankle joint, particularly the tibia 260, as possible. The sagittal guides are used to appropriately evaluate and position the proximal/distal resection placement of tibial and talar resections. In some embodiments, the talar size and talar chamfer preparations are estimated with the talar profile 486 on the distal side of sagittal guide. The tibia tray length is also indicated with the tibial pin length which is the proximal pin 480. The push button 476 allows for appropriate AP placement.

As described above, the sagittal sizing guide body 460 includes a combination of dowel 482 and fluoro-opaque profile 486 to advantageously enable the sizing of a talar implant 1200 and the appropriate height of the talar resection to be checked using fluoroscopy prior to resecting the talus. The height of resection height can be adjusted and locked in by adjusting knob 111 of adjustment block 100. A number of sagittal sizing guide bodies 460 can be available such that a surgeon or other health care professional can select the appropriate size based on the actual anatomy of the patient. The differently sized sagittal sizing guide bodies 460 can be swapped for one another until the appropriate sagittal sizing guide body 460 is identified.

As illustrated in FIG. 36, to resect the tibia 260, drill guide 280 is first pinned to the tibia 260 using fixation pins 287 inserted through the pin holes 282 and trimmed such that pins 287 extend slightly above the drill guide 280. Then the operator drills holes in the tibia 260 through the guides holes 281 using the drill guide 280 and drill 288. The holes thus drilled in the bone 260 define proximal corners of a resectioning cut to be performed in the tibia. The operator then removes the drill guide 280, while leaving the pins 287 in place (in the distal portion of the tibia 260 to be removed by the resectioning). While removing the drill guide 280, the adjustment block 100 can remain locked in the first coordinates with the first frame 110 adjusted to the same proximal-distal coordinate and the second frame 120 adjusted to the same medial-lateral coordinate.

With attention now to FIG. 37, a cut guide 290 corresponding to previously-utilized drill guide 280 is connected to adjustment block 100 and fixation pins 287. In some embodiments, additional fixation pins 297 are used to pin cut guide 290 to the talus bone 265. Once the cut guide 290 is positioned and pinned, the operator performs the resectioning cuts through the guide slots 295, cutting the bone to connect the previously drilled holes. In some embodiments, such as the embodiment illustrated in FIG. 37, one cut guide 290 is used for both the tibia resection and the first cut of the talar resection. The cut guide 290 is then removed from the surgery site, and detached from the adjustment block 100. The sections of the tibia 260 and talus 265 that have been cut are removed, along with the fixation pins 287 and 297. Various tools such as a corner chisel, bone removal screw, posterior capsule release tool, and bone rasp may be used to complete the resection, remove the resected portions from the surgery site, and clean the resection edges.

In some embodiments, a single coronal sizing and drill guide 380 is used in place of a drill guide 280 and cut guide 290.

As illustrated in FIG. 38, following the initial resectioning the operator inserts the tibia trial 210 into the resected joint space and seated flush against the resected tibia 260. In some embodiments, the operator leaves adjustment block 100 locked to fixation pins 150 and snaps the tibia trial 210 onto the tool holder 134. In other embodiments, the adjustment block 100 is removed and tibia trial 210 is pinned in place using fixation pins.

With tibia trial 210 in place and seated flush against the resected tibia 260, the operator drills a plurality (e.g., 3) peg holes 263 in the distal surface 262 of the resectioned tibia 260 using the tibia peg drill 299. In some embodiments, a tibial peg punch is used to prepare peg holes 263. The holes 212 (FIG. 31) of the tibia trial 210 are used to locate peg holes 263. FIG. 41 shows the distal end 261 of the tibia 260 at the completion of the peg drilling, with the three peg holes 263 in the resectioned surface 262 of the tibia.

With attention now to FIGS. 42-45, the operator now performs a trial reduction to ensure the correct height of the poly trial insert 230 and the correct position of the talus dome. Floating trial 250 and poly trial insert 230 are inserted into the resected joint space. The talar implant anterior-posterior coordinate is determined by moving the floating trial 250 to the location where it best articulates with the concave surface 232 of the poly trial insert 230. Once the position of floating trial 250 is optimized, two additional fixation pins 298 are inserted through the pin holes 253 of the floating trial 250. Floating trial 250 and poly insert trial 230 are then removed from the resectioned joint space and two additional resectioning cuts, described below, are performed to match the geometry of the talar dome to the talar implant 1200 of the ankle replacement system.

As shown in FIG. 60, the talar resection guide base 2100 is connected to the talus 265 by sliding holes 2104, 2106 of the talar resection guide base 2100 over fixation pins 298. Temporary fixation screws or pins 2154, 2156 are inserted into the two holes 2108, 2110 on either side of the base 2100 using a T-handle pin driver 2158. A bone saw 2160 is inserted through the lateral slit 2128 in the shoulder 2124 of the slot 2102 of the talar resection guide base 2100. The saw blade or bone saw 2160 is used to resect the talus 265 to create the posterior talar chamfer 2170, as illustrated in FIG. 74. Once the area is resected, the bone saw 2160 is and resected bone piece are removed from the surgery site.

As illustrated in FIG. 65, the anterior talar pilot guide 2130 is then inserted into the talar resection guide base 2100 and a talar reamer 2162 is used to make plunge cuts through the interconnecting holes 2132 of the anterior talar pilot guide 2130. As illustrated in FIG. 68, the anterior talar pilot guide 2130 is removed from the talar resection guide base 2100 and is rotated 180°. The talar reamer 2162 is then used to plunge cut through the interconnecting holes 2132 of the anterior talar pilot guide 2130 to prepare the talar surface for an anterior flat 2174 as best seen in FIG. 74. The anterior talar pilot guide 2130 is then removed from the talar resection guide base 2100.

Next, as shown in FIG. 70, an anterior talar finish guide 2142 is inserted into the talar resection guide base 2100 and the talar reamer 2162 is used to perform the finishing cuts for the anterior chamfer 2172 by sliding the talar reamer 2162 from side to side within the slot 2144 of the finish guide 2142, as indicated by arrow AR1. The anterior talar finish guide 2142 is then removed from the talar resection guide base 2100, is rotated 180°, and re-engaged with the talar resection guide base 2100. The talar reamer 2162 is then used to perform the finishing cuts for the anterior talar flat 2174 by sliding the talar reamer 2162 from side to side within the slot of the finish guide 2142, as indicated by arrow AR2. Having completed the talar finishing cuts, the anterior talar finish guide 2142, talar resection guide base 2100 and temporary fixation pins 2154, 2156 are removed from the surgery site.

Having completed resectioning the ankle joint, the tibial trial 210 is again positioned in the resectioned tibial bone space and connected to adjustment block 100. In alternative embodiments, the tibial trial 210 is again pinned in place using fixation pins. The talar implant holder 2188 is used to insert the talar peg drill guide 2180 into the joint space of the resected talus 265. The poly trial insert 230 is inserted into the tibial trial 210. A trial reduction is performed to establish optimal talar medial/lateral positioning. The foot F is slightly plantarflexed and a pin 2210 is inserted through the small hole 2182 in the center of the talar peg drill guide 2180 as a means to temporarily hold the talar peg drill guide 2180 in position, as illustrated in FIG. 78.

As illustrated in FIG. 80, anterior peg drill 2212 is inserted into each of the holes 2184, 2186 of the talar peg drill guide 2180 and is used to drill holes 2214, 2216 for the talar dome anterior pegs 1202. Pin 2210 in the talus 265 is removed and the talar peg drill guide 2180, poly trial insert 230, and tibial trial 210 are also removed from the surgery site.

With attention now to FIGS. 83-86, the tibial tray impaction insert 2220 is attached to the tibial implant 1100 in preparation for insertion of tibial implant 1100. Bone cement (not shown) may be applied to the superior, medial and lateral sides 1106, 1120, 1122 of the rectangular body 1102 of the tibial implant 1100, but the anterior face 1112 and inferior side 2238 of the tibial implant impaction insert 2220 remain free of bone cement. The insertion handle 2264 is inserted into the hole 2228 of the rectangular extension 2224 of the tibial tray impaction insert 2220. The insertion handle 2264 is used to insert the tibial implant 1100 and tibial tray impaction insert 2220 into the resected space of the tibia 260. Tibial implant 1100 is inserted and connected to tibia 260 with the three pegs 1104 of the tibial implant 1100 inserted into peg holes 263. The insertion handle 2264 is then removed, and an offset tibial implant impactor may be used to complete seating of the tibial implant 1100. Fluoroscopic imaging may be used to verify the tibial implant 1100 is fully seated.

The talar implant 1200 is then prepared for implantation. In some embodiments, bone cement is applied to portions of the talar implant 1200 which will seat on the talus 265. Talar implant 1200 is then connected to the talus 265, with talar dome anterior pegs 1202 disposed within holes 2214 and 2216. A talar implant impactor may be used to complete seating of the talar implant 1200, and fluoroscopic imaging may be used to verify the talar implant 1200 is fully seated.

The ankle joint is now prepared for a poly implant 1300. Poly inserter 3100 is assembled as shown in FIG. 90 by inserting locking tab 3112 into rectangular opening 3114, inserting plunger rod 3110 through threaded aperture 3106 and cylindrical opening 3118, and connecting push bar 3140 to the distal end 3128 of plunger rod 3110 as described above. Poly insert guide rail 3300 is then coupled to poly inserter 3100.

With attention now to FIGS. 93A and 93B, attachment screws 3500 are threadably inserted into tibial implant 1100. Poly inserter 3100 is lowered onto attachment screws 3500 such that attachment screws 3500 are disposed within opposed channels 3120. An attachment nut 3602 is threadably connected to the threaded proximal end 3504 of each attachment screw 3500 to secure poly inserter to the anterior face 1112 of the tibial implant 1100.

As illustrated in FIGS. 95A and 95B, locking tab 3112 is pulled in a direction perpendicular to elongate body 3102 such that the wider diameter base of aperture 3150 is aligned with plunger rod 3110 to permit plunger rod 3110 to slide relative to the elongate body 3102 of poly inserter 3100. Handle 3124 is used to slide the plunger rod 3110 distally such that poly implant 1300, positioned between extending rails 3302 of poly inserter guide rail 3300, is slid distally into the resected tibial bone space.

Once poly implant 1300 has been inserted into resected tibial bone space, poly inserter 3100 is removed from its engagement with poly implant 1300 by removing attachment nuts 3602 and pulling on handle 3124. Attachment screws 3500 are then unscrewed from tibial implant 1100.

With attention now to FIG. 99, upon completion of an ankle replacement procedure, tibial implant 1100 is connected to the tibia 260, with pegs 1104 disposed within peg holes 263 in the resectioned tibia 260. Talar implant 1200 is connected to the talus 265, with talar dome anterior pegs 1202 disposed within holes 2214 and 2216. Poly implant 1300 is inserted and disposed between tibial implant 1100 and talar implant 1200.

Patient-Specific Adapter

As noted above, various modifications can be made to the disclosed systems and methods. One example of such a modification is to utilize patient-specific locator mounts, such as those described in commonly assigned U.S. patent application Ser. No. 12/711,307, entitled "Method for Forming a Patient Specific Surgical Guide Mount, U.S. patent application Ser. No. 13/330,091, entitled "Orthopedic Surgical Guide," and U.S. patent application Ser. No. 13/464,175, entitled "Orthopedic Surgical Guide," the entireties of which are incorporated by reference herein, to mount the coronal sizing and drill guide 380 to a tibia 260 instead of using the adjustment block 300 and other associated instrumentation.

Figure 100:
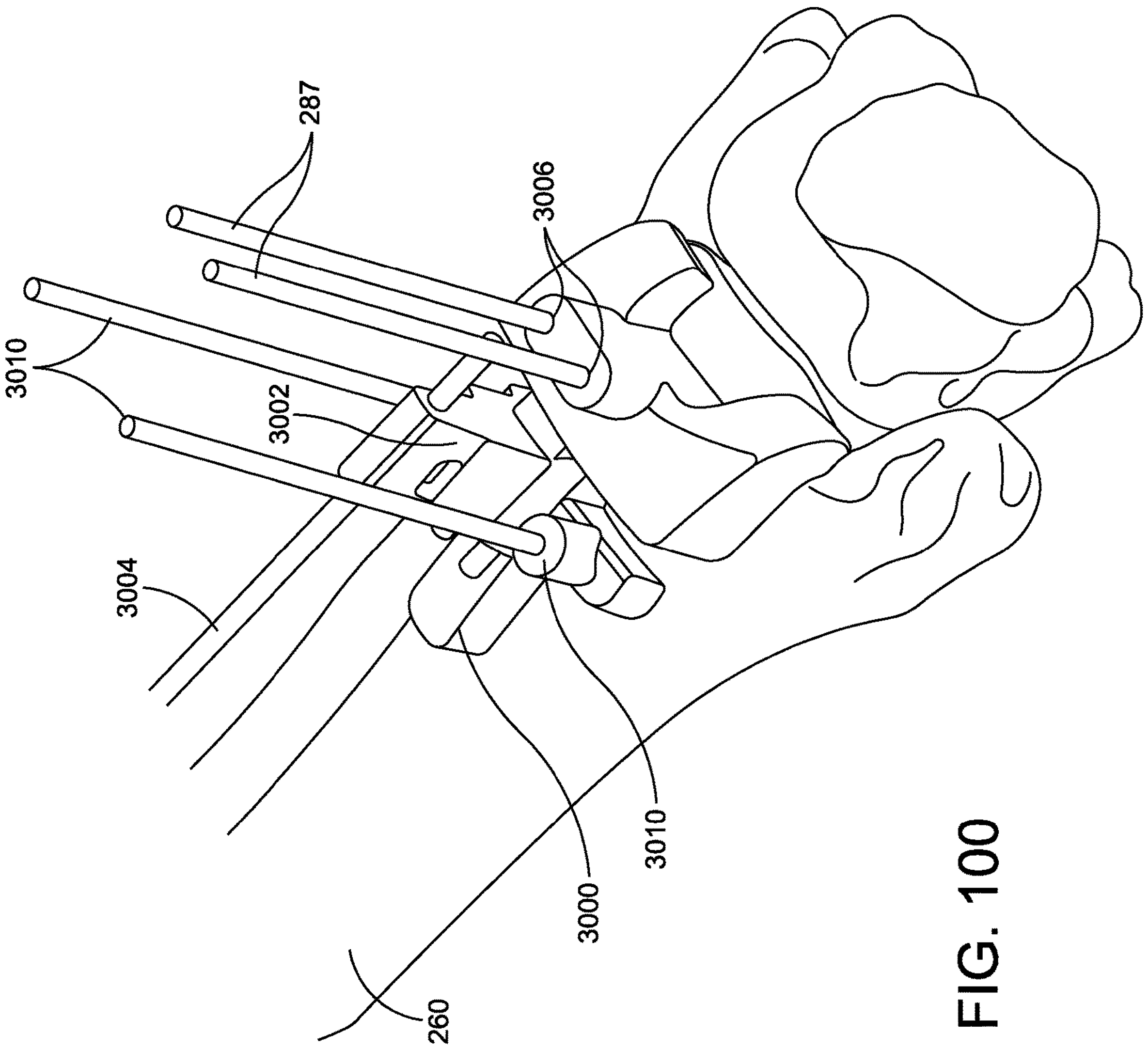
FIG. 100 is an isometric view of one example of a patient-specific locator guide coupled to a distal end of a tibia in accordance with some embodiments.

For example and referring to FIG. 100, a patient-specific mount 3000 can be fabricated to be positioned at the distal end of tibia 260. The patient-specific mount 3000 includes a pin holder extension 3002 that is configured to hold a pin 3004 in a position such that pin 2004 extends parallel to the mechanical (e.g., longitudinal) axis of the tibia 260. Pin 3004 can be used to check the proper alignment using fluoroscopy as will be understood by one of ordinary skill in the art. When the patient-specific guide is properly positioned, pins 287, such as those described above to secure cut guide 290 (FIGS. 36 and 37), are inserted through holes 3006 that are positioned to align with holes 282 of drill guide 280 or corresponding holes of cut guide 290 and/or coronal sizing and drill guide 380. Patient-specific mount 3000 also includes holes 3008 that are sized and configured to receive pins 3010. Once pins 287 and 3010 have been installed, patient-specific guide mount 3000 is slid over these pins 287, 3010 and removed.

Figure 101:
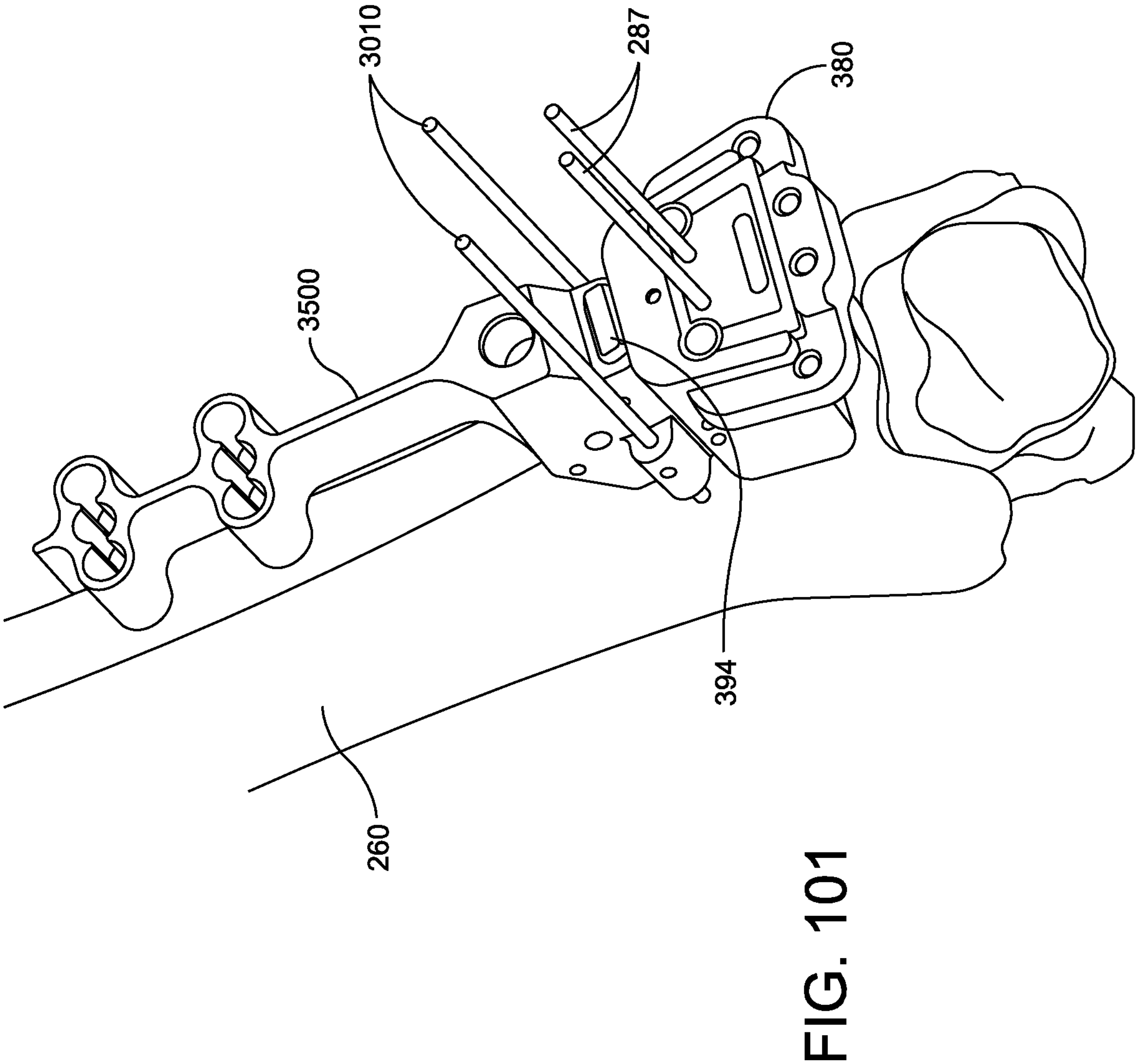
FIG. 101 is an isometric view of one example of a coronal sizing and drill guide and a conversion instrument that are positioned on a distal end of the tibia based on the pins placed by the patient-specific locator guide illustrated in FIG. 100 in accordance with some embodiments.
Figure 103:
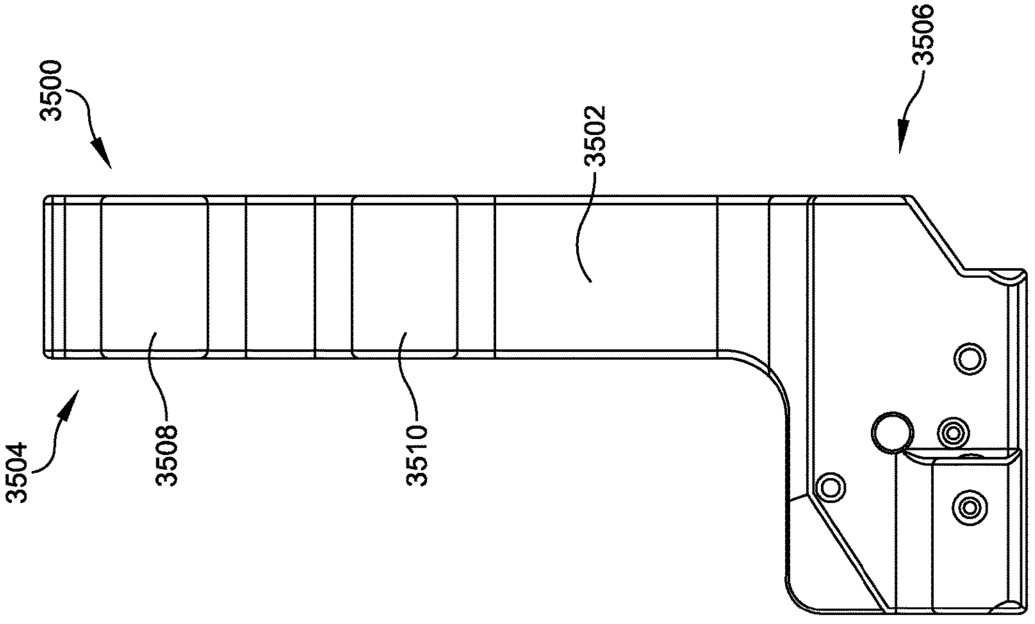
FIG. 103 is a side profile view of the conversion instrument illustrated in FIG. 101 in accordance with some embodiments.
Figure 102:
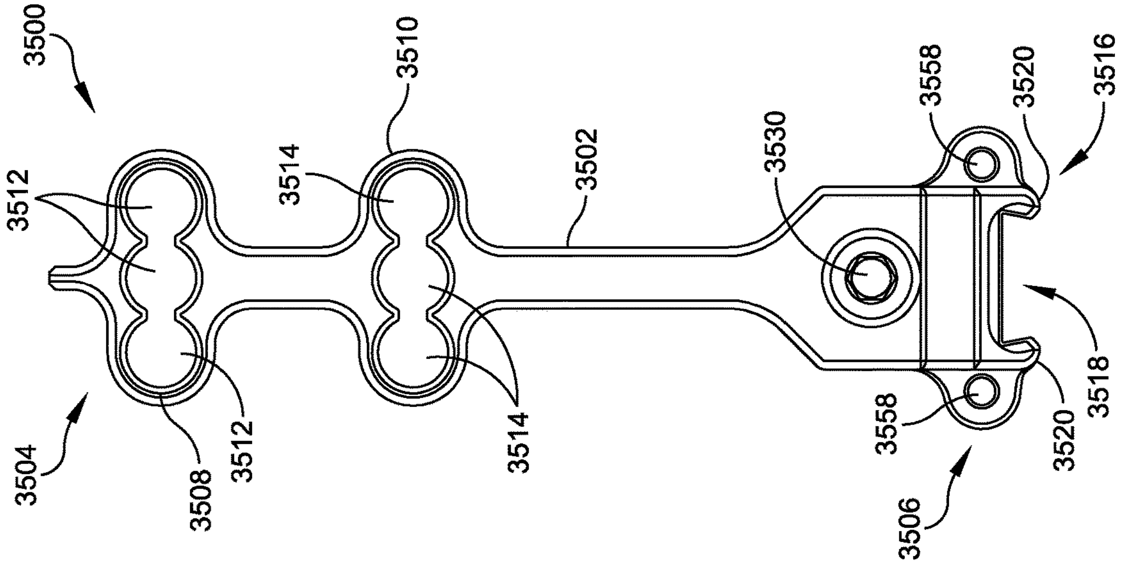
FIG. 102 is a front side view of the conversion instrument illustrated in FIG. 101 in accordance with some embodiments.

As shown in FIG. 101, coronal sizing and drill guide 380 can be slid over pins 287 and a conversion instrument 3500 is slid over pins 3010. As best seen in FIGS. 102-105, conversion instrument 3500 includes an elongate body 3502 extending from a proximal end 3504 to a distal end 3506. Conversion instrument 3500 includes a first and second oblong sections 3508, 3510 that extend transversely with respect to the longitudinal direction of instrument 3500. Each oblong section 3508, 3510 defines a respective plurality of interconnected holes 3512, 3514.

Figure 105:
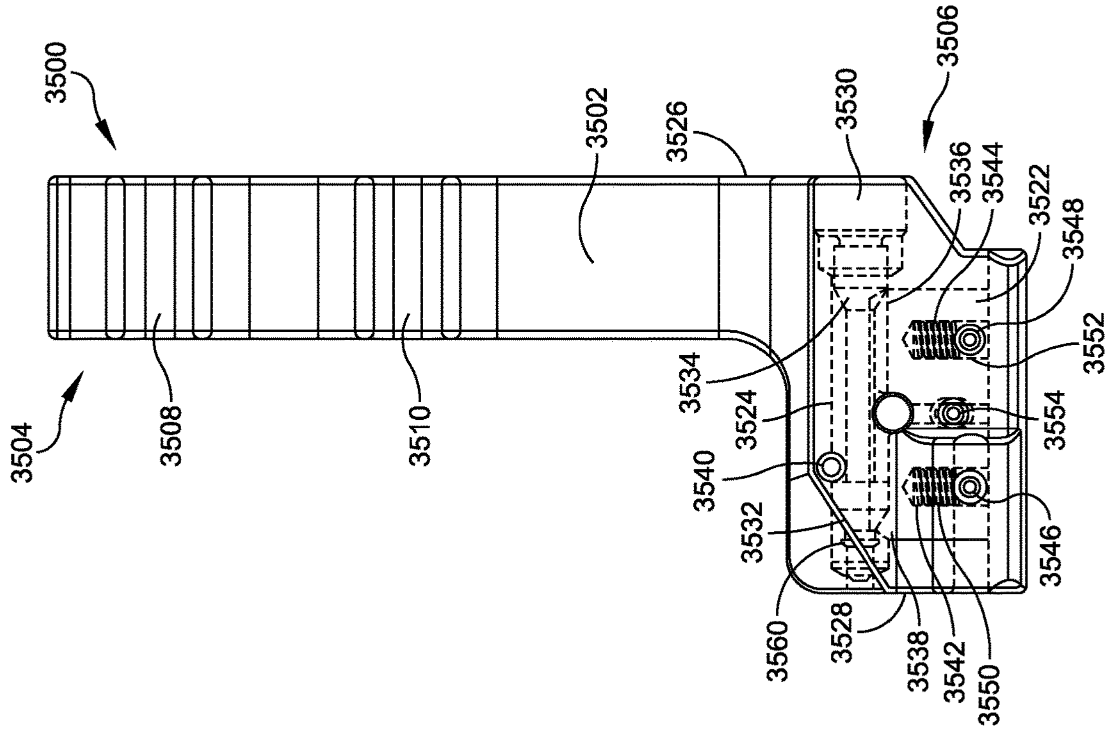
FIG. 105 is a side profile view of the conversion instrument illustrated in FIG. 101 showing the inter components in accordance with some embodiments.
Figure 104:
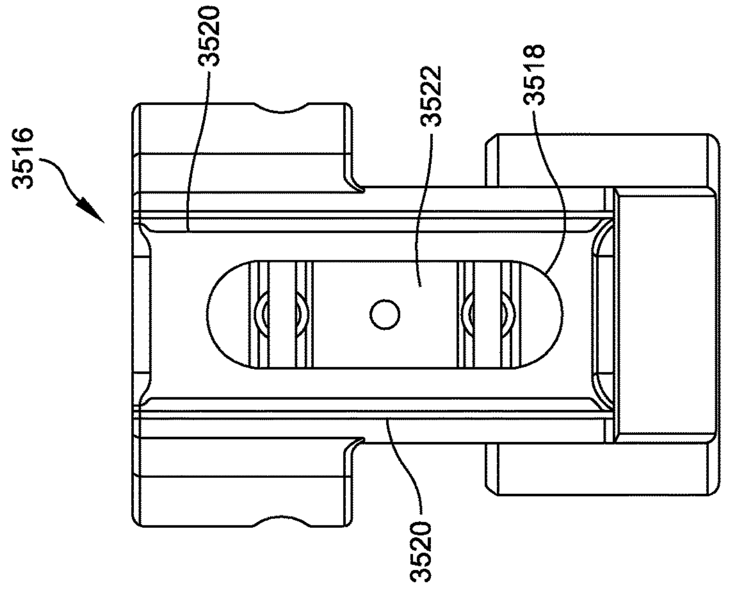
FIG. 104 is a bottom side view of the conversion instrument illustrated in FIG. 101 in accordance with some embodiments.

The distal end 3506 of instrument 3500 includes a dovetail joint 3516 having a similar construction to the dovetail joint 332 described above with respect to tool holder 330. A cavity 3518 is defined at the distal end 3506 of instrument 3500 between rails 3520. Cavity 3518 is sized and configured to receive a locking wedge 3522 as best seen in FIGS. 104 and 105. A through hole 3524 extends from a first side 3526 to a second side 3528 of the distal end 3506 of instrument 3500 and is sized and configured to receive a locking bolt 3530 therein. Locking bolt 3530 includes a pair of spaced apart shoulders 3532, 3534 along its length. Shoulders 3532, 3534 are configured to abut angled surfaces 3536, 3538 of locking wedge 3522 to press locking wedge 3522 against a dovetail member of drill guide 280, cut guide 290, and/or coronal sizing and drill guide 380. In some embodiments, locking bolt 3530 is cross-pinned within hole 3524 by a pin 3540 as best seen in FIG. 105.

Locking wedge 3522 is biased in a proximal direction by compression springs 3542, 3544, which are cross-pinned by pins 3546, 3548 such that they are disposed within channels 3550, 3552 defined by locking wedge 3522. Locking wedge 3522 also defines a vertical slot 3554 that is sized and configured to receive pin 3556 to cross pin wedge 3522 within cavity 3518. Turning back to FIG. 102, holes 3558 are defined by the distal end 3506 of instrument 3500 on either side of dovetail joint 3516. Holes 3558 are sized and configured to receive pins 3010 therein as shown in FIG. 101.

The conversion instrument 3500 can be secured to coronal sizing and drill guide 380 by having dovetail extension 394 of coronal sizing and drill guide 380 be received within dovetail joint 3516. A hex driver, such as hex driver 174 illustrated in FIG. 19, is used to tighten locking bolt 3530 within hole 3524. The rotation of locking bolt 3530 causes the engagement end 3560 (FIG. 105) of locking bolt, which can be threaded or have another engagement feature disposed thereon, engage a corresponding structure disposed within distal end of instrument 3500 and axially move such that shoulders 3532, 3534 of bolt 3530 contact angled surfaces 3536, 3538 of locking wedge 3522. The axial movement of bolt 3522 causes locking wedge 3522 to move distally compressing compression springs 3548, 3550 and forcing the bottom surface of locking wedge 3522 against dovetail extension, which is frictionally locked by rails 3520. The remainder of the surgical procedure can be carried out as described above.

In some embodiments, a surgical alignment system includes a guide arm, a ratchet arm frame configured to be coupled slidably to the guide arm, a ratchet arm configured to be coupled to the ratchet arm frame, and a sagittal sizing guide body configured to be coupled to the ratchet arm. The sagittal sizing guide body includes a first radiopaque object disposed at a first position and a second radiopaque object disposed at a second position that is spaced apart from the first position.

In some embodiments, the first radiopaque object includes a pin disposed in a first hole defined by the sagittal sizing guide body, and the second radiopaque object has a profile that corresponds to a profile of a first prosthesis component.

In some embodiments, the pin has a length that corresponds to a length of a second prosthesis component.

In some embodiments, the first prosthesis component is a talar component of an ankle replacement system, and the second prosthesis component is a tibial component of the ankle replacement system.

In some embodiments, the guide arm is configured to be coupled to a coronal sizing and drill guide.

In some embodiments, the ratchet arm frame defines an opening sized and configured to receive the guide arm slidably therein.

In some embodiments, the sagittal sizing guide body defines a channel sized and configured to receive the ratchet arm therein.

In some embodiments, the sagittal sizing guide body is configured to receive a biasing member and a push button for locking the sizing guide body relative to the ratchet arm.

In some embodiments, the guide arm extends from the ratchet arm frame in a first direction that is different from a second direction in which the ratchet arm extends from the ratchet arm frame.

In some embodiments, a method includes coupling a guide arm to a first fixture coupled to a first bone and inserting an end of the guide arm into an opening defined by a ratchet arm frame. The ratchet arm frame is coupled to a ratchet arm that extends in a first longitudinal direction that is different from a direction in which the guide arm extends along its length. The ratchet arm is inserted into a channel defined by a sagittal sizing guide body to couple the sagittal sizing guide body to the ratchet arm. The sagittal sizing guide body includes a first radiopaque object disposed at a first position and a second radiopaque object disposed at a second position that is spaced apart from the first position.

In some embodiments, the first radiopaque object includes a pin disposed in a first hole defined by the sagittal sizing guide body. The pin has a length that corresponds to a first prosthesis component. The second radiopaque object has a profile that corresponds to a profile of a second prosthesis component.

In some embodiments, a method includes using fluoroscopy to check a size of the first and second radiopaque elements of the sagittal sizing guide body relative to the first bone and a second bone.

In some embodiments, the sagittal sizing guide body is a first sagittal sizing guide body. A method includes uncoupling the first sagittal sizing guide body from the ratchet arm, and inserting the ratchet arm into a channel defined by a second sagittal sizing guide body to couple the second sagittal sizing guide body to the ratchet arm. The second sagittal sizing guide body includes third and fourth radiopaque objects that respectively correspond to a differently sized first prosthesis component and a differently sized second prosthesis component. Fluoroscopy is used to check a size of the third and fourth radiopaque elements relative to the first bone and the second bone.

In some embodiments, coupling the guide arm to the first fixture includes inserting a mating extension disposed at a second end of the guide arm into a slot defined by a coronal sizing and drill guide that is coupled to an adjustment block.

In some embodiments, the coronal sizing and drill guide includes a third radiopaque object having a size and shape of the first prosthesis component viewed in an anterior-posterior direction.

In some embodiments, a method includes inserting a dovetail extension of a coronal sizing and drill guide into a cavity of a dovetail joint of an adjustment block that is coupled to a tibia, securing the dovetail extension within the cavity, and using fluoroscopy to check a size of a radiopaque element of the coronal sizing and drill guide relative to at least the tibia. The radiopaque element has a size and shape that corresponds to a profile of a prosthesis component of a first type having a first size when viewed in an anterior-posterior direction.

In some embodiments, the coronal sizing and drill guide is a first coronal sizing and drill guide. A method includes uncoupling the first coronal sizing and drill guide from the adjustment block, inserting a dovetail extension of a second coronal sizing and drill guide into the cavity of the dovetail joint of the adjustment block, securing the dovetail extension of the second coronal sizing and drill guide within the cavity, and using fluoroscopy to check a size of a radiopaque element of the second coronal sizing and drill guide relative to at least the tibia. The radiopaque element has a size and shape that corresponds to a profile of the prosthesis component of the first type having a second size when viewed in the anterior-posterior direction.

In some embodiments, a method includes inserting pins into holes defined by the coronal sizing and drill guide to secure the coronal sizing an drill guide to at least the tibia and drilling holes in the tibia by inserting a drill into a first drill hole and a second drill hole defined by the coronal sizing and drill guide. The first and second drill holes are positioned such that they intersect the radiopaque element at two different locations.

In some embodiments, a method includes inserting a mating extension of a guide arm into a slot defined by the coronal sizing and drill guide to couple the guide arm to the coronal sizing and drill guide, and inserting an end of the guide arm into an opening defined by a ratchet arm frame. The ratchet arm frame is coupled to a ratchet arm that extends in a first longitudinal direction that is different from a direction in which the guide arm extends along its length. The ratchet arm is inserted into a channel defined by a sagittal sizing guide body to couple the sagittal sizing guide body to the ratchet arm. The sagittal sizing guide body includes a first radiopaque object disposed at a first position and a second radiopaque object disposed at a second position that is spaced apart from the first position.

In some embodiments, the first radiopaque object includes a pin disposed in a first hole defined by the sagittal sizing guide body, the pin having a length that corresponds to a length of the prosthesis component of the first type, and the second radiopaque object has a profile that corresponds to a profile of a prosthesis component of a second type.

In some embodiments, a surgical positioning system includes a first component including an elongate shaft coupled to a head. The head is configured to be disposed in a joint between a first bone and a second bone. A second component includes diverging first and second portions. The first portion defines a hole that is sized and configured to receive the shaft of the first component. The second portion defines a first channel on a first side. A third component is configured to be coupled to the second component. The third component includes a base and a pointer extension. The base includes a protrusion that is sized and configured to be received slidably within the first slot.

In some embodiments, the first channel is defined by a bottom wall and a pair of spaced apart side walls that extend from the bottom wall.

In some embodiments, the side walls extend from the bottom wall at a non-orthogonal angle.

In some embodiments, the second component defines a second channel on a second side, and the protrusion of the third component is configured to be received slidably within the second channel.

In some embodiments, the second channel is defined by a bottom wall and a pair of spaced apart side walls that extend from the bottom wall.

In some embodiments, the pointer extension defines a hole along its length that is sized and configured to receive a pin therein.

In some embodiments, the head includes a first prong and a second prong that are sized and configured to be received within a medial gutter of an ankle joint.

In some embodiments, the hole defined by the first portion is configured to receive the shaft of the first component rotatably therein.

In some embodiments, a method includes inserting a head of a first component of a surgical positioning system into a joint between a first bone and a second bone and sliding a second component of the surgical positioning system onto a shaft of the first component. The second component includes diverging first and second portions. The first portion defines a hole that is sized and configured to receive the shaft of the first component, and the second portion defines a first channel on a first side. A third component of the surgical positioning system is slid into engagement with the second component by inserting a protrusion of the third component into the first channel defined by the second component.

In some embodiments, a method includes rotating the second component relative to the first component and sliding the third component relative to the second component to align a pointer extension of the third component with an axis of the first bone.

In some embodiments, a method includes checking the alignment between the pointer extension and the axis of the bone using fluoroscopy.

In some embodiments, a method includes inserting a pin into a hole defined along a length of the pointer extension.

In some embodiments, a method includes removing the surgical positioning system from its engagement with the first and second bones while leaving the pin positioned within the first bone and coupling an alignment system to the pin.

In some embodiments, the first bone is a tibia, the second bone is a talus, and the joint is an ankle.

In some embodiments, a cutting system includes a cutting base having a body defining a slot, a first set of holes, and a second set of holes. The first set of holes being positioned along a first flange extending away from the slot in a first direction, and the second set of holes being positioned along a second flange extending from the slot in a second direction that is opposite the first direction. A first cutting guide has a body defining a plurality of holes that overlap one another to form a slot having a width that is smaller than a width of the slot defined by the cutting base. The first cutting guide includes a set of pegs that extend inferiorly from the first cutting guide and are sized and configured to be received with the first set of holes or the second set of holes to secure the first cutting guide to the cutting base.

In some embodiments, the cutting base defines a third set of holes positioned along the first flange and a fourth set of holes positioned along the second flange. The third and fourth sets of holes are configured to receive pins for securing the cutting base to a bone surface.

In some embodiments, a slit is defined along a wall defining the slot, the slit sized and configured to receive a saw blade therein for performing a chamfer cut of a bone.

In some embodiments, a second cutting guide has a body defining a slot having a width that is smaller than a width of the slot defined by the cutting base. The second cutting guide includes a set of pegs that extend inferiorly from the second cutting guide and are sized and configured to be received with the first set of holes or the second set of holes to secure the second cutting guide to the cutting base.

A method includes coupling a cutting base to a resected surface of a first bone. The cutting base includes a body defining a slot, a slit within the slot, a first set of holes, and a second set of holes. The first set of holes being positioned along a first flange extending away from the slot in a first direction, and the second set of holes being positioned along a second flange extending from the slot in a second direction that is opposite the first direction. A chamfer cut of the first bone is made by inserting a saw into the slit. A first cutting guide is coupled to the cutting guide base by inserting inferiorly extending pegs into the first set of holes. The first cutting guide has a body defining a plurality of holes that overlap one another to form a slot having a width that is smaller than a width of the slot defined by the cutting base. A reamer is plunged into each of the plurality of holes defined by the first cutting guide to form a first flat. The first cutting guide is rotated relative to the cutting guide base and is coupled to the cutting guide base by inserting the inferiorly extending pegs into the second set of holes. A reamer is plunged into each of the plurality of holes defined by the first cutting guide to form a second flat.

In some embodiments, a method includes coupling a second cutting guide to the cutting guide base by inserting inferiorly extending pegs into the first set of holes. The second cutting guide defines a slot having a width that is narrower than a width of the slot defined cutting base. A reamer is moved along the slot defined by the second cutting guide to form a first final flat.

In some embodiments, a method includes rotating the second cutting guide relative to the cutting guide base, coupling the second cutting guide to the cutting guide base by inserting the inferiorly extending pegs into the second set of holes, and moving a reamer along the slot defined by the second cutting guide to form a second final flat.

In some embodiments, a surgical device includes a body including a handle disposed at a first end and a locking protrusion extending a direction away from a longitudinal direction of the body. The locking protrusion defines an opening that is sized and configured to receive a locking tab therein and defining a hole that extends parallel to the longitudinal direction of the body. The locking tab defines an aperture having first and second portions in which the first portion is narrower than the second portion. A pair of spaced apart rails are configured to be disposed along a length of the body. A plunger rod is sized and configured to be received slidably within a threaded hole defined by the handle, the aperture defined by the locking tab, and the hole defined by the locking protrusion. The surgical device is configured to be coupled releasably to a first implant component and to guide a second implant component into position with respect to the first implant component.

In some embodiments, the plunger rod includes a handle at a proximal end and a shoulder having an enlarged diameter along a length of the plunger rod.

In some embodiments, the plunger rod includes a threaded portion adjacent to the shoulder. The threaded portion is configured to engage the threaded hold defined by the handle.

In some embodiments, the plunger rod includes a reduced diameter region adjacent to a distal end of the plunger rod. The reduced diameter region has a diameter that is sized and configured to be received within the first portion of the aperture defined by the locking tab for locking the plunger rod in a retracted position.

In some embodiments, a push bar includes an elongate body from which an extension protrudes. The extension is sized and configured to be received within a hole defined by the distal end of the plunger rod that extends axially along the plunger rod.

In some embodiments, the extension defines a circumferential groove that is sized and configured to receive a pin therein to cross-pin the push bar to the distal end of the plunger rod such that the push bar is able to rotate relative to the plunger rod.

In some embodiments, the body defines a channel along opposed lateral sides thereof each being sized and configured to receive an attachment screw for coupling the surgical device to the first implant component.

In some embodiments, a method includes coupling an insertion device to a first implant component disposed within a joint, pushing a plunger rod of the insertion device axially to advance a second implant component along a body of the insertion device between a pair of spaced apart rails until a threaded portion of the plunger rod contacts a threaded hole defined by a handle of the insertion device, and rotating a handle of the plunger rod relative to the body of the insertion device such that the threads of the threaded portion of the plunger rod engage threads of the threaded hole to advance the second implant component into engagement with the first implant component.

In some embodiments, coupling the insertion device to the first implant includes coupling first and second attachment screws to the first implant component, inserting the body of the insertion device into a space between the first and second attachment screws such that a free end of each of the first and second attachment screw is received within a respective hole defined by the handle of the insertion device, and attaching a nut to each of the respective free ends of the first and second attachment screws.

In some embodiments, a method includes pulling the plunger rod proximally with respect to the body of the insertion device and locking the plunger rod relative to the body of the insertion device by advancing a locking button relative to a locking protrusion of the body of the insertion device such that a reduced diameter portion of the plunger rod is received within a first portion of an aperture that has a narrower opening than a second portion of the aperture.

A method includes placing a guide having a patient-specific surface on a first bone. The guide includes a pin holder that engages a pin that extends in a direction that is parallel to an axis of the first bone. A plurality of pins are inserted into the guide. The guide is slid along the plurality of pins to remove the guide from contacting the first bone. A conversion instrument is slid over a first subset of the plurality of pins, and a sizing and drill guide is slid over a second subset of the plurality of pins. The conversion instrument is coupled to the sizing and drill guide by inserting a dovetail extension of the sizing and drill guide into a cavity of a dovetail joint of the conversion instrument.

In some embodiments, a method includes using fluoroscopy to check a size of a radiopaque element of the sizing and drill guide relative to the first bone. The radiopaque element has a size and shape that corresponds to a profile of a prosthesis component of a first type having a first size when viewed in the anterior-posterior direction.

In some embodiments, the sizing and drill guide is a first sizing and drill guide. A method includes uncoupling the first sizing and drill guide from the conversion instrument and the second subset of the plurality of pins, sliding a second sizing and drill guide over the second subset of the plurality of pins, and coupling the conversion instrument to the second sizing and drill guide by inserting a dovetail extension of the second sizing and drill guide into the cavity of the dovetail joint of the conversion instrument.

In some embodiments, a surgical system includes a trial and a spacer. The trial is configured to be received within a resected first bone. The trial includes a plate having a bottom surface defining a channel. The spacer has an elongate body and an extension disposed at one end thereof. The elongate body is sized and configured to be received within channel defined by the trial. The extension defining at least first and second holes that are configured to receive first and second pins positioned within a second bone.

In some embodiments, a surgical system includes a cutting guide having a front face defining a plurality of holes and a slot. A first subset of the plurality of holes is configured to receive the first and second pins such that cutting guide is positioned in a first position with respect to the first bone. A second subset of the plurality of holes is configured to receive the first and second pins such that the cutting guide is positioned in a second position with respect to the first bone that is different from the first position.

In some embodiments, one of the plurality of holes is a hole that is at least partially threaded for receiving a threaded rod to assist in removing the spacer from the channel defined by the channel.

In some embodiments, the spacer is formed from a radiolucent material.

In some embodiments, the first bone is a tibia and the second bone is a talus.

In some embodiments, a method includes inserting an elongate body of a spacer into a channel defined by a trial positioned within a resected first bone, inserting first and second pins through first and second holes defined by an extension of the spacer that extends superiorly from the elongate body; and removing the spacer and the trial while leaving the first and second pins positioned within the second bone. A cutting guide is slid over the first and second pins.

In some embodiments, the first and second pins are received within a first subset of a plurality of holes defined by the cutting guide or a second subset of the plurality of pins defined by the cutting guide.

In some embodiments, the first subset of holes is positioned at a first distance from a slot defined by the cutting guide, and the second subset of holes is positioned at a second distance from the slot that is different from the first distance.

In some embodiments, a method includes resecting the second bone by inserting a cutting instrument in a slot defined by the cutting guide to resect the second bone. In some embodiments, the first bone is a tibia and the second bone is a talus.

Although the subject matter has been described in terms of exemplary embodiments, it is not limited thereto. Rather, the appended claims should be construed broadly, to include other variants and embodiments, which may be made by those skilled in the art.

What is claimed is:

1. A method comprising:

coupling a cutting base to a resected surface of a first bone, the cutting base including a body defining a slot, a slit within the slot, a first set of holes, and a second set of holes, the first set of holes being positioned along a first flange extending away from the slot in a first direction, and the second set of holes being positioned along a second flange extending from the slot in a second direction that is opposite the first direction;

making a chamfer cut of the first bone by inserting a saw into the slit;

coupling a first cutting guide to the cutting guide base by inserting inferiorly extending pegs into the first set of holes, the first cutting guide having a body defining a plurality of holes that overlap one another to form a slot having a width that is smaller than a width of the slot defined by the cutting base;

plunging a reamer into each of the plurality of holes defined by the first cutting guide to form a first flat;

rotating the first cutting guide relative to the cutting guide base;

coupling the first cutting guide to the cutting guide base by inserting the inferiorly extending pegs into the second set of holes; and plunging a reamer into each of the plurality of holes defined by the first cutting guide to form a second flat.

2. The method of claim 1 comprising:

coupling a second cutting guide to the cutting guide base by inserting inferiorly extending pegs into the first set of holes, the second cutting guide defining a slot having a width that is narrower than a width of the slot defined cutting base; and moving a reamer along the slot defined by the second cutting guide to form a first final flat.

3. The method of claim 2 comprising:

rotating the second cutting guide relative to the cutting guide base;

coupling the second cutting guide to the cutting guide base by inserting the inferiorly extending pegs into the second set of holes; and moving a reamer along the slot defined by the second cutting guide to form a second final flat.

4. A method comprising:

coupling a cutting base to a resected surface of a first bone, the cutting base including a body defining a slot that extends transversely across the body, a first flange extending from the slot in a first direction and defining a first set of holes, and a second flange extending from the slot in a second direction that is opposite the first direction and defining a second set of holes;

coupling a first cutting guide to the cutting base by inserting pegs of the first cutting guide into the first set of holes, the first cutting guide having a body defining a plurality of interconnecting holes that cooperate to form a slot having a width that is smaller than a width of the slot defined by the cutting base;

plunging a reamer into each of the plurality of interconnecting holes defined by the first cutting guide;

removing the first cutting guide from the cutting base;

rotating the first cutting guide;

coupling the first cutting guide to the cutting base by inserting the pegs of the first cutting guide into the second set of holes; and plunging a reamer into each of the plurality of interconnecting holes defined by the first cutting guide.

5. The method of claim 4, further comprising, making a chamfer cut of the first bone by inserting a saw into a slit defined within the slot of the cutting base.

6. The method of claim 5, wherein the slit is defined along a superior side of a shoulder that extends along a circumference of the slot.

7. The method of claim 5, wherein the chamfer cut forms a posterior talar chamfer on the first bone.

8. The method of claim 4, wherein rotating the first cutting guide comprises rotating the first cutting guide 180 degrees relative to the cutting base.

9. The method of claim 4, wherein the reamer includes a solid elongate body having an end configured to be received in the plurality of interconnecting holes and a collar disposed on the end that serves as a stop for reaming depth.

10. The method of claim 4, wherein plunging the reamer into each of the plurality of interconnecting holes when the pegs are inserted into the first set of holes prepares the first bone for an anterior chamfer, and plunging the reamer into each of the plurality of interconnecting holes when the pegs are inserted into the second set of holes prepares the first bone for an anterior flat.

11. The method of claim 4, further comprising:

coupling a second cutting guide to the cutting base by inserting pegs of the second cutting guide into the first set of holes, the second cutting guide defining a slot having a width that is narrower than a width of the slot defined by the cutting base; and moving a reamer along the slot defined by the second cutting guide to form a first final surface on the first bone.

12. The method of claim 11, further comprising:

removing the second cutting guide from the cutting base;

rotating the second cutting guide relative to the cutting base;

coupling the second cutting guide to the cutting base by inserting the pegs of the second cutting guide into the second set of holes; and moving a reamer along the slot defined by the second cutting guide to form a second final surface on the first bone.

13. The method of claim 12, wherein the first final surface is an anterior chamfer and the second final surface is an anterior flat.

14. The method of claim 4, wherein the first cutting guide includes an inferior tab for ease of assembly and disassembly.

15. The method of claim 4, wherein the first bone is a talus.

16. The method of claim 4, further comprising coupling the cutting base to the first bone by sliding holes defined by the first flange or the second flange over fixation pins that are positioned within the first bone.

17. The method of claim 16, further comprising inserting temporary fixation screws or pins into holes defined on medial and lateral sides of the cutting base to further secure the cutting base to the first bone.

18. A method of resecting a bone for receipt of a prosthesis component, the method comprising:

securing a cutting base to a surface of the bone, the cutting base having a body defining a slot, a slit within the slot, and first and second flanges extending from the slot in opposite directions, the first flange defining a first set of holes disposed near the slot and the second flange defining a second set of holes disposed near the slot;

performing a chamfer resection of the bone by inserting a cutting instrument into the slit;

coupling a first cutting guide to the cutting base in a first orientation by inserting pegs that extend inferiorly from the first cutting guide into the first set of holes;

making plunge cuts through a plurality of holes defined by the first cutting guide using a reamer to form a first bone surface;

removing the first cutting guide from the cutting base, rotating the first cutting guide, and coupling the first cutting guide to the cutting base in a second orientation by inserting the pegs into the second set of holes; and making plunge cuts through the plurality of holes defined by the first cutting guide using the reamer to form a second bone surface.

19. The method of claim 18, further comprising:

coupling a second cutting guide to the cutting base by inserting pegs that extend inferiorly from the second cutting guide into the first set of holes, the second cutting guide defining a slot; and performing finishing cuts by moving the reamer along the slot defined by the second cutting guide to form a first final bone surface.

20. The method of claim 19, further comprising:

removing the second cutting guide from the cutting base, rotating the second cutting guide, and coupling the second cutting guide to the cutting base by inserting the pegs of the second cutting guide into the second set of holes; and performing finishing cuts by moving the reamer along the slot defined by the second cutting guide to form a second final bone surface.

21. The method of claim 20, wherein the first bone surface is an anterior chamfer, the second bone surface is an anterior flat, the first final bone surface is a finished anterior chamfer, and the second final bone surface is a finished anterior flat.

22. The method of claim 18, wherein rotating the first cutting guide comprises rotating the first cutting guide 180 degrees.

23. The method of claim 18, wherein the bone is a talus.

24. The method of claim 18, wherein the plurality of holes defined by the first cutting guide are interconnecting holes that cooperate to define a slot having a width that is smaller than a width of the slot defined by the cutting base.

25. The method of claim 18, wherein the slit is defined along a superior side of a shoulder of the slot and extends parallel to a longitudinal axis of the slot.

26. The method of claim 18, wherein the cutting base further defines a third set of holes and a fourth set of holes positioned along the first and second flanges, respectively, the third and fourth sets of holes configured to receive pins for securing the cutting base to the bone.

27. The method of claim 26, further comprising securing the cutting base to the surface of the bone by sliding the third and fourth sets of holes over fixation pins previously positioned within the bone.

28. The method of claim 27, wherein the fixation pins were previously positioned using a floating trial.

29. The method of claim 18, wherein the reamer has a solid elongate body and includes a collar that serves as a depth stop.

30. The method of claim 18, further comprising, after forming the first and second bone surfaces and prior to coupling the second cutting guide to the cutting base, removing the first cutting guide from the cutting base.

* * * * *